US007306910B2

(12) United States Patent
Wang

(10) Patent No.: US 7,306,910 B2

(45) Date of Patent: Dec. 11, 2007

(54) BREAST CANCER PROGNOSTICS

(75) Inventor: Yixin Wang, San Diego, CA (US)

(73) Assignee: Veridex, LLC, Raritan, NJ (US)

( * ) Notice: Subject to any disclaimer, the term of this patent is extended or adjusted under 35 U.S.C. 154(b) by 384 days.

(21) Appl. No.: 10/422,522

(22) Filed: Apr. 24, 2003

(65) Prior Publication Data

US 2004/0214179 A1 Oct. 28, 2004

(51) Int. Cl.

| | |
|---|---|
| ***C12Q 1/68*** | (2006.01) |
| ***C12Q 1/00*** | (2006.01) |
| ***G01N 33/53*** | (2006.01) |
| ***G01N 33/567*** | (2006.01) |
| ***G01N 33/574*** | (2006.01) |
| ***G01N 33/48*** | (2006.01) |
| ***G01N 1/00*** | (2006.01) |

(52) U.S. Cl. ............................... 435/6; 435/4; 435/7.1; 435/7.21; 435/7.23; 436/64; 436/174; 536/1; 536/1.11; 536/18.7; 536/22.1; 536/23.1; 536/23.5

(58) Field of Classification Search .................... 536/1, 536/1.11, 18.7, 22.1, 23.1, 23.5; 436/64, 436/174; 435/4, 7.1, 6, 7.21, 7.23

See application file for complete search history.

(56) References Cited

FOREIGN PATENT DOCUMENTS

| | | |
|---|---|---|
| WO | WO 99/33982 | 7/1999 |
| WO | WO 02/10436 | 2/2002 |
| WO | WO 02/059271 | 8/2002 |
| WO | WO 02/068579 | 9/2002 |
| WO | WO 2004/065545 | 8/2004 |
| WO | WO 2004/079014 | 9/2004 |

OTHER PUBLICATIONS

Van De, Marc J. et al., "A Gene-Expression Signature as a Predictor of Survival in Breast Cancer", The New England Journal of Medicine Massachusetts Medical Society, Boston, MA, U.S., vol. 347, No. 25, Dec. 2002, pp. 1999-2009, Vliver.

Bertucci, Francois et al., "Prognosis of Breast Cancer and Gene Expression Profiling Using DNA Arrays", Annual New York Academby of Science, New York, NY, U.S., vol. 975, Dec. 2002, pp. 217-231.

Bertucci, Francois et al., "Gene Expression Profiles of Poor-Prognosis Primary Breast Cancer Correlate with Survival", Human Molecular Genetics, Oxford University Press, Surrey, Great Brittan, vol. 11, No. 8, Apr. 2002, pp. 863-872.

Bertucci, Francois et al., "Gene Expression Profiling of Primary Breast Carcinomas Using Arrays fo Candidate Genes", Human Molecular Genetics, vol. 9, No. 20, Dec. 2000, pp. 2981-2991.

Sorlie, Therese et al., "Gene Expression Patters of Breast Carcinomas distinguish Tumor Subclasses with Clinical Implications", Proceedings of the National Academy of Sciences fo USA, National Academy of Science, Washington, U.S., vol. 98, No. 19, Sep. 2001.

Martin, Katherine J., "Linking Gene Expression Patterns to Therapeutic Groups in Breast Cancer", Cancer Research, American Association for Cancer Research, Baltimore, MD, U.S.

Perou, Charles M. et al., "Molecular Portraits of Human Breast Tumours", Nature, MacMillan Journals Ltd., London, Great Brittan, vol. 406, No. 6797, Aug. 2000, pp. 747-752.

Sofia K. et al.; "Gene expression profiling to predict outcome in breast cancer; the influence of sample selection", Breast Cancer Res 2003, 5:23-26 (DOI 10.1186/bcr548) (Print ISSN 1465-5411; Online ISSN 1465-542CX) Received: Aug. 7, 2002 Accepted: Sep. 20, 2002 Published Oct. 11, 2002, Gurvberger.

Partial European Search Report, dated Dec. 27, 2004, for European Appln. No. EP 0425 2389.

Martin, Katherine J., "Linking Gene Expression Patterns to Therapeutic Groups in Breast Cancer", Cancer Research, American Association for Cancer Research, Baltimore, MD, U.S, Apr. 15, 2000.

Dai, Hongyue, et. al, "A Cell Proliferation Signature Is a Marker of Extremely Poor Outcome in a Subpopulation of Breast," Cancer Res 2005; 65: (10). May 15, 2005.

*Primary Examiner*—Alana M. Harris

(74) *Attorney, Agent, or Firm*—Todd F. Volyn

(57) ABSTRACT

A method of providing a prognosis of breast cancer is conducted by analyzing the expression of a group of genes. Gene expresson profiles in a variety of medium such as microarrays are included as are kits that contain them.

1 Claim, 3 Drawing Sheets

BREAST CANCER PROGNOSTICS

BACKGROUND

This invention relates to prognostics for breast cancer based on the gene expression profiles of biological samples.

In breast cancers, prognosis is determined primarily by the presence or absence of metastases in draining axillary lymph nodes. However, in approximately one third of women with breast cancer who have negative lymph nodes, the disease recurs and about one third of patients with positive lymph nodes are free of disease ten years after local or regional therapy. Furthermore, an increasing proportion of breast cancers are being diagnosed at an early stage because of increased awareness and wider use of screening modalities. Universal application of systematic therapy to these patients often leads to over-treatment. According to the St Gallen and NIH consensus, 70-80% of the Stage I and II patients would not have developed distant metastases without adjuvant treatment and may potentially suffer from the side effects. These data highlight the need for more sensitive and specific prognostic assays that could significantly reduce the number of patients that receive unnecessary treatment.

Tumor size and lymphatic or vascular invasion have been found to be of significant prognostic value in several studies. Quantitative pathological features, i.e. nuclear morphology, DNA content and proliferative activity may further demarcate tumors that have a high chance of micrometastases. Known molecular genetic changes that affect patient outcome include Her2/NEU over-expression, DNA amplifications, p53 mutations, ER/PR status, uPA and PAI expression. Because the metastatic cascade is a complex process that includes multiple steps, single factors that contribute to tumor process have limitations for prognostic assessment. The gene expression profiles of this invention will provide increased prognostic power.

SUMMARY OF THE INVENTION

The invention is a method of assessing the likelihood of a recurrence or metastasis of breast cancer in a patient diagnosed with or treated for breast cancer. The method involves the analysis of a gene expression profile.

In one aspect of the invention, the gene expression profile includes 56 genes. In yet other aspects of the invention, the profiles comprise those of at least 45 genes, 26 genes, 13 genes, and 6 genes respectively.

Articles used in practicing the methods are also an aspect of the invention. Such articles include gene expression profiles or representations of them that are fixed in machine-readable media such as computer readable media.

Articles used to identify gene expression profiles can also include substrates or surfaces (such as microarrays) to capture and/or indicate the presence, absence, or degree of gene expression.

In yet another aspect of the invention, kits include reagents for conducting the gene expression analysis prognostic of breast caner recurrence or metastasis.

DETAILED DESCRIPTION

Figure 1:
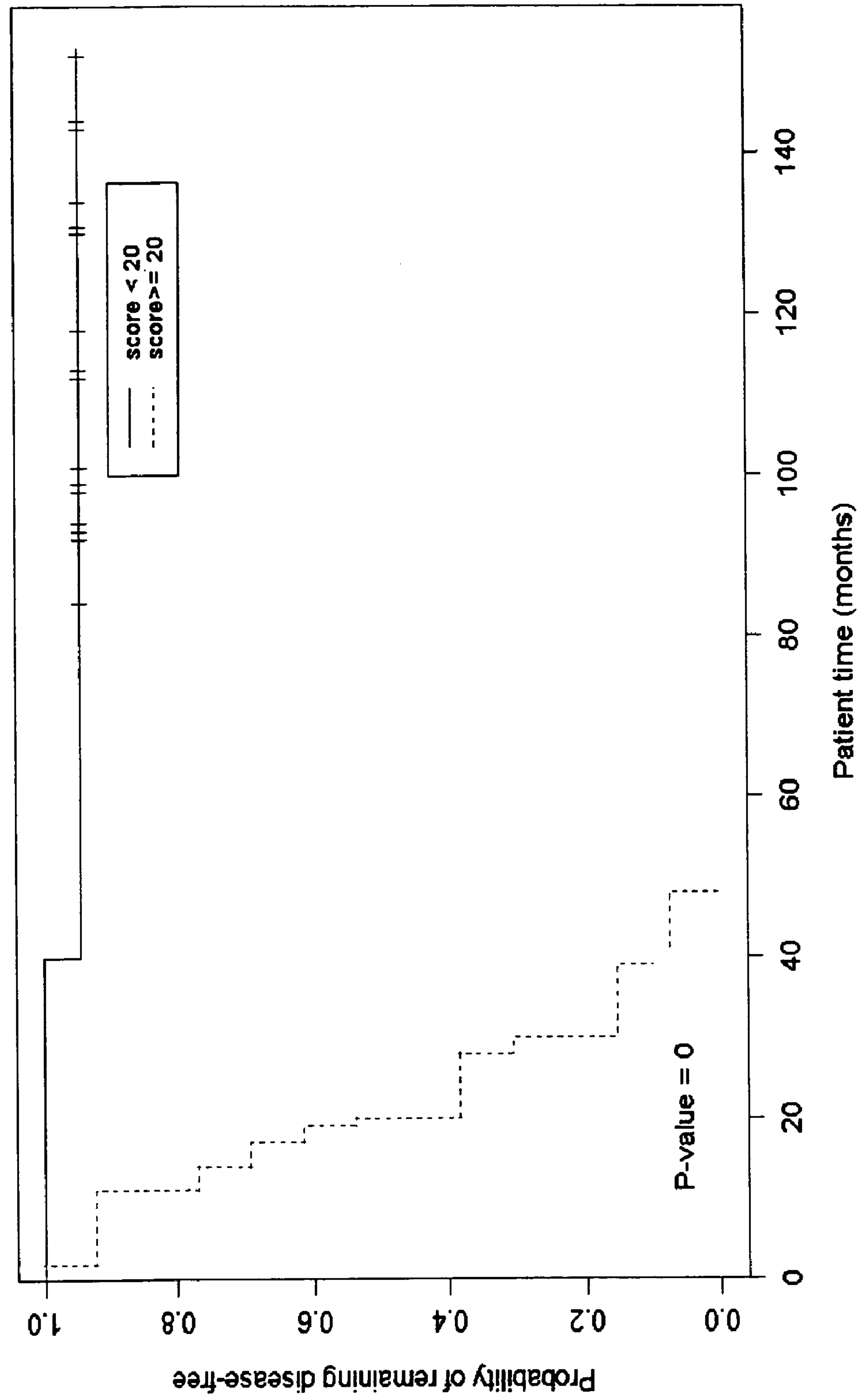
FIG. 1 is a standard Kaplan-Meier Plot constructed from the patient data as a training set as described in the Examples. Two classes of patients are indicated as predicted by the chip data of the 56-gene panel. The vertical axis shows the probability of disease-free survival among patients in each class.

The mere presence or absence of particular nucleic acid sequences in a tissue sample has only rarely been found to have diagnostic or prognostic value. Information about the expression of various proteins, peptides or mRNA, on the other hand, is increasingly viewed as important. The mere presence of nucleic acid sequences having the potential to express proteins, peptides, or mRNA (such sequences referred to as "genes") within the genome by itself is not determinative of whether a protein, peptide, or mRNA is expressed in a given cell. Whether or not a given gene capable of expressing proteins, peptides, or mRNA does so and to what extent such expression occurs, if at all, is determined by a variety of complex factors. Irrespective of difficulties in understanding and assessing these factors, assaying gene expression can provide useful information about the occurrence of important events such as tumerogenesis, metastasis, apoptosis, and other clinically relevant phenomena. Relative indications of the degree to which genes are active or inactive can be found in gene expression profiles. The gene expression profiles of this invention are used to provide a prognosis and treat patients for breast cancer.

Sample preparation requires the collection of patient samples. Patient samples used in the inventive method are those that are suspected of containing diseased cells such as epithelial cells taken from a breast or lymph node sample or from surgical margins. One useful technique for obtaining suspect samples is Laser Capture Microdisection (LCM). LCM technology provides a way to select the cells to be studied, minimizing variability caused by cell type heterogeneity. Consequently, moderate or small changes in gene expression between normal and cancerous cells can be readily detected. In a preferred method, the samples comprise circulating epithelial cells extracted from peripheral blood. These can be obtained according to a number of methods but the most preferred method is the magnetic separation technique described in U.S. Pat. No. 6,136,182 assigned to Immunivest Corp which is incorporated herein by reference. Once the sample containing the cells of interest has been obtained, RNA is extracted and amplified and a gene expression profile is obtained, preferably via microarray, for genes in the appropriate portfolios.

Preferred methods for establishing gene expression profiles include determining the amount of RNA that is produced by a gene that can code for a protein or peptide. This is accomplished by reverse transcriptase PCR (RT-PCR), competitive RT-PCR, real time RT-PCR, differential display RT-PCR, Northern Blot analysis and other related tests. While it is possible to conduct these techniques using individual PCR reactions, it is best to amplify complimentary DNA (cDNA) or complimentary RNA (cRNA) produced from mRNA and analyze it via microarray. A number of different array configurations and methods for their production are known to those of skill in the art and are described in U.S. patents such as: U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are incorporated herein by reference.

Microarray technology allows for the measurement of the steady-state mRNA level of thousands of genes simultaneously thereby presenting a powerful tool for identifying effects such as the onset, arrest, or modulation of uncontrolled cell proliferation. Two microarray technologies are currently in wide use. The first are cDNA arrays and the second are oligonucleotide arrays. Although differences exist in the construction of these chips, essentially all downstream data analysis and output are the same. The product of these analyses are typically measurements of the intensity of the signal received from a labeled probe used to detect a cDNA sequence from the sample that hybridizes to a nucleic acid sequence at a known location on the microarray. Typically, the intensity of the signal is proportional to the quantity of cDNA, and thus mRNA, expressed in the sample cells. A large number of such techniques are available and useful. Preferred methods for determining gene expression can be found in U.S. Pat. No. 6,271,002 to Linsley, et al.; U.S. Pat. No. 6,218,122 to Friend, et al.; U.S. Pat. No. 6,218,114 to Peck, et al.; and U.S. Pat. No. 6,004,755 to Wang, et al., the disclosure of each of which is incorporated herein by reference.

Analysis of the expression levels is conducted by comparing such intensities. This is best done by generating a ratio matrix of the expression intensities of genes in a test sample versus those in a control sample. For instance, the gene expression intensities from a diseased tissue can be compared with the expression intensities generated from normal tissue of the same type (e.g., diseased breast tissue sample vs. normal breast tissue sample). A ratio of these expression intensities indicates the fold-change in gene expression between the test and control samples.

Gene expression profiles can also be displayed in a number of ways. The most common method is to arrange a raw fluorescence intensities or ratio matrix into a graphical dendogram where columns indicate test samples and rows indicate genes. The data is arranged so genes that have similar expression profiles are proximal to each other. The expression ratio for each gene is visualized as a color. For example, a ratio less than one (indicating down-regulation) may appear in the blue portion of the spectrum while a ratio greater than one (indicating up-regulation) may appear as a color in the red portion of the spectrum. Commercially available computer software programs are available to display such data including "GENESPRINT" from Silicon Genetics, Inc. and "DISCOVERY" and "INFER" software from Partek, Inc.

Modulated genes used in the methods of the invention are described in the Examples. The genes that are differentially expressed are either up regulated or down regulated in patients with a relapse of breast cancer relative to those without a relapse. Up regulation and down regulation are relative terms meaning that a detectable difference (beyond the contribution of noise in the system used to measure it) is found in the amount of expression of the genes relative to some baseline. In this case, the baseline is the measured gene expression of a non-relapsing patient. The genes of interest in the diseased cells (from the relapsing patients) are then either up regulated or down regulated relative to the baseline level using the same measurement method. Diseased, in this context, refers to an alteration of the state of a body that interrupts or disturbs, or has the potential to disturb, proper performance of bodily functions as occurs with the uncontrolled proliferation of cells. Someone is diagnosed with a disease when some aspect of that person's genotype or phenotype is consistent with the presence of the disease. However, the act of conducting a diagnosis or prognosis includes the determination of disease/status issues such as determining the likelihood of relapse or metastasis and therapy monitoring. In therapy monitoring, clinical judgments are made regarding the effect of a given course of therapy by comparing the expression of genes over time to determine whether the gene expression profiles have changed or are changing to patterns more consistent with normal tissue.

Preferably, levels of up and down regulation are distinguished based on fold changes of the intensity measurements of hybridized microarray probes. A 2.0 fold difference is preferred for making such distinctions or a p-value less than 0.05. That is, before a gene is said to be differentially expressed in diseased/relapsing versus normal/non-relapsing cells, the diseased cell is found to yield at least 2 times more, or 2 times less intensity than the normal cells. The greater the fold difference, the more preferred is use of the gene as a diagnostic or prognostic tool. Genes selected for the gene expression profiles of the instant invention have expression levels that result in the generation of a signal that is distinguishable from those of the normal or non-modulated genes by an amount that exceeds background using clinical laboratory instrumentation.

Statistical values can be used to confidently distinguish modulated from non-modulated genes and noise. Statistical tests find the genes most significantly different between diverse groups of samples. The Student's t-test is an example of a robust statistical test that can be used to find significant differences between two groups. The lower the p-value, the more compelling the evidence that the gene is showing a difference between the different groups. Nevertheless, since microarrays measure more than one gene at a time, tens of thousands of statistical tests may be asked at one time. Because of this, one is unlikely to see small p-values just by chance and adjustments for this using a Sidak correction as well as a randomization/permutation experiment can be made. A p-value less than 0.05 by the t-test is evidence that the gene is significantly different. More compelling evidence is a p-value less then 0.05 after the Sidak correction is factored in. For a large number of samples in each group, a p-value less than 0.05 after the randomization/permutation test is the most compelling evidence of a significant difference.

Another parameter that can be used to select genes that generate a signal that is greater than that of the non-modulated gene or noise is the use of a measurement of absolute signal difference. Preferably, the signal generated by the modulated gene expression is at least 20% different than those of the normal or non-modulated gene (on an absolute basis). It is even more preferred that such genes produce expression patterns that are at least 30% different than those of normal or non-modulated genes.

Genes can be grouped so that information obtained about the set of genes in the group provides a sound basis for making a clinically relevant judgment such as a diagnosis, prognosis, or treatment choice. These sets of genes make up the portfolios of the invention. In this case, the judgments supported by the portfolios involve breast cancer. As with most diagnostic markers, it is often desirable to use the fewest number of markers sufficient to make a correct medical judgment. This prevents a delay in treatment pending further analysis as well inappropriate use of time and resources.

Preferably, portfolios are established such that the combination of genes in the portfolio exhibit improved sensitivity and specificity relative to individual genes or randomly selected combinations of genes. In the context of the instant invention, the sensitivity of the portfolio can be reflected in the fold differences exhibited by a gene's expression in the diseased state relative to the normal state. Specificity can be reflected in statistical measurements of the correlation of the signaling of gene expression with the condition of interest. For example, standard deviation can be a used as such a measurement. In considering a group of genes for inclusion in a portfolio, a small standard deviation in expression measurements correlates with greater specificity. Other measurements of variation such as correlation coefficients can also be used in this capacity.

A preferred method of establishing gene expression portfolios is through the use of optimization algorithms such as the mean variance algorithm widely used in establishing stock portfolios. This method is described in detail in the patent application entitled "Selection of Markers" by Tim Jatkoe, et. al., filed on Mar. 21, 2003 (application Ser. No. 10/394,087, incorporated herein by reference). Essentially, the method calls for the establishment of a set of inputs (stocks in financial applications, expression as measured by intensity here) that will optimize the return (e.g., signal that is generated) one receives for using it while minimizing the variability of the return. Many commercial software programs are available to conduct such operations. "Wagner Associates Mean-Variance Optimization Application", referred to as "Wagner Software" throughout this specification, is preferred. This software uses functions from the "Wagner Associates Mean-Variance Optimization Library" to determine an efficient frontier and optimal portfolios.

Use of this type of software requires that microarray data (i.e. intensity measurements) be transformed so that it can be treated as an input in the way stock return and risk measurements are used when the software is used for its intended financial analysis purposes.

The process of portfolio selection and characterization of an unknown is summarized as follows:

1. Choose baseline class
2. Calculate mean, and standard deviation of each gene for baseline class samples
3. Calculate (X*Standard Deviation + Mean) for each gene. This is the baseline reading from which all other samples will be compared. X is a stringency variable with higher values of X being more stringent than lower.
4. Calculate ratio between each Experimental sample versus baseline reading calculated in step 3.
5. Transform ratios such that ratios less than 1 are negative (eg. using Log base 10). (Down regulated genes now correctly have negative values necessary for MV optimization).
6. These transformed ratios are used as inputs in place of the asset returns that are normally used in the software application.
7. The software will plot the efficient frontier and return an optimized portfolio at any point along the efficient frontier.
8. Choose a desired return or variance on the efficient frontier.
9. Calculate the Portfolio's Value for each sample by summing the multiples of each gene's intensity value by the weight generated by the portfolio selection algorithm.
10. Calculate a boundary value by adding the mean Portfolio Value for Baseline groups to the multiple of Y and the Standard Deviation of the Baseline's Portfolio Values. Values greater than this boundary value shall be classified as the Experimental Class.
11. Optionally one can reiterate this process until best prediction accuracy is obtained.

Alternatively, genes can first be pre-selected by identifying those genes whose expression shows some minimal level of differentiation. The pre-selection in this alternative method is preferably based on a threshold given by $$1 \le \left|\frac{(\mu_t - \mu_n)}{(\sigma_t + \sigma_n)}\right|,$$

where $\mu_1$ is the mean of the subset known to possess the disease or condition, $\mu_n$ is the mean of the subset of normal samples, and $\sigma_1$, $+\sigma_n$ represent the combined standard deviations. A signal to noise cutoff can also be used by pre-selecting the data according to a relationship such as $$0.5 \le \left|\frac{(\mu_t - \text{MAX}_n)}{(\sigma_t + \sigma_n)}\right|.$$

This ensures that genes that are pre-selected based on their differential modulation are differentiated in a clinically significant way. That is, above the noise level of instrumentation appropriate to the task of measuring the diagnostic parameters. For each marker pre-selected according to these criteria, a matrix is established in which columns represents samples, rows represent markers and each element is a normalized intensity measurement for the expression of that marker according to the relationship:

$$\left|\frac{(\mu_t - I)}{\mu_t}\right|$$

where I is the intensity measurement.

It is also possible to set additional boundary conditions to define the optimal portfolios. For example, portfolio size can be limited to a fixed range or number of markers. This can be done either by making data pre-selection criteria more stringent $$\left(\text{e.g.,}\ \ .8 \le \left|\frac{(\mu_t - \text{MAX}_n)}{(\sigma_t + \sigma_n)}\right| \ \text{instead of}\ \ 0.5 \le \left|\frac{(\mu_t - \text{MAX}_n)}{(\sigma_t + \sigma_n)}\right|\right)$$

or by using programming features such as restricting portfolio size. One could, for example, set the boundary condition that the efficient frontier is to be selected from among only the most optimal 10 genes. One could also use all of the genes pre-selected for determining the efficient frontier and then limit the number of genes selected (e.g., no more than 10).

The process of selecting a portfolio can also include the application of heuristic rules. Preferably, such rules are formulated based on biology and an understanding of the technology used to produce clinical results. More preferably, they are applied to output from the optimization method. For example, the mean variance method of portfolio selection can be applied to microarray data for a number of genes differentially expressed in subjects with breast cancer. Output from the method would be an optimized set of genes that could include some genes that are expressed in peripheral blood as well as in diseased tissue. If samples used in the testing method are obtained from peripheral blood and certain genes differentially expressed in instances of breast cancer could also be differentially expressed in peripheral blood, then a heuristic rule can be applied in which a portfolio is selected from the efficient frontier excluding those that are differentially expressed in peripheral blood. Of course, the rule can be applied prior to the formation of the efficient frontier by, for example, applying the rule during data pre-selection.

Other heuristic rules can be applied that are not necessarily related to the biology in question. For example, one can apply the rule that only a given percentage of the portfolio can be represented by a particular gene or genes. Commercially available software such as the Wagner Software readily accommodates these types of heuristics. This can be useful, for example, when factors other than accuracy and precision (e.g., anticipated licensing fees) have an impact on the desirability of including one or more genes.

One method of the invention involves comparing gene expression profiles for various genes (or portfolios) to ascribe prognoses. The gene expression profiles of each of the genes comprising the portfolio are fixed in a medium such as a computer readable medium. This can take a number of forms. For example, a table can be established into which the range of signals (e.g., intensity measurements) indicative of disease/relapse is input. Actual patient data can then be compared to the values in the table to determine whether the patient samples are normal or diseased. In a more sophisticated embodiment, patterns of the expression signals (e.g., flourescent intensity) are recorded digitally or graphically. The gene expression patterns from the gene portfolios used in conjunction with patient samples are then compared to the expression patterns. Pattern comparison software can then be used to determine whether the patient samples have a pattern indicative of recurrence of the disease. Of course, these comparisons can also be used to determine whether the patient is not likely to experience disease recurrence. The expression profiles of the samples are then compared to the portfolio of a control cell. If the sample expression patterns are consistent with the expression pattern for recurrence of a breast cancer then (in the absence of countervailing medical considerations) the patient is treated as one would treat a relapse patient. If the sample expression patterns are consistent with the expression pattern from the normal/control cell then the patient is diagnosed negative for breast cancer.

Numerous well known methods of pattern recognition are available. The following references provide some examples:

Weighted Voting:

Golub, T R., Slonim, D K., Tamaya, P., Huard, C., Gaasenbeek, M., Mesirov, J P., Coller, H., Loh, L., Downing, J R., Caligiuri, M A., Bloomfield, C D., Lander, E S. *Molecular classification of cancer: class discovery and class prediction by gene expression monitoring. Science* 286:531-537, 1999

Support Vector Machines:

Su, A I., Welsh, J B., Sapinoso, L M., Kern, S G., Dimitrov, P., Lapp, H., Schultz, P G., Powell, S M., Moskaluk, C A., Frierson, H F. Jr., Hampton, G M. *Molecular classification of human carcinomas by use of gene expression signatures*. Cancer Research 61:7388-93, 2001

Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. *Multiclass cancer diagnosis using tumor gene exprésvion signatures* Proceedings of the National Academy of Sciences of the USA 98:15149-15154, 2001

K-nearest Neighbors:

Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. *Multiclass cancer diagnosis using tumor gene expression signatures* Proceedings of the National Academy of Sciences of the USA 98:15149-15154, 2001

Correlation Coefficients:

van 't Veer L J, Dai H, van de Vijver M J, He Y D, Hart A A, Mao M, Peterse H L, van der Kooy K, Marton M J, Witteveen A T, Schreiber G J, Kerkhoven R M, Roberts C, Linsley P S, Bemards R, Friend S H. *Gene expression profiling predicts clinical outcome of breast cancer*. Nature. 2002 Jan. 31;415(6871):530-6.

The gene expression profiles of this invention can also be used in conjunction with other non-genetic diagnostic methods useful in cancer diagnosis, prognosis, or treatment monitoring. For example, in some circumstances it is beneficial to combine the diagnostic power of the gene expression based methods described above with data from conventional markers such as serum protein markers. A range of such markers exists including such analytes as Estrogen Receptor (ER) with ER+ results indicating a greater likelihood of recurrence or metastasis. Other markers such as the protein (or peptides) produced by the estrogen regulated gene sequence pLIV1 can be used in this capacity as described in U.S. Pat. No. 5,693,465 (incorporated by reference in this specification). In one such method, blood is periodically taken from a treated patient and then subjected to an enzyme immunoassay for one or more serum markers. When the concentration of the marker(s) suggests the return of tumors or failure of therapy, a sample source amenable to gene expression analysis is taken. Where a suspicious mass exists, a fine needle aspirate is taken and gene expression profiles of cells taken from the mass are then analyzed as described above. Alternatively, tissue samples may be taken from areas adjacent to the tissue from which a tumor was previously removed. This approach can be particularly useful when other testing produces ambiguous results.

Articles of this invention include representations of the gene expression profiles useful for treating, diagnosing, prognosticating, and otherwise assessing diseases. These profile representations are reduced to a medium that can be automatically read by a machine such as computer readable media (magnetic, optical, and the like). The articles can also include instructions for assessing the gene expression profiles in such media. For example, the articles may comprise a CD ROM having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms such as those incorporated in "DISCOVERY"

and "INFER" software from Partek, Inc. mentioned above can best assist in the visualization of such data.

Different types of articles of manufacture according to the invention are media or formatted assays used to reveal gene expression profiles. These can comprise, for example, microarrays in which sequence complements or probes are affixed to a matrix to which the sequences indicative of the genes of interest combine creating a readable determinant of their presence. Alternatively, articles according to the invention can be fashioned into reagent kits for conducting hybridization, amplification, and signal generation indicative of the level of expression of the genes of interest for detecting breast cancer.

Kits made according to the invention include formatted assays for determining the gene expression profiles. These can include all or some of the materials needed to conduct the assays such as reagents and instructions.

The invention is further illustrated by the following non-limiting examples.

EXAMPLES

Genes analyzed according to this invention are typically related to full-length nucleic acid sequences that code for the production of a protein or peptide. One skilled in the art will recognize that identification of full-length sequences is not necessary from an analytical point of view. That is, portions of the sequences or ESTs can be selected according to well-known principles for which probes can be designed to assess gene expression for the corresponding gene.

Example 1

Sample Handling and LCM

Fresh frozen tissue samples were collected from patients who had surgery for breast tumors. The samples that were used were from 149 Stage I and II patients (staged according to standard clinical diagnostics and pathology). Clinical outcome of the patients was known. Seventy four of the patients have remained disease-free for more than seven years while seventy five patients had distant metastases within four years. One hundred and three patients were lymph node negative while forty six were lymph node positive.

The tissues were snap frozen in liquid nitrogen within 20-30 minutes of harvesting, and stored at −80° C. thereafter. For laser capture, the samples were cut (6 μm), and one section was mounted on a glass slide, and the second on film (P.A.L.M.), which had been fixed onto a glass slide (Micro Slides Colorfrost, VWR Scientific, Media, PA). The section mounted on a glass slide was after fixed in cold acetone, and stained with Mayer's Haematoxylin (Sigma, St. Louis, Mo.). A pathologist analyzed the samples for diagnosis and grade. The clinical stage was estimated from the accompanying surgical pathology and clinical reports to verify the staging of the tumor. The section mounted on film was after fixed for five minutes in 100% ethanol, counter stained for 1 minute in eosin/100% ethanol (100 μg of Eosin in 100 ml of dehydrated ethanol), quickly soaked once in 100% ethanol to remove the free stain, and air dried for 10 minutes.

Before use in LCM, the membrane (LPC-MEMBRANE PEN FOIL 1.35 μm No 8100, P.A.L.M. GmbH Mikrolaser Technologie, Bernried, Germany) and slides were pretreated to abolish RNases, and to enhance the attachment of the tissue sample onto the film. Briefly, the slides were washed in DEP $H_2O$, and the film was washed in RNase AWAY (Molecular Bioproducts, Inc., San Diego, Calif.) and rinsed in DEP $H_2O$. After attaching the film onto the glass slides, the slides were baked at +120° C. for 8 hours, treated with TI-SAD (Diagnostic Products Corporation, Los Angeles, Calif., 1:50 in DEP $H_2O$, filtered through cotton wool), and incubated at +37° C. for 30 minutes. Immediately before use, a 10 μl aliquot of RNase inhibitor solution (Rnasin Inhibitor 2500 U=33 U/μl N211A, Promega GmbH, Mannheim, Germany, 0.5 μl in 400 μl of freezing solution, containing 0.15 mol NaCl, 10 mmol Tris pH 8.0, 0.25 mmol dithiothreitol) was spread onto the film, where the tissue sample was to be mounted.

The tissue sections mounted on film were used for LCM. Approximately 2000 epithelial cells/sample were captured using the PALM Robot-Microbeam technology (P.A.L.M. Mikrolaser Technologie, Carl Zeiss, Inc., Thornwood, N.Y.), coupled into Zeiss Axiovert 135 microscope (Carl Zeiss Jena GmbH, Jena, Germany). The surrounding stroma in the normal mucosa, and the occasional intervening stromal components in cancer samples, were included. The captured cells were put in tubes in 100% ethanol and preserved at −80° C.

Example 2

RNA Extraction and Amplification

Zymo-Spin Column (Zymo Research, Orange, Calif. 92867) was used to extract total RNA from the LCM captured samples. About 2 ng of total RNA was resuspended in 10 ul of water and 2 rounds of the T7 RNA polymerase based amplification were performed to yield about 50 ug of amplified RNA.

Example 3 cDNA Microarray Hybridization and Quantitation

A set of cDNA microarrays consisting of approximately 23,000 human cDNA clones was used to test the samples by use of the humanU133a chip obtained and commercially available from Affymetrix, Inc. Total RNA obtained and prepared as outlined above and applied to the chips and analyzed by Agilent BioAnalyzer according to the manufacturer's protocol. All 149 samples passed the quality control standards and the data were used for marker selection.

Marker selection was performed by analyzing the 103 lymph node negative patients. Genes that allow the discrimination of distant metastases and survivors were identified using Cox proportional hazard model. Chip intensity data was analyzed using MAS Version 5.0 software commercially available from Affymetrix, Inc. ("MAS 5.0"). An unsupervised analysis was first conducted followed by a supervised analysis.

The chip intensity data obtained as described was the input for the unsupervised clustering software commercially available as PARTEK version 5.1 software. This unsupervised clustering algorithm identified a group of 22 patients with a significant low expression of many genes including estrogen receptor. ER/PR are known prognostic factors for poor outcome in breast cancer so this group of 22 patients were excluded from subsequent analysis to identify additional factors (gene markers) with independent value as prognostic indicators. The remaining 81 patients were further filtered to remove potential effects of the well-characterized prognostic indicators of age and tumor size. Twentyseven patients older than 55 years or having tumors larger than 5 cm were thus excluded too.

A Cox proportional hazard model was used for gene selection. In each cycle of the total 31 cycles, each of the 31 patients in the training set was held out, the remaining 26 patients were used in the univariate Cox model regression to assess the strength of association of gene expression with the patient survival time. The strength of such association was evaluated by the corresponding estimated standardized parameter estimate and P value returned from the Cox model regression. P value of 0.01 was used as the threshold to select top genes from each cycle of the leave-one-out gene selection. The top genes selected from each cycle were then compared in order to select those genes that showed up at least 28 times in the total of 31 leave-one-out gene selection cycles. A total of 56 genes were

TABLE 1

Breast Cancer Prognostic Gene Markers.

| Gene | Modulation (Standardized Coefficient) | P. value | Sequence I.D. No. |
|---|---|---|---|
| 202984_s_at | 3.8521 | 0.0001 | Sequence I.D. No.: 1 |
| 208777_s_at | 3.4922 | 0.0005 | Sequence I.D. No. 2. |
| 222133_s_at | 3.1841 | 0.0015 | Sequence I.D. No. 3 |
| 218185_s_at | 3.1379 | 0.0017 | Sequence I.D. No. 4 |
| 219571_s_at | 3.1131 | 0.0019 | Sequence I.D. No. 5 |
| 201138_s_at | 3.1075 | 0.0019 | Sequence I.D. No. 6 |
| 209155_s_at | 3.1018 | 0.0019 | Sequence I.D. No. 7 |
| 212468_at | 0.0019 | 0.0022 | Sequence I.D. No. 8 |
| 217593_at | 0.0019 | 0.0022 | Sequence I.D. No. 9 |
| 212973_at | 3.0325 | 0.0024 | Sequence I.D. No. 10 |
| 202971_s_at | 2.9994 | 0.0027 | Sequence I.D. No. 11 |
| 204444_at | 2.9926 | 0.0028 | Sequence I.D. No. 12 |
| 205169_at | 2.9911 | 0.0028 | Sequence I.D. No. 13 |
| 219751_at | 2.9707 | 0.0030 | Sequence I.D. No. 14 |
| 217988_at | 2.9649 | 0.0030 | Sequence I.D. No. 15 |
| 212942_s_at | 2.9460 | 0.0032 | Sequence I.D. No. 16 |
| 208993_s_at | 2.9423 | 0.0033 | Sequence I.D. No. 17 |
| 219105_x_at | 2.9324 | 0.0034 | Sequence I.D. No. 18 |
| 220085_at | 2.9001 | 0.0037 | Sequence I.D. No. 19 |
| 206640_x_at | 2.8799 | 0.0040 | Sequence I.D. No. 20 |
| 205062_x_at | 2.8663 | 0.0042 | Sequence I.D. No. 21 |
| 209385_s_at | 2.8115 | 0.0049 | Sequence I.D. No. 22 |
| AFFX-M27830_5_at | 2.7868 | 0.0053 | Sequence I.D. No. 56 |
| 215170_s_at | 2.7814 | 0.0054 | Sequence I.D. No. 23 |
| 207663_x_at | 2.7634 | 0.0057 | Sequence I.D. No. 24 |
| 212229_s_at | 2.7422 | 0.0061 | Sequence I.D. No. 25 |
| 215206_at | 2.7317 | 0.0063 | Sequence I.D. No. 26 |
| 206241_at | −2.7281 | 0.0064 | Sequence I.D. No. 27 |
| 219813_at | −2.7406 | 0.0061 | Sequence I.D. No. 28 |
| 210969_at | −2.7522 | 0.0059 | Sequence I.D. No. 29 |
| 207865_s_at | −2.7691 | 0.0056 | Sequence I.D. No. 30 |
| 202520_s_at | −2.7702 | 0.0056 | Sequence I.D. No. 31 |

| Gene | Modulation (Standardized Coefficient) | P. value | Sequence I.D. No. |
|---|---|---|---|
| 216516_at | −2.7708 | 0.0056 | Sequence I.D. No. 32 |
| 211646_at | −2.7853 | 0.0053 | Sequence I.D. No. 33 |
| 219463_at | −2.7860 | 0.0053 | Sequence I.D. No. 34 |
| 204532_x_at | −2.7921 | 0.0052 | Sequence I.D. No. 35 |
| 210365_at | −2.7931 | 0.0052 | Sequence I.D. No. 36 |
| 222098_s_at | −2.8121 | 0.0049 | Sequence I.D. No. 37 |
| 212800_at | −2.8267 | 0.0047 | Sequence I.D. No. 38 |
| 205582_s_at | −2.8350 | 0.0046 | Sequence I.D. No. 39: |
| 219096_at | −2.8393 | 0.0045 | Sequence I.D. No. 40 |
| 216944_s_at | −2.8667 | 0.0041 | Sequence I.D. No. 41 |
| 208923_at | −2.8766 | 0.0040 | Sequence I.D. No. 42 |
| 209309_at | −2.9149 | 0.0036 | Sequence I.D. No. 43 |
| 207981_s_at | −2.9294 | 0.0034 | Sequence I.D. No. 44 |
| 210160_at | −2.9448 | 0.0032 | Sequence I.D. No. 45 |
| 206862_at | −2.9676 | 0.0030 | Sequence I.D. No. 46 |
| 213110_s_at | −2.9857 | 0.0028 | Sequence I.D. No. 47 |
| 201906_s_at | −3.0124 | 0.0026 | Sequence I.D. No. 48 |
| 201057_s_at | −3.0133 | 0.0026 | Sequence I.D. No. 49 |
| 220798_x_at | −3.0270 | 0.0025 | Sequence I.D. No. 50 |
| 218650_at | −3.0513 | 0.0023 | Sequence I.D. No. 51 |
| 220986_s_at | −3.2095 | 0.0013 | Sequence I.D. No. 52 |
| 214451_at | −3.4431 | 0.0006 | Sequence I.D. No. 53 |
| 203844_at | −3.4965 | 0.0005 | Sequence I.D. No. 54 |
| 202966_at | −3.5864 | 0.0003 | Sequence I.D. No. 55 |

Construction of a multiple-gene predictor: The prediction index is defined as the sum of the product of the 56 genes' expression values (log 10 based) and their corresponding cox model parameter estimates. The parameter estimate from the cox models measures the hazard ratio of the patient when the gene expression value increases. Therefore, patients with high scores using the index have poor survival outcomes. This prediction index was applied to the training set to obtain an estimate of the prediction accuracy (FIG. 1).

Figure 2:
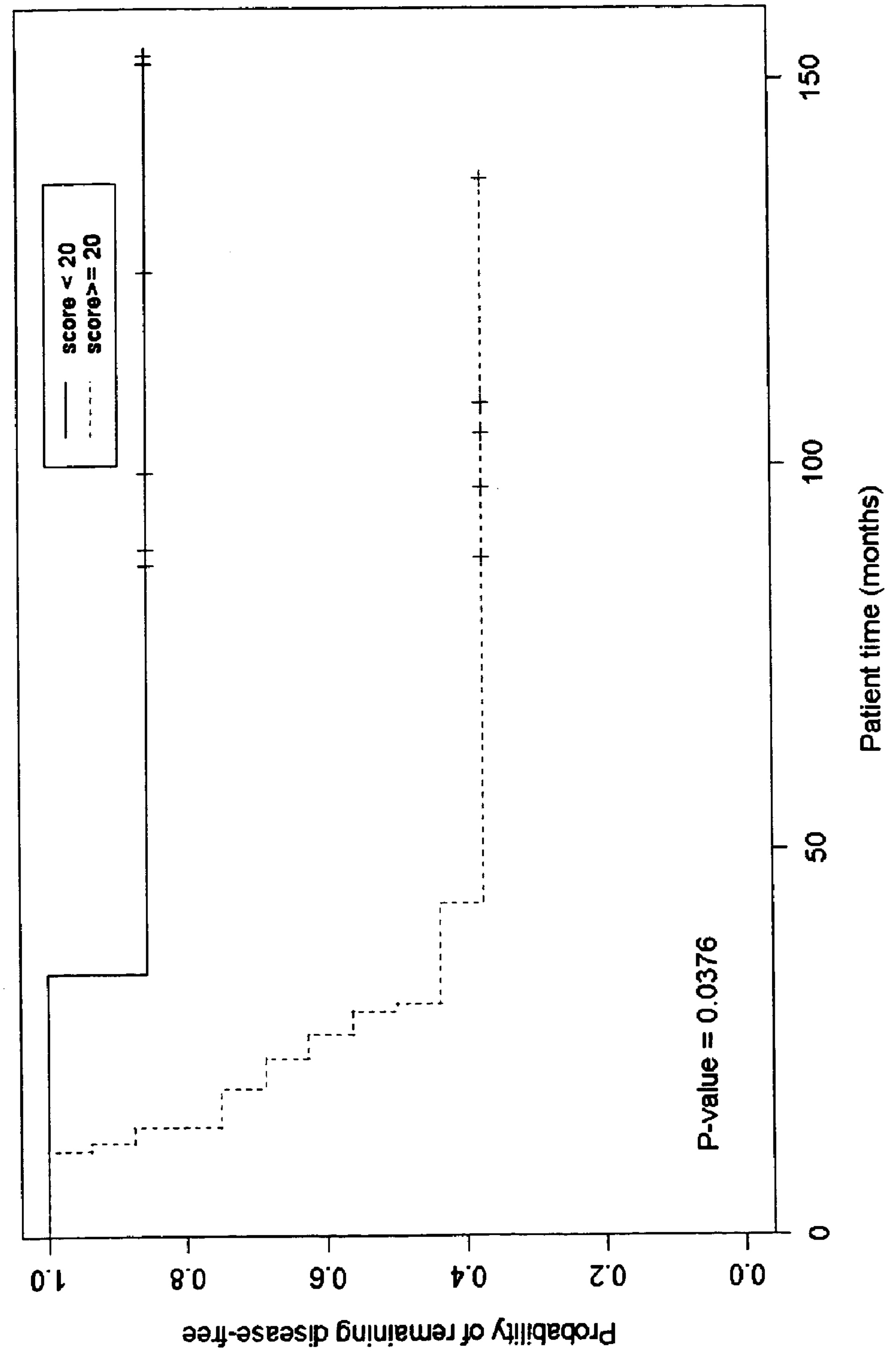
FIG. 2 is a standard Kaplan-Meier Plot constructed from the patient data as a testing set as described in the Examples. Two classes of patients are indicated as predicted by the chip data of the 56-gene panel. The vertical axis shows the probability of disease-free survival among patients in each class.

Cross-validation and evaluation of predictor: Performance of the predictor should be determined on an independent data set because most classification selected. Gene expression for those genes having Seq. ID No 1 to 26 and Seq ID No. 56 were up-regulated at least two fold and genes having Seq. ID No 27 to 55 were down regulated at least two fold.

methods work well on the examples that were used in their establishment. The 23 patients testing set was used to assess prediction accuracy. The cutoff for the classification is determined using the ROC curve with 90% sensitivity. With the selected cutoff, the numbers of correct prediction for relapse and survival patients in the test set are summarized in (Table 1). The Kaplan-Meier curve was constructed on the predicted relapsers and survivors (FIG. 2).

Figure 3:
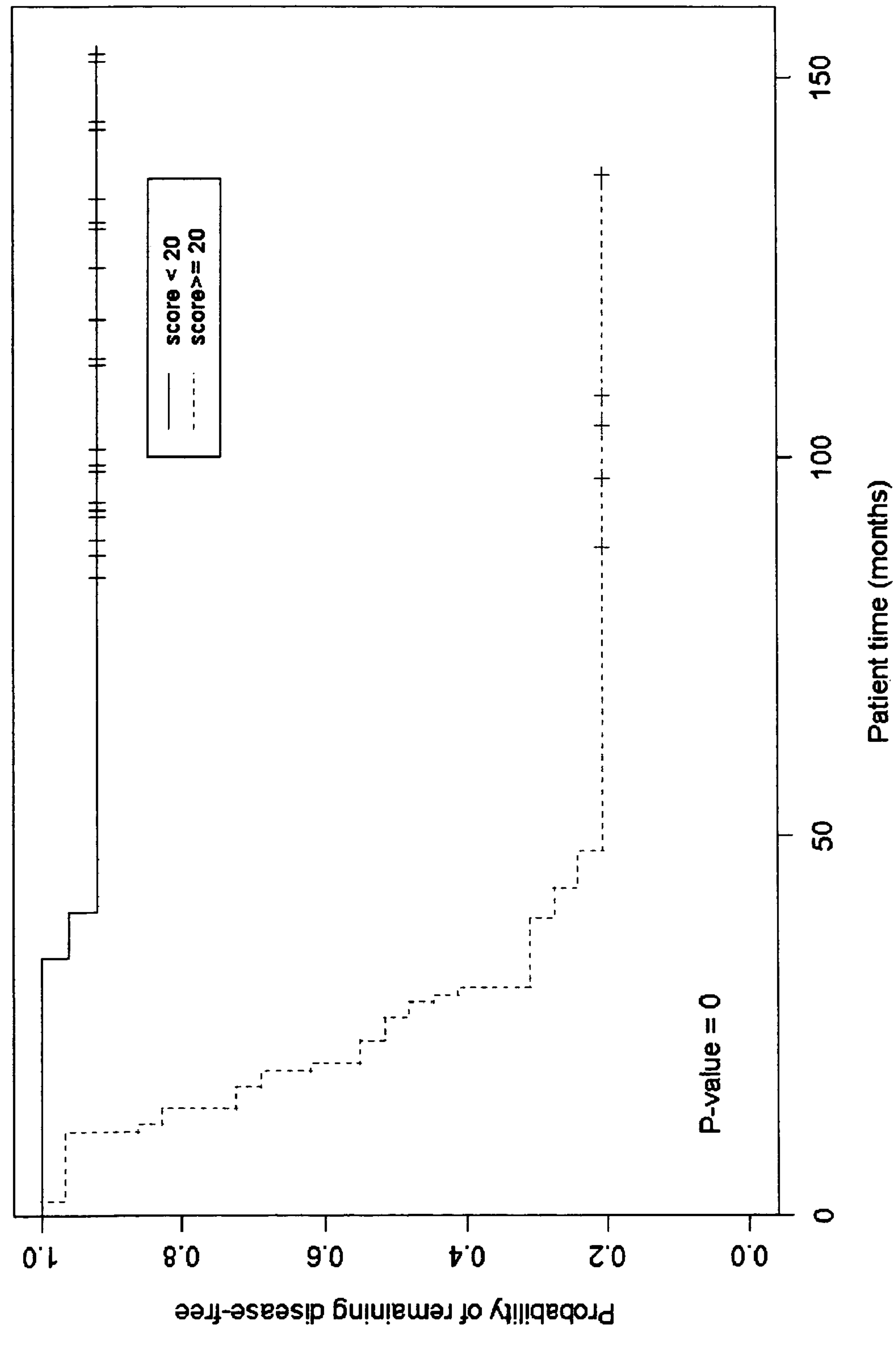
FIG. 3 is a standard Kaplan-Meier Plot constructed from the patient data of 54 patients (training and testing data combined) using a 56-gene expression profile. Two classes of patients are indicated as predicted by the chip data of the 56-gene panel The vertical axis shows the probability of disease-free survival among patients in each class.

Overall prediction: Gene expression profiling of 54 Stage I and II breast cancer patients led to identification of 56 genes that have differential expression in these patients. Thirty-six of the patients have remained disease-free for more than 7 years while 27 patients had distant metasteses within 4 years. Using the 56-gene predictor, 22 of the 27 relapse patients and 27 of 36 disease-free patients were identified correctly. This result represents a sensitivity of 82% and a specificity of 75%. The positive predictive value is 71% and the negative predictive value is 84% (Table 2) The Kaplan-Meier curve was constructed on the predicted distant metastases and survivors (FIG. 3).

An independent study was previously published (Van 't Veer et al., Nature 415, 530-535, Vijver et al., NEJM347, 1999-2009) in which a 70-gene predictor was constructed to predict patient outcomes in Stage I and II lymph node negative breast cancer. Only one gene overlaps between the 70-gene of the Van't Veer et al. study and the 56-gene predictor of this specification.

TABLE 2

Prediction accuracy based on testing set using 56-gene predictor.

| Study Prediction | Number of Sample | Correct |
|---|---|---|
| Relapse | 11 | 10 |
| Survivor | 12 | 6 |
| Sensitivity | 91% | |
| Specificity | 50% | |

TABLE 3

Prediction accuracy based on all patients using 56-gene predictor.

| Study Prediction | Number of Sample | Correct |
|---|---|---|
| Relapse | 25 | 23 |
| Survivor | 29 | 23 |
| Sensitivity | 92% | |
| Specificity | 79% | |

Example 4

Further Portfolios

The 56 gene portfolio was subjected to different treatments to fashion further portfolios that provide clinically significant benefits with fewer numbers of gene expression signatures for analysis.

a. In a first treatment, correlation coefficients among the 56 genes were calculated by Spearman rank correlation and Pearson's correlation. Using 0.7 as the correlation cutoff, a portfolio of 45 modulated genes was established. The genes are shown in Table 4.

b. In a second treatment, the 56 genes were tested with t-tests using either the training or testing dataset. The genes that displayed significant p values (<0.05) in both training and testing data were selected as a portfolio. A portfolio of 26 modulated genes was thus established. The genes are shown in Table 5.

c. The 26 gene portfolio of (b) and Table 5 were then evaluated based on the known biological functions of the genes in the portfolio. Those having a biological relationship to a metastatic pathway were selected. A portfolio of 13 modulated genes was thus established. The genes are shown in Table 6.

d. A two gene pair exhibiting the best classification performance was selected from the 56 gene portfolio. In serial, one additional gene was added to the portfolio and tested to determine whether the addition of that signature improved the overall classification accuracy in both training set and testing set of the two gene combination. This procedure was repeated until no further improvement was achieved. A portfolio of 6 modulated genes was established. The genes are shown in Table 7.

The sensitivity and specificity for each of the portfolios shown in Tables 4-7 was determined based on predicted versus known outcomes for the samples described above. These values are shown in Tables 8-11.

TABLE 4

45 Gene Set

| Gene | Modulation (Standardized Coefficient) | Sequence I.D. No. |
|---|---|---|
| 220986_s_at | −3.2095 | Seq. I.D. No. 52 |
| 220798_x_at | −3.0270 | Seq. I.D. No. 50 |
| 220085_at | 2.9001 | Seq. I.D. No. 19 |
| 219751_at | 2.9707 | Seq. I.D. No. 14 |
| 219105_x_at | 2.9324 | Seq. I.D. No. 18 |
| 218650_at | −3.0513 | Seq. I.D. No. 51 |
| 214451_at | −3.4431 | Seq. I.D. No. 53 |
| 212973_at | 3.0325 | Seq. I.D. No. 10 |
| 208993_s_at | 2.9423 | Seq. I.D. No. 17 |
| 205582_s_at | −2.8350 | Seq. I.D. No. 39 |
| 205169_at | 2.9911 | Seq. I.D. No. 13 |
| 203844_at | −3.4965 | Seq. I.D. No. 54 |
| 202984_s_at | 3.8521 | Seq. I.D. No. 1 |
| 202966_at | −3.5864 | Seq. I.D. No. 55 |
| 201057_s_at | −3.0133 | Seq. I.D. No. 49 |
| 222133_s_at | 3.1841 | Seq. I.D. No. 3 |
| 219096_at | −2.8393 | Seq. I.D. No. 40 |
| 218185_s_at | 3.1379 | Seq. I.D. No. 4 |
| 212942_s_at | 2.9460 | Seq. I.D. No. 16 |
| 210160_at | −2.9448 | Seq. I.D. No. 45 |
| 209155_s_at | 3.1018 | Seq. I.D. No. 7 |
| 204444_at | 2.9926 | Seq. I.D. No. 12 |
| 202971_s_at | 2.9994 | Seq. I.D. No. 11 |
| 201138_s_at | 3.1075 | Seq. I.D. No. 6 |
| 222098_s_at | −2.8121 | Seq. I.D. No. 37 |
| 219813_at | −2.7406 | Seq. I.D. No. 28 |
| 216944_s_at | −2.8667 | Seq. I.D. No. 41 |
| 215206_at | 2.7317 | Seq. I.D. No. 26 |
| 212800_at | −2.8267 | Seq. I.D. No. 38 |
| 212229_s_at | 2.7422 | Seq. I.D. No. 25 |
| 211646_at | −2.7853 | Seq. I.D. No. 33 |
| 210365_at | −2.7931 | Seq. I.D. No. 36 |
| 209385_s_at | 2.8115 | Seq. I.D. No. 22 |
| 209309_at | −2.9149 | Seq. I.D. No. 43 |
| 208923_at | −2.8766 | Seq. I.D. No. 42 |
| 207663_x_at | 2.7634 | Seq. I.D. No. 24 |
| 205062_x_at | 2.8663 | Seq. I.D. No. 21 |
| 202520_s_at | −2.7702 | Seq. I.D. No. 31 |
| AFFX-M27830_5_at | 2.7868 | Seq. I.D. No. 56 |
| 216516_at | −2.7708 | Seq. I.D. No. 32 |
| 215170_s_at | 2.7814 | Seq. I.D. No. 23 |
| 210969_at | −2.7522 | Seq. I.D. No. 29 |
| 207981_s_at | −2.9294 | Seq. I.D. No. 44 |
| 206241_at | −2.7281 | Seq. I.D. No. 27 |
| 204532_x_at | −2.7921 | Seq. I.D. No. 35 |

TABLE 5

26 Gene Set

| Gene | Modulation (Standardized Coefficient) | Sequence I.D. No. |
|---|---|---|
| 205169_at | 2.9911 | Seq. I.D. No. 13 |
| 203844_at | −3.4965 | Seq. I.D. No. 54 |
| 205062_x_at | 2.8663 | Seq. I.D. No. 21 |
| 202971_s_at | 2.9994 | Seq. I.D. No. 11 |
| 201906_s_at | −3.0124 | Seq. I.D. No. 48 |
| 212942_s_at | 2.9460 | Seq. I.D. No. 16 |
| 206862_at | −2.9676 | Seq. I.D. No. 46 |
| 202966_at | −3.5864 | Seq. I.D. No. 55 |
| 201057_s_at | −3.0133 | Seq. I.D. No. 49 |
| 219105_x_at | 2.9324 | Seq. I.D. No. 18 |
| 217593_at | 3.0584 | Seq. I.D. No. 9 |
| 202520_s_at | −2.7702 | Seq. I.D. No. 31 |
| 210365_at | −2.7931 | Seq. I.D. No. 36 |
| 215206_at | 2.7317 | Seq. I.D. No. 26 |
| 212229_s_at | 2.7422 | Seq. I.D. No. 25 |
| 211646_at | −2.7853 | Seq. I.D. No. 33 |

TABLE 5-continued

26 Gene Set

| Gene | Modulation (Standardized Coefficient) | Sequence I.D. No. |
|---|---|---|
| 219813_at | −2.7406 | Seq. I.D. No. 28 |
| 216944_s_at | −2.8667 | Seq. I.D. No. 41 |
| 219096_at | −2.8393 | Seq. I.D. No. 40 |
| 218185_s_at | 3.1379 | Seq. I.D. No. 4 |
| 213110_s_at | −2.9857 | Seq. I.D. No. 47 |
| 212468_at | 3.0663 | Seq. I.D. No. 8 |
| 208993_s_at | 2.9423 | Seq. I.D. No. 17 |
| 208777_s_at | 3.4922 | Seq. I.D. No. 2 |
| 220085_at | 2.9001 | Seq. I.D. No. 19 |
| 219751_at | 2.9707 | Seq. I.D. No. 14 |

TABLE 6

13 Gene Set

| Gene | Modulation (Standardized Coefficient) | Sequence I.D. No. |
|---|---|---|
| 202971_s_at | 2.9994 | Seq. I.D. No. 11 |
| 201906_s_at | −3.0124 | Seq. I.D. No. 48 |
| 206862_at | −2.9676 | Seq. I.D. No. 46 |
| 202966_at | −3.5864 | Seq. I.D. No. 55 |
| 219105_x_at | 2.9324 | Seq. I.D. No. 18 |
| 210365_at | −2.7931 | Seq. I.D. No. 36 |
| 212229_s_at | 2.7422 | Seq. I.D. No. 25 |
| 219813_at | −2.7406 | Seq. I.D. No. 28 |
| 219096_at | −2.8393 | Seq. I.D. No. 40 |
| 218185_s_at | 3.1379 | Seq. I.D. No. 4 |
| 213110_s_at | −2.9857 | Seq. I.D. No. 47 |
| 208777_s_at | 3.4922 | Seq. I.D. No. 2 |
| 220085_at | 2.9001 | Seq. I.D. No. 19 |

TABLE 7

6 Gene Set

| Gene | Modulation (Standardized Coefficient) | Sequence I.D. No. |
|---|---|---|
| 205169_at | 2.9911 | Seq. I.D. No. 13 |
| 202966_at | −3.5864 | Seq. I.D. No. 55 |
| 206862_at | −2.9676 | Seq. I.D. No. 46 |
| 219105_x_at | 2.9324 | Seq. I.D. No. 18 |
| 205062_x_at | 2.8663 | Seq. I.D. No. 21 |
| 201138_s_at | 3.1075 | Seq. I.D. No. 6 |

TABLE 8

45-gene Prognostic Portfolio

| Study Prediction | Number of Sample | Correct |
|---|---|---|
| Relapse | 11 | 10 |
| Survivor | 12 | 6 |
| Sensitivity | 91% | |
| Specificity | 50% | |

TABLE 9

26-gene Prognostic Portfolio

| Study Prediction | Number of Sample | Correct |
|---|---|---|
| Relapse | 11 | 10 |
| Survivor | 12 | 10 |
| Sensitivity | 91% | |
| Specificity | 83% | |

TABLE 10

13-gene Prognostic Portfolio

| Study Prediction | Number of Sample | Correct |
|---|---|---|
| Relapse | 11 | 10 |
| Survivor | 12 | 8 |
| Sensitivity | 91% | |
| Specificity | 67% | |

TABLE 11

6-gene Prognostic Portfolio

| Study Prediction | Number of Sample | Correct |
|---|---|---|
| Relapse | 11 | 10 |
| Survivor | 12 | 8 |
| Sensitivity | 91% | |
| Specificity | 67% | |

I claim:

1. A method of predicting breast cancer recurrence comprising identifying differential modulation of each gene in a combination of genes selected for their ability to predict breast cancer recurrence wherein the genes comprise Seq. ID No. 1-56.

* * * * *

SEQUENCE LISTING

```
<160> NUMBER OF SEQ ID NOS: 56

<210> SEQ ID NO 1
<211> LENGTH: 533
<212> TYPE: DNA
<213> ORGANISM: Human

<400> SEQUENCE: 1

aaaggcccat taacttaatt taaatgttcc catccttatg aatttactca ctaaggaaaa     60
```

-continued

```
ctataagctc agattttaca aacaaaagca acttacaagg tattattgct ggtcctttat    120

cccttctctt taatgcaatc tcaaaggttt tttggctatt agttttcata attttcttat    180

gttgcacaca aaaacaagat tcctctctaa aacgtagagg atggggaaaa tgcagatgct    240

gtttttccaa ctaaaaatgt ttacaaaaga acagactgtc tgaacaaaca aaaaaacccc    300

accccgttaa gctgggtagg accaatcagg ccttataagt gaaaaaaaag ccttctatcg    360

agcataatga aacagaacat gtactgcttg tgtttgaacc ttactcttat ttaaccaaaa    420

atttcccctt tctcataatt ttcctagtat tatgtaaggt tatgcctagt tctagattct    480

gaaagacctg cattttaatg cttgcacaac ccatttaaaa tctacaaaag ctg           533


<210> SEQ ID NO 2
<211> LENGTH: 1450
<212> TYPE: DNA
<213> ORGANISM: Human

<400> SEQUENCE: 2

cgtcggcggc cgcggccggg gacggtgtga gagcggtaag atggcggcgg cggcggtggt     60

ggagttccag agagcccagt ctctactcag caccgaccgg gaggcctcca tcgacatcct    120

ccactccatc gtgaagcgtg acattcagga aaacgatgaa gaggcagtgc aagtcaaaga    180

gcagagcatc ctggaactgg gatctctcct ggcaaagact ggacaagctg cagagcttgg    240

aggactcctg aagtatgtac gacccttctt gaattccatc agcaaggcta aagcagctcg    300

cctggtccga tctcttcttg atctgtttct tgatatggaa gcagctacag ggcaggaggt    360

cgagctgtgt ttagagtcca tcgaatgggc caagtcagag aaaagaactt tcttacgcca    420

agctttggag gcaagactgg tgtctttgta ctttgatacc aagaggtacc aggaagcatt    480

gcatttgggt tctcagctgc tgcgggagtt gaaaaagatg gacgacaaag ctcttttggt    540

ggaagtacag cttttagaaa gcaaaacata ccatgccctg agcaacctgc cgaaagcccg    600

agctgcctta acttctgctc gaaccacagc aaatgccatc tactgccccc ctaaattgca    660

ggccaccttg gacatgcagt cgggtattat ccatgcagca gaagagaagg actggaaaac    720

tgcgtactca tacttctatg aggcatttga gggttatgac tccatcgaca gccccaaggc    780

catcacatct ctgaagtaca tgttgctgtg caaaatcatg ctcaacaccc cagaagatgt    840

ccaggctttg gtgagcggga agcttgcact tcggtatgca gggaggcaga cagaagcatt    900

aaaatgcgtg gctcaggcta gcaagaacag atcactggca gattttgaaa aggctctgac    960

agattaccgg gcagagctcc gggatgaccc aatcatcagc acacacttgg ccaagttgta   1020

tgataactta ctagaacaga atctgatccg agtcattgag ccttttttcca gagtacagat   1080

tgaacacata tctagtctca tcaaactctc caaggccgac gtggaaagga aattatcaca   1140

gatgattctt gacaagaaat ttcatgggat tttggaccag ggggagggtg tcctgattat   1200

tttcgatgaa cccccagtag ataaaactta cgaagctgct ctggaaacaa ttcagaacat   1260

gagcaaagta gtggattccc tctacaacaa agccaagaaa ctgacataga gttggatctg   1320

tagcggtcct ttggagagtg tgtgtggcgg gagagtgaaa ccttggggga aaatgctagg   1380

agattctttt ttctttttgt tctacttttc gctcggaaag tttttaaatc ctcatttggt   1440

gcatctgtat                                                          1450


<210> SEQ ID NO 3
<211> LENGTH: 1633
<212> TYPE: DNA
<213> ORGANISM: Human
```

-continued

<400> SEQUENCE: 3
ctcaagatga gtaaaaagcc cccaaatcgc cctggaatca cttttgagat tggtgctcgt 60
ttggaggcac tggactactt acaaaaatgg tatccatcac gaattgaaaa aattgactat 120
gaggagggca agatgttggt ccattttgag cgctggagtc atcgttatga tgagtggatt 180
tactgggata gcaatagatt gcgacccctt gagagaccag cactaagaaa agaagggcta 240
aaagatgagg aagatttctt tgattttaaa gctggagaag aagttctggc tcgttggaca 300
gactgtcgct attaccctgc caagattgaa gcaattaaca aagaaggaac atttacagtt 360
cagttttatg atggagtaat tcgttgttta aaaagaatgc acattaaagc catgcccgag 420
gatgctaagg ggcaggattg gatagcttta gtcaaagcag ctgctgcagc tgcagccaag 480
aacaaaacag ggagtaaacc tcgaaccagc gctaacagca ataaagataa ggataaagat 540
gagagaaagt ggtttaaagt accttcaaag aaggaggaaa cttcaacttg tatagccaca 600
ccagacgtag agaagaagga agatctgcct acatctagtg aaacatttgg acttcatgta 660
gagaacgttc caaagatggt ctttccacag ccagagagca cattatcaaa caagaggaaa 720
aataatcaag gcaactcgtt tcaggcaaag agagctcgac ttaacaagat tactggaaga 780
gaccagctgt gtattttata gctaatatag aatactggaa ggttgtaact ttattggttt 840
gttggcatcc aaagctgttg ggttgatgg tgctgaaaaa aaggaagact acaatgaaac 900
agctccaatg ctggagcagg cgatttcacc taaacctcaa agtcagaaaa aaaatgaagc 960
tgacattagc agttctgcca acactcagaa acctgcactg ttatcctcaa ctttgtcttc 1020
agggaaggct cgcagcaaga aatgcaaaca tgaatctgga gattcttctg ggtgtataaa 1080
accccctaaa tcaccacttt ccccagaatt aatacaagtc gaggatttga cgcttgtatc 1140
tcagctttct tcttcagtga taaataaaac tatgcctgat gttgcacatt tgccacttga 1200
gaagctggga ccctgtctcc ctcttgactt aagtcgtggt tcagaagtta cagcaccggt 1260
agcctcagat tcctcttacc gtaatgaatg tcccagggca gaaaaagagg atacacagat 1320
gcttccaaat ccttcttcca aagcaatagc tgatggaaga ggagctccag cagcagcagg 1380
aatatcgaaa acagaaaaaa aagtgaaatt ggaagacaaa agctcaacag catttggtat 1440
caggagttgg gatttctcag cactgctaat gaagatcccc tcttatagtc caataagctt 1500
atcaggactt ccagagtcat gacatgaaca gtttaattga acccatccac tctgggcagg 1560
taagagaaaa gaaaaagata aggaaagaag agagaagaga gacaaagatc actacagacc 1620
aaaacagaag aag 1633

<210> SEQ ID NO 4
<211> LENGTH: 2666
<212> TYPE: DNA
<213> ORGANISM: Human

<400> SEQUENCE: 4
ggcacgaggg tcacctggga agagtctgca gagcctttgc ccgccagcgc cttcgctctt 60
tggctccctg agttaatccg gttgtttgcg atcgccgcgg ccggggctgc gaaccgaagg 120
gctcgctccg cgccgcctgg gtctctacct catccgtagg tgtggccctg atggtgtggc 180
aggctctgga ctcctaaagc tctggagcga atttaagatt ttattcatgt gcatggcata 240
gaagatgaat tcttccactt ccaccatgag tgaagagcct gacgctctat cggtagttaa 300
ccagttacgg gatctagcag cagatccgtt aaacagaaga gccatcgtcc aggatcaggg 360

-continued

```
atgtctgcct ggccttattt tatttatgga ccatcccaac cctccagtcg tccactccgc    420
tttgcttgct cttcgatact tggcagaatg ccgtgcaaac agagaaaaga tgaaaggaga    480
actgggtatg atgttgagct tacaaaatgt tatacagaaa actacaactc caggagaaac    540
aaaacttctg gcctctgaaa tctatgacat tcttcagtcc tccaatatgg cagatggtga    600
tagttttaat gagatgaatt cacgtcgaag gaaagctcaa ttttttctgg gaactacaaa    660
caaacgtgcc aaaacagtgg ttttgcatat agatggcctt gatgatacgt ctcggagaaa    720
tctatgtgaa gaggctttgt taaaaattaa aggtgttatt agctttactt ttcaaatggc    780
tgttcaaagg tgtgtggtgc gaatccgttc agatttgaaa gctgaggctt tggcatcagc    840
aatagcatca accaaggtta tgaaagctca gcaagttgtg aaaagtgaaa gtggagaaga    900
gatgttggtc ccattccaag atactcctgt ggaagttgaa cagaacacag agctacctga    960
ctacctgcct gaggatgaga gtcccacaaa ggaacaggac aaagcggtgt cccgggtcgg   1020
ctcacaccca gaaggtggag ctagctggct tagcacagct gcaaactttt tatccagatc   1080
attttattgg tgacttcact tttgggctca aggactgtgt gaaccaacaa ggggccagtt   1140
ttccattgtt gtggtgaact gtcaagtgca atttgcaata agttatcatg aaaagttttt   1200
agattacacg atcgcatatg ctgcatttca cattttattg gacattttac cccactgagt   1260
ggtaaaaagg acagaggcta cagatggagt tgctttgttt atgaaagtat tttggtttgt   1320
tttctttcat ttaattgcct catatttaaa aaccatgggt ccactgttaa aaccacatgt   1380
gtatgtgcag ctttacattt tattttacgt gaagcatgtg attaggaaaa ctcattttct   1440
tttcaagcct caggacctac ctgaagagaa gttttcttgt agctcaagtt gtgcatgaat   1500
tactgaatat tttactgtgc ttttcttcat gaagggtaca tgctttgtac tcttcactga   1560
aagctgaaaa catttcttgt taccctcttt tgtgcctttt tattttgcca accgtgttta   1620
tagaaaggac attactaatg acattttgca gattaaaaac attcatttga acacagtagt   1680
cccctagaaa aacaactcta caaaaatttt gcagccttat tcattataat tttgataaaa   1740
ttaacacaaa atcagtcaag aaggaaacat gtatattagt gaagtgtttt tggagactgt   1800
ttgaatgtga ccaaatgtgg ttctagttga cttcttttca ctttggctta tatcaattct   1860
tgagagttaa tgtgatcatg atattgcaaa caactataaa tggtctctag gccttacttt   1920
gtgattatac gttatctccg gctagaaaaa aataatggta gtaaagaaac tgacaaactg   1980
aaaataagaa aacaaaaatc aaatgcctat aataccataa tgccagtttg gtatagagtc   2040
caactttaaa acatgaattg ctcgacagag ttctattcag taggtgtttc tttgtattgt   2100
cttttgtgaa tttattatga aaatgctgcg ttgtgttgaa tgaaaaagac ccaaattact   2160
gcttatgaag aaataaagcc agcattgatc acttaatcct gtttctcatg tccagccaga   2220
aaaaagaact tcagtgaagg taagataaat aaatacatac acatatgttt ttttggtaga   2280
taagtgctaa ttacatatat gtaatgcttt attaaatttc tgaaatattt ggtaactaaa   2340
attttctttt tggaaattaa taaatccaga tacatattaa tgttgatatg agtaaaaaca   2400
aataggaaga aattgaaatt tcttttcatc aacatgtaga gctgctattt tactatttgg   2460
agaatatgat gtgaaaattg gacctcaaag ggtttccttg tgttttcatt gtaaaatacc   2520
atcatcagtg agagtcttga gttcactaac attgtcacct tctggagaga gagttaatgg   2580
ggggcattga ggatgatatt tttttacatg tgtttggttt ctgattcaag tgacacgcac   2640
aaactgaaaa aaaaaaaaaa aaaaaa                                        2666
```

-continued

<210> SEQ ID NO 5
<211> LENGTH: 2445
<212> TYPE: DNA
<213> ORGANISM: Human

<400> SEQUENCE: 5
tcctgtgcgt ccccaggtca ccgctcgccc tagttcccag gctttggcct ccggtgggcg 60
agaatcgcgg agcctgcggg gctgggcgcc gaagagccgg gccggcaccc aagcgggcgc 120
ggggctgtgc gggccaggcg gaggctcaag cggggatccc cgagcacgac ccccggagcc 180
gacggcgctg gggcccaagg ggccggccgg gcggtgacga cggcggaggc gaaggggcgg 240
cgggacccgg gcccggcccg tgtgcgtcct cgacggcccg gccccggctc cgcaggacgg 300
tgagccccag ggagacggat ctgggctccg ggagggacgc cccgtctgga tttgtcccgt 360
aggcccggcc cgggcccctc tggagcagaa cggccttggt gaggtggaca ggaagggacc 420
tcgcgagcag acgcgcgccc gcgacagcaa tcccgccccg gcctgtcggg agcggtgggg 480
cagaggctgc ggagccccag gaggatctgc ctccgctttc acagtcctcc agatttttcc 540
aagagcagca gaaaatgaat aaatccctgg ggccagtgtc attcaaggac gtggctgtgg 600
acttcaccca ggaggaatgg cagcagctgg atcctgagca gaagataact tacagggatg 660
tgatgctgga gaactacagc aatctagttt ctgtggggta tcacattatc aaaccggatg 720
ttatcagcaa gttggagcaa ggagaagagc catggatagt agaaggagaa ttcctacttc 780
agagctatcc agatgaagtc tggcaaactg atgacctaat agagagaatc caggaagagg 840
aaaataaacc ttcaaggcaa actgtgttca ttgagaccct gattgaagag agaggtaatg 900
ttcctggtaa aacttttgat gtagaaacga accctgttcc ttcaagaaaa atagcctata 960
aaaatagcct ctgtgactca tgtgaaaagt gtttaacgtc tgtttcagaa tatattagta 1020
gtgatggaag ctatgcaaga atgaaagctg atgaatgtag tggatgtggg aaatcactcc 1080
tccatattaa gcttgagaaa actcatccag gagatcaagc ttatgaattt aatcaaaatg 1140
gggaacctta tactctaaat gaagaaagtc tttatcagaa aattcgtatt ttggagaaac 1200
cttttgaata tattgaatgc cagaaagcct tccaaaagga cactgttttt gttaatcaca 1260
tggaagaaaa gccctataag tggaatggat ctgaaatagc ctttctccag atgtcggacc 1320
tcactgtaca tcagacatct catatggaaa tgaagcccta tgaatgcagt gaatgtggga 1380
aatccttctg taaaaagtca aaatttatta tacatcagag gactcacaca ggagagaaac 1440
cttacgaatg taatcagtgt gggaaatcct tctgccagaa gggaaccctt actgtgcatc 1500
agagaacaca cacaggggag aagccctatg aatgtaatga atgtgggaag aacttttacc 1560
agaagttaca cctcattcag catcagagaa ctcactcagg agagaagccc tatgaatgta 1620
gttattgtgg aaaatccttt tgccagaaga cacacctcac acaacatcag agaacacatt 1680
caggagagag accttatgtt tgtcatgact gtgggaaaac cttctcgcag aagtcagcac 1740
ttaatgacca tcagaaaatt cacacaggtg tgaaactcta caagtgtagt gaatgtggga 1800
aatgcttctg ccgcaagtct actctcacga cccacctgag gacccacaca ggagagaaac 1860
cgtatgaatg taatgagtgt ggaaaattct tctctcggtt gtcatatctc actgtacatt 1920
atagaactca ttcaggagag aaaccctatg agtgtactga atgtggaaaa aaattctacc 1980
acaaatcagc attcaacagc catcagagaa ttcataggag aggcaatatg aatgtaatag 2040
atgtgggaag gcttctctga agtcagacct cattttatat cagagaaccc tttcagtata 2100
gtgaatcaga aactcctgcc tgaagtcaaa caccttgtac atcagagagt tcacacaggt 2160

-continued

```
tagtgtggac atccccttgt gtgttggact cataatctga agactcacag aatggaaacc   2220

atgattataa caagaccaca tggtataaca atactagact atagacaagt aaaaatttat   2280

aaatattaag aatgtatata catgtcacca tggattggaa ctgttttgca tatcagggaa   2340

atcatagcca aggggaaatc tatcagtata aggaatgtgg aagacataat cctttggaaa   2400

ctgttaatac taaaagatat gtttctgata caatagcaaa cttga                   2445
```

<210> SEQ ID NO 6
<211> LENGTH: 701
<212> TYPE: DNA
<213> ORGANISM: Human

<400> SEQUENCE: 6

```
taacggtccc catcttcttg gatcgcttaa cagctggccg gcggttcaca aagtgagtct     60

gctgtgctgt gtgacctgtg cgcggtctgt ggccggacct aaagatagac cgcaatggct    120

gaaaatggtg ataatgaaaa gatggctgcc ctggaggcca aaaatctgtc atcaaattga    180

gtattatttg gcgacttcaa tttgccacgg gacaagtttc taaaggaaca gataaaactg    240

gatgaaggct gggtaccttt ggagataatg ataaaattca acaggttgaa ccgtctaaca    300

acagacttta atgtaattgt ggaagcattg agcaaatcca aggcagaact catggaaatc    360

agtgaagata aaactaaaat cagaaggtct ccaagcaaac ccctacctga agtgactgat    420

gagtataaaa atgatgtaaa aaacagatct gttatattaa aggcttccca actgatgcaa    480

ctcttgatga cataaaagaa tggttagaag ataaaggtca agtactaaat attcagatga    540

gaagaacatt gcataaagca tttaagggat caatttttgt agtgttgata gcattgaatc    600

tgtaagaaat ttgtagagac ccctggcaga aagtacaaga aacagacctt gctattactt    660

tcaaggacga ttactttgcc aaaaaaaatt gacgatgaaa a                        701
```

<210> SEQ ID NO 7
<211> LENGTH: 3364
<212> TYPE: DNA
<213> ORGANISM: Human

<400> SEQUENCE: 7

```
gattgttgcc gtgcgctgga gccgagtttc gctctgctgc ccaggctgga gtacagtgat     60

gtgatctcct gacgtcaagt gatccattcg cctcggcctc ccaaagttct gggattacaa    120

gtaatacaaa atacagttaa taaaatgtca acctcctgga gtgatcggtt acagaatgca    180

gcagatatgc ctgctaacat ggataagcat gccctgaaaa agtatcgtcg agaagcctat    240

catcgggtgt ttgtgaaccg aagtttagca atggaaaaga taaagtgttt tggttttgat    300

atggattata cccttgctgt gtacaagtcc ccagagtatg agtcccttgg ttttgagctt    360

actgtggaga gattagtttc tattggctat ccccaggagt tgctcagctt tgcttatgat    420

tctacattcc ctaccagggg acttgtcttt gacacactgt atggaaatct tttgaaagtc    480

gatgcctatg gaaacctctt ggtctgtgca catggattta actttataag gggaccagaa    540

actagagaac agtatccaaa taaatttatc cagcgagatg atactgaaag attttacatt    600

ctgaacacac tattcaacct accagagacc tacctgttgg cctgcctagt agattttttt    660

actaattgtc ccagatatac cagttgtgaa acaggattta aagatgggga cctcttcatg    720

tcctaccgga gtatgttcca ggatgtaaga gatgctgttg actgggttca ttacaagggc    780

tcccttaagg aaaagacagt tgaaaatctt gagaagtatg tagtcaaaga tggaaaactg    840

cctttgcttc tgagccggat gaaggaagta gggaaagtat ttcttgctac caacagtgac    900
```

-continued

```
tataaatata cagataaaat tatgacttac ctgtttgact tcccacatgg ccccaagcct    960
gggagctccc atcgaccatg gcagtcctac tttgacttga tcttggtgga tgcacggaaa   1020
ccactctttt ttggagaagg cacagtactg cgtcaggtgg atactaaaac tggcaagctg   1080
aaaattggta cctacacagg gcccctacag catggtatcg tctactcagg aggttcttct   1140
gatacgatct gtgacctgtt gggagccaag ggaaaagaca ttttgtatat tggagatcac   1200
atttttgggg acattttaaa atcaaagaaa cggcaagggt ggcgaacttt tttggtgatt   1260
cctgaactcg cacaggagct acatgtctgg actgacaaga gttcactttt cgaagaactt   1320
cagagcttgg atattttctt ggctgaactc tacaagcatc ttgacagcag tagcaatgag   1380
cgtccagaca tcagttccat ccagagacgt attaagaaag taactcatga catggacatg   1440
tgctatggga tgatgggaag cctgtttcgc agtggctccc ggcagaccct tttgccagt    1500
caagtgatgc gttatgctga cctctatgca gcatctttca tcaacctgct gtattaccct   1560
ttcagctacc tcttcagggc tgcccatgtc ttgatgcctc atgaatcaac ggtggagcac   1620
acacacgtag atatcaatga gatggagtct cctcttgcca cccggaaccg cacatcagtg   1680
gatttcaaag acactgacta caagcggcac cagctgacac ggtcaattag tgagattaaa   1740
cctcccaacc tcttcccact ggccccccag gaaattacac actgccatga cgaagatgat   1800
gatgaagagg aggaggagga ggaagaataa ggaggaaaac caaaacccca agcacccatt   1860
aaacaagtcc tggcaggact cacaggaaca aacgaggtcc ctgttagggt tctactcggg   1920
ggagggaggg ggctccatga aaggtacgtc tgaaaagttt ctgaagattt tattatcata   1980
gatacttgtt ttggttttgt gtatctgtac tctctgcaga tggtccaaaa ttgtaatgga   2040
gtctgtatta gaagaaaata agggtaaaat caggctgaac tgcatgtata tggctccact   2100
gtggcttgtg acacttttaa aatcatccgt atgtcagtgt atctggatac acgaggaaaa   2160
ggaaagagtc tcagagtgga acaaagagtg ggaagaggtg atctgtaatg ttacaaattg   2220
tgctattact ccaaggtcca acttttccag tgcattacat ggtattgtat atcagtggag   2280
aaatgtatta tttccatgat caaatgtagt ctctgttaag gtcaagtttt cttttataag   2340
cctttaattc atcctcagtg actctggcaa ggctgcttct ctatcactgg ctttgcacag   2400
aagtatgctc tacttgcgtt gctttagggc aggattctat tttgagggaa aagacagtat   2460
ccttattacc ttttgtttgt ttaatagcac aaatgcttat ttgttatcca aaaacaacct   2520
ccttcttatc tgtgataaat ctatagaaag aatttagctg caagtggaca aaggaacaag   2580
cccccagaaa agaaagggaa gaactgcctt cttatactac agaacatgca ttagtgtggg   2640
ctatatagct gtggctcatg ctacccaatt ccagatttct ttgtcctcta agagttgatt   2700
gctgtatatt aaaattgaac atcagaggat gggaagaggg ctctgtaagc cagaacctta   2760
ctaaagtaga gggcacaatc agtgtgaata aattcacttc agaatctcaa gtcaaggcca   2820
ggcacggcgg ctcacgcctg taatcccagc actttgggag gccgagacag gcggatcacc   2880
tgaggtcggg agttcgagac cagccttacc aacatggaga aaccccatct ctactaaaaa   2940
tacaaaatta cctgggcgtg gtggtgcatg cctgtaatcc catcatctac tcaggaggct   3000
gaggcaggag aattgcttga acccaggagg cggaggttgc agtgagccag gattgtgcca   3060
ttgcactcca gcctgggcaa caagaacaaa actccatctc aaaaaataaa aatcccaatc   3120
ccaagtcgaa atcacctctt gttttaaaca agaatgaatc attactgtgt atgttagggt   3180
attaaaactg tttcaccagt acagtgaaag ttgtttcaac attttaaaca aacagtggtt   3240
```

-continued

```
atagactctt tctttaacca ttgtatattt tcttccattc ttgtcattgg tcaatagggg   3300

agggtagatt agctgctcca gaattcaata aagtgtaata tttctaaaaa aaaaaaaaaa   3360

aaaa                                                                3364
```

<210> SEQ ID NO 8
<211> LENGTH: 3825
<212> TYPE: DNA
<213> ORGANISM: Human

<400> SEQUENCE: 8

```
aagacaactt gagctgaaag cgaaaaacta tgctgaccag attagcagac ttgaagaaag     60

agaagcagaa ctgaagaagg aatataatgc attacatcaa agacacactg agatgatcca    120

taattatatg gaacatttag aaagaacaaa acttcatcag ctctcaggga gtgatcaact    180

agaatccaca gctcatagta gaattagaaa agaacgccct atatcattag gaattttccc    240

attacctgct ggagatggat tgcttacacc tgatgctcag aaaggaggag agacccctgg    300

atctgagcaa tggaaatttc aggaattaag tcaaccacgt tctcatacca gcctgaagga    360

tgagctttct gatgttagcc aaggcggatc taaagctacc actccagcat caacagctaa    420

ttcagatgtg gcaacaattc ctactgatac tcccttaaag gaagaaaacg aaggatttgt    480

gaaggttaca gatgcgccaa ataaatcaga gataagcaaa cacattgaag tacaggtagc    540

ccaggaaact agaaatgtat ctactggctc tgctgaaaat gaagaaaagt cagaagttca    600

agcaatcatc gaatctactc ctgagctgga tatggacaaa gatctcagtg gatataaagg    660

ttcaagcact cccaccaaag gcatagagaa caaagctttt gatcgcaata cagaatctct    720

ctttgaagaa ctgtcttcag ctggctcagg cctaatagga gatgtggatg aaggagcaga    780

tttactagga atgggtcggg aagttgagaa tcttatatta gaaaatacac aactgttgga    840

aaccaaaaat gctttgaaca tagtgaagaa tgatttgata gcaaaagtgg atgaactgac    900

ctgtgagaaa gatgtgctgc aaggggaatt ggaggctgtg aagcaagcca aactgaaact    960

agaggaaaag aacagagaat tggaggaaga gcttaggaaa gctcgggcag aagctgaaga   1020

tgcaaggcaa aaagcaaaag atgacgatga tagtgatatt cccacagccc agaggaaacg   1080

gtttactaga gtagaaatgg cccgtgttct catggagcga aaccagtata aagagagatt   1140

gatggagctt caggaagctg ttcgatggac agagatgatt cgggcatcac gagaaaatcc   1200

agccatgcag gaaaaaaaaa ggtcaagcat ttggcagttt ttcagccgac ttttcagctc   1260

ctcaagtaac acgactaaga agcctgaacc acctgttaat ctgaagtaca atgcacccac   1320

gtctcatgtt actccgtccg tcaagaaaag aagcagcacc ttatctcagc tccctgggga   1380

taagtccaaa gcctttgatt tccttagtga agaaactgaa gctagtttag cctcacgcag   1440

agaacaaaag agagagcagt atcgtcaggt aaaagcacat gttcagaagg aagacggtag   1500

agtgcaggct tttggctgga gtctgcctca gaagtacaaa caggtaacca atggtcaagg   1560

tgaaaataag atgaaaaatt tacctgtgcc tgtctatctc agacctctgg atgaaaaaga   1620

tacatcaatg aagctgtggt gtgctgttgg agtcaattta tctggtggga agaccagaga   1680

tggtggttct gttgttggag caagtgtatt ttacaaggat gttgctggtt tggatacaga   1740

aggcagtaaa cagcgaagtg cctctcagag tagtttagat aagttagatc aggaacttaa   1800

ggaacagcag aaggagttaa aaaatcaaga agaattatcc agtctagttt ggatctgtac   1860

cagcactcat tcggctacaa aagttcttat tattgatgct gttcaacctg gcaacatcct   1920

agacagtttc actgtttgca actctcatgt tctgtgcatt gcaagtgtgc caggtgcacg   1980
```

-continued agaaacagac taccctgcag gagaagatct ttcagaatct ggtcaggtag acaaagcatc 2040
tttatgtgga agtatgacaa gcaacagctc agcagagaca gacagcctgt taggaggcat 2100
cacagtggtt ggttgttctg cagaaggtgt gacgggagct gccacttccc ctagtacaaa 2160
tggtgcttct ccagtgatgg ataaaccacc agaaatggaa gcagaaaata gtgaggttga 2220
tgaaaatgtt ccaacagcag aagaagcaac tgaagctaca gaagggaatg cggggtcagc 2280
tgaagacaca gtggacatct cccaaactgg cgtctacaca gagcatgtct ttacagatcc 2340
tttgggagtt cagatcccag aagacctctc cccagtgtat cagtcgagca atgactcaga 2400
tgcatataaa gatcaaatat cagtactgcc aaatgaacaa gacttggtga gagaagaagc 2460
ccagaaaatg agtagtcttt taccaactat gtggcttgga gctcaaaatg gctgtttgta 2520
tgtccattca tctgtagccc agtggaggaa atgtctccat tccattaaac ttaaagattc 2580
gattctcagt attgtacacg tgaagggaat cgtgttagta gccctggctg acggcaccct 2640
tgcaatcttt cacagaggag tggatgggca gtgggatttg tcaaactatc acctcttaga 2700
ccttggacgg cctcatcatt ccatccgttg catgactgtg gtacatgaca aagtctggtg 2760
tggctatagg aacaaaatct atgtggtgca gccaaaggcc atgaaaatag agaaatcttt 2820
tgatgcacat cccaggaagg agagccaagt gcgacagctt gcgtgggtgg gggatggcgt 2880
gtgggtctcc attcgcttgg attctacgct ccgtctctat catgcacaca cttatcaaca 2940
tctacaggat gtggacattg agccttatgt aagcaaaatg ttaggtactg gaaaactggg 3000
cttctctttt gtgagaatta cagctcttat ggtgtcttgt aatcgtttgt gggtggggac 3060
aggaaatggt gtcattatct ccatcccatt gacagaaaca aataaaacct caggtgtacc 3120
aggaaatcgt cctggaagtg taatccgtgt atatggtgat gaaaacagtg ataaagtgac 3180
tccagggaca tttataccct attgttcaat ggcacatgca cagctttgct tccatgggca 3240
ccgggatgct gtgaaattct ttgtggcagt cccaggtcaa gtcatcagcc cacaaagtag 3300
cagtagtggc acggatctga cgggtgacaa agcagggcca tctgcacagg agcctggtag 3360
tcagacgccc ttgaagtcta tgcttgtcat cagtggagga gagggctaca tcgacttccg 3420
aatgggtgat gaaggtggag aatcagaact tcttggagag gatcttccac ttgaaccttc 3480
tgtcaccaaa gcagaaagga gtcacttgat agtgtggcaa gtgatgtatg gcaatgagtg 3540
agcccatggg aaacaggtgg agatggggaa gccgtctctt ctgcatggtt tattttccct 3600
ctatcctttt atttaatgct cttttgtgag ataagtttca ccacataatg tgtgagcatt 3660
ttttcctgtt aactttatat tacaaaatcc gttctaccat aacaatacag aggaactagc 3720
tgtgttactg caccagtgtt ataggtaact tcagtatatt atgaacaaat caaagaatgt 3780
ttacttcctg caaactggtg aattatagaa agcaatccag atgtg 3825

<210> SEQ ID NO 9
<211> LENGTH: 471
<212> TYPE: DNA
<213> ORGANISM: Human
<220> FEATURE:
<221> NAME/KEY: misc_feature
<222> LOCATION: (468)..(468)
<223> OTHER INFORMATION: any kind of base

<400> SEQUENCE: 9
tttggtttgt ttgtttttta aagacagggt cttgctctgt cacctaggct ggagtgcagt 60
ggcatgatct tggctcactg caacctccac ctcctggact caagcaatcc tcccacctca 120

-continued gcctcccaag tagctgggac taaaagtgcg gacccggcta atttttgtat tttttgtaga 180
gatggggtct ccctatgttg cccaggctgg tctcgaatgc ccgggctcaa gtgatctgcc 240
cgccttggct tcccaaagtg ctgcgattac aggcatgagg cactgtgcct ggccttcgtg 300
gaaatcctaa aaagcaacac cacatagtgc tgggctgtat ccaggccagt gggcaccttc 360
cgtgctggta atgaacagcc acaaaacttc tggaaaacca catggaagtt tctattttat 420
gtgaaatgtc gaactcacac accacttgcc cagtggtcct gaggagtnca c 471

<210> SEQ ID NO 10
<211> LENGTH: 565
<212> TYPE: DNA
<213> ORGANISM: Human
<220> FEATURE:
<221> NAME/KEY: misc_feature
<222> LOCATION: (476)..(476)
<223> OTHER INFORMATION: any kind of base
<220> FEATURE:
<221> NAME/KEY: misc_feature
<222> LOCATION: (482)..(482)
<223> OTHER INFORMATION: any kind of base

<400> SEQUENCE: 10
ggcaccatac tgttttattt aaacctgcaa acaatataaa gaggtaagga cttctgacgc 60
caaaccatgc aagtaataac aaaggaacag agaaaaatat taataacaaa aagaaaatca 120
ttaaaaataa aaaaacaaag tacttcacat ttcacagcag tgctttggca gtactggcaa 180
gcatttctgg tcaactgctt ccaacagcag gaatatgaag aaaccccag atcttagcaa 240 aagtgtaaca acattttctc cctgacagct tacattccaa gtcattccat accataccgc 300
tccactccac agttttataa acctgatctt aagatgtaac taggtactat gtgtgctcac 360
aataaaaact aactaaaaac aaatcagagg gtagcagaca agtaaacaaa gtttccagta 420
aggcatcagg agatcactgc tggtgggccc ctcactttac cagcttaaag aagttntgat 480
tnttatttct cagcaaactc aatattcaga agctttacca gcagactcaa gtcaaaggtt 540
ttaaatacag tttacctcat ttttt 565

<210> SEQ ID NO 11
<211> LENGTH: 3615
<212> TYPE: DNA
<213> ORGANISM: Human

<400> SEQUENCE: 11
ggactgtgtg tgtctggctg tagcagacgc gaggcggcga cgaggcgccg gggacccgcg 60
cgaggggcgg ccgggaggcg gcggcggcgg ccgccagaag tagcagcagg accggcggcg 120
gcgacggcag ccctgaaatg cattttcctc tccagcggcc atgttaacca ggaaaccttc 180
ggccgccgct cccgccgcct acccgaccgg ccgaggtggg gacagcgccg ttcgtcagct 240
tcaggcttcc ccggggctcg gtgcagggcc cacccggagc ggagtgggga ctggcccgcc 300
ctcccccatc gccctgccgc ctctccgggc cagcaacgct gccgccgcag cccacacgat 360
tggcggcagt aagcacacaa tgaatgatca cctgcatgtc ggcagccacg ctcacggaca 420
gatccaggtt caacagttgt ttgaggataa cagtaacaag cggacagtgc tcacgacaca 480
accaaatggg cttacaacag tgggcaaaac gggcttgcca gtggtgccag agcggcagct 540
ggacagcatt catagacggc aggggagctc cacctctcta aagtccatgg aaggcatggg 600
gaaggtgaaa gccaccccca tgacacctga acaagcaatg aagcaataca tgcaaaaact 660
cacagccttc gaacaccatg agattttcag ctaccctgaa atatatttct tgggtctaaa 720

-continued

```
tgctaagaag cgccagggca tgacaggtgg gcccaacaat ggtggctatg atgatgacca    780
gggatcatat gtgcaggtgc cccacgatca cgtggcttac aggtatgagg tcctcaaggt    840
cattgggaag gggagctttg ggcaggtggt caaggcctac gatcacaaag tccaccagca    900
cgtggcccta aagatggtgc ggaatgagaa gcgcttccac cggcaagcag cggaggagat    960
ccgaatcctg gaacacctgc ggaagcagga caaggataac acaatgaatg tcatccatat   1020
gctggagaat ttcaccttcc gcaaccacat ctgcatgacg tttgagctgc tgagcatgaa   1080
cctctatgag ctcatcaaga agaataaatt ccagggcttc agtctgcctt tggttcgcaa   1140
gtttgcccac tcgattctgc agtgcttgga tgctttgcac aaaaacagaa taattcactg   1200
tgaccttaag cccgagaaca ttttgttaaa gcagcagggt agaagcggta ttaaagtaat   1260
tgattttggc tccagttgtt acgagcatca gcgtgtctac acgtacatcc agtcgcgttt   1320
ttaccgggct ccagaagtga tccttggggc caggtatggc atgcccattg atatgtggag   1380
cctgggctgc attttagcag agctcctgac gggttacccc ctcttgcctg ggaagatga    1440
aggggaccag ctggcctgta tgattgaact gttgggcatg ccctcacaga aactgctgga   1500
tgcatccaaa cgagccaaaa attttgtgag ctccaagggt tatccccgtt actgcactgt   1560
cacgactctc tcagatggct ctgtggtcct aaacggaggc cgttcccgga gggggaaact   1620
gaggggccca ccggagagca gagagtgggg gaacgcgctg aaggggtgtg atgatcccct   1680
tttccttgac ttcttaaaac agtgtttaga gtgggatcct gcagtgcgca tgaccccagg   1740
ccaggctttg cggcacccct ggctgaggag gcggttgcca aagcctccca ccggggagaa   1800
aacgtcagtg aaaaggataa ctgagagcac cggtgctatc acatctatat ccaagttacc   1860
tccaccttct agctcagctt ccaaactgag gactaatttg gcgcagatga cagatgccaa   1920
tgggaatatt cagcagagga cagtgttgcc aaaacttgtt agctgagctc acgtcccctg   1980
atgctggtaa cctgaaagat acgacattgc tgagccttac tgggttgaaa aggagtagct   2040
cagacctgtt tttatttgct caataactct actcatttgt atcttttcag cacttaattt   2100
taatgtaaga aagttgttca ttttgttttt ataaaataca tgaggacaat gctttaagtt   2160
tttatacttt cagaaacttt ttgtgttcta aaagtacaat gagccttact gtatttagtg   2220
tggcagaata ataacatcag tggcaggcca ctgattactt catgactgcc acgcatttac   2280
agattggtgt caaagacatt cactatgttt ttatggttca tgttatatcc tccccagggt   2340
gacagcccct taaggccctc cttttccctc catgctccag gtccatgcac aggtgtagca   2400
tgtcctgctt ccgtttttca taaattaatc tgggtgttgg gggtagtggg aggagaacgg   2460
tcagaatcaa agtgacattc taagaaaaac tgtaccttag agattttcct ctagtgctca   2520
aacaaataca aaataagatc cccaaggttt aaactgccca gttagcattc tgacattcta   2580
aaagccggca aagcagcttt tagtggataa atgggaatgg aaacgtgtgt gttcctccaa   2640
attttctagt atgatcggtg agctgttttg taaagaagcc tcatattaca gagttgcttt   2700
tgcacctaaa tttagaattg tattccatga actgttcctc ccttttctct gcttttctcc   2760
tctctgttcc tcttttaata ccacacgtct gttgcttgca tttagtttgt cttcttcctt   2820
cagctgtgta tcccagactg ttaatacaga aaagagacat ttcagctgtg attatgacca   2880
ttgtttcata ttccaattaa aaaaagaaca gcagcctagc tacttaaggt ggggatttca   2940
tagttccaaa gaagatttag cagattagag tgagttcaca cttttcaggt gccactgtaa   3000
ggttctctca gcctgggaaa ctatcaactc tttctttaaa aagaaagagg gttgaaaatc   3060
```

-continued ctctggacga acagaagtca ctttggctgt tcagtaaggc caatgttaac aacacgttta 3120
gaggaggaaa agttcaacct caagttaaat ggtttgactt attcttcgta tcattagaag 3180
aaccccagag atagcattcc tctattttat tttactttct tttggattgc actgattgtt 3240
tttgtgggaa tgacacttta tctggcaaag taactgagag tttggtaaaa gaatattttc 3300
ttctctgaat aataattatt ttcacagtga aaatttcagt attttatcac taatgtatga 3360
gcaatgatct atatcaattt caaggcacgt gaaaaaaatt ttttagtatg tgcaatttaa 3420
tatagaaaga tttctgcctg tttggacaat aggttttggg tagtacagat taggataagt 3480
aagcttatat atgcacagag attattgtat tacctgtaaa ttgatttaca agtacttaaa 3540
agcgtggtcc ccagtgaggc caagaaagtt tccggttaag ttctttaata ataatcctac 3600
agtttatctt aagaa 3615

<210> SEQ ID NO 12
<211> LENGTH: 4908
<212> TYPE: DNA
<213> ORGANISM: Human

<400> SEQUENCE: 12
acctgcgtgc agtcggtcct ccaggccacg cagcgcccga gagtaccagg gagactccgg 60
cccctgtcgg cgccaagccc ctccgcccct cacagcgccc aggtccgcgg ccgggccttg 120
attttttggc ggggaccgtc atggcgtcgc agccaaattc gtctgcgaag aagaaagagg 180
agaaggggaa gaacatccag gtggtggtga gatgcagacc atttaatttg gcagagcgga 240
aagctagcgc ccattcaata gtagaatgtg atcctgtacg aaaagaagtt agtgtacgaa 300
ctggaggatt ggctgacaag agctcaagga aaacatacac ttttgatatg gtgtttggag 360
catctactaa acagattgat gtttaccgaa gtgttgtttg tccaattctg gatgaagtta 420
ttatgggcta taattgcact atctttgcgt atggccaaac tggcactgga aaaactttta 480
caatggaagg tgaaaggtca cctaatgaag agtataccta ggaagaggat ccccttggctg 540 gtataattcc acgtaccctt catcaaattt ttgagaaact tactgataat ggtactgaat 600
tttcagtcaa agtgtctctg ttggagatct ataatgaaga gctttttgat cttcttaatc 660
catcatctga tgtttctgag agactacaga tgtttgatga tccccgtaac aagagaggag 720
tgataattaa aggtttagaa gaaattacag tacacaacaa ggatgaagtc tatcaaattt 780
tagaaaaggg ggcagcaaaa aggacaactg cagctactct gatgaatgca tactctagtc 840
gttcccactc agttttctct gttacaatac atatgaaaga aactacgatt gatggagaag 900
agcttgttaa aatcggaaag ttgaacttgg ttgatcttgc aggaagtgaa aacattggcc 960
gttctggagc tgttgataag agagctcggg aagctggaaa tataaatcaa tccctgttga 1020
ctttgggaag ggtcattact gcccttgtag aaagaacacc tcatgttcct tatcgagaat 1080
ctaaactaac tagaatcctc caggattctc ttggagggcg tacaagaaca tctataattg 1140
caacaatttc tcctgcatct ctcaatcttg aggaaactct gagtacattg gaatatgctc 1200
atagagcaaa gaacatattg aataagcctg aagtgaatca gaaactcacc aaaaaagctc 1260
ttattaagga gtatacggag gagatagaac gtttaaaacg agatcttgct gcagcccgtg 1320
agaaaaatgg agtgtatatt tctgaagaaa attttagagt catgagtgga aaattaactg 1380
ttcaagaaga gcagattgta gaattgattg aaaaaattgg tgctgttgag gaggagctga 1440
atagggttac agagttgttt atggataata aaaatgaact tgaccagtgt aaatctgacc 1500
tgcaaaataa aacacaagaa cttgaaacca ctcaaaaaca tttgcaagaa actaaattac 1560

-continued

```
aacttgttaa agaagaatat atcacatcag ctttggaaag tactgaggag aaacttcatg   1620
atgctgccag caagctgctt aacacagttg aagaaactac aaaagatgta tctggtctcc   1680
attccaaact ggatcgtaag aaggcagttg accaacacaa tgcagaagct caggatattt   1740
ttggcaaaaa cctgaatagt ctgtttaata atatggaaga attaattaag gatggcagct   1800
caaagcaaaa ggccatgcta gaagtacata agaccttatt tggtaatctg ctgtcttcca   1860
gtgtctctgc attagatacc attactacag tagcacttgg atctctcaca tctattccag   1920
aaaatgtgtc tactcatgtt tctcagattt ttaatatgat actaaaagaa caatcattag   1980
cagcagaaag taaaactgta ctacaggaat tgattaatgt actcaagact gatcttctaa   2040
gttcactgga aatgatttta tccccaactg tggtgtctat actgaaaatc aatagtcaac   2100
taaagcatat tttcaagact tcattgacag tggccgataa gatagaagat caaaaaaagg   2160
aactagatgg ctttctcagt atactgtgta acaatctaca tgaactacaa gaaaatacca   2220
tttgttcctt ggttgagtca caaaagcaat gtggaaacct aactgaagac ctgaagacaa   2280
taaagcagac ccattcccag gaactttgca agttaatgaa tctttggaca gagagattct   2340
gtgctttgga ggaaaagtgt gaaaatatac agaaaccact tagtagtgtc caggaaaata   2400
tacagcagaa atctaaggat atagtcaaca aaatgacttt tcacagtcaa aaattttgtg   2460
ctgattctga tggcttctca caggaactca gaaattttaa ccaagaaggt acaaaattgg   2520
ttgaagaatc tgtgaaacac tctgataaac tcaatggcaa cctggaaaaa atatctcaag   2580
agactgaaca gagatgtgaa tctctgaaca caagaacagt ttatttttct gaacagtggg   2640
tatcttcctt aaatgaaagg gaacaggaac ttcacaactt attggaggtt gtaagccaat   2700
gttgtgaggc ttcaagttca gacatcactg agaaatcaga tggacgtaag gcagctcatg   2760
agaaacagca taacattttt cttgatcaga tgactattga tgaagataaa ttgatagcac   2820
aaaatctaga acttaatgaa accataaaaa ttggtttgac taagcttaat tgctttctgg   2880
aacaggatct gaaactggat atcccaacag gtacgacacc acagaggaaa agttatttat   2940
acccatcaac actggtaaga actgaaccac gtgaacatct ccttgatcag ctgaaaagga   3000
aacagcctga gctgttaatg atgctaaact gttcagaaaa caacaaagaa gagacaattc   3060
cggatgtgga tgtagaagag gcagttctgg ggcagtatac tgaagaacct ctaagtcaag   3120
agccatctgt agatgctggt gtggattgtt catcaattgg cggggttcca tttttccagc   3180
ataaaaaatc acatggaaaa gacaaagaaa acagaggcat taacacactg gagaggtcta   3240
aagtggaaga aactacagag cacttggtta caaagagcag attacctctg cgagcccaga   3300
tcaaccttta attcacttgg gggttggcaa ttttattttt aaagaaaact taaaaataaa   3360
acctgaaacc ccagaacttg agccttgtgt atagatttta aaagaatata tatatcagcc   3420
gggcgcggtg gctcatgcct gtaatcccag cactttggga ggctgaggcg ggtggattgc   3480
ttgagcccag gagtttgaga ccagcctggc caacgtggca aaacctcgtc tctgttaaaa   3540
attagccggg cgtggtggca cactcctgta atcccagcta ctggggaggc tgaggcacga   3600
gaatcacttg aacccaggaa gcggggttgc agtgagccaa aggtacacca ctacactcca   3660
gcctgggcaa cagagcaaga ctcggtctca aaaacaaaat ttaaaaaaga tataaggcag   3720
tactgtaaat tcagttgaat tttgatatct acccattttt ctgtcatccc tatagttcac   3780
tttgtattaa attgggtttc atttgggatt tgcaatgtaa atacgtattt ctagttttca   3840
tataaagtag ttcttttata acaaatgaaa agtatttttc ttgtatatta ttaagtaatg   3900
```

-continued

```
aatatataag aactgtactc ttctcagctt gagcttaaca taggtaaata tcaccaacat   3960

ctgtccttag aaaggaccat ctcatgtttt ttttcttgct atgacttgtg tattttcttg   4020

catcctccct agacttccct atttcgcttt ctcctcggct cactttctcc ctttttattt   4080

ttcaccaaac catttgtaga gctacaaaac ctatcctttc ttattttcag tagtcagaat   4140

tttatctaga aatcttttaa cacctttttta gtggttattt ctaaaatcac tgtcaacaat   4200

aaatctaacc ctagttgtat ccctccttta agtatttaaa acttgttgcc ccaaatgtga   4260

aagcatttaa ttcctttaag aggcctaact cattcaccct gacagagttc acaaaaagcc   4320

cactttagag tatacattgc tattatggga gaccacccag acatctgact aatggctctg   4380

tgccacactc caagacctgt gccttttaga gaagctcaca atgatttaag gactgtttga   4440

aacttccaat tatgtctata atttatattc ttttgtttac atgatgaaac tttttgttgt   4500

tgcttgtttg tatataatac aatgtgtaca tgtatctttt tctcgattca aatcttaacc   4560

cttaggactc tggtattttt gatctggcaa ccatatttct ggaagttgag atgtttcagc   4620

ttgaagaacc aaaacagaag gaatatgtac aaagaataaa ttttctgctc acgatgagtt   4680

tagtgtgtaa agtttagaga catctgactt tgatagctaa attaaaccaa accctattga   4740

agaattgaat atatgctact tcaagaaact aaattgatct cgtagaatta tcttaataaa   4800

ataatggcta taatttctct gcaaaatcag atgtcagcat aagcgatgga taatacctaa   4860

taaactgccc tcagtaaatc catggttaat aaatgtggtt tctacatt                4908
```

<210> SEQ ID NO 13
<211> LENGTH: 3302
<212> TYPE: DNA
<213> ORGANISM: Human

<400> SEQUENCE: 13

```
ggcacgaggc ggcagtctct tcgcggcgtc caccacttag acgcaagttg ctgaagccgg     60

ccggggagaa ggtgttgttg ccggagctga gaccgggcgg ccacagtccg cagggatgaa    120

cctcgagttg ctggagtcct ttgggcagaa ctatccagag gaagctgatg gaactttgga    180

ttgtatcagc atggctttga cttgcacctt taacaggtgg ggcacactgc ttgcagttgg    240

ctgtaatgat ggccgaattg tcatctggga tttcttgaca agaggcattg ctaaaataat    300

tagtgcacac atccatccag tgtgttcttt atgctggagc cgagatggtc ataaactcgt    360

gagtgcttcc actgataaca tagtgtcaca gtgggatgtt ctttcaggcg actgtgacca    420

gaggtttcga ttcccttcac ccatcttaaa agtccaatat catccacgag atcagaacaa    480

ggttctcgtg tgtcccatga aatctgctcc tgtcatgttg accctttcag attccaaaca    540

tgttgttctg ccggtggacg atgactccga tttgaacgtt gtggcatctt ttgataggcg    600

aggggaatat atttatacgg gaaacgcaaa aggcaagatt ttggtcctaa aaacagattc    660

tcaggatctt gttgcttcct tcagagtgac aactggaaca agcaatacca cagccattaa    720

gtcaattgag tttgcccgga aggggagttg ctttttaatt aacacggcag atcgaataat    780

cagagtttat gatggcagag aaatcttaac atgtggaaga gatggagagc ctgaacctat    840

gcaggaattg caggatttgg tgaataggac cccatggaag aaatgttgtt tctctgggga    900

tggggaatac atcgtggcag gttctgcccg gcagcatgcc ctgtacatct gggagaagag    960

cattggcaac ctggtgaaga ttctccatgg gacgagagga gaactcctct tggatgtagc   1020

ttggcatcct gttcgaccca tcatagcatc catttccagt ggagtggtat ctatctgggc   1080

acagaatcaa gtagaaaact ggagtgcatt tgcaccagac ttcaaagaat tggatgaaaa   1140
```

-continued

```
tgtagaatac gaagaaaggg aatcagggtt tgatattgaa gatgaagata agagtgagcc   1200
tgagcagaca ggggctgatg ctgcagaaga tgaggaagtg gatgtcacca gcgtggaccc   1260
tattgctgcc ttctgtagca gtgatgaaga gctggaagat tcaaaggctc tattgtattt   1320
acccattgcc cctgaggtag aagacccaga agaaaatcct tacggccccc caccggatgc   1380
agtccaaacc tccttgatgg atgaaggggc tagttcagag aagaagaggc agtcctcagc   1440
agatgggtcc cagccaccta agaagaaacc caaaacaacc aatatagaac ttcaaggagt   1500
accaaatgat gaagtccatc cactactggg tgtgaagggg gatggcaaat ccaagaagaa   1560
gcaagcaggc cggcctaaag gatcaaaagg taaagagaaa gattctccat ttaaaccgaa   1620
actctacaaa ggggacagag gtttacctct ggaaggatca gcgaagggta aagtgcaggc   1680
ggaactcagc cagcccttga cagcaggagg agcaatctca gaactgttat gaagaccttc   1740
gaagttcttc attctttctc actttgccat catgtggcct ctggacactg tggtcagtca   1800
tttgaaaatt gactttaatt taaaacaaag gcctgtgctc cacccaggag gtgggaggtg   1860
aattttatgt ttaaatgaag aagtgaatta tggaagaagg tatacgacct tcccttcctt   1920
ttcaagcata agtccaaata gactctcagg aatgaagatt tgtgaagaca tcagatagga   1980
attttggact catttaaact ttgatgctta gttatgttgc tggagaaaag atacttatgt   2040
tttgctcatc taacttcatt gtacccagcg tcattttgac atgtcatttc ctatctccca   2100
tttgccttcg gtcctcaatg catgtctttg agtgacttct tatctgaaat tttgctactg   2160
gtatcctagg aaagcttttg ttggatactc tcattttaaa cttctcctct ccccagatac   2220
ctcctatatt tccatattgt gtgcaaagga tgggcagaaa agaaagtgct tgaaagattt   2280
caaattttca gaaagggaac aacgaaggcc ctctcttcct ctcataccac gttttgctca   2340
agaagctggg ctgtaacaat tcaggttttt cccttgtttt cctctcattg catgtttccc   2400
tccaatattg gttcattgtc atcaatcatg gtttttgaag atagctagtt ttatccatct   2460
ccagcaaaga atcatcaata gtttatattg ctttacctgt gctggcttcc agagatggaa   2520
acaaacccag gtgtctctca acaagctact tttttactgg ggtgggggaa tctatgcaag   2580
gagtaaagta aaaccatcca gaatcaaagc agcaaccaca tagttcaaat caaagatcaa   2640
ggtgaatttt ttgtatcact gcctgtggaa atctatcctc atcagtcatt gcatttttcc   2700
ctgcctatac ctgtgctcct ttttcttact gtgttttcag tcacttcctt tctgtgaaag   2760
gttgcttagc tttttttttg acatttgttg ttctttatat aaaaataaca gattggatag   2820
atgtgtacat ttggtgtttg aaattctctg aaaatcccat taggaaacca ggtgtgaaaa   2880
gggctcagta gcttctctga gtggcgtttt tagctgactg gaagtgctta atctggatcg   2940
tctttttttt tttttttttt ttcaatattt taaaaggaga atttaaatac tgtgcttact   3000
gtgaaatata tcagttggtg agccgggcgt ggtgggtcac gcctgtaatc ccagcacttt   3060
gggaggccaa ggcgggtgga tcacccgagg tcaggagttc aagaccagcc tggccaacgt   3120
ggtgaaagcc tgtatctatt aaaagacaaa aattagctgg gcgtggtggt acatgcctgt   3180
aatcccagct acactggagg ctgagtcagg agaatcactt gaacgtggga ggcagaggtt   3240
gcagtgagtg gagatcgcac cactgccctc cagcctaggt gacagaatga gactctatct   3300
ca                                                                  3302
```

<210> SEQ ID NO 14
<211> LENGTH: 1999
<212> TYPE: DNA

-continued

<213> ORGANISM: Human

<400> SEQUENCE: 14

```
acgcgctctt agaccatggc gacccaggcg aagcgtccac gggtggcggg gcccgtggac     60
ggcggcgacc tggatcctgt ggcctgcttc ctgagctggt gccggcgggt ggggctggag    120
ctgagtccca aggtggcggt cagccggcag ggcacggtgg ccggctacgg catggtggcc    180
cgggagagcg tgcaggccgg agagctgctg ttcgtggtgc cgcgggccgc gctcctgtcg    240
cagcacacct gctccatcgg cggcctgctg gagcgagagc gagttgcgct gcagggccag    300
tcgggctggg tgccactgct gctggcgctg ctccacgagc tgcaggcccc ggcctcacgc    360
tggaggccct actttgcgct ctggcccgag ctgggccgct tggagcaccc gatgttctgg    420
ccagaggagg agcgccggtg cctgctccag ggcacaggcg tacctgaggc cgtggagaag    480
gatttggcca acatccgcag cgagtaccag tccatcgtgc tgcccttcat ggaagcccac    540
cccgatctct tcagcctcag ggttcgctcc ctagaactct accaccagct ggtggccctt    600
gtgatggcct atagctttca ggtaccactg gaggaagaag aggatgaaaa ggagcccaac    660
tcccccgtga tggtgcctgc tgcagacata ctaaaccact tagccaatca caacgccaat    720
ctagaatact ctgcgaattg tcttcggatg gtagccactc agcccattcc taaaggccat    780
gagattttca acacttatgg gcaaatggct aactggcaac tgattcatat gtacggtttt    840
gttgaaccat atcctgacaa cacagatgac acagctgaca ttcagatggt gacagttcgt    900
gaggcagcat tacagggaac aaaaactgaa gctgaaaggc acctagtgta cgagcgctgg    960
gatttcctat gcaaactgga gatggtaggg gaagagggag cctttgtgat agggagggag   1020
gaggtgctga ctgaagagga gctgaccacc acactaaagg tactgtgcat gcctgctgag   1080
gagttcagag agcttaaaga ccaggatgga gggggagatg ataaaaggga agagggcagc   1140
ctgacgatca caaatattcc caagctcaaa gcatcgtgga gacagctgct tcaaaacagt   1200
gttctactga ctttgcagac ctatgccaca gacttaaaaa ctgaccaagg tttactcagt   1260
aataaggaag tctatgcgaa actcagctgg agggaacagc aagccttaca ggttcgctat   1320
ggtcagaaga tgatcttaca tcagttgttg gaactgacaa gttagcagtt tccctgttcc   1380
ctgaaggaac agcaataaga actttattct aagctaatac tcattgatgt ttgaaaaaga   1440
ggaaaatttg gatctttctt ttgcttacta aacaccaaga ggaaaagtag caaagttggt   1500
gtgctaggat taactcaggt aagggtgatg tgttttagga ttgagaacag cagacttggg   1560
aatcactgct aattgttact taaagcatgt tacagctgtt ttgttctcag ttttaaccaa   1620
agccagtgga catacggtag taataactaa gtcttgttgt gtttcagcat ttaataatag   1680
actttggagg tagaccccctg gtttaaatct aagtctagtt tgaggaagtc acttaacctt   1740
tattgaaaag actctggatt taataagctg tgtaactggt actcgatagt tacccaaagt   1800
tcagtctaga tggcacaaac cacctctcag ggaataaacc ctaagacatc actcaaggag   1860
gacttcaatt atttaatttt gaactgtttt gtcctctctg gccataaaac ttgacagtca   1920
tgaaaggtaa ggcaaatttt aagtgggtta agtttttaaa tacgtatcta ctcattttct   1980
ttaaaaaaaa aaaaaaaaa                                                 1999
```

<210> SEQ ID NO 15
<211> LENGTH: 1503
<212> TYPE: DNA
<213> ORGANISM: Human

<400> SEQUENCE: 15

-continued

```
ggggctccac tttctttccc tctccgtttt ggtgggctgg ttggagatga aatccactga     60
ggagggaagt ccagcaccct gtgtgccagt cctgaactgg cccatctgta gaccccctga    120
aaatcatatg ggcttggatt tggatattct caacagaaag ggttaaaggc tgatggtacc    180
taaagcctgg tacttgaatt ttgatcaaga taagctgcct taagttctct tcattacaca    240
aatgatccta gataattgat agatcctgtg gttcaactgg atttctagat agaagctgga    300
ttcatgtgat gccagaggag taaaatttca agagactgaa accagatctg agtttcgctg    360
ttccagtctg gacctctttg gagctgtaaa tcctggatat actgtagatg agtactgcgt    420
ttttctttta tggactctct tcagcttctg gagacctcac tatcctatta tgtctttgtg    480
tgaagacatg ctgctttgta attatcgaaa gtgtcgcatc aaactctctg gctatgcatg    540
ggtcactgcc tgctctcaca tcttctgtga tcagcatggc agtggtgagt ttagtcgctc    600
accagctatc tgtcctgcct gcaacagtac cctttctgga aagctagata ttgtccgcac    660
agaactcagt ccatcagagg aatataaagc tatggtattg gcaggactgc gaccagagat    720
cgtgttggac attagctccc gagcgctggc cttctggaca tatcaggtac atcaggaacg    780
tctctatcaa gaatacaatt tcagcaaggc tgagggccat ctgaaacaga tggagaagat    840
atatactcag caaatacaaa gcaaggatgt agaattgacc tctatgaaag gggaggttac    900
ctccatgaag aaagtactag aagaatacaa gaaaaagttc agtgacatct ctgagaaact    960
tatggagcgc aatcgtcagt atcaaaagct ccaaggcctc tatgatagcc ttaggctacg   1020
aaacatcact attgctaacc atgaaggcac ccttgaacca tccatgattg cacagtctgg   1080
tgttcttggc ttcccattag gtaacaactc caagtttcct ttggataata cacctgttcg   1140
aaatcggggc gatggagatg gagattttca gttcagacca ttttttgcgg gttctcccac   1200
agcacctgaa cccagcaaca gctttttttag ttttgtctct ccaagtcgtg aattagagca   1260
gcagcaagtt tctagcaggg ccttcaaagt aaaaagaatt tgagccacgc atagtgtcac   1320
gcacctgtga tcccagctac ttaggaggtt gaggctggga ggatcacttg agcccaggag   1380
tctgaggctt tagtgatcta agatcatgcc actgcactcc agcctgggca acagagtgag   1440
accctgtttc taaaaaaaaa taaagataat ttagctaact tcaaaaaaaa aaaaaaaaaa   1500
aac                                                                 1503
```

<210> SEQ ID NO 16
<211> LENGTH: 5776
<212> TYPE: DNA
<213> ORGANISM: Human

<400> SEQUENCE: 16

```
gctcacccag gaaaaatatg caatcgtccc attgatatac aggccactac aatggatgga     60
gttaacctca gcaccgaggt tgtctacaaa aaaggccagg attataggtt tgcttgctac    120
gaccggggca gagcctgccg gagctaccgt gtacggttcc tctgtgggaa gcctgtgagg    180
cccaaactca cagtcaccat tgacaccaat gtgaacagca ccattctgaa cttggaggat    240
aatgtacagt catggaaacc tggagatacc ctggtcattg ccagtactga ttactccatg    300
taccaggcag aagagttcca ggtgcttccc tgcagatcct gcgcccccaa ccaggtcaaa    360
gtggcaggga aaccaatgta cctgcacatc ggggaggaga tagacggcgt ggacatgcgg    420
gcggaggttg ggcttctgag ccggaacatc atagtgatgg gggagatgga ggacaaatgc    480
taccccctaca gaaaccacat ctgcaatttc tttgacttcg atacctttgg gggccacatc    540
```

-continued

```
aagtttgctc tgggatttaa ggcagcacac ttggagggca cggagctgaa gcatatggga    600
cagcagctgg tgggtcagta cccgattcac ttccacctgg ccggtgatgt agacgaaagg    660
ggaggttatg acccacccac atacatcagg gacctctcca tccatcatac attctctcgc    720
tgcgtcacag tccatggctc caatggcttg ttgatcaagg acgttgtggg ctataactct    780
ttgggccact gcttcttcac ggaagatggg ccggaggaac gcaacacttt tgaccactgt    840
cttggcctcc ttgtcaagtc tggaaccctc ctcccctcgg accgtgacag caagatgtgc    900
aagatgatca cagaggactc ctacccaggg tacatcccca agcccaggca agactgcaat    960
gctgtgtcca ccttctggat ggccaatccc aacaacaacc tcatcaactg tgccgctgca   1020
ggatctgagg aaactggatt ttggtttatt tttcaccacg taccaacggg cccctccgtg   1080
ggaatgtact ccccaggtta ttcagagcac attccactgg gaaaattcta taacaaccga   1140
gcacattcca actaccgggc tggcatgatc atagacaacg gagtcaaaac caccgaggcc   1200
tctgccaagg acaagcggcc gttcctctca atcatctctg ccagatacag ccctcaccag   1260
gacgccgacc cgctgaagcc ccgggagccg gccatcatca gacacttcat tgcctacaag   1320
aaccaggacc acggggcctg gctgcgcggc ggggatgtgt ggctggacag ctgccggttt   1380
gctgacaatg gcattggcct gaccctggcc agtggtggaa ccttcccgta tgacgacggc   1440
tccaagcaag agataaagaa cagcttgttt gttggcgaga gtggcaacgt ggggacggaa   1500
atgatggaca ataggatctg gggccctggc ggcttggacc atagcggaag gaccctccct   1560
ataggccaga attttccaat tagaggaatt cagttatatg atggccccat caacatccaa   1620
aactgcactt tccgaaagtt tgtggccctg gagggccggc acaccagcgc cctggccttc   1680
cgcctgaata atgcctggca gagctgcccc cataacaacg tgaccggcat tgcctttgag   1740
gacgttccga ttacttccag agtgttcttc ggagagcctg ggccctggtt caaccagctg   1800
gacatggatg gggataagac atctgtgttc catgacgtcg acggctccgt gtccgagtac   1860
cctggctcct acctcacgaa gaatgacaac tggctggtcc ggcacccaga ctgcatcaat   1920
gttcccgact ggagaggggc catttgcagt gggtgctatg cacagatgta cattcaagcc   1980
tacaagacca gtaacctgcg aatgaagatc atcaagaatg acttccccag ccacccctctt   2040
tacctggagg gggcgctcac caggagcacc cattaccagc aataccaacc ggttgtcacc   2100
ctgcagaagg gctacaccat ccactgggac cagacggccc ccgccgaact cgccatctgg   2160
ctcatcaact tcaacaaggg cgactggatc cgagtggggc tctgctaccc gcgaggcacc   2220
acattctcca tcctctcgga tgttcacaat cgcctgctga agcaaacgtc caagacgggc   2280
gtcttcgtga ggaccttgca gatggacaaa gtggagcaga gctaccctgg caggagccac   2340
tactactggg acgaggactc agggctgttg ttcctgaagc tgaaagctca gaacgagaga   2400
gagaagtttg ctttctgctc catgaaaggc tgtgagagga taaagattaa agctctgatt   2460
ccaaagaacg caggcgtcag tgactgcaca gccacagctt accccaagtt caccgagagg   2520
gctgtcgtag acgtgccgat gcccaagaag ctctttggtt ctcagctgaa aacaaaggac   2580
catttcttgg aggtgaagat ggagagttcc aagcagcact tcttccacct ctggaacgac   2640
ttcgcttaca ttgaagtgga tgggaagaag taccccagtt cggaggatgg catccaggtg   2700
gtggtgattg acgggaacca agggcgcgtg gtgagccaca cgagcttcag gaactccatt   2760
ctgcaaggca taccatggca gcttttcaac tatgtggcga ccatccctga caattccata   2820
gtgcttatgg catcaaaggg aagatacgtc tccagaggcc catggaccag agtgctggaa   2880
aagcttgggg cagacagggg tctcaagttg aaagagcaaa tggcattcgt tggcttcaaa   2940
```

-continued

```
ggcagcttcc ggcccatctg ggtgacactg gacactgagg atcacaaagc caaaatcttc   3000
caagttgtgc ccatccctgt ggtgaagaag aagaagttgt gaggacagct gccgcccggt   3060
gccacctcgt ggtagactat gacggtgact cttggcagca gaccagtggg ggatggctgg   3120
gtcccccagc ccctgccagc agctgcctgg gaaggccgtg tttcagccct gatgggccaa   3180
gggaaggcta tcagagaccc tggtgctgcc acctgcccct actcaagtgt ctacctggag   3240
cccctggggc ggtgctggcc aatgctggaa acattcactt tcctgcagcc tcttgggtgc   3300
ttctctccta tctgtgcctc ttcagtgggg gtttggggac catatcagga gacctgggtt   3360
gtgctgacag caaagatcca ctctggcagg agccctgacc cagctaggag gtagtctgga   3420
gggctggtca ttcacagatc cccatggtct tcagcagaca agtgagggtg gtaaatgtag   3480
gagaaagagc cttggcctta aggaaatctt tactcctgta agcaagagcc aacctcacag   3540
gattaggagc tggggtagaa ctggctatcc ttggggaaga ggcaagccct gcctctggcc   3600
gtgtccacct ttcaggagac tttgagtggc aggtttggac ttggactaga tgactctcaa   3660
aggccctttt agttctgaga ttccagaaat ctgctgcatt tcacatggta cctggaaccc   3720
aacagttcat ggatatccac tgatatccat gatgctgggt gccccagcgc acacgggatg   3780
gagaggtgag aactaatgcc tagcttgagg ggtctgcagt ccagtagggc aggcagtcag   3840
gtccatgtgc actgcaatgc caggtggaga aatcacagag aggtaaaatg gaggccagtg   3900
ccatttcaga ggggaggctc aggaaggctt cttgcttaca ggaatgaagg ctgggggcat   3960
tttgctgggg ggagatgagg cagcctctgg aatggctcag ggattcagcc ctccctgccg   4020
ctgcctgctg aagctggtga ctacggggtc gccctttgct cacgtctctc tggcccactc   4080
atgatggaga agtgtggtca gaggggagca atgggctttg ctgcttatga gcacagagga   4140
attcagtccc caggcagccc tgcctctgac tccaagaggg tgaagtccac agaagtgagc   4200
tcctgcctta gggcctcatt tgctcttcat ccagggaact gagcacaggg ggcctccagg   4260
agaccctaga tgtgctcgta ctccctcggc ctgggatttc agagctggaa atatagaaaa   4320
tatctagccc aaagccttca ttttaacaga tggggaaagt gagcccccaa gatgggaaag   4380
aaccacacag ctaagggagg gcctggggag ccccacccta gcccttgctg ccacaccaca   4440
ttgcctcaac aaccggcccc agagtgccca ggcactcctg aggtagcttc tggaaatggg   4500
gacaagtccc ctcgaaggaa aggaaatgac tagagtagaa tgacagctag cagatctctt   4560
ccctcctgct cccagcgcac acaaacccgc cctccccttg gtgttggcgg tccctgtggc   4620
cttcactttg ttcactacct gtcagcccag cctgggtgca cagtagctgc aactccccat   4680
tggtgctacc tggctctcct gtctctgcag ctctacaggt gaggcccagc agagggagta   4740
gggctcgcca tgtttctggt gagccaattt ggctgatctt gggtgtctga acagctattg   4800
ggtccacccc agtccctttc agctgctgct taatgccctg ctctctccct ggcccacctt   4860
atagagagcc caaagagctc ctgtaagagg gagaactcta tctgtggttt ataatcttgc   4920
acgaggcacc agagtctccc tgggtcttgt gatgaactac atttatcccc tttcctgccc   4980
caaccacaaa ctctttcctt caaagagggc ctgcctggct ccctccaccc aactgcaccc   5040
atgagactcg gtccaagagt ccattcccca ggtgggagcc aactgtcagg gaggtctttc   5100
ccaccaaaca tctttcagct gctgggaggt gaccataggg ctctgctttt aaagatatgg   5160
ctgcttcaaa ggccagagtc acaggaagga cttcttccag ggagattagt ggtgatggag   5220
aggagagtta aaatgacctc atgtccttct tgtccacggt tttgttgagt tttcactctt   5280
```

-continued

```
ctaatgcaag ggtctcacac tgtgaaccac ttaggatgtg atcactttca ggtggccagg   5340

aatgttgaat gtctttggct cagttcattt aaaaaagata tctatttgaa agttctcaga   5400

gttgtacata tgtttcacag tacaggatct gtacataaaa gtttctttcc taaaccattc   5460

accaagagcc aatatctagg cattttcttg gtagcacaaa ttttcttatt gcttagaaaa   5520

ttgtcctcct tgttatttct gtttgtaaga cttaagtgag ttaggtcttt aaggaaagca   5580

acgctcctct gaaatgcttg tctttttttct gttgccgaaa tagctggtcc tttttcggga   5640

gttagatgta tagagtgttt gtatgtaaac atttcttgta ggcatcacca tgaacaaaga   5700

tatattttct atttatttat tatatgtgca cttcaagaag tcactgtcag agaaataaag   5760

aattgtctta aatgtc                                                   5776
```

```
<210> SEQ ID NO 17
<211> LENGTH: 2695
<212> TYPE: DNA
<213> ORGANISM: Human

<400> SEQUENCE: 17

gcgggcttta gcgccttttc tggcggcggt agatttgaag cgcttcaaag gaccggaccc     60

agagaagagg aaaactctac cggtgcagga gcacagggat cagttgtcct tgtttttttt    120

tggtcttttc ttcatttgaa gattaagtat tggagccatg ggaataaagg ttcaacgtcc    180

tcgatgtttt tttgacattg ccattaacaa tcaacctgct ggaagagttg tctttgaatt    240

attttctgat gtgtgcccca aaacatgcga gaactttcgt tgtctttgta caggtgaaaa    300

ggggaccggg aaatcaactc agaaaccatt acattataag agttgtctct ttcacagagt    360

tgtcaaggat tttatggttc aaggtggtga cttcagtgaa ggaaatggac gaggaggggga    420

atctatctat ggaggatttt ttgaagacga gagtttcgct gttaaacaca acaaagaatt    480

tctcttgtca atggccaaca gagggaagga tacaaatggt tcacagttct tcataacaac    540

gaaaccaact cctcatttag atgggcatca tgttgttttt ggacaagtaa tctctggtca    600

agaagttgta agagagattg aaaaccagaa aacagatgca gctagcaaac cgtttgcgga    660

ggtacggata ctcagttgtg gagagctgat tcccaaatct aaagttaaga aagaagaaaa    720

gaaaaggcat aaatcatcat catcttcctc ctcctcatct agtgactcag atagctcaag    780

tgattctcag tcctcttctg attcctctga ttccgaaagt gctactgaag agaaatcaaa    840

gaaaagaaaa aagaaacatc ggaaaaattc ccgaaaacac aagaaagaaa agaaaaagcg    900

aaagaaaagc aagaagagtg catctagtga gagtgaagct gaaaatcttg aagcacaacc    960

ccagtctact gtccgtccag aagagatccc tcctatacct gaaaatagat tcctaatgag   1020

aaaaagtcct cctaaagctg atgagaagga aaggaaaaac agagagagag aaagggaaag   1080

agagtgtaat ccacctaact cccagcctgc ttcataccag agacgacttt tagttactag   1140

atctggcagg aaaattaaag gaagaggacc aaggcgttat cgaactcctt ccagatccag   1200

atcaagggat cgtttcagac gtagtgagac tcctccacat tggaggcaag agatgcagag   1260

agctcaaaga atgagggtat caagtggtga aagatggatc aagggggata agagtgagtt   1320

gaatgaaata aaagaaaatc agagaagtcc agttagagta aaagagagaa aaataacaga   1380

tcacaggaat gtatctgaga gtccaaacag aaaaaatgaa aaggagaaga aagttaaaga   1440

ccataaatct aacagcaaag agagagacat cagaagaaat tcagaaaaag atgacaagta   1500

taaaaacaaa gtgaagaaaa gggccaaatc taaaagtagg agtaagagca aagagaaatc   1560

aaagagtaaa gaaagagatt caaaacataa tagaaatgaa gaaaagagga tgaggtcaag   1620
```

-continued

```
gagtaaagga agggatcatg aaaatgttaa agaaaaagaa aagcagtctg attctaaagg   1680
aaaagatcag gaaaggagta gaagtaaaga gaagtctaaa cagttagaat caaagagtaa   1740
tgagcatgat cacagtaaaa gtaaggaaaa ggatagacgc gcacaatcca ggagtagaga   1800
atgtgatata actaaaggta aacacagtta taatagcaga acaagagaac gaagcagaag   1860
tagggacaga agcagaagag tgcgatcaag aacccatgac agagatcgca gcagaagcaa   1920
ggagtaccat agatacagag aacaggaata caggagaaga ggacggtcac gaagccgaga   1980
gagaagaaca ccaccaggaa gatcaagaag taaagatagg aggagaagga ggagagactc   2040
acggagctca gagagagaag aaagtcaaag cagaaacaaa gacaaataca gaaaccaaga   2100
gagtaagagc tcacacagaa aagaaaattc tgagagtgag aaaagaatgt actctaaaag   2160
tcgtgatcat aatagctcaa ataacagcag ggaaaaaaag gctgatagag atcaaagtcc   2220
cttctcaaaa ataaaacaaa gcagtcagga cgatgaatta aagtcctcca tgttgaaaaa   2280
taaggaggat gagaagatca gatcctcagt ggaaaaagaa aaccaaaaat caaaaggtca   2340
agaaaatgac catgtacatg aaaaaaataa aaaatttgat catgaatcaa gccctggaac   2400
agatgaagac aaaagcggat gagtgagtta tataaactta cttccattct gtttcggatt   2460
ttaagtttga gagacttgct aatgaatctc ctttatgttg ttttcctttt cattgttttt   2520
ggattgtttt atgtttgtcc ttttttttct taatgtggat ttcattgagt tgattttttg   2580
ataatctgca atctggataa tttgtactgc taaagtttta ataaactcga catgagaaaa   2640
acaaaaaaaa aaaaaaaaaa aaaaaaaaaa aaaaaaaaaa aaaaaaaaaa aaaaa        2695
```

<210> SEQ ID NO 18
<211> LENGTH: 1635
<212> TYPE: DNA
<213> ORGANISM: Human

<400> SEQUENCE: 18

```
ggcacgagcg cggcgttcac gggaattgtt cgctttagtg ccggcgccat ggggtcggag     60
ctgatcgggc gcctagcccc gcgcctgggc ctcgccgagc ccgacatgct gaggaaagca    120
gaggagtact tgcgcctgtc ccgggtgaag tgtgtcggcc tctccgcacg caccacggag    180
accagcagtg cagtcatgtg cctggacctt gcagcttcct ggatgaagtg cccccttggac   240
agggcttatt taattaaact ttctggtttg aacaaggaga catatcagag ctgtcttaaa    300
tcttttgagt gtttactggg cctgaattca aatattggaa taagagacct agctgtacag    360
tttagctgta tagaagcagt gaacatggct tcaaagatac taaaaagcta tgagtccagt    420
cttccccaga cacagcaagt ggatcttgac ttatccaggc cacttttcac ttctgctgca    480
ctgctttcag catgcaagat tctaaagctg aaagtggata aaaacaaaat ggtagccaca    540
tccggtgtaa aaaaagctat atttgatcga ctgtgtaaac aactagagaa gattggacag    600
caggtcgaca gagaacctgg agatgtagct actccaccac ggaagagaaa gaagatagtg    660
gttgaagccc cagcaaagga aatggagaag gtagaggaga tgccacataa accacagaaa    720
gatgaagatc tgacacagga ttatgaagaa tggaaaagaa aaattttgga aaatgctgcc    780
agtgctcaaa aggctacagc agagtgattt cagcttccaa actggtatac attccaaact    840
gatagtacat tgccatctcc aggaagactt gacggctttg ggattttgtt taaactttta    900
taataaggat cctaagactg ttgcctttaa atagcaaagc agcctacctg gaggctaagt    960
ctgggcagtg ggctggcccc tggtgtgagc attagaccag ccacagtgcc tgattggtat   1020
```

-continued

```
agccttatgt gctttcctac aaaatggaat tggaggccgg gcgcagtggc tcacgcctgt   1080

aatcccagca ctttgggagg ccaaggtggg tggatcacct gaggtcagga gctcgagacc   1140

agcctggcca acatggtgaa accccatctc tactaaaaat acaaaaatta gccaggtgtg   1200

atggtgcatg cctgtaatcc cagctcctca gtaggctgag acaggagcat cacttgaacg   1260

tgggaggcag aggttgcagt gagccgagat tgcaccaccg cactccagcc tgggtgacag   1320

agcgagactt atctcataaa taaatagata gatactccag cctgggtgac agagcgagac   1380

ttatagatag atagatagat agatggatag atagatagat agatagatag atagataaac   1440

ggaattggag ccattttgct ttaagtgaat ggcagtccct tgtcttattc agaatataaa   1500

attcagtctg aatggcatct tacagatttt acttcaattt ttgtgtacgg tatttttttat   1560

ttgactaaat caatatattg tacagcctaa gttaataaat gttatttata tatgcaaaaa   1620

aaaaaaaaaa aaaaa                                                      1635
```

<210> SEQ ID NO 19
<211> LENGTH: 3165
<212> TYPE: DNA
<213> ORGANISM: Human

<400> SEQUENCE: 19

```
ggggatttgg ctagaaggct gggccggcag cggttgtgag gagttagctc gcggcattgc     60

aggctctgag aggaggggac ccggttcccg ggtgagtgtc caggcatgcc agcggaacgg    120

cccgcgggca gcggcggctc ggaggctcca gcaatggttg aacaactgga cactgctgtg    180

attaccccgg ccatgctaga agaggaagaa cagcttgaag ctgctggact agagagagag    240

cggaagatgc tggaaaaggc tcgcatgtct tgggatagag agtcgacaga aattcggtac    300

cgtagacttc aacatttgct tgaaaaaagc aatatatact ccaaattttt attgacgaaa    360

atggaacagc aacaattaga ggaacagaag aagaaagaaa aattggagag aaaaaaggag    420

tctttaaaag ttaaaaaggg taaaaattca attgatgcaa gtgaagagaa gccagttatg    480

aggaaaaaaa gaggaagaga agatgaatca tacaatattt cagaggtcat gtcaaaagag    540

gaaattttgt ctgtggctaa aaaaaataaa aaggagaatg aggatgaaaa ctcctcctct    600

actaatctct gtgtggaaga tcttcagaaa aataaagatt cgaatagtat aattaaagat    660

agattgtctg aaacggttag gcagaatact aaattctttt ttgacccagt ccggaagtgt    720

aatggtcagc cagtaccttt tcaacaacca aagcacttca ctggaggagt gatgcgatgg    780

taccaagtag aaggcatgga atggcttagg atgctttggg aaaatggaat taatggcatt    840

ttagcagatg aaatgggatt gggtaagaca gttcagtgca ttgctactat tgcattgatg    900

attcagagag gagtaccagg accttttctt gtctgtggcc ctttgtctac acttcctaac    960

tggatggctg aattcaaaag atttacacca gatatcccta caatgttata tcatggaacc   1020

caggaggaac gtcaaaaatt ggtaagaaat atttacaaac ggaaagggac tttgcagatt   1080

catcctgtgg taatcacgtc atttgaaata gccatgagag accgaaatgc gttacagcat   1140

tgctattgga aatacttaat agtagatgaa ggacacagga ttaagaatat gaagtgccgt   1200

ctaatcaggg agttaaaacg attcaatgct gataacaaac ttcttttgac tggtactccc   1260

ttgcaaaaca atttatcaga actttggtca ttgctaaact tttgttgcc agatgtattt   1320

gatgacttga aagctttga gtcttggttt gacatcacta gtctttctga aactgctgaa   1380

gatattattg ctaaagaaag agaacagaat gtattgcata tgctgcacca gattttaaca   1440

cctttcttat tgagaagact gaagtctgat gttgctcttg aagttcctcc taaacgagaa   1500
```

-continued

```
gtagtcgttt atgctccact ttcaaagaag caggagatct tttatacagc cattgtgaac   1560
cgtacaattg caaacatgtt tggatccagt gagaaagaaa caattgagtt aagtcctact   1620
ggtcgaccaa aacgacgaac tagaaaatca ataaattaca gcaaaataga tgatttccct   1680
aatgaattgg aaaaactgat cagtcaaata cagccagagg tggaccgaga aagagctgtt   1740
gtggaagtga atatccctgt agaatctgaa gttaatctga agctgcagaa tataatgatg   1800
ctacttcgta aatgttgtaa tcatccatat ttgattgaat atcctataga ccctgttaca   1860
caagaattta agatcgatga agaattggta acaaattctg ggaagttctt gattttggat   1920
cgaatgctgc cagaactaaa aaaaagaggt cacaaggtgc tgcttttttc acaaatgaca   1980
agcatgttgg acattttgat ggattactgc catctcagag atttcaactt cagcaggctt   2040
gatgggtcca tgtcttactc agagagagaa aaaaacatgc acagcttcaa cacggatcca   2100
gaggtgttta tcttcttagt gagtacacga gctggtggcc tgggcattaa tctgactgca   2160
gcagatacag ttatcattta tgatagtgat tggaaccccc agtcggatct tcaggcccag   2220
gatagatgtc atagaattgg tcagacaaag ccagttgttg tttatcgcct tgttacagca   2280
aatactatcg atcagaaaat tgtggaaaga gcagctgcta aaaggaaact ggaaaagttg   2340
atcatccata aaaatcattt caaaggtggt cagtctggat taaatctgtc taagaatttc   2400
ttagatccta aggaattaat ggaattatta aaatctagag attatgaaag ggaaataaaa   2460
ggatcaagag agaaggtcat tagtgataaa gatctagagt tgttgttaga tcgaagtgat   2520
cttattgatc aaatgaatgc ttcaggacca attaaagaga agatggggat attcaagata   2580
ttagaaaatt ctgaagattc cagtcctgaa tgtttgtttt aaagtggagc tcaagaatag   2640
cttttaaaag ttcttattta catctagtga tttccctgta ttgggtttga aatactgatt   2700
gtccacttca cctttttat tatatcagtt gacatgtaac tagtaccatg cgtacttaaa   2760
tagatggtaa ttttctgagc cttaccaaga acaaagaagt atccatatta agtttagatt   2820
ttcagttaat ttttgagact gagtagtatt cttggataca ggctgatgtg tacttaacca   2880
cttccagatt tatacagtct tcctgtggaa gtttagtaaa tgtcttttc cctcctttct   2940
tctagtaatg cagttcatgg gctttaggta cttcagttat gaagtaggct tttcatgggg   3000
agagattggg attatgctct ctgttgttta agaaactgtt tgattttaga gtctatttct   3060
atgagatagt ttaccaaata aatgttcctt ataagatgaa aaaaaaaaaa aaaaaaaaaa   3120
aaaaaaaaaa aaaaaaaaaa aaaaaaaaaa aaaaaaaaaa aaaaa                   3165
```

<210> SEQ ID NO 20
<211> LENGTH: 526
<212> TYPE: DNA
<213> ORGANISM: Human

<400> SEQUENCE: 20

```
tggttcctgc cgtccggact ctttttcctc tactgagatt catctgtgtg aaatatgagt     60
tggcgaggaa gatcgaccta ttattggcct agaccaaggc gctatgtaca gcctcctgaa    120
atgattgggc ctatgcggcc cgagcagttc agtgatgaag tggaaccagc aacacctgaa    180
gaaggggaac cagcaactca acgtcaggat cctgcagctg ctcaggaggg agaggatgag    240
ggagcatctg caggtcaagg gccgaagcct gaagctcata gccaggaaca gggtcaccca    300
cagactgggt gtgagtgtga agatggtcct gatgggcagg agatggaccc gccaaatcca    360
gaggaggtga aaacgcctga agaaggtgaa aagcaatcac agtgttaaaa gaaggcacgt    420
```

-continued

```
tgaaatgatg caggctgctc ctatgttgga aatttgttca ttaaaattct cccaataaag    480

ctttacagcc ttctgcaaag aaaaaaaaaa aaaaaaaaaa aaaaaa                   526


<210> SEQ ID NO 21
<211> LENGTH: 4834
<212> TYPE: DNA
<213> ORGANISM: Human

<400> SEQUENCE: 21

cgaggtcaga ggggaggagg actctggagc tgacagcgcg cacttcaccc gcagttgttc     60

tagcgactgc gaagatagct cgctgagctg gaaccccaca gatcaccaac aaaaatgaag    120

gcggcagatg agcctgccta cctgacagtg ggaaccgatg tcagtgccaa gtaccgaggt    180

gccttctgtg aggcaaagat taagactgtg aaaaggctgg tgaaagttaa ggtactcctg    240

aaacaggata ataccacaca attggtacaa gatgaccaag taaagggtcc tttaagagtt    300

ggagctattg ttgaaacaag gacatctgat ggatcttttc aggaagctat tatcagcaag    360

ttgacagatg ctagttggta taccgtggtg tttgatgatg gtgatgagcg aacattgaga    420

cgtacctcac tttgtctgaa aggagagaga cattttgcag agagtgagac acttgaccag    480

cttccattaa caaatccaga gcattttgga actccagtaa ttgcaaagaa gacgaacaga    540

ggaaggagat cttctcttcc tgttactgaa gatgaaaagg aagaagaaag cagtgaagag    600

gaagatgaag acaagcgccg tctcaatgat gaattactag gaaaagttgt aagtgtggtg    660

tctgcaacgg agaggactga atggtatcct gctttggtaa tatctcccag ctgtaatgat    720

gacatcacag tgaaaaagga tcagtgttta gttcgatcat ttattgattc taaattttac    780

tctatagcaa gaaaggacat taaggaagta gacattctca atctaccgga atctgagctc    840

tccactaaac cagggcttca gaaagcaagc atcttcttaa aaactagagt tgttcctgat    900

aattggaaaa tggatataag tgaaatcctt gagtcatcca gtagtgatga tgaagatggc    960

ccagctgaag aaaatgatga agagaaggaa aaggaggcca aaaagacaga agaagaggtg   1020

cctgaggaag aacttgatcc tgaagagagg gacaacttcc tccagcagct tttataagttt  1080

atggaagaca gaggtactcc aatcaacaaa ccacctgttt tgggctataa agatctcaat   1140

ctcttcaaac tcttcagact ggtttatcat cagggtggat gtgacaatat tgatagtggt   1200

gctgtatgga agcaaattta tatggacctt ggcattccta ttttgaattc agctgcttcc   1260

tacaatgtaa aaactgctta tagaaagtat ctctatggtt ttgaggagta ctgccgttcg   1320

gcaaatattc agttcagaac tgttcatcac catgaaccaa aagtaaaaga ggaaaaaaaa   1380

gacttagaag aatcaatgga agaggctctc aaattagatc aagaaatgcc tttaacagaa   1440

gtgaagagtg aacctgagga aaatatcgat tcaaacagtg aaagtgaaag agaagagata   1500

gaattaaaat ctccgagggg acgaaggaga attgctcgag atgtaaattc tattaaaaag   1560

gaaattgaag aagagaaaac agaagacaaa ttaaaagata atgatacaga aaataaggat   1620

gtagatgatg actatgaaac tgcagagaaa aaagaaaatg agctactact ggggagaaaa   1680

aatacaccaa agcaaaaaga gaagaaaatt aaaaaacagg aggattctga caaagactca   1740

gatgaagagg aagagaaaag ccaagagagg gaagaaactg aaagcaaatg tgactctgaa   1800

ggagaggaag atgaggaaga catggaaccc tgcctaacag gaaccaaagt gaaagtaaaa   1860

tatggacgag ggaagactca gaaaatttat gaagccagta ttaaaagcac tgaaattgat   1920

gacggagaag ttttatattt ggtacattac tatggatgga atgtcaggta tgatgagtgg   1980

gtgaaggctg acaggataat ctggcctttg gacaaaggtg gaccaaagaa aaaacagaag   2040
```

-continued

```
aaaaaagcta aaaataaaga agatagtgaa gtggacgaaa agagagatga ggagaggcag   2100
aagtcaaaac ggggacgacc tcctttaaaa tcaaccctct catcaaacat gccgtatggc   2160
ttatctaaga cagcaaacag tgaaggaaaa tcagactctt gttcatctga tagtgaaaca   2220
gaagatgctt tagaaaagaa tttaataaat gaagaacttt ctcttaaaga tgaactagaa   2280
aaaaatgaaa atttgaatga tgataagcta gatgaagaaa atccaaagat ttctgcacat   2340
atattaaaag aaaatgatag gactcaaatg cagcctttag aaaccctgaa gttagaagtt   2400
ggagagaatg aacaaatagt acagattttt gggaacaaaa tggaaaaaac agaagaagtt   2460
aagaaagaag ccgaaaaatc tccaaaagga aagggaagac gaagcaagac aaaagatctt   2520
tctttagaaa ttataaagat ttcatcattt ggccagaatg aagcaggaag tgaacctcat   2580
atagaagctc atagtcttga attgtcttca ttagacaata aaaacttttc ttctgctaca   2640
gaagatgaaa ttgaccaatg tgtgaaagaa aagaagttga aacggaaaat actaggacaa   2700
tcatcgccag agaaaaaaat aagaattgag aatggaatgg aaatgacaaa tactgtatct   2760
caagaaagga ccagtgattg tattggatct gagggaatga aaaacttaaa ttttgaacag   2820
cactttgaaa gagaaaatga aggaatgcca tcattgatag cagagtcaaa ccaatgcatc   2880
caacaactga ctagtgaaag atttgatagt ccagctgaag aaactgtaaa tattccacta   2940
aaagaagatg aggatgcaat gcctctgatc gggcctgaaa ccttggtttg ccatgaagta   3000
gatttggatg atttggatga aaaggataag accagcattg aggatgtagc agttgaaagc   3060
tctgagtcta actctcttgt ttctattcca cctgccctac ctcctgtagt ccaacataac   3120
ttttcagtag cttcaccact tactcttagt caagatgagt ctcgaagcgt aaaaagtgag   3180
agtgatataa cgattgaagt tgatagtatt gctgaagaat ctcaagaagg tctctgtgag   3240
agggaatcgg caaatggatt tgaaactaat gttgcctctg gtacctgtag tataattgta   3300
caagagagag agagcagaga gaagggtcag aagaggccaa gtgatggaaa tagtggatta   3360
atggcaaaaa agcaaaagcg taccccaaag cgaacaagtg ctgcagccaa aaatgaaaag   3420
aatggaacag gacaaagcag tgatagtgaa gatcttcctg tcctagacaa ttcaagtaaa   3480
tgtaccccag taaagcatct taatgtatct aagccacaga aacttgcacg atctcctgca   3540
agaatatccc cgcacatcaa agatggagag aaagataaac acagagaaaa acatccgaat   3600
tcatccccta ggacatataa atggagcttt cagctcaatg aattagataa tatgaacagt   3660
acagagagaa tctcatttct ccaagaaaaa ctacaggaaa tcagaaaata ttatatgtct   3720
ttgaagtctg aagttgcaac catagacagg aggagaaaaa gattaaaaaa gaaagacagg   3780
gaagtgtctc atgcgggagc ctccatgtca tctgcttcat cagacactgg aatgagtccc   3840
tcatcatcgt ctcccccaca aaatgtactt gctgtagaat gtaggtgata aacattttct   3900
ctaccttccc agcagtttgc tgccatggac ataaatcccc aaaccctgaa ttacaaccac   3960
agaaagcact caactggttt gacattgcta agtatatcct gtatactttt ccaggctgga   4020
ttgtatctat gcccctctct cttctttttt cttgttgcaa aaaataagct gattaataag   4080
tgaaggttaa gcagcctgcc atatttgtca taatttttcc tctttacttt tgtttttcgt   4140
ttgttgtgat atagaacaaa gggcacttag caaatttgaa tttgtataat aaagctttca   4200
ggtgttacag aaatcgtaga caagcaagtg cacatgataa acaatcaaaa tattacccag   4260
ctgaatagtt actgctgcac tttcactaag atgtatttga acacttggtg agtagggggt   4320
ttatgttgtg ttttttttca ttatcgtttt ttttattttt gtgaagcact tgctatttag   4380
```

-continued aactgccaaa gtatatgttc agcagtgtgc ccaggattga aggtgtaaat gggacaaaat 4440
aaattgtgaa aggaagtgta gttgactgaa aactacagtt gtaataagtc ttccactttt 4500
tataggattt ttgagcacac aattatgcaa atattttaat gtttattaat gtttacagtg 4560
gaattgtgaa taagttttca gtggactatc ttatcccttg acaaaaatat tttgtctttt 4620
ttctatgtaa tttcagagtt tttattttgt tacaaaaaga caaaaatgaa atatataaca 4680
acaatgaagt tatttaacaa gatttctaaa gctgaaattt ttgtgtaaaa taaggtatta 4740
tcttgcaact tgttaaatat atttattcag acattggatg ttgtattttt atgtattttt 4800
taaaatatta ataaaattta aaaaaaaaaa aaaa 4834

<210> SEQ ID NO 22
<211> LENGTH: 1713
<212> TYPE: DNA
<213> ORGANISM: Human

<400> SEQUENCE: 22
ggggggtgtg agccacgggc tgccgggggc ctggggctcg gcgtcggtcc ccgggggatg 60
tggagagctg gcagcatgtc ggccgagctg ggagtcgggt gcgcattgcg ggcggtgaac 120
gagcgcgtgc agcaggctgt ggcgcggcgg ccgcgggatc tcccagccat ccagccccgg 180
ctagtggcgg tcagcaaaac caaacctgca gacatggtga tcgaggccta tggacatggg 240
cagcgcactt ttggcgagaa ctacgttcag gaactgctag aaaaagcatc aaatcccaaa 300
attctgtctt tgtgtcctga gatcaaatgg cacttcattg gccacctaca gaaacaaaat 360
gtcaacaaat tgatggctgt ccccaatctc ttcatgctgg aaacagtgga ttctgtgaag 420
ttggcagaca aagtgaacag ttcctggcag agaaaaggtt ctcctgaaag gttaaaggtt 480
atggtccaga ttaacaccag cggagaagag agtaaacatg gccttccacc ttcagagacc 540
atagccatcg tggagcacat aaacgccaag tgtcctaacc tggagtttgt ggggctgatg 600
accataggaa gctttgggca tgatcttagt caaggaccaa atccagactt ccagctgtta 660
ttgtccctcc gggaggagct gtgtaaaaag ctgaacatcc ctgctgacca ggttgagctg 720
agcatgggca tgtccgcgga tttccagcat gcggttgaag taggatctac aaatgtccga 780
ataggaagca cgatttttgg agagcgggat tactcaaaga aacccacccc ggacaagtgc 840
gcagcagacg tgaaggcccc gctggaggtg gcacaggagc actgagccag ggaatactga 900
gagcactaac tatgcactaa cctagatttt catttcgata ttccctgtgt cccagcgcag 960
tcctgctctc ctgtgacctg tggagagcac taatgatcac gtgtgttgat ggaaaccatc 1020
tgtgcttagt ctctgacata ggaagcttgc ttcaggcaat ggctttggat tgagtttgag 1080
aaattcaaac atttctgcag aacagatacc aaatcaatag ctaggaatca tgttcaatat 1140
tgaattctgc ccaggagcat gaactgatcc atgaatgcct tttccaggtt aaaatttggt 1200
cactgatgcc tataatcgtg gaagtcagag ggattcccct ttttcatctc attttaatag 1260
gaaaattcct tatggttaac atctccctac aaactcctac tacgtcgtct aaattgctgc 1320
tctggaataa ggtgatttct gcccccagat tcttccctag ccggtagata cgtgaagata 1380
ttcccaactg tggaatggca gtgtaggtag cttcaggaaa tggctcaggt taattctcaa 1440
aacacaaatt gttgctggcc aggcatggtg actcatgcct gtaatcccag caatttggga 1500
gacagaggcg gaaggatcac ctgagcctag gagttcaaga ccagcctcag caacagcagg 1560
agccccaccc cccgtctcta caaaaatatt taaaaattaa ctgggcatgg tggctgaggt 1620
ggaagaatgg aagaatcact tgagcccagg agtttgaggc tgcagtgagc tatgattgca 1680

-continued ccactgtact cctgccttaa aaaaaaaaaa aaa 1713

<210> SEQ ID NO 23
<211> LENGTH: 4344
<212> TYPE: DNA
<213> ORGANISM: Human

<400> SEQUENCE: 23
gggatctgct agaagttggt cttccgccag gactagagtt tcctcgcggt aacagcctcc 60
gtggcctccg gaggaccatg tcattagact ttggcagtgt ggcactacca gtgcaaaatg 120
aagatgaaga gtatgacgaa gaggactatg aaagagagaa agagttgcag cagttactca 180
cagaccttcc ccatgacatg ctggatgacg acctctcctc tccagagctc cagtattcgg 240
actgcagcga ggatggcaca gacggacaac cacatcatcc tgagcaattg gagatgagct 300
ggaatgagca aatgctgccc aaatctcaaa gtgtaaatgg tcccagttgt caaggtttgg 360
aaccgtataa taaagtgaca tataaacctt atcagtcttc tgcccagaat aatggctcac 420
cagcccagga gataacagga agtgacacat tcgaaggcct gcaacaacaa tttttaggag 480
ctaatgagaa ctctgcagaa aatatgcaga ttattcaact tcaggttctt aacaaagcaa 540
aagagagaca actggagaac ttaattgaaa agttaaatga aagtgaacgt caaattcgat 600
atctgaatca ccagcttgta ataataaaag atgaaaagga tggtttgact ctcagccttc 660
gagaatcaca gaaactcttt cagaatggaa aagaaagaga gatacagctt gaagctcaaa 720
taaaagcact ggagactcag atacaagcat taaaagtcaa tgaagaacag atgatcaaga 780
agtccagaac aactgaaatg gctctggaaa gcttgaagca gcagctggtg gaccttcatc 840
attctgaatc acttcaacga gctagagaac agcatgagag cattgttatg ggcctcacaa 900
agaagtacga agagcaagta ttgtccttac aaaagaattt ggatgccaca gtcaccgcac 960
ttaaagaaca ggaagacatt tgctctcgtc tgaaagatca cgtgaaacaa ctggaaagga 1020
atcaagaagc aatcaagtta gaaaagactg agatcattaa taagttgaca agaagtctag 1080
aggagagtca aaagcagtgt gcccacttgt tgcagtccgg gtcagtacaa gaggtggctc 1140
agctacagtt ccagctgcag caagcacaga aggcacatgc tatgagtgca aacatgaaca 1200
aggctttgca agaagaatta acagaactaa aagatgaaat ttctctctat gaatctgctg 1260
caaaactagg aatacatcca agtgactcag aaggagaatt aaatatagaa ctcactgaat 1320
cgtatgtgga tttgggtatt aaaaaggtca actggaaaaa atccaaagtt accagcattg 1380
tacaagaaga agacccaaat gaagagcttt caaaagatga gttcattctg aagttaaagg 1440
cagaagtaca gcgtttgctg ggtagcaact caatgaagcg tcatctggtg tctcagttac 1500
aaaatgacct caaagactgt cataagaaaa ttgaagatct ccaccaagtg aagaaggatg 1560
aaaaaagcat tgaggttgag actaaaacag atacctcaga aaaaccaaag aatcaattat 1620
ggcctgagtc ttctacttct gatgttgtca gagatgatat tctgctgctt aaaaatgaaa 1680
ttcaagtttt acaacaacaa aatcaggaac ttaaagaaac tgaaggaaaa ctgagaaata 1740
caaatcaaga cttatgtaat caaatgagac aaatggtaca agattttgac catgacaaac 1800
aagaagctgt ggataggtgt gaaaggactt atcagcagca ccatgaagcc atgaaaactc 1860
aaatacgtga aagcctatta gcaaagcatg ctttggagaa gcagcagctc tttgaggctt 1920
atgagagaac tcatttgcaa ctgaggtctg agttggataa gttgaataag gaggtgactg 1980
ctgtgcagga atgttaccta gaagtgtgca gagagaagga taatctagaa ttgactctca 2040

-continued

```
ggaagaccac tgaaaaggag caacagactc aggagaagat caaagaaaaa ctcattcaac   2100
agcttgaaaa ggagtggcag tctaagctgg atcaaactat aaaggcaatg aaaaagaaga   2160
ccttagattg tggcagccaa actgaccaag taaccaccag tgatgttatt tccaagaaag   2220
agatggcaat tatgatagaa gagcagaagt gcacaatcca gcaaaactta gaacaagaga   2280
aggacatagc catcaagggg gctatgaaga aactcgaaat tgaattggaa ctcaaacatt   2340
gtgaaaatat taccaaacag gtagaaatag ctgtgcaaaa tgctcatcag cgatggctgg   2400
gagaactacc agagctggca gagtatcaag cacttgtgaa ggcagaacag aaaaagtggg   2460
aagaacagca tgaggtctct gtgaacaaaa ggatatcatt tgctgtttct gaagctaaag   2520
agaaatggaa gagtgagctt gaaaatatga ggaaaaatat acttcctgga aaggaattgg   2580
aagagaagat tcattctctt cagaaggaac ttgagttaaa gaacgaagaa gtccctgtgg   2640
tcatcagggc tgagttagct aaggctcgga gtgaatggaa caaagaaaag caagaagaaa   2700
tccacagaat ccaagaacaa aatgagcaag attaccggca atttttagat gatcaccgaa   2760
ataaaattaa tgaggtgctt gcggcagcta aagaagactt tatgaaacaa aaaactgaac   2820
tacttcttca gaaggagaca gaattacaaa cttgtctaga ccagagtcgt agagaatgga   2880
ctatgcagga agccaagcgg atccaactgg aaatctatca gtatgaggaa gacatcctga   2940
ctgtacttgg ggttctttta agtgataccc aaaaggagca catcagtgat tctgaggaca   3000
agcagctttt ggaaatcatg tcgacttgtt cttcaaaatg gatgtctgtg caatattttg   3060
aaaaactaaa gggctgcata cagaaagcat ttcaagatac acttcctctg cttgtagaaa   3120
acgctgaccc agaatggaaa aagagaaata tggccgagct ctctaaggat tctgccagcc   3180
agggcactgg ccaaggagac cctggacctg ctgctggaca ccatgctcag cccttggcct   3240
tacaagcaac agaagcagaa gctgataaga aaaaggtcct tgaaattaag gatttatgct   3300
gtggacactg cttccaagaa cttgaaaagg caaagcagga atgtcaagat ctgaaaggaa   3360
aactggagaa atgctgtagg catcttcagc atttagaaag gaagcacaaa gctgtagtgg   3420
aaaaaattgg agaagagaat aataaagttg ttgaagaatt aatagaagaa aacaacgaca   3480
tgaagaataa attggaagaa ttgcaaacac tttgtaaaac accaccaagg tcattgtcag   3540
caggggccat tgaaaatgct tgcctgccat gcagtggggg agccttggaa gaacttcgtg   3600
ggcagtacat taaagctgta aaaaaaatta aatgtgacat gcttcgttat attcaggaga   3660
gtaaggaacg agctgcagaa atggtaaaag cagaggtact gcgagaacgt caagaaaccg   3720
cccgaaagat gcgcaaatat tatttgattt gcctccaaca gattttgcag gatgatggaa   3780
aagaaggggc tgagaaaaag attatgaatg ctgctagcaa acttgctaca atggcaaaat   3840
tactggaaac acctatttct agtaagtccc aaagcaaaac tacacagtca ggtatgtcaa   3900
agtgagtcgc caaatggttt ttctatcttt tcttctttag ctatttaata ttttcagtat   3960
gaagaaggca gggaaggtaa ggagtgagag ttaatttgtg aagttttgta tgttttactt   4020
aaactagaag tttacgcaaa aagagtacac agtttccaat ttaagtaggc agactgagca   4080
tgcccatcag tttcctattg ctgcttccat ccctcgaaat gatagaaaag attttaaaca   4140
gcaaataaag aatgagaaaa agaagaaatt ataagtgggt tttaaaaagt tgcagtgggc   4200
caggcatcat ggctcacacc tgtaatccca gcactttggg aggctgaggt gggaggatcc   4260
cttgatccca ggaatttgag gttgcagtaa gctatgattg tgccactgta ctccagcctg   4320
ggtgacagag tgaggccctg tctc                                          4344
```

-continued

<210> SEQ ID NO 24
<211> LENGTH: 552
<212> TYPE: DNA
<213> ORGANISM: Human

<400> SEQUENCE: 24
ctcatatttc acacagatga gttggcgagg aagatcgacc tattattggt ctaggccaat 60
aataggtcga tcttcctcgc caactcatat ttcacacaga tgaatctcag tagaggaaaa 120
tcgacctatt attggcctag accaaggcgc tatgtacagc ctcctgaagt gattgggcct 180
atgcggcccg agcagttcag tgatgaagtg gaaccagcaa cacctgaaga aggggaacca 240
gcaactcaac gtcaggatcc tgcagctgct caggagggag aggatgaggg agcatctgca 300
ggtcaagggc cgaagcctga agctgatagc caggaacagg gtcacccaca gactgggtgt 360
gagtgtgaag atggtcctga tgggcaggag atggacccgc caaatccaga ggaggtgaaa 420
acgcctgaag aaggtgaaaa gcaatcacag tgttaaaaga aggcacgttg aaatgatgca 480
ggctgctcct atgttggaaa tttgttcatt aaaattctcc caataaagct ttacagcctt 540
ctgcaaagaa aa 552

<210> SEQ ID NO 25
<211> LENGTH: 2899
<212> TYPE: DNA
<213> ORGANISM: Human

<400> SEQUENCE: 25
aaaaaaaaaa gtacgcggac aagatggcgg cggcagcagt cgacagcgcg atggaggtgg 60
tgccggcgct ggcggaggag gccgcgccgg aggtagcggg cctcagctgc ctcgtcaacc 120
tgccgggtga ggtgctggag tacatcctgt gctgcggctc gctgacggcc gccgacatcg 180
gccgtgtctc cagcacctgc cggcggctgc gcgagctgtg ccagagcagc gggaaggtgt 240
ggaaggagca gttccgggtg aggtggcctt cccttatgaa acactacagc cccaccgact 300
acgtcaattg gttggaagag tataaagttc ggcaaaaagc tgggttagaa gcgcggaaga 360
ttgtagcctc gttctcaaag aggttctttt cagagcacgt tccttgtaat ggcttcagtg 420
acattgagaa ccttgaagga ccagagattt tttttgagga tgaactggtg tgtatcctaa 480
atatggaagg aagaaaagct ttgacctgga aatactacgc aaaaaaaatt ctttactacc 540
tgcggcaaca gaagatctta aataatctta aggcctttct tcagcagcca gatgactatg 600
agtcgtatct tgaaggtgct gtatatattg accagtactg caatcctctc tccgacatca 660
gcctcaaaga catccaggcc caaattgaca gcatcgtgga gcttgtttgc aaaacccttc 720
ggggcataaa cagtcgccac cccagcttgg ccttcaaggc aggtgaatca tccatgataa 780
tggaaataga actccagagc caggtgctgg atgccatgaa ctatgtcctt tacgaccaac 840
tgaagttcaa ggggaatcga atggattact ataatgccct caacttatat atgcatcagg 900
ttttgattcg cagaacagga atcccaatca gcatgtctct gctctatttg acaattgctc 960
ggcagttggg agtcccactg gagcctgtca acttcccaag tcacttctta ttaaggtggt 1020
gccaaggcgc agaaggggcg accctggaca tctttgacta catctacata gatgcttttg 1080
ggaaaggcaa gcagctgaca gtgaaagaat gcgagtactt gatcggccag cacgtgactg 1140
cagcactgta tggggtggtc aatgtcaaga aggtgttaca gagaatggtg ggaaacctgt 1200
taagcctggg gaagcgggaa ggcatcgacc agtcatacca gctcctgaga gactcgctgg 1260
atctctatct ggcaatgtac ccggaccagg tgcagcttct cctcctccaa gccaggcttt 1320

-continued

```
acttccacct gggaatctgg ccagagaagg tgcttgacat cctccagcac atccaaaccc   1380

tagacccggg gcagcacggg gcggtgggct acctggtgca gcacactcta gagcacattg   1440

agcgcaaaaa ggaggaggtg ggcgtagagg tgaagctgcg ctccgatgag aagcacagag   1500

atgtctgcta ctccatcggg ctcattatga agcataagag gtatggctat aactgtgtga   1560

tctacggctg ggaccccacc tgcatgatgg gacacgagtg gatccggaac atgaacgtcc   1620

acagcctgcc gcacggccac caccagcctt tctataacgt gctggtggag gacggctcct   1680

gtcgatacgc agcccaagaa aacttggaat ataacgtgga gcctcaagaa atctcacacc   1740

ctgacgtggg acgctatttc tcagagttta ctggcactca ctacatccca aacgcagagc   1800

tggagatccg gtatccagaa gatctggagt ttgtctatga aacggtgcag aatatttaca   1860

gtgcaaagaa agagaacata gatgagtaaa gtctagagag gacattgcac ctttgctgct   1920

gctgctatct tccaagagaa cgagactccg gaagaagacg tctccacgga gccctcggga   1980

cctgctgcac caggaaagcc actccaccag tagtgctggt tgcctcctac taagtttaaa   2040

taccgtgtgc tcttccccag ctgcaaagac aatgttgctc tccgcctaca ctagtgaatt   2100

aatctgaaag gcactgtgtc agtggcatgg cttgtatgct tgtcctgtgg tgacagtttg   2160

tgacattctg tcttcatgag gtctcacagt cgacgctcct gtaatcattc tttgtattca   2220

ctccattccc ctgtctgtct gcatttgtct cagaacattt ccttggctgg acagatgggg   2280

ttatgcattt gcaataattt ccttctgatt tctctgtgga acgtgttcgg tcccgagtga   2340

ggactgtgtg tctttttacc ctgaagttag ttgcatattc agaggtaaag ttgtgtgcta   2400

tcttggcagc atcttagaga tggagacatt aacaagctaa tggtaattag aatcatttga   2460

atttattttt ttctaatatg tgaaacacag atttcaagtg ttttatcttt tttttttaa    2520

atttaaatgg gaatataaca cagttttccc ttccatattc ctctcttgag tttatgcaca   2580

tctctataaa tcattagttt tctattttat tacataaaat tcttttagaa aatgcaaata   2640

gtgaactttg tgaatggatt tttccatact catctacaat tcctccattt taaatgacta   2700

cttttatttt ttaatttaaa aaatctactt cagtatcatg agtaggtctt acatcagtga   2760

tgggttcttt ttgtagtgag acatacaaat ctgatgttaa tgtttgctct tagaagtcat   2820

actccatggt cttcaaagac caaaaaaatg aggttttgct tttgtaatca ggaaaaaaaa   2880

aaattaatga accttaaag                                                2899
```

<210> SEQ ID NO 26
<211> LENGTH: 2289
<212> TYPE: DNA
<213> ORGANISM: Human

<400> SEQUENCE: 26

```
ttgtaccctt aaaattattt tttcctatgc agaattgact ttgattaaaa aatgtttttg     60

atgactattt tcctgattcg tcagtatatc taattgtgtt catattactc atgaaaaatc    120

ttgtctatga gggacgtatt tttagtaaca tttttatagc atataagaac ttttacagca    180

aaaacaggaa tcattaagtg tgtgtgcttt tatcataact tctcttttaa tggaacttaa    240

aatcttaact cgtgtttttg cagcactttt tttgcacatg gtaggttctt aatatttgaa    300

tggaattcag tgtgactgtt ctttgtgttc tcaaaagtct gatctttgta acaatttgtc    360

tttcacttga gacttttttt ttctttgcat atgtgcacgt ctcactcttg gttttcctta    420

atcttttttta actaaacaca tctatgactc atatttccct atttatgaat aggagcaatt    480

taaaatttcc caacatggtg gtatgtgatg taacataacc aaaggctaca tgtttaccct    540
```

-continued

```
tgtttaatta cccttcattt gtggaaagat gacgtatgta tttatgatgt aaatgtcttt    600

cagaatgacc tttgggacta agcttttttt ttttttttcc caccaaaaaa tggtcatgac    660

ctaggaagcc ttgttagtaa aatttaaaaa ggaaaagttg gctgggcatg gtggctcatg    720

cctgtaatct caacactctg ggaggccgag gtgggtgtat caattgaggt cagagttcga    780

gaccagcctg ggtaacatgg tgaaaccccg tctctactaa aaatacaaaa attagctggg    840

catggtggcc tgtgcctgtg atcccagcta ctcgggaagc agagacatga gaattgcttg    900

aacctaggag gtggaggttg cagtgagtgg agattgtgcc actgcacgcc aacctgggtg    960

acagagcgag acttcatctc aaaaataaaa taaaataaaa ataaacagga aaaatctggt   1020

caaatgcccc ttgttcttct tcaacagata catagtgagt tgtgtaaaaa aggagttgga   1080

aaaggaatat gtagattcaa agtgacttaa agaatagaaa aaaaatttgt tttaaaaaat   1140

ggccaagact aaatcatagt gtctagggag gtacacctga ataataaaac tataaagaaa   1200

tacaaaatat ggttactact aagaatagtc tgttgccagt agtacacaga atgagcactc   1260

aaattataac agaagcattt tggtattcat aaatgttctt tttttaaaaa agaacacaat   1320

cgaaattata ggctgtaagt actgatttta attgtagtga atgtgaaagt gttgttaatg   1380

aaaatataaa gaatatttgt taaagtgtgg acctagccag gaatactagg tagaaaaggt   1440

aactctttaa aaacattttt ttaattgtga agttaattta ttgtcacttt gtttgatatt   1500

tattattaga gtccctaggt taattctgtt tttattgctt ttcagaataa ttaagaccta   1560

aatcttctgc cgaattctgt ttggtttcct tatttctttt gccatgttct ttcattccac   1620

aaatgttatt gagcacttcc agtgtaccaa gccttgtgtt tactgctttg atgataaatg   1680

caataaggta atgctgcttt taaggatcct tcaggatagg ctcttgtagc agtaaggact   1740

tagtattttt gctatagaag tgtatggaga gctatctatg gtgcaataac tgtggaaata   1800

cagtttttat tctatttggt tcccatatac attgagtcct cctttggtgg gaatttgatc   1860

aggttggtct cagttgaatc ctggctgcat atgcctcagt aaggaagaag gcctagggga   1920

ctgtggaaag cctggtggtg gtcctggaag gcttgagaat acctggagct ggaagctcct   1980

tgctcattgg tgaccttttt catatgcagc agagctcttg gcattcctag catactacct   2040

tgaaaggact gtgtcttgcc tcctagaaat tctggacttg gtagaatcat ttgtttatgt   2100

tattttaaaa agaaaaaaaa ctctgaaatg tactttttgg aagaaaaatg aacttgtttt   2160

tggacttttc tgtgtgttgt ttctttaatt gaaaattctg tctggagatt gattttcaac   2220

ccccttcctt tccctctagt tttaaattgt aacattgctt tccaagcatt tcaaaaaaaa   2280

aaaaaaaaa                                                           2289
```

<210> SEQ ID NO 27
<211> LENGTH: 1694
<212> TYPE: DNA
<213> ORGANISM: Human

<400> SEQUENCE: 27

```
atgccatggc tagtccaggg aaagataact atagaatgaa aagttataag aataaagccc     60

taaatcctca agagatgcgt agacgaagag aagaagaagg aatacagctt agaaaacaaa    120

aaagagaaga acagttgttc aaacgcagaa atgtctattt gcccagaaat gatgaatcta    180

tgcttgaaag tcctatacag gattcagata ttagttccac tgtacccatt ccagaggaag    240

gagttgttac tacagatatg gttcaaatga ttttttctaa taatgctgat caacagctaa    300
```

-continued

```
cagcaacaca gaaatttaga aagctgcttt ctaaagaacc taatccacca atagatcaag    360

ttatacagaa accaggagtt gtacagagat ttgtgaaatt tcttgaaaga aatgaaaatt    420

gcactttaca atttgaagct gcatgggcat taacaaatat agcatctgga acttttctgc    480

ataccaaggt agtgattgaa actggggctg ttccgatttt tatcaaactt cttaattctg    540

aacatgaaga tgttcaggaa caggctgttt gggcacttgg taatattgct ggtgacaatg    600

cagaatgcag agattttgtt ttgaattgtg aaatacttcc acctctttta gagttattaa    660

caaattcaaa cagactcaca acaacaagaa atgccgtgtg ggccctctca aatttatgta    720

gaggcaaaaa ccctcctcca aactttagta aggtttcacc ttgcttaaat gtcctgtcac    780

gactgttgtt tagcagtgac ccagatgtgt tagcagacgt gtgttgggcc ctttcttatc    840

tttccgatgg acccaatgat aaaattcaag cagtcattga ttctggagtc tgtcgaagat    900

tggtggaact tttgatgcac aatgattata aagttgtatc acctgcatta agggcagttg    960

gtaatattgt gactggtgat gatattcaaa cacaggtaat tttgaattgt tctgcattac   1020

cctgtctctt acatttattg agtagcccaa aggagtcaat tagaaaagaa gcctgctgga   1080

ctgtttctaa catcactgct ggaaatagag ctcagattca ggctgttata gatgcaaata   1140

tttttcctgt tttgattgag attcttcaga aagcagagtt tcgtaccaga aaagaagcag   1200

cttgggctat aactaatgca acatcaggag gtactccaga gcaaataagg tatttggtag   1260

ctttaggctg cattaaacca ctttgtgatc ttttgactgt tatggactcc aaaatagtcc   1320

aagtggcttt aaatggactt gaaaatattt tacgtcttgg agaacaagaa tctaagcaga   1380

atggaatagg cattaatcca tactgtgctc tcattgaaga agcatatggt ctggataaaa   1440

ttgagttttt gcaaagccat gaaaatcagg aaatttacca gaaggcattt gatctgattg   1500

aacattactt tggtgtagaa gaagatgacc ccagcattgt acctcaggtg gatgaaaacc   1560

aacaacagtt tatatttcag cagcaggaag caccaatgga tggatttcaa ctttaactta   1620

ctggaggaaa aaaaatttat ggctaaaaag ggtagcttca ggtaactcct ctttgttgcc   1680

aatgtaagga actg                                                     1694
```

<210> SEQ ID NO 28
<211> LENGTH: 4756
<212> TYPE: DNA
<213> ORGANISM: Human

<400> SEQUENCE: 28

```
gcgacgctca cgaacgatca gagctgcggg cgacgcaacg aagcccggag gccgcaggct     60

gcgcgctccc tcgcagcagc cgggcgggca aaagccccca gtcctcggcc cccgcgcaag    120

cgacgccggg aaatgcccac atccgggaaa cctgcagcgg agtgcggcgg cggcgacact    180

gagtggaagg caaaatggcg gcggcggcgg cggtggcctg gtgttaaggg gagagccagg    240

tccttacgac ccctgggacg ggccgcgctg gcccgcggca gcccccccgt tcgtctcccc    300

gctctgcccc accagggata cttggggttg ctgggacgga ctctggccgc ctcagcgtcc    360

gccctcaggc ccgtggccgc tgtccaggag ctctgctctc ccctccagag ttaattattt    420

atattgtaaa gaattttaac agtcctgggg acttccttga aggatcattt tcacttttgc    480

tcagaagaaa gctctggatc tatcaaataa agaagtcctt cgtgtgggct acatatatag    540

atgttttcat gaagaggagt gaaaagccag aaggatatag acaaatgagg cctaagacct    600

ttcctgccag taactatact gtcagtagcc ggcaaatgtt acaagaaatt cgggaatccc    660

ttaggaattt atctaaacca tctgatgctg ctaaggctga gcataacatg agtaaaatgt    720
```

-continued

```
caaccgaaga tcctcgacaa gtcagaaatc cacccaaatt tgggacgcat cataaagcct    780
tgcaggaaat tcgaaactct ctgcttccat ttgcaaatga aacaaattct tctcggagta    840
cttcagaagt taatccacaa atgcttcaag acttgcaagc tgctggattt gatgaggata    900
tggttataca agctcttcag aaaactaaca acagaagtat agaagcagca attgaattca    960
ttagtaaaat gagttaccaa gatcctcgac gagagcagat ggctgcagca gctgccagac   1020
ctattaatgc cagcatgaaa ccagggaatg tgcagcaatc agttaaccgc aaacagagct   1080
ggaaaggttc taaagaatcc ttagttcctc agaggcatgg cccgccacta ggagaaagtg   1140
tggcctatca ttctgagagt cccaactcac agacagatgt aggaagacct ttgtctggat   1200
ctggtatatc agcatttgtt caagctcacc ctagcaacgg acagagagtg aacccccccac  1260
caccacctca agtaaggagt gttactcctc caccacctcc aagaggccag actccccctc   1320
caagaggtac aactccacct ccccccttcat gggaaccaaa ctctcaaaca aagcgctatt  1380
ctggaaacat ggaatacgta atctcccgaa tctctcctgt cccacctggg gcatggcaag   1440
agggctatcc tccaccacct ctcaacactt cccccatgaa tcctcctaat caaggacaga   1500
gaggcattag ttctgttcct gttggcagac aaccaatcat catgcagagt tctagcaaat   1560
ttaactttcc atcagggaga cctggaatgc agaatggtac tggacaaact gatttcatga   1620
tacaccaaaa tgttgtccct gctggcactg tgaatcggca gccaccacct cccatatcctc  1680
tgacagcagc taatggacaa agcccttctg ctttacaaac aggggggatct gctgctcctt  1740
cgtcatatac aaatggaagt attcctcagt ctatgatggt gccaaacaga aatagtcata   1800
acatggaact atataacatt agtgtacctg gactgcaaac aaattggcct cagtcatctt   1860
ctgctccagc ccagtcatcc ccgagcagtg ggcatgaaat ccctacatgg caacctaaca   1920
taccagtgag gtcaaattct tttaataacc cattaggaaa tagagcaagt cactctgcta   1980
attctcagcc ttctgctaca acagtcactg caattacacc agctcctatt caacagcctg   2040
tgaaaagtat gcgtgtatta aaaccagagc tacagactgc tttagcacct acacaccctt   2100
cttggatacc acagccaatt caaactgttc aacccagtcc ttttcctgag ggaaccgctt   2160
caaatgtgac tgtgatgcca cctgttgctg aagctccaaa ctatcaagga ccaccaccac   2220
cctacccaaa acatctgctg caccaaaacc catctgttcc tccatacgag tcaatcagta   2280
agcctagcaa agaggatcag ccaagcttgc ccaaggaaga tgagagtgaa aagagttatg   2340
aaaatgttga tagtggggat aaagaaaaga aacagattac aacttcacct attactgtta   2400
ggaaaaacaa gaaagatgaa gagcgaaggg aatctcgtat tcaaagttat tctcctcaag   2460
catttaaatt ctttatggag caacatgtag aaaatgtact caaatctcat cagcagcgtc   2520
tacatcgtaa aaaacaatta gagaatgaaa tgatgcgggt tggattatct caagatgccc   2580
aggatcaaat gagaaagatg ctttgccaaa aagaatctaa ttacatccgt cttaaaaggg   2640
ctaaaatgga caagtctatg tttgtgaaga taaagacact aggaatagga gcatttggtg   2700
aagtctgtct agcaagaaaa gtagatacta aggctttgta tgcaacaaaa actcttcgaa   2760
agaaagatgt tcttcttcga aatcaagtcg ctcatgttaa ggctgagaga gatatcctgg   2820
ctgaagctga caatgaatgg gtagttcgtc tatattattc attccaagat aaggacaatt   2880
tatactttgt aatggactac attcctgggg gtgatatgat gagcctatta attagaatgg   2940
gcatctttcc agaaagtctg gcacgattct acatagcaga acttacctgt gcagttgaaa   3000
gtgttcataa aatgggtttt attcatagag atattaaacc tgataatatt ttgattgatc   3060
```

-continued

```
gtgatggtca tattaaattg actgactttg gcctctgcac tggcttcaga tggacacacg   3120

attctaagta ctatcagagt ggtgaccatc cacggcaaga tagcatggat ttcagtaatg   3180

aatgggggga tccctcaagc tgtcgatgtg gagacagact gaagccatta gagcggagag   3240

ctgcacgcca gcaccagcga tgtctagcac attctttggt tgggactccc aattatattg   3300

cacctgaagt gttgctacga acaggataca cacagttgtg tgattggtgg agtgttggtg   3360

ttattctttt tgaaatgttg gtgggacaac ctcctttctt ggcacaaaca ccattagaaa   3420

cacaaatgaa ggttatcaac tggcaaacat ctcttcacat tccaccacaa gctaaactca   3480

gtcctgaagc ttctgatctt attattaaac tttgccgagg acccgaagat cgcttaggca   3540

agaatggtgc tgatgaaata aaagctcatc catttttttaa aacaattgac ttctccagtg   3600

acctgagaca gcagtctgct tcatacattc ctaaaatcac acacccaaca gatacatcaa   3660

attttgatcc tgttgatcct gataaattat ggagtgatga taacgaggaa gaaaatgtaa   3720

atgacactct caatggatgg tataaaaatg gaaagcatcc tgaacatgca ttctatgaat   3780

ttaccttccg aaggtttttt gatgacaatg gctacccata taattatccg aagcctattg   3840

aatatgaata cattaattca caaggctcag agcagcagtc ggatgaagat gatcaaaaca   3900

caggctcaga gattaaaaat cgcgatctag tatatgttta acacactagt aaataaatgt   3960

aatgaggatt tgtaaaaggg cctgaaatgc gaggtgtttt gaggttctga gagtaaaatt   4020

atgcaaatat gacagagcta tatatgtgtg ctctgtgtac aatattttat tttcctaaat   4080

tatgggaaat ccttttaaaa tgttaattta ttccagccgt ttaaatcagt atttagaaaa   4140

aaattgttat aaggaaagta aattatgaac tgaatattat agtcagttct tggtacttaa   4200

agtacttaaa ataagtagtg ctttgtttaa aaggagaaac ctggtatcta tttgtatata   4260

tgctaaataa ttttaaaata caagagtttt tgaaattttt ttgaaagaca gttttagttt   4320

tatcttgctt taaccaaata tgaaacatac cccctatttt acagagctct tttttcccct   4380

cataaccttg tttttggtag aaaataagct agagaaatta agccatcgtg ttggtgagtg   4440

ttcctaggct aatgataatc tgtataattc acatcctgaa actaaggaat acagggttga   4500

aaaaatatta atatgtttgt cagaaggaaa aataatgcat ttattttccc ccccaccccc   4560

cgccccatgg aatatttaat ctatttaatc ttcttgcatt tatttctcaa gaattactgg   4620

ctttaaaaga agccaaagca ctactagctt tttttccata ttggtatttt tgatgctgct   4680

tccaatttta aaagggaaca aagctgccat aaatcgaaat gttcaatact aaaagctaaa   4740

atatttctca ccatcg                                                  4756
```

<210> SEQ ID NO 29
<211> LENGTH: 2306
<212> TYPE: DNA
<213> ORGANISM: Human

<400> SEQUENCE: 29

```
ggaggcagga gaatcgcttg aaccctggag gcagaggttg cagtaagccg agatcgcgcc     60

acagcactcc agtctgggcg acaaagcgag actccgtctc aaaaaacaaa aacaaaaaca    120

aaaaacaaac aaaaaaccat aaattcacag ttcagtggca attttaaatg gaaagacacg    180

ccttattcac tatgatgctt ttattgctaa ttcattcagt gaagaggaat tatgcaaggt    240

ttaaaatggc ttgcctgtcc tggtatatcc aaaactctta attcagaaga ttcatctatt    300

tctccaagag aagaagctcg tggtggggct ggaggaggtt caggctcaag atcaaagtcc    360

aatttggtta ctgtagaatc gcttatagaa gataaagtaa ctcaccaaaa cagtaataga    420
```

-continued

```
aagtctgtat tttaaacagc tttaaaatta aagcaaacaa tttacttttt aagtaaacag    480

aacactactt tcaaaatact acttgggaaa aaagcaagac tcagtacacc tgctataatc    540

agtacgtaag aatgtcccaa taactttgta taagagatgc ttaaaatctc agacacatac    600

ctagctggag gtgctagttg agggatgcgt acatcaacca ctggcactgt agtaggcaca    660

ggagcttgag ggctgaaggt gccagaatga tttactgtag gaatagctct tcttactagc    720

cttccccaag tggcaatatt aatattcatt tgaggagctc tgagaaatgt tttgccttgt    780

tgctttgaaa aaattttctt ttgtctttga agttttggtc ttctttcaat aactggatta    840

aaaaaggtaa cctctgcaaa taaagtaccc tgtggttcca aatagagaca catgccatgc    900

cgttggttgt ctaaaaaatc ttctaacctc agaaaatttt acagcacaca gagaccgcca    960

atcacgccaa taaactgaaa tttccagttc acgtgacctg tccagttcca gtgtaaactt   1020

ctggtcccat gactgattgg aaatgggttt ccagctagtt tggccaacca cagtattatc   1080

gagcttcaaa acagcacaga catcattgga caagtcatcg gtttttagaa gatttcgact   1140

acttccgctt ttacttttac tcgttctgct catgaaagat gatctggttt cacttggact   1200

ccaaccaggc agtgcaactg atgttgcttt tgaccgtcca gggacattct ctaggatatc   1260

ttggcagccc ataagacgaa cttccaaagt acctgttagt gctgctggtt tggatagtgt   1320

actatattga ttttgcgtag atatcatact ttgacgtgga cttagtgttg gtgatgcagc   1380

aacaagtgaa agttcttcaa taataatcct gcttttggga tgattcttgg ggacttcgtt   1440

taatctttgc tctaatgaat actttaaaag gtccaacttc tgacttgatt cattaaatct   1500

tgcttgagct tctgaaagtg cttttctgtc tgttactttt cctgagccaa gtaatttcat   1560

tacattcttt gcaccttctg ctactgcaaa ctctatccta aaatgatgcc ttaattcttc   1620

catccgaagt tcaagaggac ttatcacagg ttttgcatta tcaaaagcca attcattagt   1680

ctggactgcc tgaagaatct gcattcgtat gacttctatt tttgtcttgc tgtcctggag   1740

cagttgctga gctgtaccat ggagtttccg atcctttgaa gatccatttg aatacatctg   1800

tatcatattc tctgcacctt gttttacttt aagttctata tccaattgtt tttgtagggc   1860

cttcaatcta ttggtgctag tagaacaacg agggtcatta tttggagtat ctggagtcct   1920

tgggcaatct gtaatatctt ctggatctga tacaacaata tgtgcattta attcctgcag   1980

cttgtgatgt agttcttcta atttttattt gatttttttca aaatgttgtc tacataagcc   2040

aaactttttt tatctgttgt gactttcctc agattttcag ctccttcttt gattttcagt   2100

tctttcctta tttctctctt aattcgatcc ttgatatcat ccaatttctg ctgcaccatt   2160

gtatctgaaa agtctaattt ttgaacagca ctcacattct cagaaaacgg aagacttcgg   2220

gaatcccccct gcagttccgt gagcagaatc tccccccgtt cggggttgga cgccattgcg   2280

ctccggtatg gactccgcac ctggac                                        2306
```

<210> SEQ ID NO 30
<211> LENGTH: 1842
<212> TYPE: DNA
<213> ORGANISM: Human

<400> SEQUENCE: 30

```
ccacagtggc gccggcagag caggagtggc tggaggagct gtggttggag caggaggtgg     60

cacggcaggg ctggagggct ccctatgagt ggcggagacg gcccaggagg cgctggagca    120

acagctccca caccgcacca agcggtggct gcaggagctc gcccatcgcc cctgcgctgc    180
```

-continued

```
tcggaccgcg gccacagccg gactggcggg tacggcggcg acagacggat tggccgagag     240
tcccagtccg cagagtagcc ccggcctcga ggcggtggcg tcccggtcct ctccgtccag     300
gagccaggac aggtgtcgcg cggcggggct ccagggaccg cgcctgaggc cggctgcccg     360
cccgtcccgc cccgccccgc cgcccgccgc ccgccgagcc cagcctcctt gccgtcgggg     420
cgtccccagg ccctgggtcg gccgcggagc cgatgcgcgc ccgctgagcg ccccagctga     480
gcgcccccgg cctgccatga ccgcgctccc cggcccgctc tggctcctgg gcctggcgct     540
atgcgcgctg ggcgggggcg gccccggcct gcgacccccg cccggctgtc cccagcgacg     600
tctgggcgcg cgcgagcgcc gggacgtgca gcgcgagatc ctggcggtgc tcgggctgcc     660
tgggcggccc cggccccgcg cgccacccgc cgcctcccgg ctgcccgcgt ccgcgccgct     720
cttcatgctg gacctgtacc acgccatggc cggcgacgac gacgaggacg gcgcgcccgc     780
ggagcggcgc ctgggccgcg ccgacctggt catgagcttc gttaacatgg tggagcgaga     840
ccgtgccctg ggccaccagg agccccattg gaaggagttc cgctttgacc tgacccagat     900
cccggctggg gaggcggtca cagctgcgga gttccggatt tacaaggtgc ccagcatcca     960
cctgctcaac aggaccctcc acgtcagcat gttccaggtg gtccaggagc agtccaacag    1020
ggagtctgac ttgttctttt tggatcttca gacgctccga gctggagacg agggctggct    1080
ggtgctggat gtcacagcag ccagtgactg ctggttgctg aagcgtcaca aggacctggg    1140
actccgcctc tatgtggaga ctgaggacgg gcacagcgtg gatcctggcc tggccggcct    1200
gctgggtcaa cgggccccac gctcccaaca gcctttcgtg gtcactttct tcagggccag    1260
tccgagtccc atccgcaccc ctcgggcagt gaggccactg aggaggaggc agccgaagaa    1320
aagcaacgag ctgccgcagg ccaaccgact cccagggatc tttgatgacg tccacggctc    1380
ccacggccgg caggtctgcc gtcggcacga gctctacgtc agcttccagg acctcggctg    1440
gctggactgg gtcatcgctc cccaaggcta ctcggcctat tactgtgagg gggagtgctc    1500
cttcccactg gactcctgca tgaatgccac caaccacgcc atcctgcagt ccctggtgca    1560
cctgatgaag ccaaacgcag tccccaaggc gtgctgtgca cccaccaagc tgagcgccac    1620
ctctgtgctc tactatgaca gcagcaacaa cgtcatcctg cgcaagcacc gcaacatggt    1680
ggtcaaggcc tgcggctgcc actgagtcag cccgcccagc cctactgcag ccacccttct    1740
catctggatc gggccctgca gaggcagaaa acccttaaat gctgtcacag ctcaagcagg    1800
agtgtcaggg gccctcactc tctgtgccta cttcctgtca gg                       1842
```

<210> SEQ ID NO 31
<211> LENGTH: 2524
<212> TYPE: DNA
<213> ORGANISM: Human

<400> SEQUENCE: 31

```
attggctgaa ggcacttccg ttgagcatct agacgtttcc ttggctcttc tggcgccaaa      60
atgtcgttcg tggcaggggt tattcggcgg ctggacgaga cagtggtgaa ccgcatcgcg     120
gcgggggaag ttatccagcg gccagctaat gctatcaaag agatgattga gaactgttta     180
gatgcaaaat ccacaagtat tcaagtgatt gttaaagagg gaggcctgaa gttgattcag     240
atccaagaca atggcaccgg gatcaggaaa gaagatctgg atattgtatg tgaaaggttc     300
actactagta aactgcagtc ctttgaggat ttagccagta tttctaccta tggctttcga     360
ggtgaggctt tggccagcat aagccatgtg gctcatgtta ctattacaac gaaaacagct     420
gatggaaagt gtgcatacag agcaagttac tcagatggaa aactgaaagc ccctcctaaa     480
```

-continued

```
ccatgtgctg gcaatcaagg gacccagatc acggtggagg accttttta caacatagcc    540
acgaggagaa aagctttaaa aaatccaagt gaagaatatg ggaaaatttt ggaagttgtt   600
ggcaggtatt cagtacacaa tgcaggcatt agtttctcag ttaaaaaaca aggagagaca   660
gtagctgatg ttaggacact acccaatgcc tcaaccgtgg acaatattcg ctccatcttt   720
ggaaatgctg ttagtcgaga actgatagaa attggatgtg aggataaaac cctagccttc   780
aaaatgaatg gttacatatc caatgcaaac tactcagtga agaagtgcat cttcttactc   840
ttcatcaacc atcgtctggt agaatcaact tccttgagaa aagccataga aacagtgtat   900
gcagcctatt tgcccaaaaa cacacaccca ttcctgtacc tcagtttaga aatcagtccc   960
cagaatgtgg atgttaatgt gcaccccaca aagcatgaag ttcacttcct gcacgaggag  1020
agcatcctgg agcgggtgca gcagcacatc gagagcaagc tcctgggctc caattcctcc  1080
aggatgtact tcacccagac tttgctacca ggacttgctg gcccctctgg ggagatggtt  1140
aaatccacaa caagtctgac ctcgtcttct acttctggaa gtagtgataa ggtctatgcc  1200
caccagatgg ttcgtacaga ttcccgggaa cagaagcttg atgcatttct gcagcctctg  1260
agcaaacccc tgtccagtca gccccaggcc attgtcacag aggataagac agatatttct  1320
agtggcaggg ctaggcagca agatgaggag atgcttgaac tcccagcccc tgctgaagtg  1380
gctgccaaaa atcagagctt ggagggggat acaacaaagg ggacttcaga aatgtcagag  1440
aagagaggac ctacttccag caaccccaga aagagacatc gggaagattc tgatgtggaa  1500
atggtggaag atgattcccg aaaggaaatg actgcagctt gtaccccccg gagaaggatc  1560
attaacctca ctagtgtttt gagtctccag gaagaaatta atgagcaggg acatgaggtt  1620
ctccgggaga tgttgcataa ccactccttc gtgggctgtg tgaatcctca gtgggccttg  1680
gcacagcatc aaaccaagtt ataccttctc aacaccacca agcttagtga agaactgttc  1740
taccagatac tcatttatga ttttgccaat tttggtgttc tcaggttatc ggagccagca  1800
ccgctctttg accttgccat gcttgcctta gatagtccag agagtggctg gacagaggaa  1860
gatggtccca aagaaggact tgctgaatac attgttgagt ttctgaagaa gaaggctgag  1920
atgcttgcag actatttctc tttggaaatt gatgaggaag ggaacctgat tggattaccc  1980
cttctgattg acaactatgt gccccctttg gagggactgc ctatcttcat tcttcgacta  2040
gccactgagg tgaattggga cgaagaaaag gaatgttttg aaagcctcag taaagaatgc  2100
gctatgttct attccatccg gaagcagtac atatctgagg agtcgaccct ctcaggccag  2160
cagagtgaag tgcctggctc cattccaaac tcctggaagt ggactgtgga acacattgtc  2220
tataaagcct tgcgctcaca cattctgcct cctaaacatt tcacagaaga tggaaatatc  2280
ctgcagcttg ctaacctgcc tgatctatac aaagtctttg agaggtgtta aatatggtta  2340
tttatgcact gtgggatgtg ttcttctttc tctgtattcc gatacaaagt gttgtatcaa  2400
agtgtgatat acaaagtgta ccaacataag tgttggtagc acttaagact tatacttgcc  2460
ttctgatagt attcctttat acacagtgga ttgattataa ataaatagat gtgtcttaac  2520
ataa                                                               2524
```

<210> SEQ ID NO 32
<211> LENGTH: 158980
<212> TYPE: DNA
<213> ORGANISM: Human

<400> SEQUENCE: 32

-continued

```
gatcagtcta aagagaattg gcaatatcta cacctgtaaa gtgtaaaatt aggaaaacaa     60
ctcaaaattg ttataaatgt acaataaata ctgctcattc aataacggct aacaacagac    120
tcattgttga aactgcaagt gttgaggatt ttagtaactt gattatgtaa atgagataaa    180
gccttgttta tagatataca aatttaacag gtaattatta atgttttgtt gtatatatga    240
gtgtgctcct gtgtgatgta aaaacagaga catgtttgag aaactatgaa taccttgtac    300
aaacaattta gttgctttat cttagaattt tttgttttac tgtgccttct ttcggctcaa    360
aaggaattat tgcctaagtc agtgattatc tgggcaacag aattaatgtt ctagctacag    420
cattgcacta tttcacagga tctattgatt actttttaaa aatttttctc atctgtcctg    480
ttctcattat tctactatta ttattttagt ttgggcctta tttaacaatt aactaaataa    540
ttacatttgc ccccaaatgg tatccctgcc atctatattc tctctctctc cctctccact    600
catcacctgt ctaccaatat atttattgtc tactactttc catgttcctc attaatttct    660
ggtattagta aactgatacc aaatgttgcc tcccttaaga aactgacagc ctagtccggt    720
ttactactgt tccgtagaac cttgcatctt tcttctttaa aaatctttaa cacctttcag    780
tggcttttag aaaagggttc acatttttca gagcttttga cactctttac cttttgacac    840
aatatattat tattatttgg gggaacagca ggaaccaggg atgattaatt tcctacaatg    900
tgcagggcag ttctatataa caaaattatt tgtcccacat tttacatgac tttcaaatgc    960
cccacaaaat gttcaaagac atgagaatct catctgaact cagagctcaa ctctgttttt   1020
ttataatgta caaagctttg attttattta ttttttggaa aagctttgat tttatttatt   1080
ttttggaatc attttaatat gcactgattt tgatgctaat ttcaacccac ctaattcctt   1140
gcccaactga tagatccatc ttctattttt aaactttagg aagtagaata ggtcagtgaa   1200
gagcattgtg ataaaaaccc agggtattcc cacactgttg ccctctgaac aatttttttag   1260
gatgtgagtg tgtgtgtgtg tttgtgcatg tgtgtgtgtg aaggcgactt tcgcttggat   1320
aggatgccac tccataaaac agttagagaa taaaataaaa agagtacagt tggagtcctg   1380
ttcttgctct gcttaccccc attatcttgt gacacacagt acctgttcca aatccccact   1440
cagaattctt aacccagtat ctcaggagta aattctggca ctaaaggggt tctttccttc   1500
tgaggagcta agaaaaacag atggagaaaa tctgacctca agcagatgtg tctctgcccc   1560
tcattctcca aattcttggg agagtgttac tcagtcttac tgcacagtga cattatcaat   1620
ggaactttaa gaaatactaa tgcctaggtc tcattctaat ggcttctgat ttaattgctt   1680
tagggtatgc cctggtgatt ctgaaatggt tctctcacaa cctaggacta gggacttata   1740
atctaaggtg tatgtcctcc aaatgctgat tctacatagg gcagtaaaga gtggaaagtg   1800
aagacttgac ctgtgatttt ggtggtgggg aagagaaagg ctattttggt atttctggct   1860
ctttatctta agagtcatca atcctctact tgcactgtca gacacattgg gctgacacat   1920
tcgaaaatac acattgcctg accgtgtggc tgatactcct agagaagcgg tttctaaatt   1980
ttatagccca ttggaatcac ttggacatct ttaacaaaca ctgatacccg gctcctactc   2040
ctagacatgc cgatttaatt tctatggagt ggcacctggc tttaggattt ttaaaaagtt   2100
gtgcagcttg ttctaatgag cagcaaagat tgggacccag tcccagtgaa aaaaagctcg   2160
tagaacaata caacaggaca tttaaggagc acagccattt caaaacaata ttctgttaaa   2220
aattatagat gtccatatag ctgaaatagt aagacagatt gtgaatttaa aactagggaa   2280
gatatttgaa agattaaaaa aaggagtgga tagccaaatt cataccatat acacatatga   2340
aggtttccag gtcagaagac caacaaagaa tctaaagtaa gacagacatt aggtttttca   2400
```

-continued

```
acagtaaata ctatatgcaa gaagatgaca aagggatatt ttataagttc tgaaggaaaa   2460
taatttaaaa tatagaattt cccatcaagc caaacagtct tcaaatatgt cagcataagg   2520
aaaggttttg gaagcataga aagtcccaag aggtttgcca tgcagaaact cacatagaca   2580
acagttttgg ataaagtcag aggaaagaaa aatccaagag atgctgcaaa agatatctgt   2640
ataaaaggtg attgaatata ttggcaaagt ttgttcttgt cttggccatt tatttaaagt   2700
caaataaaaa gaggaaaaat attcataata atccacaatt aaaagtctgg aaaaaaaaag   2760
tcatggggat ttttgtggag aactaaggaa cttaagaatt ggccaatttc ttgccttaat   2820
agggagtaac ttttttttta ggagacagca ttaaaaagaa atagaaaagg taaacataaa   2880
caaaaaataa gttaaggttg gagaaacatg tccaagtata ccagtaataa tgattaatgt   2940
aagtagacta gattcaccaa tgtaaagtcc aatattgaaa aactgagtat taaaaaaagc   3000
cagatacata ttgtttaaaa agtatgtgga cttcacttgt gcccaacatg gagcaacaga   3060
aaccagattt acccttatat ctgaaacaac tgagaaactg ggtaaatata ggaaagaaca   3120
gctttcaagg cattggcatc aagcaacaca gaaccgtgat ccctggcaga cagcaaacaa   3180
atgaggtgag ccctctgatt ttactcaaga gaatttccag gccatcagaa ggggaaaccc   3240
aagtggagac cagtggactc cctgagtgaa ggagatgaag ctaagaatac aggaagaaga   3300
atgcagctaa ggttaacatg gcaactcaag caccaaagga gagagagcca cacagagata   3360
aaactctgga caactacaga aaaattgccc tttaatattc agcaaattac tgatcagtgc   3420
atgtatttga aggaaaaaac ctcaatcata attgagggat caattatcaa ctacccaaaa   3480
tgattaaagg aaacaggact cagcactcac ccagaatggg ggaaagtgct tgttccccac   3540
gaggcagact ggtaaaccat acaattcaca gggctttggg taagggatct tgtcttggca   3600
gtggggagta attaacccta gaccaaacat ggtgctgttc ttgcttaata agtcttaaaa   3660
gcaggacacc aaatggtcaa actgtttcaa gtaacttaac tgcatttcaa aaaaactcat   3720
gatactttta gaatacaaaa tattcaacat ccaacaaggt agaattaacg attcctggct   3780
tctaatagca tgaacccagg aggcagagct tgcagtgagc agagattgcg ccactgcact   3840
ccagcctgga caacagagtg agactccatc tcaaaaaaaa aaaaaaaatc agttcatcaa   3900
aattgatcaa tcaatcagaa ctgataaacc aatcagaatg gataaagatg tagtaattac   3960
cagacaagaa cattaaaata cttaaactct acatgctaaa aatagcagaa gaaagattga   4020
acattatatt aagagaactg gaaaatataa gagaaccaaa tagaactttt agggatgaaa   4080
actacagtgt cagagatgaa aaacacacaa agtagtatta acagcagacc aagcactgaa   4140
gaaaaaacca aaagtttagt gaatttatag gcttagcaat ataaattatc caaaatgaaa   4200
gaagtagaaa aaaagattta aaaagaaaat gaaccgtgtg ttagttagct ctgagacaat   4260
ttcaagtttc ctaatgcaca tgtaattgta gtctctgaag gagcaggagc agagaaatgg   4320
ttgaagaaac aatggcctaa aattttccaa atctaatgaa agctgcaaac ccacaagttc   4380
aaaggaaagc aatgaactcg aagtataaga gacataaacc tggccgggca cagtggctca   4440
cacctgtaat cccagcactt tgggaggctg aggggggtgg atcatttgag gtcaggagtt   4500
cgagaccagc ctcacaaaca tggtgaaact ttgtctctac taaaatacaa aaattagctg   4560
gacctggtgg cggtcacctg taatcccagc tactcgggac gctgaggcag gagaatcgct   4620
tgaacccggg aggcggaggt tgcagtgagc caagatcttg ccactgcact ccagcctggg   4680
tgacagagtg agactctatc tcaaaaaaaa aaaaaaaaaa aaaaaaaaaa aaaggcctaa   4740
```

-continued

```
acctacatat aattaacttg cttaaagtaa gtgataaaga gaaaatctta aaagaaatca   4800
gagcaaaaaa aagatatcac aactgagaaa caaagataag gatgctagga gactttgcac   4860
tggcaaatct gagaggatag tagagcagca tcattaaaga attatgggaa aaagaaacgt   4920
gtgcaccagg tgttctatga ttagcaaaaa tatatttcaa aaataatgtg aaaatacaga   4980
tttttcagat tatctagtca caagaatgaa gaaaaccaca aataacactg taggtacata   5040
taaaataatt tttcttctca tcagtatctc ttcaaaagat aattgatggt ttgaaaagtt   5100
ataccatgct tttgggggat ttataacata gccataatta aaatgcatgt catcaattgc   5160
ataaaggtag agagggaaca catggaaata taagagcata agagtgttat atgtgaagtg   5220
gtaaaatatt gctggaagta ggctctaata agatagaaaa aggctcagct aaaacataat   5280
aacaatcaaa ggttggatat aatgtcgact aagaaaagta ggtgtaggta tgttaggacc   5340
agataaaata acattgaatc attagagata aagaggagca caccataatg atataggctt   5400
ttaaaacatg cttatactta atacaagagt ttccaattat atgaagcaaa agtccgcaaa   5460
agtccattaa aatgctatag aaataaactg ataaatccaa catcaaaatg agaaatttta   5520
acacacccct ttaattttta gttggtcaaa gtgaagaaaa taaaagccag tatataaaag   5580
agatgaaaat aaaatcaaca aagatgactt aatcaacaca cgtagaattc tgcataccac   5640
aattgcagaa tacacattgt tctattgaag acacagaaag catataatag gcccttaaaa   5700
agccatgctc tttcacaaga caattaagtt aaaagttggt aacaaaaaca ataaattact   5760
agaaattaag aacatttcaa gaattttcta agcttgtagc ttcggtgcaa ataaagcata   5820
ttttgtttga aattttataa acagtgtttc accattttgg caaatgacat cacaatgtca   5880
cattaactat gttaacagtg catgaattag ggtgaggcaa gtgaggcaac caaggtgcaa   5940
aattcaagga atcaaccacc cgtggaatca tgtaaatacc tgtttacgta tttttgtccc   6000
aggagcttcc taggtttacc ccagttctgg ccctggtatt tgagtcatct caacaagtca   6060
cttgtgttgg tctacacttg tagctgttgc atataaatat gctaaatagg agattcgtgg   6120
ctcattttta acagatttag aacaccatta aattaacagt gaaacagcaa agtcagggat   6180
gctattacat ctcactagta aaggtaactt taaaaatatt tcatattttt taacctacgt   6240
atttttgatt tattctggaa tccattgata aattaatctg ctgtgaaaag agcagagtga   6300
aattatttat ataatttgga gttggcaatc tttttcaaac taactcagat aaatgtcctg   6360
caggataatt ttacaatttc tctacagatt cttattttat agttgggctg tttgtatatt   6420
ttatatttgc tcttaatcca tcctttcttc cccatcttca atagatatac ttcaagattt   6480
cagcaccaaa gcctaatata tgctttgaca agtagcaggc tttccagaga tgagatatgc   6540
cttctgtcat gatatgttac tgtctcattc catgcagtga cataaggaaa tatttttgact   6600
ttataaagct cagctcattt gtgagggtat tatatttcat tttccgcccc tatgtcactt   6660
tgtcatttgt cttgacttat cacccctact tcaattaagg ttatgtccca ctttctttta   6720
tcacagaagt aatactagtc tgttttactt attgcatcaa ttctttttat tgctgctgta   6780
acaaatattc acaaacttgg cttgaaagag caaacattta tgacctgata gttctacagt   6840
tgagaagtct gacacaggtc tcactgggct aaaatcaagg ttttgacagg acaatgttcc   6900
tttctagagg ctctagggat gaatctgttt cctggtgttt cctctagagg ctgccagcat   6960
gccttaatgc gtggcctcct ccatccacaa agccagcaaa ggtaagcggt gcccttctct   7020
catctgcagc actctcacct ggcttctctc tccgcatttc tttctctggc tctgggtctc   7080
tcttccactt ttaatgatcc tcgtgattac atggggccca cccagacaat ccagaaaaat   7140
```

-continued ctttcttttt aaggtcagcc aattaacaat cttaattcta cctgtgcaac cttaaattct 7200
ctttggcagg taacataata tattcacatg ttccaaggat tcagatgtgg atattttttg 7260
gtaggggcat tattctgcct gtaatatatt ttttcgaaca ccagttgttg ttctagtgtt 7320
catgcccatg tttgttgttt cattttccta ggcttctaca aaatgagttc acctcacttg 7380
tcacaaattg tatcttattc atttcctgta ggcacatgca tttgaaactt ttatacatct 7440
tctggtgtat acaagtcctt acatgatgaa atgtaaatta ttttaaatta ttttcctatt 7500
atggctctaa aattgtatgg ttggggcatc ctccctccct cctttccccc cttccttgct 7560
tcctcctttg aaattatgtg tgttggtagg ttgcattaat catcagtttt atttcagggt 7620
cataaaagga gtgtaacaaa ataagtataa taaaaaagga atgttggata tgttatgact 7680
gagaggcacc ttagcagaag ccaaaagttg actccttgga ctataagaga agcctcttca 7740
aggaaaattg tagtgctctg tccataaaga actgtgcaaa cactacctac ccccacctcg 7800
aaatactttg gatattcagg cagagccaga gctactgtca gtggaaatat tgaccttagt 7860
atgtcattta attacctgag ctctatcaag aaccttgtag acctgtgagc agaatatgaa 7920
atagagctta cctcctatag tttgataaga gctccacaga gccacagtgg aaaattaagc 7980
aaattcctag acaatttcaa taaaaatggt ctatttttaa agttattcta aataaaaatt 8040
aaaaatttgt gttaacctta ttttggttac taaatgataa tgaacatacc ttttcaaaat 8100
taaaataaag tttacattct tcttgtgggg acacttttaa tttctgctta gatgatttat 8160
aatggaattc atcaccaaaa gataatttaa ttatatgacg gtagtttaca tataaattag 8220
aaagttttag gctgggcaca gtggctcatg cctgtaatcc cagctctttg ggaggccaag 8280
gtgggtggat catttgaggt caggagtttg agatcagcct ggccaacatg atgaaacccc 8340
gcctctacta aaaatacaaa aattagccgg gtgtggtggc atgtgcctgt agtcccagct 8400
acttgaaggg aggctgaggc aggagaatca cttgagcaca ggaggtggag gctgcagtga 8460
gccgaaatca caccactacg ctccaacctg ggtgacaggg ggagactctt tctcaaaaaa 8520
aaaaaaaaga aagttttagg tttaaatttt tttttttctt cttggtgaga cggagtctct 8580
ctctaacgcc caggctggag tgcagtggca cgatctcggc tcactgcaag ctccgcctcc 8640
cgggttcacg ccattctcct gcctcagcct cccaagcagc tgggactaca ggcgccggcc 8700
accactccca gctaattttt tgtactttta gtagagaggg ggtttcaccg tgttaccatg 8760
gtctcgatct cctgacttcg tgatccacct gccttggcct ccgaaagtgc tgggattaca 8820
ggcgtgagcc accacgcctg gccttaattt tttttttaat tctttacatt ttccaatgga 8880
gtaattatat ccctgagtta caagtcaaat gcgagcctcc atcagatttc ttggctccct 8940
tcctaaagac aatagagcaa ctcattactc tgcttcagaa tctttctccc aacctttagg 9000
cttctctagc tatgtagtga tgggaggaaa ggtggtggta gggtggggtt gggcacaaat 9060
tcctattcct ttcatgactg ttttacagtt gcttccttgt agggacatgc cacagaaaga 9120
agacactaca ggatccagaa atacttaaat aagataattt gtggaaatct tatcccttaa 9180
atatcttcag ggagaagtat ccttagcaac ttcttctttc tataggcaaa tcatggctgg 9240
gtaggtggtg gtcttctgct tccaagaaac cggcaatcaa caactcaagt tgcctcactt 9300
ctcatataca agtcccagca agagcctaga tgaattcact aatgcacttc atcctcctgc 9360
cctcttcctg gttcaggcaa taataatcat agatcgccat tgtcaattct tttttgttag 9420
acatgatgct ttttaacatt atttcatcta atgctcacag aatctctatg tggttagaaa 9480

-continued

```
tactattact ttacaaatga aagaacgcaa aataattgag ggatgtagat aactctctcg   9540
agataatgca gtaaacaaag ggtgatatca ttttgctgtg tccccaccca aatctcatct   9600
tgaattgtag ctcccataat tccacgtgtt gtaggaggga cctggtagga gataattaga   9660
tcctgggggt ggtttcccct atactgttct tgtggtagtg aataagtctt aggagacctg   9720
attgttttat aggggttttc ctcttttgct tggctctcat tttctctctt gtctgctgcc   9780
atgtaagatg tgcctttcac ctttggccat gattgtgagg tctttccagc catgtggaac   9840
tgtgcatcca ttaagcctct ttttctttat aaattacccct gtctcgggta tgcctttatc   9900
agcaatgtga aaatggacta atataaatgg cagggcccat aaatgaactc tattctgttt   9960
aacaccagtg tgtatcgttc attcattcaa caaaacaatt cagttactta atatgtgcca  10020
agcagtgagt taggtattga aaaagcaatg attaaaaaga cagaaggtac ctttctcctg  10080
ggaggttaaa ttttactgaa ggaaatagag ggaaccaagg aaataaaatt aagtagttac  10140
aatatgtaat aattttgatg aagaaatcac atagggatcc ccaggagggc agaaaggtat  10200
ttcaagcaga aagttcaaga aaggtctctc tgagtaatga ccatttaagc taagtcttta  10260
ggaagacaaa gggtgtggcc tggaaaggct ggtgggggca gaaagagcat tccagagatg  10320
cacaccagcc agtgcagagg atgactcaca cgcagtttgg tgaagactga aggggtcata  10380
aaagtaaagc attttttgga gtgtaatttg gcaatagcca tccacatttt aagtacattt  10440
aaattttctt tgggtgcagc aatttctttt cttgtgggct ttaaaataag tgttgcatat  10500
gtgaactaag ccacacaatc aggtagacat tacactttcc taagggacag agagacatgg  10560
gatctcaggt tttcttgct gttttctttt tttaatgttt tcttcctctt cttattttaa  10620
tcttctgggc tataagttat aatgctcctt ttagactttt tttttcctac cctgcaggca  10680
gtcacctgat agagaggttt cctggaatag taataggaaa ataatgcaca gcaaagctga  10740
cacaccacat gccgagctgt actgaaggca caatcataac ttttaataac gaaagtttct  10800
tttggtaaaa taatatcttt ccagctgtcc taacagatac taatgtgaaa tgctcccttg  10860
ggacaggacg gtggagagaa gtcacccccg ttccagaggg gcatgccctt ggctcagaac  10920
ctcagagcac taacataatg tagtactaag attgcagtga caccagtaaa acctgctctg  10980
taggactgca acaggctaca ttttttttat ttgtgctttt gttttcctgt aaatcacttt  11040
tgagtttctg tttctcaagt ctggaagcag caggtgtgta attttggcag aacttttccc  11100
agccattatc tagtggttta ttgtttattt agagtgtggg ggtgagttat aataaagaga  11160
ttggccctgt gggttaagac tgggcacatt tctatttaca gtcctaccag gtcttcacat  11220
tctaggcaaa atgaaaggct aagccagtta tccagatagt tcaggccaaa aggtaaacac  11280
aaagagagga tgatttagtg ctgtcccacc tccggcttac gcttctgagg taacaaccac  11340
agggttctgc tttggtttgg caatggaaat ctgagttctc ctagctgtga cttgtgttag  11400
gaacgtagac tctgtccagc tcagtaggct gtgacataga aaatacatga agttaacttg  11460
ggcatagaga tagacatgat ccaattcccg gttcaaaact tatcccctat tgccttgttt  11520
cttttccttt tatatgctct tacatctcta gtgaagtttg ccatcagtat atttagttgt  11580
attaaaaatt ctccaggttc agttaatgcg gtcattttgg gtagactgtg acatacattt  11640
gcatggattt ggtctccctc cctccctccc tcccttcttg ccccgcttca ttgctctctt  11700
atttcttttc ttcctttctt actcccttcc ctcatcactt ccttcctttc ttccacattt  11760
atttaatgtc tataaccaga acccatgcta catatttgag aaacaaagtc aaacaaagca  11820
tacatttatt ttctaataaa ctaacagtgt agttgttggg gaaaaagaaa agtaaatgaa  11880
```

-continued

```
aaattataat attttggtta aaatatacat tggaagctgc tggaaaagaa ttcatgaaca  11940
caacttagtt gtttttagtt ttacaggaag tgaacctgat atacaattat tggtggtcta  12000
gaaatacaga tgaactggat aaaataattt tgaaaaagag gtttaatctt tctcactgaa  12060
aatccattac agtatggaac atatttattt cttctttgaa ttatatacat ttcctaacac  12120
ataatagatg cttaattaaa atgtttgaaa gaaaggagat gtaaatgtca caattttaaa  12180
aagtaatgat ttggctgggc atagtggctc gtgcctgtaa tctcagcact ttgggaggct  12240
gagatgcaag gatcgcttga gcccaggaat ttgggaccag cctgggcaac aaagtgagac  12300
ctcgtgtcta caaaaataaa agaataaaaa taaaaagtac ccaggcacag tggcccattc  12360
ctgtagtccc aggtactcag gaaactgagg caggaggatt gctctagcct cggaattgga  12420
ggctgtggta agctatgatc atgccactgc aatccagcct gggtgacaga gcaaggccca  12480
atctttaaaa aaaaaaaaaa aaagaacaga aaaaaaaaga aatgattctt ttttgtagag  12540
agtatttaga aaacatttta tgccatgctt ttctgtatta gtgaggaaaa aactgaatat  12600
aatttacctt ttctttgaga actcaatcat cagtatgaac aatgattact taagtgaact  12660
ttaggtgttc aggcagagga agatgtaggg tatagggcca gtgggtagca acacgagcaa  12720
gtgcatcaca tattctttat tgaaatgatc tcatttgctg aatgcttgct tctagtttat  12780
ttttattgga tagtttcctt tctcacatat gtggaagaaa accaatgtat tgcttggccc  12840
ctagggaagt gtaatgtggc tattctttcc caatgtaaat catggaataa aaatccacag  12900
ccttctctca aattattttc ttaccctcca gaaaaattcc tttctctcct tgtcatttga  12960
tttctcaata acattcagat cattatctct ttttccaacc tgtcactatt aacatatcaa  13020
cttcaatata ttttctatat atttacacta tcatttattg aacaaatatt tattgaacac  13080
ctgctatgta tcagacattg ttctaagagt tgaaggtgca tcattaagca aaagtcagaa  13140
tccctaactt cacagagttt acaatacagt acatgtaact gaagtgtctc tctcactatc  13200
aagaatttgt gttcgtgtaa ttgggagggt tctttttctc tttctctttc tctctttctc  13260
gtttccttct tttcctttct ttctttcttt ctttgttttt ctttgtttct ctcttttttt  13320
ttttttgatg gagttttgct cttgttgccc aggctggagt gcaatggcac catcttggct  13380
cactgcaacc tccaccttcc aggttcaagt gattctcctg cctcagcctc ctgagtagct  13440
gggattacag gtgcctgcca ccatgcgcag ctaacttttg tatttttagt agagacatgg  13500
tttcaccatg ttggtcaggc tggtcttgaa ttcctgacct caggcgatcc gcctgccttg  13560
gcctccgaaa atgctgggat tacaggcgtg agccaccgtg cccggcccca gggctttttc  13620
aaagtgtatt tcataataac aagaatgcct attcattaaa ggttttataa gattttacag  13680
ttgacaatgc tcttttagag aatacattct cattggaatt tcacagtaac ttttaagata  13740
cataggatag gcgttattat tgttttttttg tactgtgcag atgcagaact tgggtttaga  13800
cagagtaaat tacttctcaa gatcccagag gtgtaagtag caaatacttg agtttagaat  13860
atttaaaaat tccaaaactg ccttagtact tttaaatttg gaaaatattt ttatatttat  13920
tattttattt gttcttcaaa atgatctgtg tggtaattac tgattcctct ctaatcttcg  13980
tgcccgatga tgtggaattg ttgcattatc tgcccagatt tatctagctg gtaatggtag  14040
aactgaaaat ccaactatgt tcattgaaaa aatcaactgt ggaagctgaa cacaaatatt  14100
ttctttaatc tttctatatt cttataggca aatggaattt taaaaattta ttataaatat  14160
aatagagatt tttaaatgct ttataaatta atttcccatg aagttaattt ttctcataac  14220
```

-continued

```
attatatatt ctaaataaca cccaggtata cagtttgaac aatgaagtga cagtggcagg  14280
cagtaaaatc ataaaacaat tacctgacac attctgcttt tcagagtatt ttctacaatt  14340
ttcttaagtc aacctgtcat tcagacaagg tttaaaaaag tacatttcag cttccaaaat  14400
aaggttaaaa caactagaaa aacaaaacaa aacagagctc tagcacccct ccttgtatgt  14460
ataatacata tcttgtaaat acagagctgg aaatgtacat tatttttgac agatagagct  14520
ttcaatagtg agggttttat tacataaaag acagcaggaa tggtatatgc aaaagccgtt  14580
aaggtctccc ttttcttctt aaactcagca gtttgtgatt attactattt ggcaagcagg  14640
agtaaattgg accacaattt caacagcctc atagaagtat tccaggagac agtgttgata  14700
aatgagtcct agaatgccat ataattttcc tgcagtttca ttgtttgatg acttactttt  14760
catggataca ctctgccctc aggtttcatg tcctgctgcc aaatgtgaaa gctgtttgtc  14820
agaaatcaat gggttcaagt ggcccatcaa aagcttctgc ctttttgttg ataggaaaca  14880
ctttgtatag gaatctgctt tctggagaac tcattgctat ccctttttgta tatacctgaa  14940
ccttgtcctg gctattatta tggtttcctt tgccagggga ttccccagtg aagggtgctc  15000
tgcctagtac tgcttgggtt actctcaaga tgacaacccc tccaatacag caatgactgc  15060
aaagctccta aggacaatag gattcagagt gtcttcttcc accaaaagct gagctaaata  15120
tagcctaaat atagcttttt gtattttgtt ctagggggtc attgatgtat ttacaataag  15180
ggatagatag gaaattttca tatattgtga atctattatg tagcaggcac tgaggtgctt  15240
tccacatgct atcttcttaa attgtcatac gaaaactctc tataaattat gtattatccc  15300
cattttacag atgagcaatc tgctactcaa gaaagatagt atttgctgaa aggcaaataa  15360
cagaggtggg atttcaaatt cagttttatc ttactcccaa gatcatgctc tttctactta  15420
gcatttggtt aaccgggttt aatttgcact aagaccaaat gacagcaaaa gaatttctct  15480
tctgataggc aaactgacaa atcaaatcta tgcttttgaa aagtctgtta cttcccatga  15540
ctctgttttt tgtttgtttt ctattggtga gaatagagta catccagtca aaagtaagtc  15600
tggttaaggt gggattttga aagttgggtg gaagttaagt gtctgactag ttctgtccac  15660
tctttgtccc aaatctccat tgtgataggt aggatctcct cagtccaggt gtctgtatgt  15720
gacaataggt tagaaagatt cttgtacttg aggctttatg aagttgacca aaagacatta  15780
agaatgacta agtgggccag gtgtggtggc tcacacctgt aatcctggta ctttcagagg  15840
tcaaggtagg cggatcgctt gaggctagga gtttgagacc agcctggcca acatgaagaa  15900
atcctttctc tactaaaaaa tacaaaaatt agtcaggcgt ggtggcacat acctgtattc  15960
ccagctactc gggaggctga ggcatgagaa tcacttgaac ccgggaggtg gaggttgcag  16020
tgagctgaga ttgcaccaca gcactccaat ctgggtaaaa gagtgaggct ccatctaaaa  16080
aaaaaaaaag aacgactaac tgcacttagg aatggggact acattcattt tttctgtata  16140
gatactggag gtcttactag ggggttgtgg gattagtttc catatgtaat tgttctaaat  16200
gctttgcaac ctcacagttt tgagtctttt gatccctttg gtggtttatc caggctttac  16260
tacctggaac tgctgatact tggttccaga actcttatta gcaagatctt ggttagtcct  16320
tgcatctaca aatagctcaa gttcacctta agtagaaagc ttatcaatag atttctgtgg  16380
agactgcgga tccctccaat acacttgttg cttgatttat ttactagctc tcctctcttc  16440
ttggctttat ctcttactgt ttaagtagga gtttgttttc tcttttgttt gttttatttt  16500
tggttaaagc agcagagaac ccagctcaaa ttggcttaaa aagtgaaagt gattaaagtt  16560
ttcgtggtat tgtgggcttc agcttttgat cagtgaagaa tctggctcta tttctctgct  16620
```

-continued attcttttgg ctctggtttt gcagttgtag ctttgcccta agtctggctt gtcctatggt 16680
tataaaacgg ctgccagcaa cttctgaagt gacccgtttc tccattcagg tttatagaaa 16740
agaaagagag aattgcttct caagccattg aattgaagtt ctaaattttt ctctgaagga 16800
atcaatcatg gatgcttggg gtaaatgaga ttaacctgat ttattctaat caaggtgcac 16860
ccctggaaga ggtcaactct tccaacaaat gcacggtttc tatacaatga agagtgacaa 16920
agacttgttt ggaggtaatc aaaatgccca ccacatttca ctgaacctaa atattaaatt 16980
tgtctttact tttttgttgt ctgttttaca actagcaatg gagcagagaa agttggagga 17040
aggttattgg gatctttttg aagagcaaat cacattctca ttggtaacca tgatgaaaac 17100
atattttctt ccttgtgtgg gtctgagaca gtgtcataaa ctgctttcag caatagttag 17160
tatggtctaa ccgagtggtt ctcaatcagt tctaatcagt ggctccttct cccaggccag 17220
cagcatcagc atctcctgga aatgtttaga aatgcaaata ttgaaacaga aactctgggg 17280
atggggcaaa tctgagtttt aatgaacact gccattgatt ctgatcatgc tgaagtttag 17340
aaaccactgg tttgatgctt atttgcacta ttatactgtg gtttacatat gggcttgaca 17400
ggtccattta ctttcattta cttgctattt gagattttgt ctggccagac aactgagcct 17460
cagataaatt attttcttac taaattctgg taaataccaa taaaaccttg aatacaacca 17520
acataggaca gtcagttctg ctataatgat ttttaaaatg ggaatttgtt tcaatgcaat 17580
taatatattg ggaaacaaat ttagcataag gcaaattttg catttatttg tgcactactt 17640
catctgctag accaactagg tgaatgtagg aaccatacac agctgagctg agtctcatag 17700
gaacacataa aacacacaca cacctctcaa ggacaatcag tggcccagac ccatgcacat 17760
ctactattac aacttcttgt ccatttccac cacttcactg ttattaatac aagctgcaag 17820
tcttccacaa actaacttca ggtggttttc aagataaagt gccatattgc ttgcagtatt 17880
tatgtatttt ttaatcattt aatgaatgta aaactatgct accatttatt agctgcttct 17940
ttttaaaaat gttccactga caaatgtttt gagtattatg ccccgaggcc tatgattttt 18000
attgtgttct tttgcattgc acagagaatt ttagcaatcc ctatgttgca ctaaagcaga 18060
attgagacta atttgagcaa aacttagcaa cttataactg ttacaatcct tatttcaggg 18120
caaacttttc attttataat cataattatt ttgtttcctc ttgagtagca cacacacaca 18180
cacacacaaa tctaaggtgt tcactatcac agaataatag cctttaaaat gtttaccagt 18240
tttcatattg atatattttg tttgactctg tcattccggg ctttaagtac taaaatatat 18300
tagtcttttt cagaaaacat tccaagaaaa aagttgaatt cctacctagt ttcctctctc 18360
tttgataacc tattgtcata gtaatataca aatacctgaa aattgcccag attattcttt 18420
tcttcttgga acacagattt gttgataagt gccaaaggat tttttacaaa aacatgagaa 18480
gtttgacatc acagtaagat ttaaaaggaa aggctgttta ttgttattat catcattgct 18540
actactattt ccgttagtat atatttcttt gtcttatttg tccttttcca aaagattttt 18600
gttcttatat ttttaattag ctctttaaag aaatcaagaa ctgcttgttg attatagaca 18660
tccttattgt ataaagaggg agaagttctt tggtaattag ctgtgtatag gttctgttca 18720
aacaattggc tcaagtgagg ttgtacagaa agaactcttg tattttctta tttttcagta 18780
tattctccac tccatcacac ctctttttcc aaagatgcag tgcaaagaaa gtataatctc 18840
tggagtaatt aaagctcagt gaggaaatga tatcacctga tggccctatg aagcattcag 18900
caataaaagg tgagttgccc aaaatgcatt taccctgaac aggaatacaa tgaaactacc 18960

-continued

```
aagttttatc tttataatga ttcgtggctt attattttgt tgtttgtata tgttctgttt  19020
cccacatcag tgttgtctta cattattatc tgtcttaact tagactctgt tttctaaatt  19080
gctctgtgca attaaatgct ttgtgatcat aataaaaagc atcatgataa cttttagact  19140
agaggtttcc atacaaagct gtatcccatg gagagcagct actggcactg aacaatggct  19200
agagatactc tacataggga aggggctgac aattattcag tttaaatcaa tcacttgtgc  19260
atatatctcg atagaacact aggctagttc gttgtgtgtg tgtgtgtgcg tgtgtgtgtg  19320
tgcatgtgtg tgtgtgtgta tgtatgtaat tcactgctta ctctataaca gagagaatat  19380
caattaaatt gggccatata ggaagatcaa ttaatatatt tgttaattga ggaacttttg  19440
atggccttgt tgatccccta tggtttgatc tttaaatctg tagtgtttat tagactcact  19500
acagactctc tgtaaatcgt aagacattta catctataaa tgcattttaa aacatcaaat  19560
tttaaatttt gcagcactaa aatgtgtcag acaatattct caattaactt gcattaatat  19620
ttgcttagtg tctgataaaa tgtgtagtgt aggacaaaat gtcctacata atcaacaaaa  19680
cactcttcca aaattaaaca taatatttgt taagatggtc actgtttttt taaaaaaaga  19740
gcactactac acagatcaag ccaatgagcc ccagtcagtt gacagaagta catatttggg  19800
actccttctc taaatttttt ataaaaatac ctgaagaaga tgaatagtca tttgctttct  19860
tattttaaaa gatctgtccc cccaactaac tttttaatct tctacttgtt accaaatacg  19920
ataaaaagga gagggggaaa aaagcagaca ccagtttcat tcgtgaatgt aaactttggt  19980
tttttggttt tcttttcttt ttttttttga gacagggtct cactctgtca cctaagccgg  20040
agtgcagtgg aacgatctca gctcactcac tgcaacctcc acctcccagc tcaagccatc  20100
ctcttacctc aacctcccaa gtaattggga ttacaggcgc agccaccacg cctggctttt  20160
tttagtagag agagggtcca tgttgcccaa gctgacctct aactcctggg ctcaggtgat  20220
ccacccacct cagcctcccg aagtgctggg attacacatt gcacctggct gaacttctga  20280
aatgaatgaa gtgctcctaa atgaatgaac atcttgaatg gcaaattaag tttcaagtga  20340
catataagcc aacaagtatt tctaaatttc taaaataaat ttccaaattc gaagtcattc  20400
tttcttttct ttcttttttt ttttttgttg ttgttgtttg tttgtttttt tgtgtgtgtg  20460
tttttgccgg tctgttttta atcgtggcag cgcctcacac acacattcag ggttcagatc  20520
ttgttcaaag ctgcgatgtc gacactctgc acatgctcct caaacttggt gatctcctcc  20580
tccagcaagt ctgtccccac tttgtcgtcc tccaccacac actgaatctg catcttccgg  20640
ataccatagc ccacggacgc cagcttggag gccccgctca ctagcccatc cagctggata  20700
gagcgcacac atgcctccag ctgggtcatg tccgtcttat tgtcccaagg cttgatgtcc  20760
agcaggatgg aggacttggc caccagcgag ggattcttgg ccttcttggc gtacagccgc  20820
agccgctcct cccgcagccg ccttgcctcc ttgtcttcct ccttattgtc gctgccaaca  20880
gatcaatgtc atcgtcctcg ttatcctctg cttcttggcc ggggtcgtag taagggggc  20940
gaggggaggg gcgctccact tggcgcatgg gagacacgtg ctgtgtctgc gggactgtgg  21000
accatggcca ggcgagctct tctctcttct ccggcatgtt cagccaggcc tccaggttgg  21060
agaccgcctg ctgcagctcc tgcaccacgc cgcgcaggct ctggttctcc acttccaggc  21120
tggcgatctg gaggacgagc tcgctgtggt cttccctggg gccgagctct ggcgggaggc  21180
gctggccaca ggcccattca tctgcttgta gaatttcctt tctgtatctt catatttgaa  21240
tttgtcgagc cagatcttct catgtgctag gaattttgta gccatttttc tgacgcctgc  21300
caagaatgcg gctaccagaa atgaggaatc ggtagacgca ggacgcctaa gggcgaagtt  21360
```

-continued

```
gctctttcat aatgtacaaa acccttaagt cttcaacaga aagcaccttt tttatttaaa  21420
agaaaatcct gcagtttgca aataaaagtt tgtatttcag agagttggtg aggaaataat  21480
ccattaaaga ctgcctttat aaacataaac tgctgggaat aaagtaagat ttttaaaaga  21540
caatgaaaac attctgacat ctcaacagga gttagcctga tgaatccatc tcataccaga  21600
agtctttgtt ttctatttct ggctccttca ggagctcaag gttttacctt ggacaggtca  21660
tttcatctgt cagagccttg tttctcttac atcaaaggaa gaggcttgtc tgtaaaatct  21720
ttaaagttct tctttttctc aaatataaaa ttatcattca gatactcttg gtataatatt  21780
taaaaattat ttaaatattt aaagaaaaat gttttgaata tttttctata tactgagctg  21840
ctatgttgag aaatcccaga ggtattattt cagtgtacta ttgctctgat gaccagctac  21900
cactggagag gggtactatt tcttccttaa aacttgtata ttcccctcaa atactgatgg  21960
aggaaagagt acatgaatct ttatagtaaa agatagacaa ttagatataa ttgatcttaa  22020
tagatctgta gataatatgg accattatct acatatcatt tgttaaatta atgccttcta  22080
gcactcagct aaactaattg tatcgtgtgt gtgtatttct taagcaaagt ttgtttcata  22140
gatcagtgcc cctgggctag acaggaaaat gtcaaagctc ttaaaccagt ccaccaaagt  22200
atgtcaacta aaagcctcag aactagtagt atttctcgtt aggttttcag ttgcagggta  22260
gagaaagaaa gcaaaatcac aaggcaggta tttttctaca gcagtttgat ttagcaaatg  22320
ttgaacaaat aaaccattaa ctaaataaaa tattgcatat atatatatat atatatatat  22380
gtatattgtg tttattttca tgttgtctga catcctgaca actaaaggga aaataatata  22440
gaagtatttc tacattattt tgtgtctctg agtttgtgtc tctgagtttc ctgggcaaac  22500
tttgtgtctc tgagtttcct gggcctgaaa taattggcag ggtgaatctg aaatgcagac  22560
acagaaagtc acccttggtt tgatgccctt ttttttttcc ttttcatgtt tatattttgg  22620
tgcatttccc cccgatatca aatattacct tggtactaaa aaaatcaaga agggaaaatg  22680
caggcaggag aacgaggaga atcaccttgt tacttctctc ccatatatga ttgggctcat  22740
gtgattggtg cattagactt tgtagtgtca tttcactcct ttctctgtag acatcaatac  22800
taacaaatga actgcaaaat cctaaagtgt gaggataaac accaattatt tatgtatgca  22860
catcatttgt atggatttct aactattgat cttcaggtaa atgtctagac agaagtagat  22920
ttaaatgtat aggtagttgt gctatatttt tacatttata gtaattaaca tctagaaaag  22980
caagaaggaa gagacaaaat atcagttatt attttgccta cttgcctctg caaaaaagaa  23040
gaaataaaag gattgccttc tatctacctg agacagacat ttaaactata gtgaattcag  23100
aatctttagg cattctcctc aaagtttcct tcagtgaaaa ttgatttgaa tcaaaaattt  23160
atgttaaaaa aaatggcagg gccaatgttc ctagcagagt tatctgaatg atttgctagg  23220
tcaagcaatc ggtcaactat tttcctctag atcataggat tagcatatca ggccagatac  23280
ttatcctgtg caatgttgag cacagttatt tttggaatct aagagatcat atgatttgac  23340
actcctaaag gagaccttct aagactttac ttccaaaaaa ctgactggat attatagtaa  23400
aatataattc ctatactaaa atacagctgt aaaaaccaaa atgcagcttg aatacattta  23460
gagggagtct tcagtgcttt gtccattaga taaaaagatt gcaaattaaa agtactcaaa  23520
aattgcagtt gacattcaga aactcattag cttctttctt tcccaaaatc accatagcaa  23580
ttagtctaca ctttaattgg tcaaaattat tcatcattaa aacactgatt tctaaaagac  23640
catttttttt cccctctgtc ttggacttaa attttttagg aatttaaatc ttctttctct  23700
```

-continued

```
accagtttct gaaatgatta agcacatttg cattttatct gtctagagaa gatattcctt  23760
cccttgaact ctctcattct ggcctcttct gcttggtcaa ctgtctgtgg aaattctgtg  23820
ctgatcatct atagattaca tgctaatcta tatttcctaa gaaaaatagg aaaaatatgt  23880
acacagggtt cagtttacat ttagaaatct caggatcttc tgtcaattct tacccaattt  23940
tcatgataat ccctacattt ttttcttaat ttaacttatc cagtttaaga tgttgcttcc  24000
ttattaaaat atttatcacc ttaaaattgt ccactacaat ttaatatata gaagctttta  24060
tattccttcc ttccttcctt cacatgtcca gtcaattagt catttattca ttcagtatct  24120
tccagtgcca gcactgtgct agaaacatgg aatgaaaaga ggaaagaggt gtgttctatg  24180
atctaaaaat gttcctaaag gtcaggtaaa caaataagtg catttaaatg ttaagagaac  24240
aaagacaaga gaatatgcag gacatgccgg aggcccaatg gaaggtagga attttcccat  24300
ctgggaggca ggtggtgaac cagaaggttt ataggtgaag acgatgcttg aactgtgttc  24360
acaggtgctt tttgccagat agtctaacag attaaggtgc tctccctata gagggagaac  24420
cagagggctg gaaactgaag gatgaattca gggaaaatga caagtagtgc agtctggcta  24480
aagcagaaag gcatatcagt ggggcaggga ccagttaatg gataataaca agacagagag  24540
tttggatttc aaaccacaaa atatggtcaa gggaaaaatc agcagagtta agccagaaca  24600
ataatatgat atatattttt tcatttagac agaatgcact ggatatttaa agaaatagaa  24660
ataaaacatt tcagaatcta gcttttgctt ctcattgaca aagtctttac taagatggaa  24720
taaaaatgga agcatggaac agagagagag aagttgtatt tcttcatggg atgacaagaa  24780
gggtagatga ggctcgccca agtacagtga tgtttacacc taattgatca caaccagtta  24840
cagatttctt agttctttct ctactcccat tgcttcactt gactagactt agaaatgaaa  24900
aaaagaaaag aaaaagggtg gattatagag cttaagatct gtgctttggt ccccatattt  24960
ccaatccttg tcaccaatgc ttggtaaata tgtgggtata taaaaaatta tatttaatta  25020
attaattaac tatttttttg agatggaatt tcgctctcat tgcccaggct agagtgcagt  25080
agtgcgatct cagctcactg caacctccac ctcccgggtt caagtgattc tcctgcctca  25140
gccttccaag tagctgggat tacaggcatc cgccaccatg cccagctaag tttttgtatt  25200
tttagtagag acggggcttc accatgttgc ccaggctggt cttgaacttc tgacctcagg  25260
tgatacaccc gcctcagcct cccaatgtgc tgggattaca ggtgtgagcc acaatgcccg  25320
gcccttaatt atgttttttt aaagctatat gacagtaacc aaaactatat gattgaggaa  25380
atatttgtag aaatgatata tatgacaaca gtagcaaaaa ggacaagggt aaataaacag  25440
aagtcatatt tttcaaaatt cttgcacttt attagaagta ttataaaatt aattgtaagt  25500
agattgtggt acttaataat gaatgttgta aaccctacag catacactaa aaataatgta  25560
aaaatgtata tttaaaaagc caatagagga attcaaagga atattttata acaacatcag  25620
ttaaccttaa agaagacaga aaataaggaa gacaggaaca aaaatacagg tgagacaaac  25680
agaaaagaca tagcaagtta tagttgggtc ttgattttca aaatctgggc taagaatttc  25740
catcttttaa tggggagaag taatctattt ataacaaata taattgtcaa ttaagttggg  25800
cttaagtcct attaaaatat atagattttt agcctggata aaaatgtatg gccccattat  25860
atcctgtcca taagagaaaa actttttgtt aagaaaatac agattgattg aagcaaaata  25920
atggaaaaaa ttataccatg cattcaataa acataggcaa tatggagtgc ctatattaat  25980
accagaaaaa aatagacttc aatgtaaaga gtattatcag atatgaagaa gaatattaca  26040
taataataaa ctgctgattc attaaggaaa tataacaatt atatatgtgg gaaggtggag  26100
```

-continued

```
caagatggca gaatagaagg ctctaccgat tgtccccact accctgcaag gacaccaaat  26160
taacacctat ctacacagaa aaaaatatct tcagaagaat caaaaatcag gtgagcaact  26220
cagtacctgg ttttaacttt attgctgaat gaggcactga agaaatagaa aaaaacagtc  26280
ctgaatccca atgccttcct ccctacccac agaaactgag tgtggtgtgg aaagcatctc  26340
tcagtgctga gggaggagaa tacagcaatt atgaggcatt gaactcagta ctgttctttt  26400
agagcagaaa ggaaaatcac atcaaactta gctgatgtcc acccacaaag ggagcattta  26460
aaccagcccc agccagaggg gaattgctga tcccaacagc tgaaacttga gttcctgcaa  26520
acctccacac cgagggatac aatactctat gtctccaagt aaacttgaaa ggcagtctag  26580
gccataagga ctgcaacttt taggcaagtc ctagtgctgg actaggccta gaatagtgga  26640
ctgggctggt gcagtacata ctgagacacc agctggggca gggctgcaca gggtagaggt  26700
aatgctagca ctccctgagc cagacaccac cacctctccc ttaagcctag gctgcacaag  26760
tctctccaaa agagacccct ttcttccact tgaaggagag gagaggacag aatggggagg  26820
actttgtctt gcaacttagg tattagctca gccacagcag gatagagcaa tggtcagagt  26880
caagaagccc ttgttctagg ccctaggtcc cagacatttc tagacatacc ttgggccaga  26940
agggaaccca ctgccttaaa ggaaaggacc cagtcctggt agcattcatt acttgctaac  27000
tgaagagtct ttgggccagg aatgaccatt agtgatacac aggtgctatg tcttgggcct  27060
tgggtgagtc tctgagactt tctgacttca ggtgaaactc atcatcttac tagcttggat  27120
ggctatgggt caaaactccc tctgcttgag aaaagcagag ggaaaagtaa agtcttgcac  27180
cttaggtaca agcactgcca ctggggggta gagcaccaag tggtctcttg gggtccctga  27240
ttctagcact tgactcttgg atggcatttc tgcacctgcc ctgggccaca gaggtgctca  27300
ctgccctgaa ggataagtcc caggcaaggc agcattcacc acaagctgac ttagagccct  27360
tgggttttaa gggaatattg gagatagtct ggcagtactc cttgtggcct ggggtggtgg  27420
tggcaatggg gtgaagctcc tctacctttg gaaaggggag gaaagtgtgg gaaggactgc  27480
atcttgtggt ttgagtgcca gctcagccac agtacaatag aacaccagaa gacttctaag  27540
atttttgact ctagtctctg aactaccaga ctgtagctct ggacccacgt ggggcctggg  27600
ggaccttgcc accctgaaga aaaggacaca ggcctggttg gctttgccac tggctgattg  27660
ggtagcccca gggccttgag tgaacatagg cagtagccag ggagtgacta cagcaggcct  27720
tgggcgaggc ccggtgctgc gctaacttta gatctgaccc agtgcagtca tagtagtggt  27780
ggacacagag gtgcttgtgt tactccaaat ttaggtgact tggaacagag agactttgtt  27840
catttggaag aaattaagga aagagaacaa gagtctctgc ctggtaatcc agagaatgct  27900
cctggatctt atccaagacc atcaaggcag tacttctatg agtctgcaag aaccacagtg  27960
ttactgggct tgaagtgccc ctaaatcaga cacagcttag atcataacac ctaagccctt  28020
tgaaatatct ggaaagcctt ctgaagaagg acaggtacaa atatgcccag acagtgaaga  28080
ctacaataaa tactgagttc ttcaatgccc agacaccaaa gaacatctga cagcatcaac  28140
actatccagg aaaatatgac ctcaccaaat gaactaaata aagcaccagg gaccaatcct  28200
ggagaaacag agctatgtga cctttcagaa acagcattca aaatagctgt atagaggaaa  28260
ttaaaaagaa attcacaata agacagagaa ggaattcaga attctatcag ataaatttaa  28320
caaagagaat gaaataatta aaaagaatca agcagaaatt ctgaagctga aaaatgcagt  28380
tggcatactg aagaatacat cagagtcttt taatagcaga tgtgatcgag cagaagaaag  28440
```

-continued

```
aattagtgag cttgaagaca gggtattcaa aaatcaacag tcagaggaga taaaagaaaa  28500
aaagaataaa aaacaatgaa gcatgcttac aggatttaga aaatagcttc aaaaggataa  28560
atctaagagt tattggcctt aaagaggagg tagacaaaga gatagggta gaaattttat  28620
tcaaaggaat aattacagag agttcccaaa cctagaaaaa tatataaata tccaagtaca  28680
caaaggttat agaacaccaa gcagatttaa tccaaagact acctcaaggc atttaataat  28740
gaaactctca aaggtcaagg ataaagaaag aaccctaaaa gcagcaagaa aaaaagaaac  28800
aaataacata tgatggagct ccaataagtc tggcagcaga cttttcagtg gaaattttcc  28860
aggagagagt ggtgtgccat atttaaagtg ctgaaggaaa aaaaacttgt accctagaat  28920
actatatctg gcgaaaatgt tcttcaaaca cgaaggagaa ataaatactt tctcagacaa  28980
acaaaacccg agggacttca tcaataccag acttgtccta caagaagtgc taaaaggagt  29040
acttcaatca aaagaagaca tcagtgatca ataagtaatc atctgaaggt ataacactca  29100
ctggtattaa taagtataca gaaaatcaga atattttaac gctgtaactg tggtgtgtaa  29160
gctactctta tcctaagtaa aaagactcaa tgaagaacca atcaaaaata ataactacgg  29220
caacttccca agacatagtc agtacaataa tatataaata gaaacaacaa aaagtttaaa  29280
agcagggtgg gcaatgaagt taaggcatag attttttatt tgttttcttc ttgcttgttt  29340
ctttgtttat gcaaacagtg gtaaattgtt atcagcttaa aataatgggt tataagatag  29400
catttgcaag cctcatggtt acctcaagcc aaaaaacata caatggagat gcaaaaaata  29460
aaaagcaaga aaccaagtca taacaccaaa gaaaatcacc ttcactaaag gaaggtggga  29520
aggaatgaaa gaaggaagac aagatcacaa aacaaccaga aaacaattaa caaaatggta  29580
ggagtaggtc cttacttatc agtaataaca ttgaatgtaa atggacttaa tgctccaatc  29640
aaaagacata gactggctga atggaagaaa caagacccat tggtcttttg cctccaagaa  29700
acacacatca cgtataaaaa catagactca aaataaaggg atggaaaaag atattccatg  29760
ttgatggaag ccataaaaaa gtaggagtca ttatacatat atcagacaaa atagatttca  29820
agaccaaaac tttgagaaga gacaaagaag atcactatat aatgatgaag ggtcaattc  29880
agcaagaaaa tataataatt taaaatatat atatgcaacc aacactggag cacccagata  29940
tataaggtaa atattagagc taaagagaga tatagaaccc atatacaata atagctggag  30000
acttcaacac cccactttca gcattggact tatcttctag acagaaattc aacaaagaaa  30060
catcagactt aatctgcact atagactaaa tgtatctagt ggatatttat agaacatgta  30120
atgcaatggc tgcagaatac acattctttt cctcagcaca tggattattc tcaaggatag  30180
accatgtgtt acatcacaaa agaagtctta aaatattaaa aaattgaaat aatatcaagc  30240
atcttctctg accataatgg aacaaaacta gaaattaata aaaagaagaa tttgggaaac  30300
tatactaata caaggaaatt aagcaatatg ctcctgaatg accagtgggt caataaagaa  30360
attaagaagg aaatttaaaa atgtcttgaa ataaattata atagaaacac aacataccat  30420
aacctatgag acacagcaaa agcagtacta agaggcaagt ttattgctat aagtgcctac  30480
atcaaaaaag aggaaaagct tcaaaaaaca atctaataat gcatcctaaa gaactagaga  30540
agcaagagca aaccaaaccc aaaattagtg gaaaaagaga aataataaag atcagagcag  30600
aaataaatga aattgaaatg aaaaaaaaat tcaaaggatc aatgaaacaa gaagttggtt  30660
ttttaaaaag ttaaacaaaa ttggcaagcc tttagtcaga ctaagaaaaa aaggagagaa  30720
gatctaaata aataaaatca gaattgaaaa agtagacatt acaactgata ctccagaaat  30780
tcaaaggatc attagtggct acaatgagca actatatgcc cataaatttg aagatttaga  30840
```

-continued

```
agaaatggac aaattcctag acacattcaa cctagcaaga ttgaaccatg aagaaatcca  30900
aaacctgaac agaccaataa caagtaatga aattaaagct gtaataaaaa ttttcccagt  30960
aaagagaagc ctcagacctg atggcttcat tactgaattc tatcaaacat ttaaagaact  31020
aataccaatt ctactcatac tcttattaat attctgaaaa atataggagg agggaccact  31080
tccaaattca ttctacaagg tcagtggtta ccctgacacc aaaatcagac aaaagcacat  31140
taaaaaaaag gaaactacag gtcaatatat ctgatgaata ttgatacaaa aatcctcaac  31200
aaaatactag caaacagaat tcaacaatac ataagaaaga tcattcatta tgtccaagtg  31260
agatttatcc ctgagatgca agaatggttc aacatatgca aaccaatcaa tatgatacat  31320
catatcaaca aatgaaggat aaaaaccata tgatcatttc aattgatgct gaaaaagcat  31380
ttaataaaat taaacatcac tgcatgataa aaactctaaa aaaaaaaact gggaatggaa  31440
ggaacatatg tcaacataat aaaagctatg tacatcagac ccacagctag tatcacactg  31500
aatgggggaaa aactgaaaac ctttcttcta agatctggaa catgacaagg atgcccaatg  31560
tcaccactgt tactcaacat agtattggaa gtcctagcta gagcaatcag acaagagaaa  31620
gatataaaag gcatccaaat gggaaaggaa gaagtcaaat tattcttgtt tgaaatgata  31680
tgatcttata tttggaaaaa cctacagact ccacaagaaa actattaaaa ctgataagca  31740
aattcagtga tattgcagga tacaaaatca acaaacaaaa ataagtagca tttccatata  31800
taacagtgaa caatgtgaaa aagaaataaa aatgtaaccc catttgcaat agccacacat  31860
ataattaaat aactaggagt taattgagga agtgaaaggt ctctgaaaac tatgaaatgc  31920
tgataaaaga aatcgaagag aacacaaaaa atggaaaaat atttcacatt ggtggattag  31980
aagaattaat attgttaaaa tggccacgct atccaaatca gtctacagat taaatgcaat  32040
ccctatcaaa atactaatga cattctttac agaaatagaa aaaacaatcc taaaatttat  32100
atggaaccac agaacatgca gaatagccaa atctatccta agcaaaaaga ataaaactgg  32160
aggaatcaca ttgcctgact tcaaattatg ctatagagct atagtaatca aaacagcatg  32220
gtgctggcat aagaacagac acataaacca atggaacagg atagagaacc cagaaacaaa  32280
tccactcacc tacagtgaac tcatttttga caaaagtgtc aataacttac cctgggggaaa  32340
ggaccgtgtc ttcaataaat ggtgctggga aagctagatc ttcacaggca gaaaattgaa  32400
actagacctc tatctctcac catatacaaa aatcaagtca atatggatta aacacttaaa  32460
tttaagacct caaactctga aagtactaca ggaaaacttt ggggaaaata tccaggacgt  32520
tggtctgggc aaaaatgtct tgaccaatac cccagaagca taggtaacca aagcaaaacg  32580
ggacaaatgg aatgacatca agttaaaaaa cttccacaca gctaagcata caatcaagaa  32640
agtgaagaaa caacccatgg aatgagagaa actatttgca cacttcccat ctgacaaagg  32700
attaacaacc agaatatata aggagctcaa acaactctac aggaaaaaaa tctaataatt  32760
caatttaaaa aatggtcaaa agatttgtat agacatttct caaatgaaga cataccaatg  32820
gcaaacaggc gtataaaaaa tgctcaacat cattgatcat cagagaaatg caaatcaaaa  32880
ctgcagtgag acatcatctc accccagtta aaatggcttt tatccaaaag acaggcaata  32940
acgaatgctg acgaggatgt ggagaaaagg gaacccttgt acactgttgg tgggaatgta  33000
aattaataca accactatag aggtcagttt ggaggttcct caaaaaaaaa aaaaaaaaaa  33060
atctgagctg ccatatcatc tggtaatccc actgctgagt acatagccaa aagaaaggat  33120
atcagtatac caaagatatt tacactcctg tgtttattgc agaactgttt acaataagta  33180
```

-continued

```
agatttggaa gcaacctaag tgtccaccaa caaatgaatg gataaagaaa atgtggtaca  33240
tatagacatt agagtattat tcagccataa aaagaatgag attcagtcat ttgtaacaac  33300
atggatacaa ctggagatca ttatgttaag tgaaatgaac caggcataga aagacaaaca  33360
tcacgttttc actaatttgt gggatataaa atcaaaacaa ctgaacttat taacatagag  33420
agtagaagaa tggttaccag aggctgggat gagtggtgca agcctgggaa aggaggtggg  33480
gatgaataat gggtataaaa attgtagtta gaatgaataa gacctgctat ttgatagcac  33540
aacagtgtga ctatagtcag tactaactta attgtgcatt ttaaaataaa aacagtgtaa  33600
ctgcatcatt tgtaactcaa aggataaatg cttcagggaa tggataacct attctccatg  33660
atgtgctaat ttcacgtttc atgcctgtat caaaacatct tctgtgctcc ataaatatgt  33720
acacctacta tgtacccaca actttttaa aaaattaaaa tatatatgtg tatgtactaa  33780
taacagagct tcaaattcaa tgaaaaaaaa aacacaaaat ttgacagaac cgaaaaaaga  33840
aataggcaat tccaataatt atatcacttt tctctcatta atgtagaaca actaggcaaa  33900
ggaatcagta actgtatgga atatcagaac aaaaatatca gatactttca gttaactaac  33960
atcaacagaa tacatccaat aactgcagaa tatacattct ttttaagtga acatagaaca  34020
ttcaccaatg tagctgatgt gctaaacatg tctaaataaa ttttaaaacc ttgcagtatt  34080
gctgactata atctctaacc acaatggatg taaattagaa aaaaatacga tgtctaggaa  34140
agtctggaat atttgaaaat taaataacca actctaaata atattaatat atgggccaaa  34200
ggtgaaatca caagaaatat taaacaacat tttgaagtga atgataatga aagtacaaca  34260
tataagaatt tgagaaatgg aatggcaaat tcatttgctt tcatgaggtg gtaactaata  34320
tagaattgcc ccctttctgt aaataattag aaaactggac caaatatgta aaacagttat  34380
ttttaaagat tggcctatag ataacaaagg actattattt tcttaacaaa tgagttaagc  34440
cctaccagct agaggaaaaa caggtatgta aggatgatca cagatttctc ttcatagttc  34500
aacactaact atgtgttgtc tgcatgagac acatttttaa tataatgacc cagaaatact  34560
taaaaataaa agaatgggaa tatatgtacc atgcatttaa aaactattat gatataccaa  34620
ggaggctgca gcaccacttc tgtggtattc ctgccaaaag tatgtatctt gaatctaatc  34680
atggggaaac atcagacaac ccaaggtgag ggaaaccccca caaaatgact gacctgtcct  34740
ctgcaatagt gtcaaggtta taaaagtcaa ggaaaaaccg aagagttgtt ccagatgaag  34800
aaaactaaag agaccttcaa ggggtgattc tgaactggag cttttaaata taagtcttgt  34860
tggaacaacg ggtcaaactt gaataggatt caaagaggtg gcctaaagag ttaaaagact  34920
taagtgatag tattgcatca gtgttaatct tctgattttg atggctgcat ttcattatcg  34980
tgaaagaatg ttaaatgtct ttgttcatag gaaatacaca ctaaagtagt cagggtgttg  35040
aggctttagg ttgataattt attctcagat agttcaggaa aaattctttc tgctgtttgt  35100
gcaacttttg tgtacgttgg aaaattttta tacaaaaatc aacttcaaaa ttgaccatat  35160
aaatgaatac cattgaaata tcatttaaat tatcagtagt aacattagat gctagagata  35220
gtggagtaat gccttcaaaa ttctcggggc aactgctgtt catcactgaa tcatacgcag  35280
atcacctttc aatcaagtgt gagggtaaaa cagcaacatt ttcagatata tgagaactca  35340
gagtccccat tccctctatc aaaaactgga gaatcaacct tatgcaaatg aggcaataaa  35400
aaatgcacac agtggtggag agaaacaata aaatgacagt gttctgttgg cctaagaagt  35460
taaaaagagg ggccaaaaag tagcagaatg ggagagtgtg cagagatatg tctggaaatt  35520
actattttcc aatgtagata ttttaaaata ggtgcatgca tttctttact gattatttaa  35580
```

-continued

```
aaattatatt taatatgaat ttaaagaagt gagtggggaa atgaagacgg caagtaaagc  35640
ctaatttttt taacagcaaa taaaggagaa agcagagaag gtagttaaaa aggaatctat  35700
gtttgagaga ctgtttttcc tgctaaatta agagaaataa gcatggtact gtgatctgaa  35760
ggaaagccag aaactgggtg accaaataaa atgcactaga aaagagtgct tttttactaa  35820
ggttggtaga aaggaggtga tgtaccaagt agatagaaat aatttgtagt ctagtgtgct  35880
gcagagagcc tcacttttct ttatacaaag gcatattcta agaaaaaaaa aatagggcat  35940
agatggataa agaggattgc aaagctttgc aaaaagttga aataacatcc atgcctcata  36000
gttgagggag ctaaaagagg aacacacaga agaattgccc agcagcatgg atggtcctgc  36060
tgaggaggtg aacatgaatt tttaacagca ttagccacac atttgtatag tgctttttaa  36120
agcttttatt ctaatgtttt tggcagcctg ggtgtagcta ctaaatttag atttgggatt  36180
tgcccagtct tgcaaacaag taataaccca gggtatggcg taaactaaaa agaaaaagaa  36240
gagaaactat gcaagtatgt caggcagaat tcaactggag gtcaaaattt gctgaaatag  36300
caggtagagt gggattaaag gagcaaaaag aggggattct atgaagttgt ggtccatgaa  36360
agactgagag gaggaggga agaaattcag aattgaaatt gactactcaa aaggcttgct  36420
cgtgaaaaaa actgccaata aaaaatcaag catccttgtg tacaaagaag aaaatcaaag  36480
agagatgcct agggaccttc agttgttttt aggaagttaa gctggcctag agtttcttgc  36540
tgagtatcct tgcattcgtg gggatgacat ttctgggaca aagcaaactt ccaccacatc  36600
aaactacctg tggatgataa accaactatg atgaagttgg ccttttccag gtttctacct  36660
tggcaccaat ttaacacttg catcctttct agcaaggttg tttttattt atgtttttta  36720
tttcctctgc atctcagtga tagttgtctt ggcacacagt cccagctgca gacagctttt  36780
atttttaggt ttccctattc agaaagagta gtccctgttt aggcatttca ctgtcattct  36840
aagctttcca ctgagctaca accctgcagc tttcttcaaa ttcaagtcac tggggagggc  36900
ttttgaaatg ctcaaagaac gagacaacat tttgtacaaa ggggaaaaag caaccataaa  36960
gatattccaa aaccaagtag ataccatgaa aacgaatgga aaagagaaga cagtgacagg  37020
aaccaaaagg acaaaagaca atatgttgaa tctgtaataa gccagccaga agccccaagg  37080
acaatggtag gaacctacag atagaggtct gcacataggg aaataaattc ttacttcgtg  37140
attcccaaaa gcaccaccca agttactaga ggtgacaaaa atacttcctc ttattaaaat  37200
aaggaagtta ttttgggacc acattattag tgaactggtt agttttagag agctcttcta  37260
gaaactcatt gaggtataga ttttcaaagt agttaagtac attatttgag taaaataaca  37320
ttatgttcaa cctaacttac aaaaggaata gtataattaa acagacttgt gcctggaact  37380
gaaaatatac tcagttaagc attgccatat tttataaagg atgttagaat ccctttaccc  37440
tgtatttagt aatcctagct gtgatgcaag atagattaat agataagcca caaagtaatt  37500
gtaatcaaac ataaaggtac aatttaggaa atgggtaatg tacctatagg tgcctaatcc  37560
aatatatact tcatatgatg cccaaatatg ccacattttt ggtctgttag aggagcatga  37620
aactagtgat ggtcaggaaa tgattcagaa agcaagtcct aaggcagttg caaagctgta  37680
gaaggaaagt cctggaaagc tttaatgttt tgggcttgca aatgggtctc tttgtcctca  37740
aatgttttaa gaataatttt tcagtcataa tttgtaaaaa ccaatggcat ttttgttgaa  37800
aatattttgg cctcttgagg tggacttgca gaaaatactg caacagcact tttgtacccc  37860
cactaaccat ttcgatgaac tcagctgtat catctcctgc cctcacccac tgtttcactc  37920
```

-continued

```
ctggttactg ccctctgttc ttagcatata tgataccctg ccatggctca ttcgttctca  37980
gcaaggggac aaggaactca agaactggca gcacgagagc aagttgcctc aggccagggg  38040
tcagacccgg ctataggtct tgccttgtct cctctccact ttctctattt ctttggctct  38100
cctgacaatt tctcatagct tccctgtttg agcacacatt ttgcttttcc ccttgcattt  38160
ctattgatca tccagaagct gtttgctggg gcctttgcaa ctcccagctt gcaatattta  38220
tgtccattct cttgatacct atgtgtatcc atttccctga cattttaaaa tgtgtttctc  38280
ctcagtttta gctcttctcc tgactactac tttgccctgt ccctagatat cctgccataa  38340
ttaatgttga atgaaagaat ctaatcaacc aagactggaa attcatacag actttgaaat  38400
ggggacaaaa tcttacattt gtttctagtg tgtccccata gatttgacta tcacactttg  38460
gggcatcagt ggcattaagt gacaaattac ttctgggagt tgtaggatga ttctatgtca  38520
agctctccac tcagatccaa tgagtcacta gttcctactt atgaacaggt attaacttgc  38580
ttcatttgca aaccccagca agaattttgg tcacaagcca cagttgccat aagaactggc  38640
tttggaataa gttaggcttt ggttcctatg ccagctctcc catgtcataa ctttgatcag  38700
gatagcaata ataataatat tttttctccc aagacttacc atagagtttg gtacatagaa  38760
agtacttaac tactatgatg aggcataaaa atgtttaatt aatcaccgag atttaaactg  38820
acttttagag gaactttctt agcaggtacc tggttcccca aagtttctca tgcccatgac  38880
acgcactata accttagcaa aggttatcag gatcttctgt tgactgtgct gttctttctg  38940
cacttttggc ttcttggaaa cactgtccct cccaacagtc catgctgaga gtttccaact  39000
gggtaatcac atctgtctag tcagatgcta actttctgct ccgcagaggt atgtccctca  39060
aagttcatac ctgaggaatc atttggaaag attccttcct tcaatatctc tggctgagtc  39120
atgcatacct cctcatcaaa gacaaataga aaacaaggtc aataggaaag cggtgctcac  39180
ctatcttact gtctgtacct tttcctatta tgactagcct cataatcttt aggttagaat  39240
gacttgcact aacctgttcc tagagtccct tccttgtccc ttgtggcact tgccagttgt  39300
gattgcaact ggtggtttta agcatgttac cacttcaaaa ctccaagctt tatgaaaacc  39360
aagaagatgt atgtaccatt tgactatttt tatatctccc atttctagcc caggggttgg  39420
cattatcaca tagcagttaa gagcttgtga tctggagcca gcctgcgtgg ttcagcttaa  39480
aactcaactc catattattt atgtgaattt aggcaagtca ctgaaattac tcctacttca  39540
gtttactttc ctaaaaacag gtattttcat aatagtgttt acctcttagg agagattaaa  39600
taagtcaata tgcataagca cttaggacaa tgcttggcac agagcaagta actattaaaa  39660
taggtactta gtaaatattt gctggattag caaatgccac aataggtcca gtcatcagca  39720
ttttgcagac atcatttaat caacccgaat agtccagtgg ctctagagtc tcttaatttc  39780
ttttttcatg atttttttc atttactgcc tctcaggctt tattgcattt gtgtcaaatc  39840
cacttgtcta aacatttaaa aaagcaaaac agtgttacat agttttaaaa accattataa  39900
tttgactcta tgagtttcaa aaacttcata tacaagtgct taattgtctc attcgaggtt  39960
ttacattgct gatgaaatcc actcatttaa gaggtaggta gtaatgcagt gtgtggggtg  40020
taaagtaaaa tgctaggggt gtgtgtgtgt aggtatgttt gtttatatgt gtgcttgtgt  40080
atatttttat gtgtgtatgt taggggtagc tggctgtgcc aaaggtgaat aagatgaagt  40140
tcctgctcta tagaatcttg aaatttaata aaagagataa ccatgcaaac aactaactaa  40200
atcacaaggc acaatcctct gtgagcctgt gagtatctgc atcctgctct gggaaagtgt  40260
aataatctct ttttgtgtct acgattgtac ccgggctggc atctgagtta gatcataggc  40320
```

-continued

```
tcctaacatt tcactttatc agttcgtaca atgccccaca tctctgtgag ctaaaaaaac  40380
atgttgctat cagcacaatg tgagaagaat ggtttttttt ccccgaaggg acaaaagtag  40440
tgccataaag ctatagaata ggcaagtctc tcagtaaaat gagtttccct aaaaggattt  40500
cctaaggaac atcttaaggt atttaaataa acaaacaaat aagacaactg agtagagttt  40560
aagtctgtgc cttttcctta ttctctagtc ctggttcttt tgacgtaaag tgaaacattt  40620
ttggggttat ttatttccac ccccactctg tcataatata aagagaattc tcagagggga  40680
gactatagaa gtctgtcagc agctgactct tttctggcag gaagactatt ttataaaaaa  40740
aagaagaaat ggatttcctc tccttgtagt tcaatatttt cttcctctac acattggtta  40800
aattcctcca tcctatttcc ttgaaaatgt cagggttggg ttgccccaat ctcagacagc  40860
tctcttcatt atgattatca gtgttaatgc catgtcatta atcctcacga gtatatggag  40920
gcctcacact gaatgaatgg ggaaggtcac catggaaaca tctgtctcca tagatgactc  40980
acggcaaccc ccataactgc tgaaccacat cctgtctccc aaatgcactg gatgaagcca  41040
caaatttggc atttcctaca ggaccatatt ctttttaaaa gctattaaaa atctatgcca  41100
gggaagcatt tttcagactc atggcaataa tactctttgc aatgtgttta agtgggtgat  41160
gctatgcaat tagttgttaa caccttttaa taaatgcaca cagtaaacat tacctgtggt  41220
ttttcagctc ccggtttctt tgcagtgctg tcatctctgg agacaggcgc tggcagagag  41280
aaaagtgccc atgtagaaaa taagcaaaac acctgcattc tcacatttca gaaatgatcc  41340
tccttagggg ttagtgtggt ctatcaactt gcatcacagt gaagtggagg ggaataaaat  41400
ggtctttgct ggatttattt ttttggctgc ctcaatgaaa aaagcaagca agataactca  41460
tgtagaaaaa ttacatttga ggactgcaga cttctcactt agccttatca tggaacggca  41520
ggatatcaac atttcctaga tggaaaatta ggtctatgtt gggagatatc aggcttaagt  41580
aaaatcacat gacaactact gtgtatatcc cagtcacctc ggcacagcta cgctgagcag  41640
tctttctagg gttgctatgt tcagagttgg ctgtaactat acacaccgta agcccagttg  41700
gaaaagcaaa caagggagtg aaaaagggaa cagactattt cccaggctgt acacatttgc  41760
tgaatcttca caaaggcagg ttgtcatttc ttgtttattt cttgaatcct agatggaaac  41820
ctggaacttg agtgataata atagtagacc tttgctaact gtacatatat tagctcattt  41880
gtttctgtaa atgatcatat aatgtgggta gtattcttta cttcatttga cagattaaga  41940
gactgaggca tggaaaaatt aagtgatgtt accatggtca ccaagctctt aagtagctga  42000
ggcgggacat gaacccaggc atctggcatc cagtttattt cctttaactt taagccacat  42060
atttacctct tgtagagtca tatttattcg ttttctctcc tcttgtttcc tctcctcttt  42120
ctctccctct ctctttctta ccatttttct actactcttt cacacctgcc cccaatcttt  42180
cccctcaagc ccacacccac ttcctacttc tctcctctct cctctctctc tccctctcta  42240
ttgctggaag tgatgagccc catctgggtc caccagctgg ccccagacag gggattttgg  42300
cctctcccaa attaaatcat acttgtaaag caggaaaagc tactccctgc ttccagatct  42360
ccccttccca ctgaccctcc cttgtccctc tgtcgccttc cttcttttgc ataggcttcc  42420
agttctcttg tactcttctc ccacagtttt ctcaggaaag aatgggttgt cttaaagtca  42480
tctgatatgg tttggctctg tgtccccacc cagatctcaa cttcaattgt aatctccagg  42540
tgttgaggga gagggttgat tggatcatgg gagtggtttc cccatgctg ttcttgtgat  42600
agtaagtgag ttctcacgag atctggtggt tttataagac agtttcccta cccttgcttg  42660
```

-continued

```
cttctctctc ctgccatgtg aagaaggttc ttgcttcccc ttgtcttctg ccatgattgt  42720
aagtttcctg aggcctcccg agccatgtgg aactgtgagt caattaaacc tcttttgttt  42780
ataaattatc agtcttaggt agtagcttta tagtagtgtg agaatggact aatgcattat  42840
catatagtaa attcagtctc ttcatttaca ttaaagttcc cactttatga acatttgctt  42900
tttaaaaaaa actttgttat tgaagtacag tttaccatat aaatggtgtc gtggactgaa  42960
ctctgtccca aaattcatat gttgatgcct taactcacta tgtgactata tttggagata  43020
gggcctttaa aaaggtaatt aaagttaatt aaggcctata gggtgggacc ttaatcgaag  43080
atgactggta cccttataag aaaaggaagt gacacaggga catgtataaa taaagaaaag  43140
gccatgtgag gacacagtga gaattgttga catgttgatc ttggaattcc agcttccaga  43200
attgtaagaa aattaatttg ttgttgaagc cacctagtct atgacatttt gttattccaa  43260
cgctagcagg ttaatacata tggggaaata cacaaaaata ctcaaatctt aagtattcag  43320
cttgatggat ttctatatat tcataaaccc atgaaatcac tgcagatcaa gaaacagaac  43380
atttccagta ccccagaaac ctccctcctg ccccttccca ctcacgttag cagtctgtgc  43440
ccgattttca gatctgcttc cctgcagaga gggttcactt aggcccttct ctctcatgtg  43500
gaagagcttt acttctgcaa gtgcccctgt gcctgggtct ggatatgaga gtcaattttg  43560
ggagtcaggg ttggcggggc cacttggcca aagagctaag gcaacatttt ccaagctgtt  43620
ttcacaagtg ataaagatga cacaataatc ttcatctgat ttctgcatct atttctcaat  43680
tgtttctgaa ctagggaggg gaaaagggta tcattatctc cttgatacct aacattttgg  43740
tggttggctg tgtttaagtt tggaattttt aaaaataacc tatttttatt ataaaacatt  43800
tcaaacattc aaaacatttc acacattcaa aaatgtatat actaatataa tgaactacca  43860
cctgatttca ataaataaag acgatttact atatttgcct ttgaaaaaca ttttaaacta  43920
ctttagtaaa taagagtttc ttctattatt cttgaaacct aaaggctctg ggtcttttga  43980
acaaataatg actctaataa tcaaataaaa atcacaacat gacacaaagc tctcacaatt  44040
aattctactt tttatctaat gcactttcca tcatgttgca taccatctgt taactaatga  44100
aatgccctaa ggctcaaatt gataaataca aaaatctccc tttctttgat atgtgattga  44160
ggattccacg ctgatttgga ttagatcttt gatgaagtag tagaggcaac tgaaagttta  44220
agcaaatttg ggttgtcct acatcactaa catcatcctc tgggcaggaa tgggtcttgg  44280
gatccattta ctttcccttc tctccaacca catatatagg aagagcacct ggtggatcac  44340
accttgatga tcaggcagct acaccaaatg gttacagaaa atatgaatag gtttgagagg  44400
ggaagagcgt cataaattct tcaaagaatt gctatatggg tttagaggtg acaaagctat  44460
tactggtgaa gagtcatcac ggaaagtcct gagttctgaa tgaaaatgct caaaaaatga  44520
gaaaactggg acttcaaaga taggcataaa caaatggaag catattacaa gtgaaccagg  44580
cagaacatca aattcaggcc agggttagtt attgttttgg aggaattatc tagggcagtg  44640
aatgtgaaca gctatgaatg attttgaaca taaagaactc attgacttca tgtgctcact  44700
ccagagatct aaatagcatg tttgaaaaac aaatggccaa gtcgggagag cgggagagcg  44760
ggagagcggg agagcgggag agcgggagag cgggagagcg ggagagcggg agagcgggag  44820
agcgggagag cgggagagcg ggagagcggg agagcgggag agcgggagag cgggagagcg  44880
ggagagcggg aactgaaagt ggtgagaacc ctacattagg ttgagaagaa acaagacata  44940
ttaagaaaca agttaaactg ttaatgggaa catgtcttga ttttcttgtg tgattccttc  45000
aattctttag aattatcaat atgaatgata aaccacatgc atccagtaat aaaaaatccc  45060
```

-continued

```
agtctacagc tgctgaggaa attcaaaacc catttgggtg tttgagtgag atacttctgc  45120
cagcattcag cagtagcttt gcaaggactt acattagggt cacatcctta gtctcaatcc  45180
agccctcata tccacctact cttaggagaa ggaggaactt acctgattgg tgggtttagg  45240
attagttaga tataatcaat gcagcccatt cctctctctt cttcttgagt ctgtgtgctg  45300
ggagaaggga tgtattgtgt gctctttacc acttgatacg accctgctac agtgtggtag  45360
gtctgccact ttctggctgt acttatggac agaagggaag ggtaaattt gttcatttca  45420
gaggtgaagt cttagcaagt tcgcactgcc agtgtctaag ccatagtctc caatcacttt  45480
tgttagtaat aaaagtgtat tttgttagta atatacctt tgtcactttt gttagtaata  45540
aaggtatatt ttgatgttat cccaaagttg aacatggagg aaagatatgt ttttcaacaa  45600
tactttcagc agtattctgc tctatttcct aaatgacagg atagaattaa aataaatttg  45660
caatgatgta ctaatataaa taaatgaagt atcagtaatg aatgtacgaa ttaagtcaga  45720
gcatgtagcc ttgaacaagc tggggaacag aatataaggt cttacataat catactaatg  45780
gctaatattt accaagtgtt tattctgtcc aattaatttt ggtaatattg tgagccccat  45840
tttttgtgag tcccaatatt gtgagatgac agccaaaaag acgtggagac tggattcata  45900
atcaagggct tgatctcaga gtgggttctt ttagaatata ctggaaattt attaagacaa  45960
atttgtctct gaacttcctt gaaaatagaa cttttgttat cagtgctaat agttctttcc  46020
tttttccttt ttatattgag atatattacc aggagaaaaa taaattatct gttaagacat  46080
cctgcaaaag tatactccaa aaagtttccc ccaatttatc ctgccagtaa ggggacataa  46140
gtgtgcacat tttaatccac cttggattaa gatttattta aattaaaatg tattttaaaa  46200
taggctattg tcacttttta tgtttaattt cagtcaggag agtctgtgga catccacagt  46260
atcaagcagc ctcagaactt tattgactta aaacaactta gatgtatatt ttgctcaaac  46320
tacataattt tttacaggct aggtgggtgc tctgtcctct atcctttctc tagaatccca  46380
cgcagaagag ctgtataggg ttttgcatgt gctattcaat gttcttttcc agaagtaaaa  46440
aatatcactt agttcacaat ccattagtca taacaagtca tctggcttca cccacttaca  46500
agttgcctag aagtgcaaat ctaccatgta ccaaaaagga agaaagctag acaacacttt  46560
gtgatcagca ctaggattgc tacatgtttt tacaagtttt atagctgaaa aatggcaact  46620
agccttcttt ggcatttaca ttacaagaga ggttatgcaa ttattttctc ttttgtgaat  46680
tgtttgtgca tgccctttt ttgtctgaca tattaaaatg ggtatgttgg cagagtcccg  46740
tagaaaagtt ggtggaggaa tttaagttgt tctcaagtaa tcaacaaaga ttatccattt  46800
ctactccctg ccccttaccc gctgctgtct cccttatccc ttggaactaa gaagttgtat  46860
ataggaaaat attctggagg gtggtggtta cctcatcgta acacactata agcaacatgt  46920
cttagaatgg tttccatggg ggcattgatc atttagtgtt tcctaacctg tgattgattc  46980
ataagtacat caatatcaca tgtcaggcta cttcaggtac tctgtaaaag atacctattt  47040
ttccaaggtg tatttcttag gcctctctca atttgaagtg aaataattcc aatctgaacc  47100
agttaaaaaa aacaaaacag tgtgtcctca agtaaaagtt ataggggttt cctaggttta  47160
ggcatggctg gatatgtgaa gtcaaataat aacatcagaa cttactcatt taccactaag  47220
accaaactgg gaagttaaat ttgagtcttc acttcctcat ctatgtatcg gggataatta  47280
ttatttttct cctgtgcttg ttgtgaggat tctttcatta attcatgcaa aactttattt  47340
ttgaggcgga gtttcactct tgttgcccag gctggagtgc aatggtgcaa tctcggctca  47400
```

-continued ctgcaacctc tgcctcccgg gttcaagtga ttctcctgct tcatgctccc aagtagctgg 47460
gattgcaggc gtatgccacc atgcccggct aatgttttgt atttagtaga gatggggttt 47520
caccatgttg gttaggatag tcggaactcc tgacctcagg tgatccacct gcctcagcct 47580
cccaaaatgc aggattacag gtgtgagcta ctgcacccag cacatgcaaa acttttaata 47640
caatgcctta catagtaata gaaatagaag ataactgcct actattgttc ttactacatc 47700
tactattact gtttattctt atgtatagat tgttcaatac actgaaatga cctaattgca 47760
tctgtcattc tgagatttga atttagctta actattatct ttagacttta ttattgacaa 47820
aaagatgaag gtgacaggta tgaaagattt gaaatatgtt tttcaaatat atcctaaacc 47880
agatttcagg aagagactag aaactggact tgccagattc cacatatctc aatgctgtgt 47940
ggaatttttt ttaaattttt ttttacaatt tgagatggag tctagctctg tcatcaggct 48000
ggagtgcaat ggtgtgatct tggctcactg caacctccgc ctccccggtt caagcaattc 48060
tcctgcctca gcctcctgag tagctgggac tacaggtgca tgccaccaca cctggctaat 48120
ttttgtattt ttagtagaga tgggtttcac catgttggcc aggatagtct aaatctcctg 48180
acttcgtgat ccgcgtgcct ctgcctccca aagtgctggg attacaggcg tgagccaccg 48240
ctcctggtct gagtgtgtgg aatttgacgc acctatgtgg taacaaaatg gatatatcca 48300
gtttatagct ggaactctga ttctgtacag aggtcaggat aataaacaaa agaagagtca 48360
tttgtttatg tcagagattt gttatgtggt attaaatata tccataatgt taggcaaaaa 48420
tggattgtgt atttttttcc tcctaaatag atcttaataa atgggctact ttaaatatta 48480
catacaaaga aatttagttt taaagaataa atttgcttga catgacaaat atcaaaggga 48540
actgaggagc agctacttct ttggccatga ttccaattct tcattcagta tgtatgcaca 48600
cctattcctc atttgtttgg gtcacttgct tcccctctgg aggaatttga gcactgagtc 48660
tgatcaaggg taatagagtc cttgacaaag ttcatggcta aggccagaga cctaagtgag 48720
gttgccattt ggaaacagaa gaaaaggggg ccaattatgg aagtggggag aatagccatc 48780
caaagaaact gagaagaatc agtaagaaca gcaggagaga gcagtttcac ccaagtcaaa 48840
gtaggagata gtgctatctt tttatttaca ttattattat tttttaattt tagagatgaa 48900
attttgtcct gttgaccagc tggagtgcag tggtgggatc atagctcact gcagctgcaa 48960
tctcctgggc tcaagcaata ctcctgctcc agtcttgcta gcagctggga atataggccc 49020
tcaccacggt gcctggttag ttttttaagt ctctttatag agaagaatga tcagcgccat 49080
gttcccagat aaatctaata gacttagtga aaataatcta tgaatttcat caattagaag 49140
ataatgacat acaatgaaag cagtttcact cttgtgatag ggcagaaatg tacaatactt 49200
tctgtctcta tgattttgcc tattctaagt agctcatgta agtggaatca tatggtatat 49260
gtattattgt gactggttta cttcatttag cataacacct tcaaggttca tccatgttgt 49320
agcatatatc aatatttctt ttttaatttt tttaaatgtt tttagagatg aggtctcact 49380
atgttgccta gggtgacctt gaatttctgg gctcaagcag tcttcccacc tcagcctccc 49440
taggagttgg gactacaggc atgtaccaca ttttgctttt ccattcatcc cactggtgaa 49500
cacttgagtt acttctatgt tttagctatt gtgaataatg ctgttgtaac atgggtatat 49560
aaatatctct tcaagattct gttttcaatt ctttggggtg tataccaaga attggaactt 49620
ctggatcata tgataattgt atttttaatt tttgaggact tgccatactg ttttccacag 49680
tggctataac attttgcatt ccagcaacag tgcagaagag tttctatgtc tccacattct 49740
tgtcaacata ttattttcta tgtttttaaa aaagttttcc tgtaatccca gcactttgag 49800

-continued aggccgagat gggtggatca cgaggtcagg cattcaagac cagcctggcc aacatagtga 49860
aaccccgtct ctactaaaaa taaaataaaa aaaaaagctg ggcatggtgg tggggcctgt 49920
aatcctagct acttgggagt cttgggcagg agaatcactt gaacctggga ggcggaagtt 49980
gcagtgagcc cagatcatgc cactgcactg cagcccaggt aacagtgcga gactccgtct 50040
caaaaaaaaa aaaaaaaaaa aatttatagt atccttaaca ggtgtggggt gttatctcat 50100
tgtaagtttt ggcttgcatt tccctaatga ttagtgatgc tgagcacctt tcatgtgctt 50160
attggccatt tatatatctt ctttagagaa gtgtctactc atgtcttttg cccactttta 50220
aatcaaattg ttcctttttc attgttgagt tttaggagct ctctttatat tagtatctta 50280
tcagatatgt gatttgcaaa tattttattc tgtaggttgc ctttttactc tgttgatatt 50340
gtctttaaaa atgtatatta aaaattctaa ccagcttaat atattattga caaataaaag 50400
ttatatatat ttgtggtatg caacatgata ttttgatgta tgcatacagt atgaaatgat 50460
taaatcatgt taattgacat atccattgcc tcacataatt attcacaaat ttttttcctt 50520
tccataaagt ttaatttgtc tgtttttttt cttttgtagc ctgtgccctt agaatcatat 50580
ccaagaaata attgccaaat ccaatgtcat aaagcttttg ctgtatgttt tttcttaaga 50640
gttttatagc ttcttaaggt tttaaatgta gttctttgat ccatttaaat aaatttttgt 50700
atatggtgtt aggcaagggt ccaacttcat tattttgcat gtggatatcc agttttccca 50760
gcacctgttg ttgcaaagac tcttttccat attgaatggt cttagctctc ttgtgaaaat 50820
catttaccgt atatatgagg gtttatttct gaattatcta ttctattcca ttggtctatg 50880
tcttccattg gtctatatct atgtttgtga ctgtactaca ctgttttgat tactgtagct 50940
ttgtggtaag ttttaaactc aggaactgtg actcttccag atttgttcct ttttcaagat 51000
tgttctggct attcagggaa ctttgatatt ccatatgaat tttaggatga atttttctat 51060
aaagagtatc attaggattt tgataggatt gtattgaatc tgtagatcac tttgggtagt 51120
attgctatcc taaaaatgtt gtcttctact ccataaacat aggatgagtt tctatttttt 51180
tatgccttta atttcttcca gcaatatttt gtagtttttc ttgtacatgt ctttcatctc 51240
cttggttaat tcctatgtat tttattttta tttggaaata tttattaggt gcccactttg 51300
ttccccatat tatcccaggg agttattaca aaatgatgag caagacagac atgggctcat 51360
ggggcttcct catgcatgtc ttttggtatc accaatttat ctcctgtggc ctgtggcaaa 51420
tgtatggtgt aattctagtc catgagctta gtatacttat tttcaggtac tcactcagct 51480
gtacttgttt aaaaaaatgc ctgaaacttg atttgcttgt gtggatatta agagtaaatc 51540
aactattcca tacatgtaaa gtacgtttta ttctccctgt aaaactctca atgtttttct 51600
tcaaaatata ctttatgata tatatattaa ctattatttt aagatagttg ggaaaatgaa 51660
gggaccataa tttaaaagaa atggaatatt tgatacatga tgtggctgcc tgtttttatt 51720
cttgtcacct agtctcagtt tttcaggttt ttaaaaatat tataaatgca cacatgtaca 51780
cacacttaat ttcttcttaa tctgtgatct ttcaggtttc tattacatag attaattcat 51840
gtaaattttc ctagtctttt gaaattaaag aaagtcaatg acaaaaggac catcacgtgg 51900
acaaccagtg ggaatgtttc attcactctt gtaagttact tgttcccagt gcaaaagttt 51960
aaaagaaagt ctttttattt attcaaaagt tgaaggtttt tttttttttt ctcttcagca 52020
ccggaaactg tcaggaaaag cagtatatac ccctaatgac tagttcagaa ataaatgtat 52080
cattgttttt aataatttga tacagtatat aaatgttgtt ttgtaaagtt taaattctac 52140

-continued

```
tattaactga acaaaatata aaccaggaaa ttaacatcaa agaaataacc acattcacct  52200
gttcctctcg tctctaacat tctgcttttc ctttgctccg cagggtaacc atggtgagaa  52260
agatgttgat ggcttggatg gagaacaggt actaaaattt ctcattctat gttccgcctc  52320
tactagtttg gcatttacac atgtcatgat taatctagaa atgtaaacat gcatatttaa  52380
tgtttaaagt ttatctatgt ttgttcttat cccaaatata caagaaccct agaagtctaa  52440
ctcgaatcaa cctctcccat attacatttc tttccatctt atttttgtta aatctatcac  52500
ttagacattg ttattgtttt atatagtcaa tgcttattta gccctaccat catatgtctc  52560
caattttctg gaagagttag agaaggatta gtattcattc tttaaatgtt tggtagaatt  52620
cactgaggaa gccatcaggt ccatggtttt cttcaagaga ttttttgatt attgattcaa  52680
tcttcttacc attgattcaa tcttcttacc agttgtaagt ctattcatat tttctatttc  52740
ttcaggattt agttttgcag gttttgtgtt tctggaaatt tttccatttt ataaagacta  52800
cctagttgtt ggcatacact tgttcttagt actatcttag aatgtttttt tatttttttg  52860
agacggagtc ttgctctgtt gcccaggctg gagtgcagtg gtgtgatctt ggctcactgc  52920
aatttctgcc tcctgggttc aagcgattat tctgtctcag cctcctgaat agctgggatt  52980
gcaggcgtag gctaccatgc ccacccaatt tttgtatttt tagtagagac atggttttac  53040
catttttgcc aggttggtct caaactcttg acctcaagtg acctgcctgc cttggcctcc  53100
caaagtgcta gaattacagg catgagccac ctcacccagc ctattataat tctttttatt  53160
tatgtggact cattatttcc actttcattt ttgattttat taatttaaat ttttctcttt  53220
tttttttagt tcatctggct aaaatttcat cacttttgct aatcttgagg aatcaatttt  53280
tggttttatt gattttctct attatttctc tgttctctat tttatctttg ctctaatctt  53340
tatttccttc tttctccaag ttttgagttt agttcttctt tttctagttt cttaaggtat  53400
aaagcgaagt tgttgatttg agaccttttt tgttttttaa cgataagtgt ttacagctat  53460
agtttttttcc tttagcacca cttttgctgt gtaccataag ttttcgtgtg atgtagtttc  53520
atttttcatt tgtctctaat tatattctaa tttcttttgt gatttctttg atccattggt  53580
tgttgaagac tgtgctgtat gatccttttg tagttcacaa gcctgatgat tgggttttca  53640
ttcacgtgga tgagatgcac ctccctcaaa cctggttgtt acagcatagg cacattactt  53700
gtctaacacg aaaaaaagga aaaaggagtg tgctgtgcaa tttccacaaa tttgtgaagt  53760
ttctaatttt acttgtgtta ctgagttcta atttcatcct gttgtgatca gagaagacaa  53820
tttgcataat atttatcttt tataatccat cgagaattgg tgacttaata tattgtgtct  53880
ggagttggtt cctcctggtg ggtttgtggt ctccctgact tcaagaatgg agctgcggac  53940
cttagcagtg agtgatacag ctcttaaaga tggcacggac ccaaagagtg agcagcagta  54000
atatttattg tgaagagcaa aataacaaac attccccagc acggaagggg acctgagcgg  54060
gttgccgctg ctggctgggg tgcccagctt ttattccctt atttgtcccc acccatatcc  54120
tgctgattgg tccattttac agagtgctga ttggttcact ttacagagca ctgattggtc  54180
cattttacag tgtgctgatt ggttttacaa aactctagct acagagcgct gattggtgtg  54240
tttttacaga gcattgatag gtgcatttta caaacctcta gctagctaca gagtgctgat  54300
tggtacattt ttacagagca ctgattggtg cattttacaa acccccttgta agacagaaaa  54360
gtcctccaag tccccattcg acccaggaag tccagctggc ttcacctctc aatatgatat  54420
atcttgataa atattccatg tgtacttgag aagaatgtgt atgctgttga tgttgagtaa  54480
tgctctgtat gtgtctgcta gatctagttg gtttgtgttg tgttctattt cctttcttat  54540
```

-continued

```
catctgtctg attggtgtct tcattattga gaggggagta ctgaaatctt taactattat  54600
tgtagaacta tatttctccc ttcatttctg tcagcttttg cctcatatat tttgatggtc  54660
agttattaga tgcatgaatg tttatagttt ttatatcttc tttctgtatt gaacatttta  54720
atttataatg tccttcttta tgtctttttc actttttgga tttaaagtgt attttccctg  54780
atattggtat agccactgct gctctctttt ggttactatt tgcatggaat agcttatttc  54840
tttttttctt tctttttttt tttttaaata aacacatttt tttttttttt ttttgagaga  54900
cagtctccct cttgtccagt ctggaatgct gtggtgcaat ctcagctcac cgcaacctct  54960
gcctcctggg ttcaagcaat tcttatgcct cagtctccag agaagctggg actacaagtg  55020
cacaccacca cccccggcta atgttttgta ttttagtaga gacagggttt tatcatgttg  55080
cccaggctga tcttgaactc ctgacctcag gcaatctgcc caccttggcc tcccaaagtg  55140
ctgggattat aggtgtgagc cactgcaccc agccagaata gctttttcta tcattccatc  55200
tttttttttt ttttttgaga tggagttttg ctcttgttgc ccaggctgca gtgcaatggc  55260
acaatcttgg ctcactccaa cctccgcctc ccaggttcaa gtgattctcc cacctcagcc  55320
tcccgagtag ctgggattac aggcgtgcgc caccacctca gataattttt tgtattttta  55380
gtagagacag ggtttcacca tattggccag gctggtctca aactcctgaa ctcaggtgat  55440
ccacctgcct cagcctccca aagtgctggg attacaagca taagccacca tgcctggcct  55500
atcattccat cttttcactt tctatctgtt tgtatttcta aatctaaaat gagtctcttg  55560
tagacagcat ttagttggat catgtatttt taaatctatt ctgccagtat gtatctttca  55620
attggagagt ttactccaca tttatttaaa gtaattactg ataaggagga cttacttctg  55680
ccagtttgct atttgttttc tatatgcctt atactttatt atccctcagt tcctgcatta  55740
ctgtcatctt ttgtgtttag ttgatttttt gtagggaagt gtttaaattt atttctcatt  55800
tccttgtata tagtctgtag ttattttctt tatggttgtc atgaggatta catttaacat  55860
cttaaagtaa taacactgta atttaaattt aaaccagctt aactttaata ctatacaaaa  55920
agtttactct gttatagctt catccccact tatttcagtg gctgatgtca taaaattaca  55980
gctttatata ttatgcaccc caaaacataa actaataatt cttttaaata cattagcctt  56040
ttaaattata tagaaaatga aatgtgaagt taccaaccaa agttacaata ttaggttttt  56100
gagtaataat tctttaaatg tatttttctc ttaaatcatg tagaaaataa aaagtggagt  56160
tataaaccat tattacaata atacttgatt ttatgattgc acatgtattt acctttgctg  56220
agatagttat tttttcatat gtctttgaat tactgtccag tgtcttttca tttcatgcta  56280
caggcttccc ttgagcattt ctttcagggc agctctagtg gtaatgaact ccctcagttt  56340
ttttatttgg gaatatctct tttttttttt gacaagatct tggtctgtca ctcaggctgg  56400
agtgcagtgg cacaactgta acttactgca gcctcaaact cctgggctca agtgatcctc  56460
ccacttcagc ctcccaagta gccaggacta caggcatgca ccaccatgcc cagctaatct  56520
tttttaatta ttattttttg taaggatgag gtctcactgt gattcccatg ttggttttga  56580
atgcttggcc taagcaatcc tcctgcttca ggctcccaaa gtgccaggat tacaggtgtg  56640
aatcactatg cccagccatc tgggaatacg tcttaatttc ttattttaga aggacagttt  56700
ggccagagat agaattttttg gttaatagat tttttctttt tttttttttt ttgcacttgg  56760
aatatattga cccaatgcct tttggcctcc aaagtttcaa atgagaaatc tgcttatgat  56820
cttattgaaa atctcttgta tgtagtaagt ctgtctttgt tcaatcaaag gtttgattat  56880
```

-continued

```
aatgtatctc agtgtgggtc tccttgagtt catcatattt ggattttctt gaatttcttg  56940
gatgtttata ttcatgtctg tcatccagtg tcagaagttt ttcagtcatt atttctccaa  57000
atattcactc taccccttc tctcttctcc ttctaaaact tctgcaatgt gtatgttggt  57060
ctgcttgatg atgtgctaca ggtcccttag gctctgttca cttttcttca acattttttt  57120
ctttctgttc cttagactca ataatttcca ttgtcttatc ttcaagtgtc actgattctt  57180
ttgcctctta aaacctgcct ttgaatctct ctagggaatt ttttgtttca gttatcatac  57240
ttatcatttc cagaatttat ttttggtttc tttttaggtt ttggtatctt tatatttcta  57300
ttttgttcat ttatcatttt cttgattttt ttaacatctt cctttagttt tgaaaatata  57360
tttaaggcag ttgtttcaaa gactttgtct agtggatctt ccatctgtgt tactcaggga  57420
cagttttggt tgatttattt ttgtttcctt tgagtgagcc atagtttcca tttctctgaa  57480
tgccctgtga tttttttttt tgaaaactgc atatttgaac ctaataaagt ggtaactcta  57540
gaagccagat tctcctccct ttccctgtgt ttgctgtttt ttggttacaa tttattgttt  57600
attgattttt tttttaattt gagtgtttta agctatctct gtgtcaagga tcagaatgag  57660
gtatatactt aaggtcttct caggtatttt ctgagtcagt gctttcccat gggcttgtgt  57720
ggtgataaaa gaaaaacttc agctgaatta aatttgaagg agtttaattg agcaatgagt  57780
attttgtaag ttgggcagcc cccagaagca cagctgattc acagagactc cagcacagct  57840
atgtagtgga agaagattta tagacaaaaa aggggaaatg acctacagaa attggtggtg  57900
aggtacagaa acagctggat tggttacagg ttggtgtttg ccttattgga acacagtttg  57960
aacacttagc agtctatgag tgcttggagt atggccgctg ggattgccca agacagttat  58020
tgttacaggt gcatactgtt aaattaggtt tttaatcttg tgtgactatt aagctaggtt  58080
acagttcatc cacaaggact caaatataga agtatggagt ccttctcacg ccatatttag  58140
ttttctttaa gtggtcactt tctaattttc ctcacatata ctgctgcttt tgaatgtccc  58200
agcctttaat gtctggctcc caaaaaggca aaaagaaaaa aataaagggg agagggagga  58260
ggcagtggcc cttaaaatcc cctggaagtc aattcatttg ggggtaggag ggagtagcag  58320
caatttgaga agatacaaaa caatagctgc ctgcttcttt gcacctccga gatcaaaaac  58380
aacaatcagt aatcaaagct cagatcttga tttgcaggac agagttcttt ttgtcacact  58440
gatttccaca agctgcattc aagctgctcc aggaacatgt gcattgctac ctgacaagga  58500
actgtgtgta gggtatgtgt agctcctcct gtgcaaacta aagttggcaa aagtaatagc  58560
aatacactaa acaagccttc ctttggaagg tgcaagcctt caataggatc cacagttcca  58620
aaatagttac atcagataaa ttctgtcagt acaattgtag tagggagata gattttatgt  58680
aggcagatag attttaggta gggagataga tttctggttc ttcctattct gccatcccat  58740
cttctaaaac tacacctcat gttattatca ttattactat tattattatt tatttttgag  58800
acaaagtctc gctctattgc ccaggctgga gtgcagtgat gcaatcttgg atcattacag  58860
ccttgacctc cacccacctc agcctcccaa gtagcaggga ccacaggcat gcaccactat  58920
gcctggctaa tttttatgtt tttgtagaga cagggtttca ccatgttgcc caggctggtc  58980
tcaaactcct gggctcaaca tatctgcctg acttggcctc ccaaattgct gggattacag  59040
acatgagcca ctgtggccag ccctgaattt attttttaaa tagaagattc ataaaaaaaa  59100
ttgacctcac gattataggt aactagattt tttgcaaatg aaattatctt attagaaagt  59160
atattagata taagcagtta tatttttacc cagaaccaca ggcagttctt tctattcaga  59220
gtaaagagcg atattgggta tatttccaaa ttcaaatgtc attctaaaat atatttgtat  59280
```

-continued

```
ttttatcagt gccaagtgca atggtagttt gtgcaaatta gtgctcgtag taggagtgtt  59340
ttagtactat tgaataataa cagtgtaatt tgaaaggtaa tttcattatg gcaagcttcc  59400
tgggaaaagc aagtggcctg ccttataaat ttggactcat tgttagaaat tacaagttca  59460
ttgaataatg aatacagtag tcactgggcc tttagaagtg aagttttaag ttggtgataa  59520
aaagaggtag cttcatagaa ttccttttgt acttgttttt tttttttttt ttttgtcaaa  59580
ttatcaaacc ttgctttgga tgtaagaatg agttgcgagg ggagcaaaag ggcaactgtt  59640
cttcatgcca aaagtaatca ctcatttagt tttttctaaa cattttcttt gttccagggt  59700
aaataagatt ttcaagccac tttaattata atgaatgatt gttaaaatca tactgaacaa  59760
aaaatgttat tgttattcag gattattcta ttgagtagga cactcaaaaa cttcagttaa  59820
atattaatac aagataagag cctaataaaa acagtagaac agttttatac atgttaaata  59880
gttaaaaaat acatcaatgg ttataataca tttgacaatt taccttgaaa tagtctacag  59940
tttgcttgtg aaaatgagag ttggaagaat tgcagcttgt gagttactac gtagtagtga  60000
aatgagggtt atcaaaattt gcagtctttt tgcagcctta aaaactggga catgtttgtt  60060
ttccctttga gatgcagctc cttggaagca tatgtttaca atagatacct atgtcataaa  60120
tatttaaaat ttgatccaat gcatagtctt ctccttcaat taacttcagt atccctgctg  60180
gaaatctgtg actttttcat ctacactcat agctttactg ataggaaggc tttacgaatt  60240
gcagtggtgt ttgaaaccac caaaccaccc tctagtagca ctgaaaggag caaattatgc  60300
aggatttggt gataacggtc tttgtataga gatagtgctt tctctttgat tatgttttct  60360
ctttgattgt gagaaaggtt gtttttgatc attgcactat ttggtcttca tatgctgaac  60420
aatatttcaa tttcttgtat ttctttctgc cttgttctta ttgacttcat agcacttgaa  60480
gtgatttaag atacagccat gtatttgtgc agagttgtct ctgatggtcc accatgtgga  60540
ttcctttatg cttgttgctc tggagatatc atattccctc ctttctttca aaacacttta  60600
gttcaagatg atcttcaata tcatcaatac ttaaagattt tcttttacat gcacggcttg  60660
ctggttttga acacagatgc ttggatatgt ttgagagatt aattaaaaga gtgctttttt  60720
tttgtattga aaagttcatg agttcaaaag aatggaaaaa cagaacaatg taggctaaca  60780
catgctgtgg actgaggtaa ctggtagatg gctcaggtct gagcgtgtac gtgttttgtg  60840
tactaattcc cacatggatc catctaacca tgcagttttc tgcctttatc tagtgtttct  60900
taacactagt agagatttag cagagataga aaatttgttt tatgctgaaa acattccctc  60960
gtatgtcaat catgttggaa caaattcatg ttttaaaaca agtgctatag cagaaatgac  61020
tgtgataaaa aagtttaaaa aggaataaaa acttaggtct gtcattatag taagtgttaa  61080
ttgactgaaa tctcacttta caagaccatc agattgaagt aaaaaagcac aactatgtac  61140
tgcctttaca ggaaatgcat aataacaaga gatgagcaga gatatatgcc aaatggaaac  61200
aaaataaagc aagtgtggta ttgtaaatat cagagaggct gaaatttaat gataatagca  61260
ataatcagga taaagaaaga cattatacaa taaaattact attaatgaag gagatacact  61320
gttataaact tttatgcacc aaatatagca actaagcata taaactaaaa tctatgagaa  61380
attaaaatct atttgaattt aatataatga aactttagaa taccacttta aatttcaaat  61440
atgtccagta gaaaaaaatt ttaagagatg cttttaataa aacaatatta gacaaacaca  61500
tatacaacac acatacatac atgaatatga acataaatat aatattttac agcccttaag  61560
agaaaatata gcttagtctt agattttaac atataggtaa aaaataaatt aaatattaga  61620
```

-continued

```
aaaaatctta gagtttatca aacaattgat atactatgat aaaggtttta ttttagaaat  61680
gaatggtggt tccttatcag gaagtttgtc accagaattt ttttttcatc aacttttaag  61740
ttctggggta catatgcagg atgtacaggt ttgttacata ggtaaatgtt tgccatggtg  61800
gtttgctgca cctattaacc aatcacctag gtattaaccc cagcatccat tagcttccgg  61860
atgctctccc tctccctact ccccccacag gcctcagtgt gtgttgttcc cccaccatgt  61920
gtccatgtgt tctcatcatt cagctcccac tgataagtga gaacatgcaa tgtgatcttc  61980
aacaaatctg acaaaaacaa gcaatgggga acagattcgc tatttaacaa atggtgctgg  62040
gagaactggc tagccatatg caaaaaaatt gaaactagac acctttctta caccttatac  62100
aaaaactaac tcaagatgga atgacgactt aaatgtaaca cccaaaacta taaaaacccc  62160
agaagaaaat ctagtcacca gaatttaata caaaatttaa tggtaaagag aataagcatg  62220
tggtcataat agcagatgat gaaaatgacg ttttaaaaat ttatcaggaa tttctaataa  62280
aacgaattac aaaaaacaaa aagaccattt accaaaagca cagctgaagt ttttttttc  62340
ttttgtaagt gatgaaatac taaaaatact taaaattcat tgagggtata gtttccaaat  62400
gaaaaaatag acaaaggaca tgaatgggca attcacagga cagcaaatcc aaaagggcaa  62460
caaatacata aattgatgtg caaataggcc tgatgcaggg cttatgcctg taattccagc  62520
attttgggag gctgaggtgg gcggatcact tgaggtcaag agtttgagac cagcctggcc  62580
aacatgggaa aaccccatct ctaataaaaa tccaacaatt agctagacat ggtagtgcgt  62640
gcctgtaatc ccagctacat gggaggctga agcaggagaa tcgcttgagc ccaggaggca  62700
gaggtttcag tgagccgaga tcgcaccact gcactccagc ctgggtgaca gagcgagact  62760
ctgcctctaa ataaataaat aaataaataa ataaataaat gtgcaaactc attatttata  62820
aataaataaa tagatgagtc agggaagagt gaacccggga ggcagaagtt gcagtgagct  62880
gagatcacac cactgcatac cagtctgggt gacagaatga aactccttct ctagataaat  62940
aaacaaacga ttaattaaat gatacacaaa ctcactggga gtcagaaatg tgaattaaat  63000
tgaaaatgac atattataca cctaattaga ttggccaaaa taataaaata cccatatctc  63060
cctaatattt gtggtggtgt agagaaaagt atttccaaat attgctagtg gatatgtgag  63120
gtactatatt ttttggacag aacatttagc aataaatatt aaaataaaaa atttttaaaa  63180
ccctcatata ccctttgatc cagaaatccc aaaccaggta tttaggctat agaattaaag  63240
taccagtatg tgagcataag tataaggatg tttaataact taattattgt tcatactagc  63300
aaaaaatgga ggaaaatgaa tatccattgt aatagttaac ttatggtacc tgcatataat  63360
gaattatttt gcagctatta aaacttgtca ctgtttgctg atgatatgat tgtataccta  63420
gaaaaccctg aagactcatc caaaaagctc ctagatctga taaataaatt cagtaatgtt  63480
tcaggataca aaatcaatgt acacaaatca gtagcactgc tatacaccaa caaatgacca  63540
agctgagaat caaatcaaga actcaatccc tttacaacag ctgcaaaaaa aaaaaagaaa  63600
ataaaatatt taggaatata cttaactaag caggtgaaag atctccacaa ggaaaactac  63660
aaaacactgc tgaaaaaaat cacagatgac acaaataaat ggaaacacat cccatgctca  63720
tggatgggta gaatcaatat tgtgaaaatg accatactgc caaaagcaat ctacagattt  63780
aatgtaattc catcaaaata ccatcattct tcacataact agaaaaaaca attctaaaat  63840
tcatatggag ccaaaaaaga gccttcataa ccaaagcaat attaagcaaa aagaacaaat  63900
cgggaggcat catattaccc aacttcaaac tatactacaa ggctacagtt accaaaacag  63960
catggtattg gtataatagg cacatagatc aatggaacag aatagagaac ccagaaataa  64020
```

-continued agccaaatag tgagaaccaa ctgatcttcg aaaacgcata caaaaaccta aaatgaggaa 64080
aggacaccct attcaataaa tggtgctagg ttaactggca agccacatgt aggagaatga 64140
aactggatcc tcatctctca ccttatacaa aaagtcaact caagatggat caaaggctta 64200
aatctaagac ctgaaaccat aaaaatttta gaagataaca tcagaaaaac tcttctagac 64260
attggcttaa gcaaataatt catgactaaa aacccaaaag caaatgcaac aaaaccaaaa 64320
ataaacagga cttaattaaa gtgaaaagct tctacacggc aaaagaaata atcagcagaa 64380
taaatagaca acccacagag tgggagaaaa tattcacaaa ctatgcatct aacaaaagac 64440
tgataagcaa aaaagtatat ataagatttc atttttatgt tgcaaataat tgtaaaagta 64500
tatatttttg catgtatatg ccgaaaatat ggtggaatag ttactacatt ttaaaatgtt 64560
ggaacatatt aaatatgggg aggaaaaatc gaataaatgt tataaagtgg ggaggggggg 64620
aagtggaatc aagaatagag aaaaacaagc aagtgataat agaccacaaa agaaaaaaca 64680
aaatgtttgg gaggcctagg caggcacatc acttgagcca ggagtttgag accagcctgg 64740
gcaagatggc aaagccccat ctttacaaaa aatacaaaaa ttggcagggc atggtggtat 64800
gaacctgtag aacccagcta cttgggaggc tgaagtagga gtaatgcttc ttgaacccag 64860
gaagtggagg ttgcagtgag ctgagatcat gccaccgcac tccagcctag gcaacagagt 64920
gagacagtgt cttgaaacaa aaaacaaaat gtctaatata tggtggtctc atttatgcat 64980
ttatgtaaat tagtattctg ctagtcttgt gctttttaga agagaaaaat tgatatttaa 65040
caattaatag gcttaattat aaatgcatta aaagccctaa taatgaacaa ccttaatcta 65100
ccagaatgag ttccaaaaat ggacaattat atggaaaatt tgggctttaa aatggtgtat 65160
tttgttgagg ctacacttgt atcctgcaga ccagagaggg cataggcaag atgctgacct 65220
tgccttgtct aggaaatact agggatggct ggagggttgc cgatttcaaa aggaagcagc 65280
aggattatat ttaaatgagg ggtctcaaat gggtactcat gcctgtaatc ccagcacttt 65340
gggaggctga cacaggcgga tcacctgagg tcaggagttc tagactagtc aggccaacac 65400
ggtgaaactc tactaaaaat agaaaaatta gccaggcatg gtggtatgca cctgtaatcc 65460
cagcaactca ggaggctgag gcaggagaat ggcttgaacc tgggaggcgg aggttgcagt 65520
gagcttagat tgtgccactg caatccagcc tgggcgacag agtaagactc tgtttcaaaa 65580
aaaaaaaaaa aattaaatgg tggggggtct tattactctg ctttgccttc tccattgacc 65640
actggaacaa attgctttga aggttatggc aggtagccat ctctgtatag gaatatgaac 65700
aattcctacc taactgaagg tatcaatttc taaatttacc aaaaaattct gatgcccagg 65760
ttttcattcc agagattctg attgaattgg tataagaggt gtgtggctgg ttttctgaag 65820
cccagagaga gagagagaga gagagagaga gagagaaatt taccctctca ggtttgttca 65880
gctagaatta caattcattt caaatctatc taaaatgatt gtcattacaa atgattccac 65940
attgtgctta gtaaccagat gaaacaagag ccaacaaggg ctgcattatt taattctcat 66000
ctattagtaa actaggacaa aatagagtaa ttaagtaatt atgatatcta aggcactgaa 66060
agtagggata aaagggaatg tcatcaagtg aatatacatg aggtgagaca cacagactag 66120
tatagaataa aggaaccgcc cttgacagtg cattggaatc acctggggaa ctttaaaaaa 66180
tactgatccc cacccccacc caccactcaa attctgatgc aagttgtcct gggcatagtg 66240
attttaaaag ttacccatga gattctgtta ggtagtcaga gttgaaaacc aataacctaa 66300
aaggaaatag gatgaaaaaa agtgattcgt gtagaggttc aaagaccctt taagatgggt 66360

-continued atcattcatt catttattta ttcagttcag gtattcagtt tagtcattct tttcattgca 66420
ttcaattaat tcaatattta tgaagtaccc actttgtatt tgtccctgaa ttagagtccc 66480
caacatcacc acttgatgga taaaatgcaa atttgttttg actaatttct ttgtgcctgg 66540
aaggcatctc ttattctgag tctggctcta ttagaaagag aggcaaattt tctcctcttt 66600
tctcttctct cttttctttt tctttctttc tttccttttc ttgtttggtt ttagtaaagt 66660
gggaagatta ggggattgag aaagaaagag cctaggaaac tttcatttgg tttctactgt 66720
gttagctacg gattcacatt tcacaggcag aatctcacaa atctgtgaca gaggcattat 66780
tcactccagt ttacaaatga ggattctgag actaaaaatg attaaggaac ttgtaataag 66840
taaagccact tattacaaaa ctaggatgta aactgcaaag ttacttcccc caacattttt 66900
tcttccagtt tctctaaagt caaaaagagt atagccacgt ccccttgcaa atcatatgtg 66960
tatgcacgta tttcaggaag ttgttctggc aatgttgttt ctttgaaatt tcttcttgta 67020
tctttaaaac tcacttgaat ttttatttca cccccatatg atgattaaaa tgcaaaaatt 67080
gggcttaatt tgccattagg aaaaaataat ctgtttctgc cttaagggat gcaactgcat 67140
tgagtttatc aatttcagaa aatcgtgttg actaaagaga actgactcaa catataaggc 67200
tcagcatcta ggaaattgct ctgctctgga ttgcaatcac tgaatttcat agatctgggg 67260
atacaaatgg taacagatct ttttctccgt gcttcttttt tttttttttt ttttaatcct 67320
tgagacggag tcttgctctg tcgcccaggc tggagtgcag tggcacgatc tcggctcact 67380
gcaagctccg cctcccggat tcactccatt ctcctgcctc agcctcctga gtagctggga 67440
ctacaggcgc ccgccagcac acctggctaa tttttttgtat ttttagtaca gacggggttt 67500
caccatgtta gccaggatgg tctcaatctc ctgacctcgt gatctgcccg cctcggcctc 67560
ccaaagttct ccatgcttct taaaccctca aatgctgcct gaattaaaaa ggcctctgca 67620
ttcactgacc agtctcactt aactcactga tgctgatctt ccccccaccc ccatatggta 67680
taatgcttat gtcatgaatc aagaatctcg aggacaaggc aggtggatca cttgaagaca 67740
ggagttcaag accagtctgg ccaacatggt gaaaccccat ctctactaaa aatacaaaaa 67800
ttagcagagc gtgatggcgc aggccgtaat cccagctact ggggaggctg aggcaggaga 67860
atcacttgaa tacaggaggc agagattgca gtgagctgag atcgcaccac tgcactccgg 67920
ctgaggaaat agagtgagac tctatctcaa aataataata ataataataa taataataat 67980
aataataaca atagtaatct caagtgactc atagtcccta ttagtaactc tcttcatcca 68040
gtgaaatttt atttttttgg tagtgattct gtgtctattt caaacactca tttggcagca 68100
ctttttattt ttggcaatta tttattcaac tcttgtaagt atctgtttac tttgcatatt 68160
ttctgctggt ataagctcta ggaaggtaga aacttagtct gtgtttctaa ctaatatatc 68220
ctccacacct agcattttgc ctggtagtat atatattggg catttagtat ttgttgaatg 68280
atcgcagcat aggactttca cagataattt actcctaaaa tatgcttttg acatgtcaag 68340
cttcactgac cttgaagaaa gcctgaagta atttttagtt taattgattt tgccttttta 68400
ttgtattgtt ctattcatga tttcatttca gttgcaaaac attctgaaaa cgttttgaga 68460
gatttgtttg aaatatagct ataagaatgg ttgtccaggg attttttttt tctttccttt 68520
tttttttttt tttttttga tatagagtct cactctgttg cgcaggctgg agtgcagtgg 68580
tgcaatctcg gctcactgca acctccacct cctgggttca aacaattctc ctgcctaagc 68640
ctcccgagta gctgggacta ccagcatgcg ccactacgcc catctaattt ttgtgttttt 68700
tagtagagat atgaggtttc accatattga ccaggctggt ttcgaactcc tgacctcgtg 68760

-continued

```
atccacaggc cttagcctcc caaagtgctg ggattacagg tgtgagccac cgcgctaggc  68820
ctagggattt ttaaaaaaca aaatctcact caatattcag gattatttat atttttacaa  68880
taataaaatt taaaatacaa ataagcatca aaactcacca acatgtttag tatcgatagt  68940
ttctgtgtta ccaccaattc acaagattag gttaagaaaa tatcctttgg ttgtttcttc  69000
tgtcaagatc attttaggga catctgaagg gtaactgact ccataatatt agatttctat  69060
gcatttccat tgtcttgtat gttgttactg gtttcaagtc tattttcaaa ttactggttt  69120
ttaaatcaca ctcaatattg ccagttgaac atgtaattta aaacttattt cccctcttaa  69180
gttatataaa agataacaaa tttgcttacc tatctactgt tattagaatt ttcagccaag  69240
cgcggtggct cacgcctgta attccagcac tttgggaggc cgaggcaggt ggatcacgag  69300
gtcaggagat caagaccatc ttggctaaca cagtgaaacc ccgtctctac taaaaacaca  69360
aaaaaattag ccgggcgtgg tggcgggcgc ctgtggtccc agctactcgg gactctgagg  69420
caagagaatg gcgtgaactc gggaggcgga gcttgcagtg ggccaagatc gcgccactgc  69480
actccagcct gagggacaaa gtgagactcc gtctcaaaaa aaaaaaaaga aaagaaaaac  69540
tcatgtaatt ggggagctcg tgatattggg aattagatta gtctcaaacc tgccctgtgc  69600
atatcgagta ttgagatata tgcaactact atatttcatt catggtatta ttttacgtat  69660
attccttatc aatcacctgt caaattaggt aattttatta cacacacagg tatttatata  69720
atttttagtg acacaggaca attatatatt atttcatact atcctcacac tgacagagaa  69780
gatatttgtt gttccttaaa aaatcaaaca aacaatagaa agcagctgag aatattgaga  69840
ttcagtcttg cccaaggtca cgtatgctca cacacagcta gaaccagtca cagatctgct  69900
cttcgtctgg tgctgtctac tctgattttc aaaatagtgg ctcctgttca ctctccccta  69960
ttttaatttc agagttctgg cagaatggta agaatgtaaa gaaaatggtt cactgctacc  70020
tctggtatac actttatctt gtaagaattt atggtagatg gtgttgggga acagtgcctg  70080
catggcaatt cttgcagcat ctctgctgct gtatatcatc ccattttctt atttgccaca  70140
ttgtaaatca gctttgcaaa tagccactca tacagggaag taacacttta ggctggatag  70200
tacagtactt tccaatttg tagatgtttt aggaagctat gtctgctgaa tatgccacat  70260
ttcttatcac tgtcatctca aaaccataat taatattaac cgagaaatga tgatcaaggt  70320
aatagtctca aaactctttg gcaaataaac aatgctattg cagcacaact ttgttaggca  70380
ggatgtatat aggtaattaa tacttttagg atatctaaat agctattctg tggggctgag  70440
gaagaaaaac ttcatcagga gagtggcaat aaaaaaaaat gatgcagtac agcaagatgc  70500
cgctgaaaaa taatctttgc agaaagcaga acaggcacaa agtacatatt tggagctcct  70560
tttaagaaaa gttttaagct gatccaactg agtataaagt ggagttgcat gctcagggta  70620
aggctctgca gaaagcattg accaggtgtg tgtttatggt tttcaaagct agaactagct  70680
actgtgccag tggcttttac agcatctggt gggtaggaac cagcatgagt catccgggga  70740
gcactggact agccggggca ccccagtacc cactaaagag ctgacctagc ctcttgcctg  70800
gggctgagaa gctgcatttg gtctagatca aggtcctagg gaggaactaa gcaggtggtt  70860
tgatctgaaa tacttgaact ggcacaacgt caagtaggcc agacaggtag ggcagaggca  70920
ggcatagcaa gagcaccatg aactggtgac ttagtagatg cctggcctca gttctttttg  70980
gctaagggct gctctgttgt tctttgcctt ttctgcttcc ctgtgggata gaatttgcag  71040
atctaagagg ttcaaaaagt tgagaaaagc cctgttacct ggaaaaaata tcatattctt  71100
```

-continued

```
agttccctag gaaaagtctt ctgattctga attagaactt gttattgacc tttgtcctca  71160
ctggtaaaat cattccctgg tgttagaaaa agtgaaattt gtgctaggaa aagaggagaa  71220
tcttaaaacc acggatgcat ctgtccttaa gcagtaaaat cctaacccga gagaatccat  71280
gaaatctgca gctctcctta ctttgccctt gactctgtca gctcgtttac ttaaaaaggc  71340
aatgtggggc agactgataa gatgggttcc ccagagtata tccactgcct cttcaacctg  71400
gctgcgggtt gacggtttat ataacactaa ctctgaatat gtggaactga cagttgtcaa  71460
attagtattt atacagaatt tgctccatat gtaaaaccag tcaggctcaa gttttaaaca  71520
atggacattg gttttatact ttctgatgct ttaaatgcca tcctagtata actgaacctt  71580
accttggcat agaattatgg taggataagc gccgggctac ttttagtgca cagtcattaa  71640
gtacctctca cgagataact ttatgattat ccctcaaggg aactgtgggt aagactattc  71700
ttccttttct ctcctgtcga gttccagtca caaattctca cagagaagag gcttaactaa  71760
aatttcattt tccccgtaag ttttgtacaa ctctgttaga gcttcagcat ttggaatagg  71820
ccccaaaacc ccctttaata cattcactga ccaaaagttt ctcttctctg catttacaaa  71880
atgaacaata agctaatggt atcatttctg ccagaaactg cacaagctga aaatatacat  71940
gtttaaaaaa acattttaga tacatctgag caatattgtc accatttgta aacatcatgg  72000
aagacaatta ttctcatagc aggtctcaat gacagtgaaa tggtcagagc cagtatacct  72060
gaaagttatg aagatgtttg agaaataagg ctttagtcaa tggcacctac tgaaagattt  72120
ctgagcgtgg aagtatatac aactaagagg aattaagaaa gatcatgtaa taaaatgagg  72180
aagaaaatcc tttatcactt ccccaccaga catttttatc attttatatg tttttccctt  72240
atgtagcact tggtaaattt agaattatat atatgtaagt gagtctttga agaatgcctt  72300
atttccgcaa ataaagtagg agatccacaa gggcaagaac attgcccatt ttcctcatct  72360
tgaatccccc atatactgtg tatgatgcat ggagcctgca caagatgagt gttcaattta  72420
tttttatgaa agaataaatg aattagtgaa agaatgaatg agtctagtag ataattagag  72480
gcttagacag tcaagaaagt aagtgcaagg gtgccacaga gagtcaaaag agttgacagt  72540
gaataatatg actgaagagt ttatgctctg tgccctgatt tatagcctgt tgagtaccaa  72600
tggccctgag tgcccaggta ttgaccatga ccagcaagca ttgtgagacc tgaaggtgac  72660
tcttttctct gattgtgttg gtagcagcaa gctgttatct tactctggat tctgattacg  72720
tactatgtat acagtaattg tgtaataggc caggtgagca ttaaacaaag gctgttttca  72780
tttcttaaac ttcttgtgca attctttagc ataagagatg acaaacaatt tggcagaaag  72840
tcaaatgctt taaaaatatt ttcgggatag tcattaagat atcattgttg taattcctta  72900
aagtttatgg taacttttaa ttgtatgttc aataggaaca aatccaagct ggcctatcga  72960
actggttggt tgtgtaatta atatacataa taaagacatt aaaggaccat cttagctaat  73020
aatagcaagc ttatcttcct taagtgggct atttttttcc aaaacaattt gcaacataat  73080
ttatttaggc tagtttatgt tcaccaaatt tctttatgta ctgtctacta gaagcaattt  73140
gtcttttctt cataggctta taaatttgag ttttaaagcc aattaaagaa aaaaatcaaa  73200
tgaactcagc ctaatttatt gaactaagag cttttacaga ataaaaaata tatggaattt  73260
tatgtcttac tttgtcttta atgactttcc ttttagtacc ttagacttca atgccccatt  73320
atataatttt tagaattgag ttaatacttt aactaataca tctatattta tcttctgtat  73380
ataatagatg tgttataagc tataagctcc tctaaacaat atcaaatatg aaatgttcaa  73440
cacaaacctg tattaaagaa tttgttttta cctcttgttt ggtaaagcat taaaaaaaag  73500
```

-continued tctcaatagt tttagaaaac atttattcaa ataccaggct agatgttgag gatatagtgt 73560
tgaaaatgta atcttaagtt cactgtgtat tgggaataca gataaagaag ccaaggattt 73620
cattacagtg tgataagtaa tataacagag gaattcacac aatatttaaa gatgagagca 73680
gagaatagag gcatattttt taacctaaaa attgactttg ttgtcaaaga agattttcta 73740
taggcaacta aacttaatgc atttcttgaa ggaaaagaag ataccagcca ggaggaaact 73800
cgtgtgtgtg tgtgtgtgtg tgtgtgcatg agagagagag aggtagtact ttgggtattt 73860
cgagtatgtg caaagcatgt gcaaagatat tctggcatca aatagcaatg tctcactttt 73920
aattctgtgt ggtatttagg tttagtaacc attgatgaaa agttggggga gataaacagg 73980
agacagatca tgaagaaacc tttaaaacat gctaaacaaa tggctcttta ttttaagaat 74040
aatgtggatc cactaacaaa tcttacacag aatagtcctt tttttttag gctacatact 74100
gtccttcaat atatatataa aaataatacg gcctccttta aaaaatgttg aagtgcaaaa 74160
taatcatttt ttctaagcta aagcaattgt aatctctgat aagattttct gaattaatct 74220
atcatatgat ttgtttaatt aaagaagtct cctttctttc acctacccct tccccaaccc 74280
ttagatggga ttattatatt atttccttgc agtcactcag ttgagaataa cagatttagg 74340
atcagtgtgg aatgtggata aagaaatctc agaatgacct ggggagatct gttagcaggc 74400
tcttgggtat tgcaggtaag agtgatgtgt gcctgtgctg acatagcagt gataggaact 74460
gagagaatgg gattggtata agagatacta tggaggttgc atcagtgaga cttggtggta 74520
gattgaatgg gggatggaaa gacagaatgg ttgatgttga ctgcccagtt tcttgctcag 74580
cctattgggt agatggtgac acatatcaca gtattttgaa ggggtatgga aaagaggtag 74640
aaaagatggt gagttcagtt gggtatctat tgacttagag atagtaatgt gtaataggca 74700
tatgaagata tgggttggag ctcagaagag atgtctgcta agcaattatg aatctgaaac 74760
tcattgctga acagatagtt gaagttacag gtttggccat ggtgttccag gacagagagt 74820
tgactggaat cagaagagta taaatcaaga aactttgggg aaaattccca tatttataag 74880
gagaaagagg aagataaaac ctgaaaaaaa ctgagaaaga gcaaccatag acataggatt 74940
caaatcaaga cagcaaaatt ttggaagatg ctgcaagaag taatcacagt gtcaaaagtg 75000
actgagaggt caagtaagat gaggacctac aaatgtccat tcaatttgga gttaaaaagt 75060
ccttggcaga cagattgcct catttgtaaa aattcaggtg acattttaat aattttatta 75120
agcaaaataa tttatcttga agagatgaaa ccaagccaaa ccaaaaaata ctctgatagc 75180
ataaaagcat ttcctttaca tatttttcta aatgttacaa gacactttgg tcttttggtt 75240
gaagagaaag gagagggaga gggaacatta tatttatggc attaacatcc ttattattta 75300
agtcaattat agattttagt aaatccatat attcaacatg acaaaatgtg cccctccaat 75360
ctatttcttt ctttttcatg gcagtacttg tatttctttt tataaattta aataataatt 75420
ctgagtgtca ttttctagaa tagcattagc gattctaggt tcataatata gagattataa 75480
tgtgaaatct aacaccatat taatgctttt ggaagaaggt aagagataat ataacttaaa 75540
aaataaacaa ttatagcatc ccttatgcag agaggctata ggtttcttca aggaaattag 75600
taaatttaaa agcatcaagg aagatttatt cccagagcaa ggttttttctc tctgatgcag 75660
gttttccagt ttgatcctta aacatgggaa gaaacataca tgaagtttga atctggtgac 75720
aagacaggaa acagaaggga aatacagaga cttaccagtg ttatttaaca gtattgtgaa 75780
caacaggcca acttctattt caaagtagag cgatcacaaa agctcaaaat agccttgggc 75840

-continued

```
agtacaggag agcagatgaa gcactgaact ggatgccaag atgaaatcaa tgagagagaa  75900
caggtgaaaa attgtcagca agagttacat tttgggccta ggaaagaatg tgacgattcc  75960
aaagggctac ccactctctg aaacaggatt gtatgaatta tatttcctag atatatagca  76020
cctgcagtgt ggatggttag gaattttgga gaagttaaat tgattgctta tttcattgta  76080
cgtcaatgca aacatttttc aatgaataga acatatctac aattaacaga agaaagttct  76140
agaaaatgta gcactcccta agtcagtgtc ttcttggtga ataagtagat gtgttcttat  76200
atccttgatc agcaacaccc aagggacaga gacaggactg atgaagattt ctattctctc  76260
aataagttta gcagagctga ttggagtcgt ctgccgtaga acatccacag agcaacgatg  76320
tatatatatg tcagtatatc tcagatgtcc tctaattcag attgtgaggg atggaagagc  76380
ttttgtttct ttagagtcag agggcacgct agacagttat gtgcacaaaa acattccaga  76440
aatcccccat ggcgccgtgt ctggaaatag taatttcttt gcttattgat ttaaaaatgt  76500
ctcaatctgg aaaccaatta gaatttttac gtaaatattt cagtaatcta gcattgtgtg  76560
tctgattcaa gacacctttg aaaatcactg caaggctggg tgagatggct tacgcctgga  76620
atcccagcac tttgggaggc tgaggcaggc ggatcacttg agcccaggag ttccagacca  76680
gcctgggcaa catggtgaga cccccatttc tacaaaaaat acaaaaatta gctgggtatg  76740
gtggaagggg cctctggtcc caccttctcg ggaggctgag acactcaggc atctcccagg  76800
atcacttgaa cctgggatgt tgaggctgca gtgagctgtg attgtgcccc tgcactccag  76860
cctaggtgac agagcgagac actgtgttta aaaaaaaaaa aaaaaaaagc aaatggatgt  76920
ggacacatac aagatttgga aatttgattg cgggcatgac tcagggaaat atgagattaa  76980
actctgctgt ggaaaatgtt caagtcctga tatttatgtc tataccataa tttccatctt  77040
gctaaacgtg agaatttttt aaagaactat ataaaagttg cttggaaaag cagcatactt  77100
ttctagaaag atgattaacc aaatgctaac caaacgttgt caatgaggaa taagtgattg  77160
ttcacatttc tgtgatcctt tgaaacatga taggaatatt taactactcc ataaaatttg  77220
tttcccattt tatatatgtg agagttgctg gaaacaaatg aaacaccatt ataaagtatc  77280
aaattctctc cttggaatga atcgattttc caccagagcc attgaggcaa ttccttagct  77340
cctggttgtc aaaacctggc ttcagagagt gacatctttc agaagtccaa ctcctacccc  77400
tcttgttaaa aaatattcac tgactgcata ttagttagta aataaccctc cctccatctc  77460
tcactgacaa aaaatcggac tcattttcaa attctttcca aaatgtcatc tccttcctga  77520
agtcttttct gaatcttttc aaccaaatat actctgtcct tcctctgacc tcacaaacta  77580
tctcactctt aactttgtga catttatttg tttaatttgt tcatttgcca cactattttg  77640
taacttcctt gaaggcagag tttcttcttc gggtttgtat tatctatctc attagatcag  77700
tattagattg atagattgat tgatagattg atacagagct agagagacag agagataaac  77760
aggtagataa ctcatgttcg aatatcttgt ttttagtgga attaaatttt agagaagaaa  77820
agcaggcaaa cataaaagga ttttgaaaga tagaagatac tttggccaaa aacatattta  77880
tcagcagcat acaaatgtgc ttacacatgg aggcattatg gcaacccaaa tacaaactag  77940
ttcttttttt gtcaacacat ttttcactat tgtcacagta gcttgtttac catatttttc  78000
tcttgactca cttgcctcct attattgggt cctagaatga tcatgttcct gctggataga  78060
gcaagacatg tttagaagtt ttgcttatgg aaatcaaagt tgttacaatt tcaaggtcat  78120
cttatctttg cactttaaat ctactattta gttcgtctta atctttagct tttgtctact  78180
tccaacctct gaaagtaatt ttgcctttca ttttgagctc catccctgtg tagagtttca  78240
```

-continued

```
gatgtctctt ggctctccca gtcctccctc taaacaactc acaaccctgg catgatcttt  78300
agtaagattc ttcttaggtt tttttttttt tttttttttt tttttttttt attaaagggc  78360
aaggtgggta ggggaatggc atagaagaac acatttggtt gtttttcagg gtacctaagt  78420
ttatgtaatt atcatcaggt agctcttgct ctttacatgg tttgatggtc gtttctctgc  78480
caagtggtct tgaagtcttg tcagggacac ttctgcttca gcaatgattt ctataggaaa  78540
gtgaagccca taacattcaa acttgggttt tttatcttct tgattactaa ttagctctaa  78600
cttccaatat ccacaaataa aacttcagag tcaagttaaa agtctttaat tgattacttt  78660
aaatttgaag ggtatgcata cttatttcca tggaattgca agatcaaagg ggatgaaatt  78720
cctgaaagca gtactgtgtc cctcaaatcc tctgatatta actgctctta aggatatggg  78780
gaaatgggct agtttgggat ggtctgtatc atagctctta ggaaataaaa aataagaatg  78840
gaggccgggc gcggtggctc acgcctgtaa tcccagcact ttgggaggcc gaggcgggcg  78900
gatcatgagg tcaggagatc gagaccatcc tggctaacac ggtgaaaccc cacctctact  78960
aaaaaataca aaaaattagc tgggcgtggt ggcgggcgcc tgtagtccca gctactgggg  79020
aggctgaggc aggagaatgg cgtgaatccg ggaggcggag cttgcagtga gcccagatcg  79080
cgccactgca ctccagcctg ggtgacagcg agactccgtc tcaaaaaaaa aaaaaaaaaa  79140
aaaaaagaat ggaatagatg cttcaaaata cattaggacg aaggtaaatt acacatttaa  79200
aaacttagat gtgtgtgaga atgatgtttt taacaaattt taaaaggtga ataagtaaaa  79260
taaatttaat tttgaaatag ttctacattt ttttgtaaat tatttcttcc atgatgattt  79320
agagggacta tcaacaaacc agtacaaata tttcataaat aatatctgcc tgttttctaa  79380
ccaattgagt aatttgttgc acaataagcc acttcacatc tttctgcaag taaaacatta  79440
gctgtgaata gtaaagacat tacacaatga attagggcac aattaaaatt tgatttaaat  79500
atttctttag gggagggaac accacacttc cacttaatga aaagaaacat ttttagagtc  79560
cagaggtctt ttgcttcttt tacacctatt atgccctgac tgcatagggg acaggttcca  79620
gcagctcagg ctttggttct cacaaagtat gtttccctgg gtggagcagg ctggtgcttc  79680
agttgaaccc aggaaccttt ctctttggct tctttctctg accattttcc tttatgtgtt  79740
ttaggaagcc gtctcggcac ttagagtgct taatatgctc aatatgcaca tgaattccct  79800
tggcaagaat cttgtcctta acttgtttac aacactgcca acagcatgct gggtaacact  79860
gtagattctt ccaattttgc catggtaata cttgtgaggc attccttttt gaacaggact  79920
cattcccttg atgtctacag tatcaccttt cttctaagtt tgcatgtaca tggccaaatg  79980
aacaactccc tgttttccaa atagactgga gaacatgtat cagtgcctat cctctttccc  80040
tgtgtgttca tcattttggt gaattactga aagatggtgg ttctggctga aaggctaatt  80100
ttttaattta aaaatttcta atgattctac ttttaataat ttctaattaa tttctaaaaa  80160
tcaattgtat agtattaagt aaatttcact tttcagaaat gatctaaatt tgtttttgtc  80220
taaacatacc aatatcataa tttcagattc agattgattc tgtttagcaa gccatttaaa  80280
atttgcttgt agttcccggt aatagtatga gaaggcaact tcttcttatt tatttatcca  80340
aatttgcagt actattcaat tcatacagta tttactcata tcccatttta gttttggtta  80400
atttctcttt ggagaaatat gggagacaat gaaatctcac tttggaaaag aaaaagagaa  80460
actaattctt attcagtacc tattacatac caaccactgt gtcagatact ttaatctcac  80520
aactattctt tgaggttgca aaagttttgt gcatttttat acggtttaag aaataaagta  80580
```

-continued

```
tcaagaagtt aagtaactaa gttgcaaata acctaaatga ctcaaagcta atggattgag  80640
taaacttttg tacattcatg tgttacaatg caaaaaagca atgaaagatt agtaagtatg  80700
ttattatttg atatcataaa atgcctacta gatattgcca aatttaaaaa atagtacaca  80760
caaccattta tatgtatgta tatgggtgtg tatacacaca catctgtttt ttaaaaaata  80820
aagacctaca tacaacacaa gactcacaga atcacataaa ataaaaaaac cacattaaaa  80880
cagagaaaac tggtaaaagt tgctttagca cttatatcag ggtagtgagt tacagatgat  80940
tttcattctt ttgtttattc actctaaatt tctgacgatg agtatatctc agctttatat  81000
tttaaaaaag caacgtatca tttaaaaaat acgtattcca atgttacaca gttgtaaaca  81060
ttagagctca gctttgaaat ataaggttat attctttcct ctatgatcaa agatagacta  81120
ctcaggccta aagaaaaaca ctcagatact cccgtgtggg ggctgggga cagggagaga  81180
aagagagaga gggaagaaag agtcaaagac acacactcac acacacacac acgcacacac  81240
acacgggggg gcggggtgga catagagaaa agagctttca tttggctgtt cttgacgtta  81300
gaccaccttc actctaatta ctgactgtac agttgtaaaa gcccttccca attacatata  81360
aggatatttt tgagtcctac tggttgctgt tgcaaagcta taaagatctt cataattacc  81420
ttcaggcagt taaaaattta gagatccaga gaggtctagg tatagattct tttggaatag  81480
cgggccagct gaaattgtta ggtggttatt attcagtaca agggaatttg gctcttcctg  81540
tttaaatggc aaatttaacc aatgcacaga ttagaagact ccaaaccaaa tcaattgtat  81600
atagagaaga acctagaaaa aagaaaggaa tccatttaaa cagcagagga ggtatagtaa  81660
ttgggcctat agatcacagg cccaactagt aagattgtat tactaagcca aaatcatcaa  81720
taaaagaaaa taaagccagg tgactaagtt aaggtctagt atgacaatgg tcatgaatca  81780
acacaaataa tcttggcaca aaagtttcag gacaggctgt ccaaaagcag ctgagtagaa  81840
gattcaagta aggttttatg tatggtatgt tacgctgatc ttcctccctc gcttacttcc  81900
ttgctttctc tttccctcct tcttcctatt cctccctccc tcccttcctt cccttcctta  81960
acttccttct ctcattttcc ttcttttaca aaaataatct ctactgcata cattgtttga  82020
agcacttata atgatgaata agatgtgtct ctcacctaaa aagagtttac agaatatgtg  82080
tgttgaggtc ataggttaat atttgtgttt acttattata tcttgagtac tcatttgcag  82140
tgttttagtt gttcacaatc taacatatgg atttaatgct gaacatgtgg ctcctgctgt  82200
agaaagttat gggcctttgg gcagaaaccc tactcctgac cttcaaactg aaatggatgt  82260
cctaaatgat gtaatgtgta tagctaatga tgttatacag tagaactcat ttgtaatagt  82320
ggtattgaga aactgggcta atggccacat gtagacttag taatataatg agagaaattc  82380
atgatgaaac tttaagtaag aggacatgat ttttcttcca gtataactga atctttgcta  82440
ttatgagaaa tattagggtg aaatttaata gaattacaca aaacatattg aactactgtt  82500
ggaatagtat ggaatgtgat atcaaaatca tgcttcaata gaatacaagt ttaggcttga  82560
aatatattat atttcaagtt gaaattcatg acagctgaat aagggatatg gtattgcctt  82620
ttaatgagct aatttcttcc caattttaag agtgaccaaa ggtcagccct tttggattgc  82680
acagcacaca cttgtaagaa acccttataa atcatcctta tgttcaagtg caaggcaact  82740
ataacacaag cccatgtatt aaatcaaaag tgcctttcag aatatgagag agagacgcaa  82800
atgttcacag taacagtatg ctaagggctt tatgaaatag aaaattaacc ttggaagttt  82860
ctcagtggac aaggcttaga taaaataaaa aagttattcc tttggtatgc ttagaggata  82920
ccaaacaatg tagaacaatt tgtattttaa tgtggaagtt gttccgtctt gtttatttct  82980
```

-continued gagtgtcagt ccttctgcct tatccccatt attttcaaaa ctgtaaacta catacagcat 83040
ggctctaatg aatcaggttg acagggattg ctaatgcatt ggaacatttc tgaatgttca 83100
gagaaatttg aatttagtaa gtgccatatc tgaaaccagt acagaacctg gggtggata 83160 gttggtattg gtgggtggtc agaatttgac acccatcccc aaacttcaaa agggatttag 83220
agaagtattt ctaataagac tgaagttaaa aggatatgac aatgggaata ccaattggtt 83280
taatcctttt gaatggcaaa ttattattaa gaattagcta gcattaattt agtactttct 83340
atatgccagg aactgtatta atttatttat atataattta ataactgaat tacttactat 83400
gtgtaaggat tcttaaaagt attaatgggg ccaggcacgg cggctcacac ctgtaatccc 83460
agcactttgg gaggctgaga tgggtggatc acaaggtcag gggatcgaga ccatcctggc 83520
taacacagtg aaaccctgtc tctactaaaa atacaaaaaa ttagccaggc gaggtggcag 83580
gtgcctgtag tcccagctac tcgggaggct gaggcaggag aatggcatga acctgggagt 83640
tggagcttgc agtgagctga gatcgtgcca ctgcactcca gcctgggtga cagagtgaga 83700
ttctgtctca aaaaaaaaaa aaaagtatta atggtcttga cctagtattt ctatatccag 83760
gaactcatag taataattaa tgacccatat aaagaattat gcactaaaat gtttgcttca 83820
gcattattta catagcataa agtctgaaac aaatgtccaa cactgaagaa tgcttaggaa 83880
aagttacata aaggatatta tacagtcatt gaaatcatgt ttgcagtgaa tgcttaatgg 83940
gaagatgatc tccatgcaat gttaagagaa aaacaaagta gcacgcaaaa tagtatatat 84000
aaaatacttc aaaatataat aaacaataaa cattggaact tttataaaaa gacttagagg 84060
agatacagca aaatatcaat tgtggttata tctgggtaat gagaattata aataatttta 84120
gtttttaaaa tttatttctg tattttccaa gtttttttaca aaaagtttac atcaagtata 84180
taatttgaaa aataagctta aacattttct gggtgaaaag aattcctggc ttctctacag 84240
gcagattccc ttcacacatc ttcctgccca actactgtgt cagtgggacc cctgctcatg 84300
tgaatatttc tttgtgccag tgtttgggtc tccaggctag agcaattttc ttctgggctt 84360
tggagcattt tgtttcctac ctcttagtaa tccaccccca acagttgact cctggttttg 84420
gcatccaccc tttcatgaag ccatcctcag gttgaggtgg ttaaaccatt ccattccacc 84480
attagttgct cactgccaca ctggctggct tcatgcttta gtgaagctag taaaacctca 84540
agggatgtat caagtatccc aaaatctact taaaaaattt tgggatgacc agggggcata 84600
tttagccatc tttagctctc agaatttcgg ctacatctct ctaccaataa tcctgtttat 84660
actgaggact ttactgataa gatgggttac aagaatgttt tcatgcaagt ccctaggact 84720
cctcggtaaa ttaagggtat gggactttgg gattaaaagt cagttgctct cagagacgtc 84780
ggagcattat agatactcaa gaagtatttg atgaaggaaa gaatactagg ggtgataaag 84840
gtagtcttta atatttttac taatcaaaag aataagtatt atttttcaga aaataggagg 84900
tgggaaagac atatggagga agcagggaaa tcattcagag gcagggaaaa ttgatggaat 84960
aagtgccgca ttttgggaca gatattcagg gttaataagg aaaattaaga gaatagtgtg 85020
atatgatatc aatggacatg cagataactg atatcagtcc tttaacaaag gaaattgcaa 85080
attgtttttt caagagtttc aaagaggtac aatttttatg gcctagacct tctgtggctg 85140
actgtcatag gtgaataatg gctgccccaa aatatcaagt ccaaatcgtt ggaatttata 85200
aacgttatct tctttgaaaa aaaggtcttt gcagatatta caaagttaag gattttgaaa 85260
tgaatagatt ctaccttgga tgacccagat gagctttaaa taccatcaaa agtgtcttca 85320

-continued

```
taaaatagag gccgagggag attccacgcc gacacacaga ggagacaaac agaagaggag  85380
ggtgcaatgt gaccatggag acaaaaattg gggtggcatg gccacaaaac aagaaacact  85440
cggagttgcc caaaggtgga agaggcaaga gcagatactt ccctggatcc tttggagaga  85500
ctgtagtcct actgatgcct taatttcaga ctttgggcct tcagagcagt gagggaacac  85560
attcctgttg ttttcggcta gcaaatctgt ggtaatttgt tatggcagcc ctagaaaaca  85620
cacacagtga ataaaataac tcttgtgtgg gaaaacagcc tcattctgat tggttgggga  85680
ggaaagtgat tgccaatagt gtacctgtaa gacggtagaa ggtgaaatca gctgtaaagc  85740
gtaggaaggc agtggtggta ggtgtctagg agtacggtgg ccacaatagc atctgctatt  85800
gtaagagcac tggggagtga aggtgggaga ataagagtgg aagggtcact ttcctgagtg  85860
ccctaatccc tcttttagtt gacacatcag acctagccat ccagatgaga tgacattgtt  85920
ctatttaaaa gactgggtgg gaactggagc caggatactc tgtggggtta tttatccaaa  85980
tccggggtta ttattcaaaa gtgcatggct gggcaaatag gtttatgcca tagtttatca  86040
agacggaaac caaaagaaag aaagttgcca aattaatttt tgggggcttg aagaacagtt  86100
gtttgtaaag aaatggttta aattacagat taaaaaaaaa acacacacaa aaatccgtgc  86160
tgcttcaaaa ctcaaactag actacctcca caagcattcc ttcctcaaag ccaccttgta  86220
gacaccagac ctagtaaatt tacatttgac agacaaatag gaaacttttt catgttacac  86280
aaaggcaaca ttataatcta gctgtcaggc cttagctcca ttgatgcact gagatgtggg  86340
ccagatgaag ataattcagg gaatctagct ccagcgagag tttcagggag ccctccctca  86400
gttagttgat atcccaaacg cttatcacaa aagcaagaga aacttgataa cgacctggca  86460
gtggtgacca gacttattct tcctagaaca agaaagtgat attcagagat tgacataccc  86520
ttaaaacgat caaaagggaa aagcaaggtt ttctttttag aggttcaagt catgctgagt  86580
ttggtcagat agtgtgaggg gcccagtcga gtcacttgtg agggtatata aaataaagtt  86640
gggaaacaaa ggaaacgagt gaaaagaatg aggtatttat tcactaaaag gaccaatgaa  86700
accgatcccc tctaagtgta aaaggaggag tagagattac tgtgcctgtt gtttaaaatg  86760
tgtggacaga agattatttc tagaggacac ttagtatata tttaccatgg tatgcatcaa  86820
aggcaacaga attttgttac gtcgcttacc ataaaatatt agaataaaaa atcaatattg  86880
atgtttctgt tttaaaaagt aatacatgtt cattatttaa aaaaataaac aagtgctgta  86940
ataaaagtat atagtatgga gggcgacatt ctcagagata cccacttctt ggtgtcagcc  87000
acaattaact gtttggtgta caaaatcaca gaaataaggg ctgataaatt tgtagatgct  87060
gtctaatcca attcccttat ttcatagtgg aggaagatga ggcacaaaca gggctacaag  87120
gctactgagt tactgaagat tgtccagtta gttagagaaa gatgctggtt tgctcttata  87180
ttacctacag atacagataa ttttattcac cttttttttt tctgttgagc tatcagggaa  87240
acacatccta gatattcaga accccctact aggttgacta aaacaaagca aggaaggaaa  87300
ttttaaaaat agcagagggt ctctaaagac agctgcttga ggtaagcaaa tgaacaggtg  87360
tttatgattg aattattagc ctcaataaat tgaagaaaac accatttttt tttcaaactt  87420
gaggtaaaaa cacaataaca atagagaatt tatcactctc cagaactttc tgtgttgaat  87480
acaggagtat atttttagct ttttctctag gaaaacggct tccagtttct gaatcatttt  87540
ggctaatttt tatatgcttc cgatctatcc tctgcagcac tcccgcaagc tgcttatttt  87600
gtggcaaata gtagcaaaca actttttatt tttttcagag atatccagaa tttcgccaaa  87660
tggtgatgtt ttttcctcta aaagagtcct tgtgaaaatc ccttacttct gtctaataaa  87720
```

-continued

```
tgccatattc aatatttact ttctccaggg acgattgttt cagtactatg aaaatctcag  87780
aagagcaact agagtcattt aacctactct taatctgtcc taatgccatt tctctcttaa  87840
acgtgtctcc attttttttca gaattgtatg cctcttagtt tttcaaagca gtgagtaggt  87900
tgagcagaga aagggccaat acagcatttg ttctcctcat actgctgagc atagtcatca  87960
aaatgtccta agatatgtgt atgaataatc atctaagaat atgtgtatat tctgtgttca  88020
tatagaacac atttatatac gtacatgttc tctgatacat atagggttct caatttttga  88080
ataggaaagg gacttggact ttgagatcta tagatttggg atcaaatatc aacttctact  88140
tcatggctat gtgatcttgg aaaagtcatt tagcttctga aatttagttt tctcacttac  88200
aaaatgagga taataatgac tatcttaagg tgatgttaca aggattatat atggtaatga  88260
cataaaaggt ctgtttgata aatgcttgat gtatcagtgt caacaaatgg caattattat  88320
tttctcatat aatcacatat attttcaaaa aactaaacaa tactgcctga aaatattcat  88380
catttgccct ttctgtcatc tagaaaatgc tacttctttt agatcatttg caaattgtag  88440
ctttgttcag tctttcccaa acttacactt tctcccctgc tccatatttg acagctatag  88500
ctgctctgct attatcactt tctggctcct cttgttcatg catcatttca gattggattg  88560
taacgtgctc tggaaccact tcaggtattc tgccctctgt gcaattgcct tagaatcaac  88620
ttctcccaca attagttgtc actggttaca tttttatcgg ttaaccaaaa tgcttagttg  88680
aacatagatt aggttgtcat gcctctggag agcctgcagt tcagaacttt tttactggac  88740
actttctctt gtcacttgat gctaagagga acatgtcaac agtgaaactt atctgaaagc  88800
tgaatatgaa gtaactgata gacttaggtg tcacattata tagtagacag tagtgttgct  88860
tgatagaata ttgtttgact ctatgccaaa aggcacactg ggttcactat agctgtctaa  88920
cttttcccat atcagtatgt catttagaag cttgctaaaa atgtagcaag aggccaggat  88980
tatttttagt tggaaaagct tcatttactt ctcacaaggt aaatagatct ttaataactt  89040
ctttaattta gtcttgtttt taacacatga aatgggaata aatattcagt gatttgaatg  89100
atggattctc tataacaatg aaatatttaa atgctcttac taggagcagt aatcgaccgt  89160
aacgtttctt tttgacactc acaagtattt tctgttaagt gggagtaatg tttttaaaac  89220
taaacataaa atcacaaaca tagagcattt tcaatttgaa cttttaatac ttagaagtga  89280
gcctttattc agaaggctca tagaagtatt ttccttaatt gttgcatgca taaggatctc  89340
ttctaaatta acattaattt tatgattaat tttgaaacag aaatctaatt tttactcact  89400
ggcatgaaat gtttcttgga acaggaaaga gaaatttatt tttgtttctt actaactcag  89460
tcatcattta atgccatctg atattaaata ccatattttc aacaatctaa aatgaataat  89520
ttacaaaata ttttaattat attgttatga tattaaatat ggtaggctat gtatagtaac  89580
acaagctcac caataatgaa tttgctgaga ttaactgtga aatctggttg agagatatgc  89640
ctgtggagga ttatcctccc atggtaagaa ccatgaaggt ggttcattca tttgactaaa  89700
gctttgagct catgcttatg tggtagacca cttttcctcc atttcttatc aaaaaaatgt  89760
gtagccagag gaaaacagta ttttcaaata tttcttatag tagattaaga caatagttgc  89820
tattgtttgg atgtttgttc tctgcaaata tcatgttgaa atttaattcc tagtgtggca  89880
atgctgggag gtgggtccta ggtcatggga cacatcctgc atgaacagat taatgttctc  89940
tcttggtgct gagtgaggtt tcactttatt atttcccata agagctggtt gttaaaaaga  90000
gcttagcacc tcctccttct ttgtcttggt tgctctctgt acatctgatc tctgcacact  90060
```

-continued

```
ctggctttcc ttcaccttcc agctagtgga agcagcctga ggccctcacc agatgctcaa  90120
tcttgaatgt tccagttcca gtcagcaaaa ctatgggcta cataaatttc ttttctttat  90180
aaattaccca gtctcagcta tttctttaga acaacactaa gcagactaag ccaatagctc  90240
ttctatttcc tgtatgtgta gtgcttgaga atagatcatt atgtagcaaa aattcctgat  90300
ctttgacttc accagaactg acggaggtgt attttgttgt tgctgttatt tttctccctt  90360
taaattgtct aaaggactat ttatcaatca atttctggcc atttcaaact tgtcgtattt  90420
tactgtatgg gtaggtttta gtcaggaaac cagaagccac tctggatatt cagataggaa  90480
gggtttcgat acagtaattg taggtataat cattgttagg gctgcagagt gaagatcagg  90540
aaagtctccc tgttgagtag acctacagag cattctcaaa agttcatctg gaagctgctg  90600
tgaatcttaa gaatcaacat tcctgctgcc tgagatactc aaagtggctg atttgaaagc  90660
tgtcatgcac agaagctcat gcctgcatgt gcatatttcc ttaattgttg atagaaaaga  90720
atgctttttt ctgctttgat acccttacta caagcttgct tgtcatttgc agagtaatct  90780
gtagccatcc agttaaatgg gtactgggaa gggagttttg ggtttctctt tgttgaagta  90840
gacaaaatga taaaacaggc acagtaatga tgtcaagttg aagacaaatc tggcatagcc  90900
atgttttgtc aacctagcat tcgtatatac tcttctaccc acattctaac ttcaaaaaca  90960
accatccaac ttcatgcttc cacatgatat gatctaacta tgtcttatcc agccatatat  91020
acatatacat atatgtatac actctctccc tacaggggta gacacaaagt tctataaatc  91080
actgtatgct attttggggt gatgttcatt ctttttctaa ctcagttcca attctccttt  91140
ggtatctttt aacttataga ctaaattata aggtaaatct ctattaatac acttcgcatt  91200
agataaaaga tgaggatggt ggcaaaaaac tggttaatat atgcaactat gtacatcata  91260
aatcagaaaa ggaaataggc ttagctttca catgcttcgt ttctacaagt gaataagagg  91320
ccataattgg tctttacgat tttgctttct ccctatccat ttgatttgtt ctcagtgggc  91380
gcgttatctg gtcatggttc ttcacttgat gggatgatgc aaaacctcat ttttgaaggg  91440
ctagagccac tagtagcctt gcttttttgg gttgctctac tcctttgcta accttttaca  91500
ctagatatac aagtactgag gggcaatcca gagaatcctt tgaatcctct ttgcctttat  91560
tatgcagcag caactctatt tctccttgac aatcaatatt attcactccg gttagtacag  91620
caagcccttc tttgactgtt gccttagtgg catgaagaat tcaaagtgat agtttaaatt  91680
tcacattcag tagaatcatt gttaggtcca ctagtgtaag cattcatttt ttagaaatta  91740
agtcctctaa acctgcagag ccaaaagtgg ttaagagaag tgatatggtt tggatcttta  91800
tacccaccca aatctcatct ggaattgtaa tccccaggtg ttgagggagg gacctggtgg  91860
gaggtgattg gatcatgggg atggttcccc catgctgttc ttatgaaagt gaatgagttc  91920
ccgcaacagc tgatggttat aaaagtgttt ggcagttccc cccactttct ctgtctcctg  91980
tcgccatgta agaggtgcct tacttcccct ttgccttctg ccataattgt aagtttcctg  92040
aggcctcccc aaccatgcag aactataagt caattaaacc tctctccttt gtaaattaca  92100
ttgtctcaag ttgtatcttt agagcagtgt gaaaatggac taatacaaaa agcaaatctt  92160
ttgtgattgg gtctttaaga ataacagaga gaggaaccac tcccattccc acttcttggc  92220
tcctttatcc atgtcttctg gccatgggaa aagatagtgt catgttgtca tattgtttgc  92280
tagttcagaa catatatgaa atctttcagg acagcacata gccaaacaag gtattattac  92340
ttagccagca cccaaaatga gtttttaata gggcattcca ctgttatgtc aggcaggcca  92400
acttgaggtg atgtggtaca ctgtaagacc aataaattct acagatgtga acatttccct  92460
```

-continued cattctttgc tggtcaatgt gttctttggc caggagcaaa gttatatggg catcattaaa 92520
gagaatcagg ctttccatta gcctgtggat actggtactt tacaaaggca gagcagacag 92580
ggatggcaca ttcatatcta ctgtgtttat tctggtaaaa catgctgttc tttcttccat 92640
gatggaggta gtcaacatgg ctagcagatc ccctcaagaa tagtgccaca gaaggaaatc 92700
agcatcaaac tcagctgaca acatactatg tttttagcaa ctgtgatagc tagaatagtc 92760
ttattgaaga gaagaccctg cttttgagcc catgcatagt ctctatcact gacactttga 92820
ccatttttatt tatgagccca ttggtcaagc tcaaatggct gggaagaggg tggctaatat 92880
tcacagaaag cgttatctcg actttattat tcgaaaaatg ccttgcagtt gaagcctgtt 92940
tgtgagcaat tacttggggc acaaaaaatt tcaaactctt accattccca gaggtttacc 93000
atttcttact cagacctttg tgttatcaat cccttatttt attttcttca aaatccggag 93060
aaatgagaaa accactttcc attgtccagt gtagatatgg catctctttc caaaaaagaa 93120
aaaaaaaatt gaatgcagtt ctgcccacta gaaagatttc ctttttcccc aatccttaac 93180
ggccattaca tagtgggact gaaatgctac atggtacaag actattgtgt ggacatatct 93240
acaaaccagg actgatttgt tttacctcag tcacttgatg atgaactccc cctgaggtcc 93300
caaatgtggt gtgtggtata gttgtcaatg caagcttttg atgccaaaag ttcaaatttt 93360
gccatcagtt caaattctac cccatatctc atgtttctac tctggctggt gtgaagggca 93420
acttatgcca aacttatgtg agcttgctga atttttctct atagcacaac acacctgtgc 93480
tttcaggact aattgagctc agttgcacat acgccacttc agtttgataa tggaatgctg 93540
ctatacactc tttaaaaaat taaatcaatg ttattgagat ttaatttaca taccaaaatg 93600
cattcatttt aagtgcagaa tttgatgagc tttggcaaat gttctccctg tatgaccttc 93660
acgaaaccga atatatagaa tatttccttc attcaaaaat tacccagtgc ctttttgcag 93720
tcagtacctg cacttattcc tgccccaaac aaacactgat ctgattttta tcactataga 93780
ttggttttgc ctattctgga tttttacata agtggaatca tacagtgtat agtcttttat 93840
gcctggtttt atttcactat ataaagattc tgagattcat ccatgctgtt gcgtatatca 93900
gtagttggtt ctgtttcact gctgagtagt atcccattgt ttgaatatat cacaatttgt 93960
ttacccatca ctgtgttgga tatacttgta caagttcttt ttttttaaat cttttttttt 94020
attatttata ctttaagttt tagggtacat gtgcacaatg tgcaggttag ttacatatgt 94080
atacatgtgc catgctggtg cgctacaccg actaactcgt catctagcat ttggtatatc 94140
tcccaacgct atccctcccc tcccccaacc ccacaacagt ccccagagtg tgatgttccc 94200
cttcctgtgt ccatgtgttc tcattgttca attcccacct gtgagtgaga atatgtggtg 94260
tttggttttt tgttcttgcg atagtttact gagaatgatg atttccaatt tcatccatgt 94320
ccctacaaag gacatgaact catcattttt tatggctgca tagtattcca tggtgtatat 94380
gtgccacatt ttcttaatcc ggtctatcat tgttggacat ttgggttggt tccaagtctt 94440
tgctattgtg aatagtaccg caataaacat atgtgtgcat gtgtctttat agcagcatga 94500
tttatagtcc tttgggtata tacccagtaa tgggatgggt gggtcaaatg gtatttctag 94560
ttctagatcc ctcaggaatc gccacactga cttccacaat agttgaacta gtttacagtc 94620
ccaccaacag tgtaaaagtg ttcctatttc tccacatcct ctccagcacc tgttgtttcc 94680
tgacttttta atgattgcca ttctaactgg tgtgagatga tatctcattg tggttttgat 94740
ttgcatttct ctgatggcca gtgatggtga gcattttttt catgtgtttt tggctgcata 94800

-continued

```
aatgtcttct tctttctgta aacaagtatt actaattttc ttgggtaaat aagaattaaa  94860
tgactggttt gaatgttctg ttcatgtttc gctttacaag ggactcacaa aatgttttcc  94920
aaatgatggt tgattattcc caccaacatt atagtagagt tctaattgct ccacattttt  94980
gccagtattt tgtattgtca gacttttaac tttagcaatt tctaacgggc atttggtgga  95040
cttaattttg atttttctgt tgattaatga tgtttcatat gcccattagc aatttatata  95100
tctttctatg tgatgcatca gttcaactct ctgtccattt aaaatttgat tgtttttctt  95160
attatttagt tgtaagaggt ctttatatat tctggaaact aatcctttgt cagaaatttg  95220
tactgtaaat gtttactccc agactttatc ttgccttttt atttttgtca aagtgtcttt  95280
caaagggcag tcatttttaa tcttgatgga gtacaagcat cagtttttct tttacgttca  95340
tgctttctac atagtatgta aaaataacac aaaaaacaat ataaacagta tagcaaggtc  95400
acaaatattt tctactatat tttattctag aagttttaca gttttaactt tcacacttag  95460
ggctatgatt taagttaatt tttatgtatg atttgaatta agcattaaag cttattttta  95520
ctttgctatt tttatctctg gtttgagtta ggtcttcttc atatcatcca tgtttctatt  95580
taaaatgctt aatatttcct ctattaagct taactatcct aacttaactt aactatccta  95640
acttaactta actatcctaa atatttaggc agccaacatt gggccacata aaacaaattc  95700
ttagagacct ataaagagac ttagataacc acacaataat tgtgggagac ttaacacctt  95760
actgacagtg ttagacacat cattaaggca gaaaactaac atagatatct gggacctatt  95820
ggttcttgaa cacctggata gagttgtaat aactgtttta atgtctttgt ttatatgttc  95880
tatcatcttc ataatttctg ggtcagtttt gatttaattt tttctcttcg ttatgagtct  95940
tattttcctg ctttttatg tttgtatggc agactttgtg aaatttacct cattgagtga  96000
tggatatttt tgtattacta taaatgttgt tgagctttgt tctgggacat agttaagtta  96060
ctcggaaaca gatgggttct ttcaggtctt gaatttaatc tttgttaggt gggattagag  96120
cagctaattt tgtcacgcta ctgaagaaaa gccattatgc atatactact caatgcccca  96180
ttttccactc tgactagtgg gtagagaaac tattcttggc cctgtgaaaa ctctgtaaat  96240
tttctcctct aatccttttg ggttgttctt tttccatcct cagagagttt cctcacagaa  96300
ataccctgat taatactcag ccaaagcctt gagggaaggg agatcctgtg aagatttctg  96360
aatctctgtg taactttccc ctctggtact ctgaccagca aaatgtagct ttctccaaag  96420
agacctgagc agtttgtcag ggattagagt atactggctc ctgagtggtg ttagccaggg  96480
aaatgaaatg ttttgtggtg atgtcaatca attttaaggc atcatttcct cattgtcaga  96540
catatctctc acataggcaa ggaagctcat gtcagctgac tagacatcct ctctccagga  96600
caatggtgga gattccctgt gaatctagcc ctcttggtct ccgtttcctt ttgttgcatg  96660
ccaacatacc cctgcttgat aaaccctctt tcttttgtgg taagtttgta gctctctcag  96720
tcccagtgac attacaatct ttgctaatta gtcatctcac ttggggtttc caaaactctt  96780
tattcacaaa tactgatagt cctatgagtc attcttatat atgagtaatt cagtaatttt  96840
gtgttgattt ttaccagttt tatctcaaag atcaatttca ttgtaaatgt tgtgactata  96900
attactgtga attaagaatt tttgaacata ttcctattta aaaaaaaatc tttgctagga  96960
ccatctatct tatttgtatg agctccttta taatctagat ttttgggtat tatttatttg  97020
ttaatatctt ctagtttgac cttgccctta ttttggttct atttcattgt ccatagaatt  97080
aaaataattt tttttgtggt ggattggtcg gtgaggggag gcagtggcag acagggtctt  97140
gctcttttgc ccagggtgga gtgcagtggc tcaatcatag ctttgtaaca tcaaactcct  97200
```

-continued

```
gggactccat acatgcacta tgactggcta attaaaaaaa ttattttgta gcagtggaat  97260
cttgctatgt tgcccaggct ggaacagaat taaaattcta atatagtaaa aagtataaaa  97320
tctttacatt tattgtttct tctctttaat gtatacgaat gaattaatat ttaatctaga  97380
gacctgaaaa gcattaaatt ccattttctg gtagattttt gaatatatat tttatttttg  97440
tagacatatt agagtgttgt tccgtctctc atatttttct ccttcctgac tactcctctc  97500
atcacttggc taatccatag cagcatgggg gtgggtccat aatagccctg ttggcacaat  97560
ctgattcttc ctctttgatg atggtttatt ttaatccagt gaccatctga atcaagatgg  97620
cctaattagc attattttcc tgggacttta aatctgggct gtaaaattta aattgaaaac  97680
aaggagagtc acttgaatga ataagatgta atcttaggac actgtagaag agatatctta  97740
gttatgatat cactggggtg ttcagagaaa gaggtgaata aatgaactta atgctcagta  97800
agaagcagaa gtgagaggag gaagggaatt tcctgggatt tttatgtctt ctgcttccta  97860
gttccagtgt ttctctaaaa ccagcctgca tttctgttct tggtcattaa taaaatgtac  97920
ttatatcttt ataataaatt ctctctttca cttactttag ctaaatttag tttatagtac  97980
ttctaattca ggagttttaa ctaataaaga attcaagttt tttccctttt ttgtaataag  98040
tttggtgtaa gctgtcagat ggagtatcca acattcaccc taagagtagg aactagataa  98100
attatatacc accttctggg cagcatatga aggcagttca caaaagaaag aggctgaggt  98160
caaggcagaa gctagttttg tatattacta ccagatctta taatttctaa gacaaaagaa  98220
attaagcttg agctaggtta gaaaaccgtg ggagagactg gttaagtatc aatacctagc  98280
ctggagaagg ggcagacaca aaatggaaga gtaataagag aagactggaa ataacactta  98340
gttaaactag ataatccata cagaatcaat ctagaaagag tctcatgatt aataagttta  98400
gttaatcctt tattttttttc atttagaagc tatataggca tagggtactg gacaaaaccg  98460
gcatatacag cagaaaccaa ggcaaacaca gcccttccat tatggagctc acattcttgt  98520
gggatggaga aggaaggtat taaataatta agtatacatt tattcattca ttattactgt  98580
aatgagtact gttaaggaga accattaaag tttaagctga aggaacttga ccaggtctgg  98640
gtgacaagga atgattcttt aagaaagtga aataaagtat ctttgcatat attttctagg  98700
ccagatgttt aaaatagtag acttgttcca gtgggcatgt ggattttttt ttaaaatcac  98760
tttataatta cttgtaacaa aaactggtag aaatgcaaaa gtgtatggat ttaaatttct  98820
gtgttctttt ttttatgcct ttgacattaa ttttcttctt gaaataagtg ttagtcatgt  98880
gacttaaaat gcagaaaatg atacacattg tctagctttg tcagagggat gcagtgagtg  98940
caaagaatta tcttgcctaa gaaatctaac atcctaaatg gaaaggcttc aaatatcaaa  99000
taaacccgat gctactttat ttgatacctc cttacaccat ttcatttagg cttttctttt  99060
ttctgcttcc taactcacat gctcagactt ctcgaaacct tcaggcactg ggaaggaaaa  99120
gagaacaagg aaactagaag attttaagca tgagctatgc accaggtcca ataggaggtg  99180
cttggccatt ttgggctgca tctttagcat tagaaatcca ttcttttcct caatgatctc  99240
tttatgtaat tctccaacag aacagagctt tctcaccaag gccagggacg tttggagtta  99300
ttgtgtggat ttcaggggt cagtaaaaac ttggaaaata tatatattat atatttctac  99360
atttctataa tttacaatca tatttaattg ttcttataaa cttttatttg taaaaaatat  99420
gtttagctta atgaacaaga cacatagagt tagtttattt tgttattact tgctattact  99480
gtactattta gaaaaggagc ttgtaaatgt caatttcttt tcctattatg catagtttta  99540
```

-continued

```
aaatgttaag gttagtagag taaataatat tgtttaacta ctcagtatgt tgtaggcaga  99600
ataatggctg acaaagatat ctacctcctt atctctgaat ctgtgaagat gttgtcttgg  99660
cataacctca tggcaagggg gtgtgaggtt gcaggtggaa ttaaggttgc tgatcaattg  99720
acctcagaat aagaatattt tcctgtatta ttgagatggg tgtaatgtaa acacaaaggc  99780
ccttaaatat agaagaggaa ggcagaagga ctggagtcag agttattcaa tgtgagaaag  99840
acttgccagt ctgtcgctgg ctttgaagat gttgatgtta ggagaccaca aacaggtgtt  99900
ctctagcagc aaacaaaggc aagaaaacat tctcccctga agctttgagg aaagtataca  99960
gaaaacacct tgattttagt ctagcaggac ctattttgaa cttcttatct ctggaattat 100020
aaggtaacaa atctgttttg ttttaagcca ctgaatttga agtggcaaca agaaacttac 100080
taatactatc aggtaggaac attagattac ttttattgtc cacacattgt gggccaagta 100140
aataattaag tactttacac acatgtattt ttagttctat ctgactgcag aatatacagt 100200
cttaaccatt gtgctataca acctcttttt taaattaata attcaatgaa tgattgaaat 100260
acggaacatc aagtctgtgc tcatttggag cacatacgaa gtactcagca aatgcttata 100320
aatgcttatc tgaagagtgg ctttttggcc cataggaata ttcagcaagc cagagttatt 100380
ctacctccct ggatagaggc gtcatggctg gagcaacttt gagcttagca cattctatct 100440
gagctgttca ttacattcat catttaagat atactcaagc ctttgagagt ttgtttctta 100500
caattctgaa aatatgaaga tatatgaacc tcctagtaca ccctggtgaa tcatcttaat 100560
cagggtgttt ccctcaaggt attccaaaca gacatttttt ataatatgag aaagtgaaag 100620
catattgaac ctaaggccaa gttatagatt ccctaaaagt aagcatcata taaaacaacc 100680
gatccatttt ttcttcaact ttccaaactt gtttttatcc atttgcttga aatgttttct 100740
ctcttgctct ataagtatgt tttgtgtagt gcctgattct ccctatggta tttgctttcc 100800
attaacttcc tattgatttt cagttgtgtg tacacagtac tgcaggaaca taaactgcaa 100860
acaccagact taaagaagtc cgaactctaa ctgttttatc ttggtgacac agtactacaa 100920
cgtgaatatt acctgtggcc tcttttaaaa aatgtattta aaggcagttg tgacaagtag 100980
ggtcaagtct gaataatgat gtatataaat tacagtggaa aaatatttgg cgtctcagga 101040
tgaaggatgt tcaagttgaa agggcaggtt ggaacagata aagagcagtt tttgaaaata 101100
tggcattaca gaaggtgaag caaagtataa gtcactgtaa aaagaaaggt accaaaagat 101160
gacaaaagtg aggaggagtg ggaaggaagt aacacacagc aagttgatat gacactcaaa 101220
aaggaatacc gtttttgaaa caagtgaaat ttaaagttat cttaacttaa tctgatgaat 101280
aatttctcta acatttaaga gcattcacgt ttttattgtt ttgctttata gtaagctcgt 101340
ccaactggca gcacacaaac cgcatgcagc ccaggacagc tttgaatgcg gcccaacaca 101400
aatttttaaa ctttcttaaa acattatgag ttttgccaaa agcaattgca acaaaacaca 101460
gaactgacaa atgggatcta attaaactaa acagatacag cacagcaaag aaactatcat 101520
cagagtgtac aggcaaccta cagaatggga gaaaattttt gcaatctacc atctgacaaa 101580
ggtctaatac ccagaattta caagtcagga aacaatagat gctagcgagg ctgtggagaa 101640
ataggaatgc ttttacactg ttggtgggaa tgtaaattag ttcaaccatt gtggaagaca 101700
gaatggcgat tcctcaagga tctagaacca gaaataccat ttgactcagc aatcccatta 101760
ctgggtatat acccaaaata ccaaaatagt attctactat aaggacacat gcatacgtat 101820
gtttattgca gcactattca caatagcaaa gacatggaac caacccaaat gcccatcaat 101880
gatagactgg ataaagaaaa tgtggtacat atgcaccatg gaatactatg cagccataaa 101940
```

-continued aagaaatgag atcatgtcct ttgcagggac atagatgaag ctggaagcca tcattttcag 102000
caaactaaca caagaatgga aaaccaaaca ttgtgtgttc tcacttgtaa gtgggagttc 102060
aacattgaga acatagggac acagagaggg aacaacacac accagggcct gttgggggt 102120
ggggaggtga ggggagagaa cttagaggat gggttagtag gtgcagccaa tcaccaaggc 102180
acatgtatac ctatgtaaca aacctacatg ttctgcacat gtaccccatt tttttttgga 102240
agaaataaaa aattgtgatt tttttttttt tttttttttt ttttagctca tcagctatca 102300
ttagtgtttg tgtattttat gtgtggcaca agacagttct ccttccaatg tggcccaggg 102360
aaggcaaaag attgacacac ctgctttata atctcaaaca cagtagcaca ctttgaagat 102420
cagagagaaa acacctaact tcatcagtct tggttgtgtc acctgtaaga cagagataat 102480
acatattaac tcagagagtt actgaatggc ttatgtgtat gtagagaaac tagtaaaggg 102540
cctgtgtagc ttacatatat ttttagaggt gataaaaata accaataacc atatttataa 102600
tatattgaag ttaattgaaa tgaaaaacaa taaattaaca gaaaagatta gtcataaata 102660
aaatgagttg aactaatcaa gcaaaaaaca tgtgtttaat ttctttcaat tattttatag 102720
attttgactg aagtccacag tgctgattaa atttacatct ctattaagaa gcattaataa 102780
tacagaagaa atagacaagc caaggagatt gatggcagac ataggattac tttaagttgg 102840
tgttctatga aaacaatctt aaattaaaat attgaagtgg ggttccttta tattataatc 102900
tcatgtttca caaatttgtg agtgtatgat tgtactgagc taaaattgaa attgaacatt 102960
ttttctgttt tctatatcaa atcgataaca agcaattttc tagaattttg agattgtatt 103020
cctctttcat gagtattttt agaaatggaa ctaagttata aatataagaa aattttgtca 103080
cattagtgaa aaatgtttac ataaaagacc tgaatttcgt gaagaacctt taaacaatgt 103140
tcatctccat aaacacaatg tctgctctga aacttctttc ttattagagc caggaaataa 103200
agaaaggtgt atttttggag gaaagataaa ttgcctgtga tatcttagct ttatgccttt 103260
ttttcttata cttcatttat actaatgaga attttctatt tatcttttat gagttgattg 103320
tttgaaacac tattttgtta tttttaccat attttgtttg gggtattcaa gactcttaag 103380
caagaagttt agttactgaa tattttatat tgatctagtt tcttttcttt ccaacataaa 103440
gttattttta attttttaat tttttttattt ttattttttg agatggagtt tcactgttct 103500
tgcccaggct ggagtgcaat ggcacgatct cagctcactg caacctccac ctcctgggtt 103560
caaatgattg tcctgcctca gcctcccgag tagctgggat tacaggcatg caccaccatg 103620
cccaattaat tgtgtatttt tagtagagac ggggtttctc cgtgttggcc aggctggtct 103680
caaactcctg acctcaggtg atccacctgc tttggcctcc caaagtgctg ggattacagg 103740
tatgagcttc aagtacaagg aaataatgct cagttgagac tgagttgggc tgagtgggtt 103800
tttgattaac tgtggtctgc ctgaaacaga aacagtgctc tctgtagcaa atgtatcttg 103860
aaggactgac agctatacct cctgttgttc tgttcctatt cttacactag tttcataagt 103920
atctataaga taaatagaaa attatcatta gcataaatga tatataagtt ccatttctaa 103980
ataaacaaat tattttaaaa gaagaagttt tttttttatt tattgagtgc ctattttccc 104040
agtcttaccc tcttccagga atgtactcct agttgggaaa aacatcgcct cttgataggt 104100
tacttgatat tgctatagta ttgaggtctc cttctagatc atggttcagt atagcaggtc 104160
atcatttttt ctgactggtg aagagaaagt ctagattttc aagtaccttg gaagagaata 104220
gatatgctac cacctgtggt agtcctgtta tttgatcagg gcttagctct tttcaaagga 104280

-continued actttcctta agaattctgt ctcttaatac cacttctctt gatgactggt tcaccttcca 104340
tgataccgtt acatcagagg agagcctgga agaattgggg tggattttgt gtgcatgtgt 104400
gtgtacgtga gcagtgcatg attcttattg gcttgtttcc tcataattca gctaaaggaa 104460
agcgtatggt ggcgttgatc taactggtgt ttattatcta ccttatattt ccaagaaatc 104520
agaatattct cttgagttcc atttaccaaa gtaagtttta aatcatccta atatagagcc 104580
aaaacatagt tacttttcaa aattgcaatt ccataaattt tagctttatt ttccaagatg 104640
agagaaacaa tagaggaaaa ttctcactca caacctaact cagttatcaa cagaacattc 104700
aaggctggat ctcctaatca acattgaaaa agtatcccct acattaggaa aatactctgg 104760
ttctgtcttt acttcatact gggttattca cagattggaa aggtatataa gtatggcgat 104820
tgaatctatt cccttcccca catatccctc cctttgtagt gaggtcaagc ttggctcttt 104880
cactgtgttc atgtcagcat tttgtgttag aaatttacga tgggtgtggg ggcattacag 104940
tgcattcaac attttttca gtgccttcta tttggaaata tggtgacatg tgcagccagc 105000
actgagtaaa agttttaatg ggaggggaaa ctagtataag gataggaaca gagcaacagg 105060
aggtgtagcc gtcagtcctt caagacacat ttgctacaga cagcactttt tctgtctcag 105120
gcagacaaca gttaatctta agttagaaga agaaagaagc agagctgatg caaaaaaata 105180
tatatatatg gagaaagtta agctgaatgt tgtagagcta acactcaata agtatttgga 105240
atgttagcag tacaaccttt attagcagct acaaaaatca gactacatag ttttttgata 105300
acaagatgac caattcaagg tgatacagag gcttgtgctt ggagaaggat gtcttgtaga 105360
ctattgacca atagggcaga atttcccttt gtacattcat ccctgttcag gtctaacttg 105420
catcctttta agcacggaca cctgacccat cacacccgca aaagtggata agatcaatct 105480
caagcagtga acttacactg accaagcaca caggaaatgc atataaaagt agattcctca 105540
aggccacatc tgaccagagt attcattatt tgttacagaa gactcgggaa agcattgaat 105600
ggctatctta taattgtttt ttcctcccca tctgaagctg cagacaccat ttgaaaagtg 105660
gctacatccc agcctatgat tgttctcagg tggcattttt gtttttattt tctaaatctt 105720
gatgggtacc tcactgttat tcccacatat cactcataat atttatatta tatactggta 105780
attgaatgtg ggttccatat tctacattca tttgctagac aaataattga gattctactg 105840
tatgccaagc actggagtaa tctgttaatt ggttaattca tttattagtt tctttaagac 105900
atactgtatt tactatgtat tggggactat gttagaagct tgaaatatca cagtgaacaa 105960
gttagaccat ggctactttc aaagtgtcta tagaagaatt gagaaatcaa gtgaacaatc 106020
acaatacttc tgataagaga taacacagag gaggtaatag ggttttattt ttaaagaaca 106080
atatataaat atagtggctt tggtcttgta aaatttagtg gcaatgtaat tgtataaaac 106140
aagggaaccc aagtggataa ggtaggaaat caaaatatta gctagtagta aaataattaa 106200
atgacattct ctggtctgga aattttgcca agtcttttca aataaacgaa gaaaacaaca 106260
aaaaaaactt actttggttt gtttcctaac aagtcaaaag gaaaaccaca atccaacaac 106320
aatgcaagca acagaaaatc tttaaataat gacgctgaaa ttatcttata actttaataa 106380
gtaaaagtaa aaatatggaa ataaacagaa gtttggcaga aagaacagat acaaaaattt 106440
caaaactcag gagaaaaagt cgagatcttc atgaaacaaa gctttaaaag agaaaagtta 106500
atgttagaaa accacacaaa agtctaaaag cttagaatgt tcagatccct aaagaaataa 106560
ggagagcatc atatagattt tatggggcat tttattttca caatagttga tactgaaagc 106620
aatttttttt ccaaagagaa tgtgccacat aacaactagt aaaatagcaa aaacaacagg 106680

-continued caaaattgga taaaatactc cactttctag cagtccagga gttggccctg taatctgtct 106740
tctagttttt aacttagccc atccctgact gtctcatata acaattggtt tgtagatgat 106800
cccatcattg agtagtttag cgtctctgaa tcataggcca ggtacagcat tcaaacttac 106860
ctaaaaacat cactcttttg gttcttaaaa aatattttgt gaaggagatg ccacaagctt 106920
tcccttagaa gccctgtgga aatcatctaa ctggtgggct attattagac acattatcaa 106980
agtttctgct tttttacaag tctcttctta atacagtact agcacatgat gccaacagcc 107040
catgttatta tcatgtcatt ctagtgcttt aactaatagg tccctggaag gagaagaatt 107100
cgtttattcc tttgggatta tatatagatt ttctttctta attttatcta cagtgtaaac 107160
ttatacccag atcatgtctt ttattttgta ttttatgtag caccctcttt gcctttagaa 107220
aaggtttaga agagacaatg aggaaagata gtttaagggt ggtagaaata agttgaattt 107280
gagatttgag atggatgtga aagggtttgg agaggtagtt gctgaggaag gggcaaagct 107340
gggactttgc ctttggagca ggcttcttgg acatgcagaa cagtatcttt gtcagagaac 107400
attctggacc aggaaaactg ggaacattaa tctagattag tacaggactt tgaacatagc 107460
tgtgactacc tgacttgtaa attggcatat ctgtattttt ctgctgtcct gagttagtta 107520
acttcgtatt ttaaaatact catctgaata tatctgctac ttttgcccac ccagaaccca 107580
ttaccttttc ttcagtgcag cactgttccc tccccacctt ctttggaaaa cgatgctgct 107640
ccaaccttta gggcttttgt tttggaaggg cagaccacca acctagatca agatgtagct 107700
gtcgtccagg cctacccaat gaccttattc aatttccata cctacaaagc atggttgaga 107760
agaggaaaaa aacccacact tttcagaggc aatcctaggt ttgaactttt gaaaaggagg 107820
agctctttcc actgtggtag ttgaaggtag agggctgcct ggagctgcca gtagccatct 107880
tgccactctc tgggataagc ctgaccgaat aaagtccaca cagaggaaag cagaactgag 107940
agaaagagag ggaccaagtc cctactgatc tcatttgaca cactcgatct actgccttct 108000
gaacatttct tgagcctata gattactcta cctcccttat ttcccataag tcaccatgac 108060
ttgccttttt ctgttacaac caaatcagtc ctaggaaata aaatgtttgt tttgcttcca 108120
cacccacagt ggggcttggg agcatctgta tttcaaagct gagaattctc cacagaatcc 108180
agttcccttc tatcttgttt taccttctga ggagaggacc atgaaggcag cgtcaggcac 108240
acgacacaaa tggcagctgt gtttcatctc ttctgtgcag atagcttaat aataaatacc 108300
tccttccctt tttagggaac aaaatagttt tattttacat agaaatttct tctgtagtga 108360
gtagcagtga aacgctaata tttattaaag agaaattgcc actgataccc tttggtgtag 108420
cccaagagga tgtaagaaaa aaaggaacaa atggcaccta cactctataa gctgcctaag 108480
tggaatctta atgtagaatt tgttgctttg tagtcttctt ttttttttta tctagcaaga 108540
ctagtgttac agaggatcac ggacattagt cacttgttct tgataacctc tgaagagttg 108600
gataaaagaa agaaactgcc cccagtgaaa agggatgatc tgcaatatct gaagaattat 108660
ttctgtggaa gacaatgtta ttacaagaca ctgggatatt atgactattt tggtagctta 108720
aagaaaaata aattcataat actagatatt aattatattc gatgatatac ataatttata 108780
atactaggat agaaaaaatc tttattaatt ttcaagtagt tacatcattc tctcctcact 108840
tcttagcatg aaggccattt atgtactggc aggtaaatgt caggttgaga aggctctaag 108900
tcatttcaca gtagggaaag ttggtttttc aacttggaag caaattttat tttattattt 108960
ttagaaaatt atatatatat ataacttaaa atggaaaatt gcacaaatca taagtggaca 109020

-continued gctccgtaca ttctcaccaa gagaacatat caatgtaatg aacacccaaa ttaagaaaca 109080
ctacatgggc cgggcgcggt ggctcacgcc tgtaatccca gcactttggg aggccgaggc 109140
gggtggatca tgaggtcagg agatcgagac catcctggct aacaaggtga aaccccgtct 109200
ctactaaaaa tacaaaaaat tagccgggcg cggtggcggg cgcatgtagt cccagctact 109260
cgggaggctg aggcaggaga atggcgtgaa cccgggaagc ggagcttgca gtgagccgag 109320
attgcgccac tgcagtccgc agtccggcct gggcgacaga gcgagactcc gtctcaaaaa 109380
aaaaaaaaaa aaaaaaaaaa aaaaaaaaga aacactacat gattagctcc ccaatatcct 109440
ccattcggct actgtctagc caattcccta ccaagggcaa ctgctacact gacttctaac 109500
actgtaaagt agtcactggc agagattttg aaaggcagta tgtcctgctg aaatgtgagg 109560
gaaattccac tgatgatttt aaacctaaaa cgatatgaat atctttagca acaaaaccta 109620
ctttcctcca gaccacataa gaacccgccc atgcctatgt cctatttcct ctggagcatt 109680
tttaggttaa gttttagatc ttgtagtctg gtgatatagt acattttgac ataacatgga 109740
gtaaggatgc catgaggatg cccagctcat gtagggggtg cttggctggt ctgtgatagt 109800
cactgggaga aaggtttaag ggaagggctg gcatgtcatt tccttctccc tcttatcctg 109860
ctccataatg atcaccactg tttattcttt aaataagtga aaagggaaag aaataaatgt 109920
gtcatttaaa gggttccaat ttaagtctcc tgctttattc ttaagccctg cttaatcttt 109980
cttgattcta ccctaaggag tacaaatctc ttttggctga tccactttcc tttgaggaac 110040
caaaagtgaa cacgagcaaa cagattaaaa gatagcccaa gagcactggt caacatgtgc 110100
cctgtgtggt tggatcaagt agagggaaac catgatttgc tttaaaagaa taacggtcat 110160
tgcaatgtcc tgcttctgtt ctggggttca gaatgtgata ttctgcatcc agttaaagga 110220
atctcttggc catttaccac agctaatagt aattaacaga acctactgaa aatgcagatg 110280
caccctcttc aaactagtaa gtgttactca tcatgctggg atattgagag agatttgact 110340
ttgagaagca tggagaaatg atttggttta aaactagaaa ctctggatta tacagatact 110400
catggcacta agcaaattca gaattaaaag aatgtgcctt cagagagaca aatgccacag 110460
gatctctcta tatgtgaaat ccagaaaagc caaactcata gaagtagaga ttagaatggt 110520
ggttaccaga aactgagggt ggtgatggtg gatggagaaa ggggagatgt tggttaatgg 110580
gtacaaagtt tcagttaggc agtaggcata agttctggtg atctcttcca tagcacagtg 110640
actgtagtta ataataatgt attgtatatt tcaaaattgc taaaagagaa gattttaaat 110700
gatcctacca caagaaatgg taaatatttg aggtgataga tatgctaatt agcctatcag 110760
atcattctgt gatatataca tgtattgaaa caaccttata cctcacaagt agatgcagtt 110820
attatgtcag ttaaaaataa aactaaaaaa aatttttaaa agaatgtgcc ttaaaaaata 110880
ttttgttctt ttcattaaat aataatctta gtaacactga cagtgagaat ctataaattt 110940
agcaatttcc aaagcaatca ttttaattgg atttaaaagg gatattatag tggataaaac 111000
cctcagaata ttttatgtag tagtgccatg gtttattaaa cagaattcat ttaaagtaca 111060
catgcaacac atcccgatag tttcttacaa accttgaaat aagcaattat tgagaagagt 111120
tgagagggtg attttctgag tttaacgaag aaggccttac atctagaagc ttgcagtctt 111180
cttgaagata gagattctga gttggttttg gctcagtgtc acccttgcct gaaatagtat 111240
gtggaaagcc acaataatgg gaatgagcat agtgtatctg ggggaggagt agacaggtca 111300
gtccagctga atgccgtgta tgtatgtttg tgtttgtgtg tttatacacc aagtgtaaaa 111360
taaaataaag tacaagtcat aaaattggac atgttacgga tagttttgta ttgtcataaa 111420

-continued

```
cacatttaca ctcaataaat gtggaacgaa taaatcaaag gacaaaaagc tttgaatacc 111480
taatggaacc tgagggtgtt catcctgaag gtaactagaa gatataagtt atttctctct 111540
ttgtggccag aaaggctaga attcctttta tagacagagc aatgttacta gttttcagac 111600
agatgggaat tgaaacaact tttatcttta aagacaaaat cctacccaac attgtacata 111660
tttaaattta tgtgaagttg cccacaggca gtggaatgag ttaatcaaat gataaagaaa 111720
tgtcaaaaca tcttatactt gtatataaac ctggtagttc agtatcctat aaagtacaac 111780
caatccatct gtccgaaagc ctaataccac tatttttggt gacactaaat gctttaaatt 111840
ttgtcagcaa gatttgaggc aatgtcaaat gctagagtga tcaatatcaa atactagagt 111900
gataaaaccc caatattatt atatataatt atatgtgtgt atgtatataa atatatgcca 111960
aaatgctata caaatctata cacactttat ataagtacta tatgcacaca tacacacaca 112020
taattattaa ctaagtttaa aaaattccac gtgatgagat tttttttaa ctttaaaaag 112080
tattagctca ttagacttca cttttttttt tttttttttt tttgagactg ggtcttgctg 112140
tgtcgcccag gctggagtgc agtggcgtga tctcggctca ctgtagtctc tgcctcctag 112200
gttcaagaaa ttctcctgcc tcagcctcct gagtagtgag gattacaggc taatttttgt 112260
atttttagta gacacagggt ttcaccatgt tggccaggct ggtctcgaac ccctgacctc 112320
aagtgatccg cccacttcgg cctcccaaag tgctgggatt acaggcatga gtcactgcat 112380
ctggccagct cattagactt cctgataaga tttcaaattt tatgtctttg tccgaagtca 112440
gatctataac tttaaaaata taaactagtt attttacttt gttttcattt gtttttcttt 112500
ctgatttttt aagtaattaa ttctaacaaa atggtctact tggctgtgct catgtgtata 112560
gctgatgtca gcatattaat agccagatgt agatgacata tcttgatctc tggtctcatc 112620
gctctactgt taccgtcaac attgttacca agcatgagct gggcaatgca aggcaattat 112680
tttctgaccc ttgcagtctg tataatttgg ttatccccta gatacaatct ctataaatag 112740
tgtttgttgg gttctggaaa ctagagtgga cagatggcat gggggacata atcaccaatc 112800
ttacccaagt atgtaacaga tctgagtata taaagaaagc ttgggtattt cttgtagtca 112860
gcatgatatt ttgctcataa atttccaaca taatataaat tttgaaacaa aaaggtaagg 112920
aaaataaagc tttaggactg ttttcagcct gctatttttg aggaacaagt gacagagtct 112980
ggtcatcatt ccattctgta tctttggatt attttaatgg attatgtccc agatggatat 113040
tagcgtattg gtagggcatg ggcagctaag tggtcaaaat ttttaaaaag cagcagctac 113100
tggattggct tgaactgttt ccttaaaatg gcagattagt tttaccagtg gtgtttttaa 113160
tacagcttca catcaaagca gatttgtgta atttggccac ctgctataaa catcaatttt 113220
aatcaatcac atatatcttt gccaatatag tttatcagtg gtaaatgttt aaagattttg 113280
aaataaattt tatgataaaa ttaagcagcc atctggaatt gtaatatagg tttttctaa 113340
atgatttgca agtcataaat tttaaacact atatatagag aatacacaca gtaagtgtac 113400
attcattttg tccctgttta caatattgtt tttgaggaca tttcattgtg aataatacag 113460
aaaatttacc ttctgaacag gacctatcaa cagtcttggg cagaaagaca tttgagctct 113520
gctggtctag acctgtgtgc ttagataatg agtccagcta ttcttgccag aactgcttgg 113580
tgattatgat tcaatctctg tagcttttca gtcagtgtga aattattgta aaaaacaaaa 113640
tctgctctct gatacattta tttcaagtgg tattgcttta ataatgtacc cccaatccaa 113700
gtataactta caagaaaaat gtatttagcc tgcatatgca agttagatat cctccccatt 113760
```

-continued

```
agagtagtaa cttcccaaac tgtttaggaa agatgcatcc aaagaatttg cataattatt 113820
atattgcaat ctggatttgt gaaatcaaag gtattggata tctaaattag taggaatatc 113880
tgcacacaac ccctcaatcc acttatttca ttacatggct tattttaggt tttcttttct 113940
taggcttatt tttgaataat tgatgtattc attaccagta gtaggggatg tgggggttgg 114000
tttttatctc ctctgtttta tccccctttt tatacttctt ttattgctca ttttaacatg 114060
ccacctgtgg gggtttctcc ttgacgtaac tagtattctt ctggctaagg ccatatttta 114120
ttagttttat ggcttgtctt tccttttatt caaaatctca ggtcttgaaa aagactggat 114180
acgaatgtaa aatgtaagaa agaacaaaaa tacactttaa aaagactttg gattgccaat 114240
ataaagtcca ttattagcat tcataaaata aactacttta gagccaataa ggatgaaatg 114300
ctctactttt aatttctgtg gcactattaa aaatactgta tatgggatac atcctacttt 114360
atagggatta actttcaaca tgcaaataaa caagaatcgt ataaccagtc ttacgtattt 114420
aagatttaat ctaaaattaa aatattttat atatttgatg tgtatcctta ggttatcact 114480
ttatgtagat agatgtggaa gtccttaata cttaacaaaa cacatataat aggctgggta 114540
cgtacctata tcatctgata taaaactcct gtgaggtaac tagggctgac tctggataac 114600
aagctatcat caatatacca cagtacttct cacataagct atatttgtga cacagcttga 114660
tgtgtggtat aatattcata gttatgaata agcatatgtt tggataatac aggaggatgc 114720
aactcgctct tccttgaata gtaatgattt cacagagaaa ctaatattta tattgggaca 114780
cgaggaatgc ataggaattt atccagtcca atttaattat tgtacaacga aagttaaaaa 114840
gagaaaacgc cattgacttt ggaaagtagg aactccagct atgaaagttg gaggtgaaga 114900
gtattccaac aaaaagagta gtatgaaata atatagtcag ttaagggaaa gccaagaaat 114960
tgaagttcat aagattggga aggtaaacaa aatggtggag aagtagagta aggggcttcg 115020
aactcatcta aggtcaggtt atcaagggca ttattgccaa gataaggaat aattctgcag 115080
gcatagagag ctagccaata ttttaaagcg ataagactga catcagttta tgacttttat 115140
aaagagatta tcaacttata ttgtggagat tgtaccaaac aggaacagat tgatagcagg 115200
gccaattata caaaaatgat actgatctat tattttttta gcagaaaagg aagccatggg 115260
tttttctagg aagagctctc ttatatgtaa ctaattagca ttggttttac tgctagatta 115320
caataaaata tataaagatt agagaatatt gttcatactt aatttttttc atttttttatt 115380
ttcaacaaga cagtttatca agatagttta tataatgatt tgaatacatc ttcatttttt 115440
tcatactttt taaaataatt tttttcacat gttcaagtta ctgttcatcc atgtggttga 115500
cagaggccca tgaggttgat aaatgaactc cactgtaacc aaaacaactg tttttaaaaa 115560
taaatacatc tcctttacca agattttgaa gacatctgaa agcaaaagca attgatctgt 115620
tttaccttcc ttacctgaca cttcctgcaa agcaaacaca atgtaaattg ttagaaaaag 115680
attcaaaagg cagctgactg aaaagaaaag gtgaagaaag tacataaacg agcaacacac 115740
caaatgacaa tttaattctt gtacaatgaa agttgaaaag acaaaatatc attgactttg 115800
gaaagtagga actcttgcta tgaagattat tattactcat atataatgcc tttattattt 115860
attctgtctt atttatactg ttcaaaatct ctactgtgat agattatgaa acagagaata 115920
ttcttgtgcc tggaattgtt tgtccatgtc aagtattgtt tgatggtttt gacttgattt 115980
gacaagtcag gttaatcaaa acaatcaagg ctctatacca tatctagtct cattatactg 116040
tcaaaattta gatgttttgt aatagtaaag catattaatt gtttgctgca agaagttcag 116100
ggtccttagc tgtccttcta gcatggaaaa tgttgttcat tttagtgaat atgtaaagga 116160
```

-continued atagttgggt taacttttgg gcaaagcaat ttattttctt acttaatgca agactagtac 116220
taatgattct tgtaacaatt gtcataaaga tgattcatat ttttctatgt ggctttataa 116280
atgcaccatc tatcataaga tagaagattc tagtttaatt gctaacattt atctttttgg 116340
gtctcatttt ccccctggag taacatttct agaaatgata aaaaaaatca ttacttaaaa 116400
gattgggctt taaaattgga attcaaggtt attagataca aatttctgtg ggggaggaaa 116460
gcacatgtat tatcctaagt tatatattat tttgtctgtt aagccattga tataattaag 116520
gggttaattg ttacaatcgt ctttggagat caaagtttag attgaatgag caattgaaac 116580
ttgctatgtt ttaaatgtaa gaaaagtagg aatttgcttt acagttatcc ttttaaataa 116640
gaccttacag gagagttctt ttctgtcatt ctccctctct tgccctctgc cttctccaat 116700
ctccattact tccctttgc ctcttttccc tccacaaata tttattgaga gattactgaa 116760
tgagtacaaa atgtattaat gtagtgacaa atatattgct gtacaaacaa atgcaaaact 116820
ttcttagact aaaatactgt taaggttagt tttgagcaat atttgaagaa ggaaagggct 116880
gcagtgttgg agggaagata tcaagagtgg acagtaacta catcaggata aaactgacca 116940
tttaggagca agtccaaaag cccaattagg taaaaggagt cttagaggca tggtagcact 117000
ggcaggcaag aagtcatgtt caagctagca gagggggaag ttctattaga tgatgactca 117060
agtaaggaaa taataaacta cagttctagc aggctttcat gagggaaaat tgcatggtac 117120
agaaaggggc attggcaatg agaagggagg cacaagcagt gttgggctat caaagaggat 117180
agattcattt taagagaaac caggtcactt tggcttcaac agtaaacatt ggttggtcca 117240
tagagtggat aaacaaacag agtgaacctt tgtcaaaaat attaatttaa attgtttggt 117300
tacctgctac tgttgttgtt gttttgaggg gagattatgg ctatcatgca atcaaaatag 117360
tacctaaggg ggacaatttc agagagcata gtgattaaga gcatgtactt tggagtcgga 117420
ctgcctgaat tcaaatccta gtttcactat ttacaaactt tgtgactttg ggcaaattat 117480
ttaacctctt tgtacctcag tgttcttata tttaaaatgg ggagaatagt agcacatacc 117540
tcaaaagatt gccataaaca ttaattgaaa tatttgtaaa gtgcttagaa taatacctga 117600
ccaatagtaa atggttgtta agtgtatatg tatatgagtg tgtatatata tatgtgtgtg 117660
tgtgtgtgtg tgtttgtgta ataaaggctg tatgcttgag tagctcatga cagaaatggt 117720
aaacactacc atttaaggga gcaaaagaca aatgtatggt aatgtttgaa cttgaagtaa 117780
agcttgcagt atgtaaagga tggagtggat ctagagttta tttattctgg ttttaccagg 117840
ccaatctagc atgttcttgc ccaaacatgc taaattagcc tagatgtact gttagttcag 117900
ccaggtaagt attaaaaggt ctaaagtttc aaactcctgc tttagggaac aaggactatt 117960
gagattccaa actactctag agttagcaaa attggaccaa gcttctcttt ctaggagtct 118020
tgagaatatt cagggctaga aaccttggtg cttctgagaa caccatacca catagtctac 118080
ataaatccag actccaaaca aacatgtcaa atacaagacc ggaaaggatt ttagagctgg 118140
ttcagaggct gttacctgta ttttgctcat tcatgaattg ctggcccttg tgattttttg 118200
tgggtggcac ctgggacttt ttgacatttg aaagtctctt tcaatatttg catctatgat 118260
gcatccattt ggaaagtcct aaaaatatga agatattttg tagaaatttt aggatgatgc 118320
agattaagaa acggttaatt tatggaacca aaaaagagcc cacattgcca agtcaatcct 118380
aagccaaaag aacaaagctg gaggcatcat gctacctgac ttcaaactat atacaaggct 118440
acagtaacca aaacagcatg gtactggtac caaaacagag atatagacca atggaacaga 118500

-continued

```
acagagccct aagaaataat gccgcatatc tacagctatc tgatctttga caaacctgac 118560
aaaaccaaga aacagagaaa ggattcccta tttaacaaat ggtgttggga aaactggcta 118620
gccatatgga gaaagctgaa actgcatccc ttccttacac cttatacaaa aattaattcg 118680
agatggatta aagacttaaa tgttagacct aaaaccataa aaaccctaga agaaaaccta 118740
gacaatacca ttcaggacat aggcatgggc aaggacttca tgtctaaaac accaaaagca 118800
atggcaacaa aagccaaaat tgaccaatgg gatctaatta aactaaagag cttctgcaca 118860
gcagaagaaa ctaccatcag agtgagcagg caacatacag aatgggagaa aatttttgca 118920
atctacttat ctgacaaagg gctaatatcc agaatctaca atgaattcaa acaaatttac 118980
aagaaaaaaa caaccccatc aacaagtggg cgaaagatat gaacagacac ttctcaaaag 119040
aagacattta tgcagccaac agacacatga aaaaatgccc atcatcactg gccatcagag 119100
aaatgcaaat caaaaccaca atgagatacc atctcacacc atttagaatg gcaatcatta 119160
aaaagtcagg aaacaacagg tgctggagag gatgtggaga aataggaaca cttttacact 119220
gttggtggga ctgtaaacta gttcaaccat tgtggaagtc agtgtggcga ttcctcaggg 119280
atctagaagt agaaatacca tttgacccag ccatcccatt actgggtata tacccaaagg 119340
attataaaac atgctgcaat aaagacacat gcgcacgtat gtttattgcg gcactattca 119400
caatagcaaa gacttggaac caacccaaat gtccaacagt gatagaccag attaagaaaa 119460
tgtggcacat atacaccatg gaatactatg cagccataaa aaaggatgag ttcatgtcct 119520
ttgtagggac atggatgaag ctggaaacca tcattctcag caaactatcg caaggacaaa 119580
aaaccaaaca ccgcatgttc tcactcatag gtgggaattg aacaatgaga acacatggac 119640
acaggaaggg gaacatcaca caccggggac tgtcgtgggg tggggagagg ggggagggat 119700
agcattagga gatatatcta atgttaaatg atgagttaat gggtgcagca cacccacgtg 119760
gcacatgtat acatatgtaa caaacctgca cgttgtacac atgtacccta aaacttaaag 119820
tataaaaaaa aaaagtagga atcaggcaaa aaaaaaaaaa ggttaattgt cctgttgaga 119880
ggttgattca gattttctgt tattctaggg ggagagttct attgatgaca aaaatgtaaa 119940
tttctttcta tgtcattttg ttcagtctgg ggagtagcaa aggattattc tttacagtat 120000
gttttctaat gatttgtcca aactgatttt gtattccaga atcacatact gctcttgggt 120060
ttttctcccc acatttccct tcagtggatt atttatactt ttaacaaaat gatgaatggg 120120
tcgttgtata ttcaaaatgt gttcacttcc cctggagaat ctgagtgaaa caagtacatt 120180
cttgcagaag aatcctaata tggttaccta gtcctttgaa attggtttta tctttgattc 120240
tgagaattct ctacaaattc aatgctgtat attaaaaagt tacaatattt catattttta 120300
atagcagaga taaaattgta gaaacaagtt ataatagaga aaagatttta gtttcttctg 120360
gagagcagta tttcataaca taaaataaat ccacttaggg atttatagaa tattttctct 120420
acatattact atgaaacttt taagacataa tttttttttc tctttcctgg aaatcctttc 120480
tctctcttcc tctctgttgc ccttatctat cccccacccc attattgtac tttagcactt 120540
aagcatttaa ctacagtttt gaccaacaga tgtatctgtt tgtttccata tagtaatata 120600
tgtttatttt agagaagaaa aaataagaca aagtaaaaat atacagcaac tgaggcacaa 120660
aattctgcag tgacttgctt catttttccc ttcctattta atcaaagtac tatcaaaaat 120720
tctatttaaa tttctcaaat tagaatatag gaaatatcat tcagatattt taaaaaatgt 120780
aattatatac ataagcataa gtaatagtac agaatgttgc atgagatgaa aatgtatata 120840
agcttagctg tcattgatca tactgaaaat tatttctaag atggacttta ataggctaca 120900
```

-continued gatttttaag atttttaaaa ttgtaagctc tgatcaaggc actgtgttac ttacaggggg 120960
atgtatgcat gtgcatgact tggtccatac tttccagaaa tttataattt agttgaagag 121020
aaaagaagta gacaccatga cgatacaatc tagtttgtga gtggcacaga ttttgctata 121080
gctcagaaga ataaaggcat ttttaaattt caatagtttt tggggaacaa gtggtgcttt 121140
atcacataga taagttcttt agtggtgatt tctgagattt tggtgcaccc atcacctgag 121200
cagtgtacac tgtacccaat gtgtaatctt ttctccctca ccccccctggc actcttcccc 121260 ctgagtcctc aaagtccatg gtggtattct tgtgatgcct atctcccact tataagtgag 121320
aacataagat gtttggtttt ccattcctga gttacttcac ttagaataat gatttccaac 121380
tccatccagg ctgctgcaaa tgccattatt ttgttccttt ttatggccga gtagtattcc 121440
atgatacaca aacacacaca cacacacaca cacacacaca ccacacacac acacacacac 121500
acaccacatt tcccttatcc acttgttgat tgatgggcat ttgggctggt tccatatttt 121560
tggaattaca aattgtgcta ctctaaacat gcatgtgcaa gtatcttttt catataatgg 121620
cttcttttcc tcttgggatt cctggatcaa atggtagact tacttttagt tccttaagga 121680
atcttcatac tgttttccat agtggctgta ctagtttaca tttgaccagc agtgtaaaag 121740
tggtcccttt tcaccacatc caagccaaca tctatttttt taattttttt aaattatggc 121800
caatttttgc atgagtaagt tggtatctca ttgtgatttg aatttgcatt tccctgatca 121860
ttagtgatgt tgaccatgac ctattttggg ttcaagtttg gctttgggaa gtgctttgga 121920
gcttcttctg agtccagcca ctgagctggt catcaacagt tgtataaaat ccacttttca 121980
ttgcatgtca caattcgatc tagaaatggt ttgtcgtttt tgtgttgaat aagagaatat 122040
gacacttcca aatgacattt ttttaaattt tcagtcagct catgaggcac tcacttactg 122100
agctttttca cctttccaat ttgcttcaaa tgccaaacga ccatagaatg gtcaatgttg 122160
agttcttctg caacttcttg tgtagttgta ggaggattag cttcaatgat ggctctcaat 122220
tagtcattgt caacttctga tggctggcca ctatgcttca catcttcaac actctcacct 122280
cctttgcaaa acttcttgaa ccaccactgc actgtatgtt cattagcagt tcctgggtca 122340
aatgcattgt tgatgttgtg agttatctcc actgctttat gacccatttt gaactcaaat 122400
aagaaaatcg cccgaatttg tgttttgtct aacatcattt ccatagtcta agataaatct 122460
aaaataaaca gcaagtaagt cattagcaaa acaacataaa gcaagaaatg cacattaaaa 122520
tgatgtataa cataacaaca cttatttaag actgtatttc aatatcaaac agcaaatttc 122580
aacaatgcaa aaaccgcagt tatgtttgca ccaacctaat aactgtgaaa tatactttgc 122640
tttaggctgt ttctgtcaat gaagctgact agttacaatc ttactaggtg ctgagaattg 122700
aaaggaaggt gctacagttg acacagatca ccagtcctac actattcaaa attttaaatt 122760
aaaaaatatt tattgagtag tttttatgtt caagggactg taaaagacaa tggaaataat 122820
tttctagaag agtaaaaaac agttttgtct ccaaaaattt caccatccac attcggaaac 122880
aatcaagcta aaaagtcaaa ccaaacaaat caagctttaa tgaaacatgg ttggaggaac 122940
tcagaaaaaa gggtgtctaa ttctgttttg gggtatctgg taagctatga ccagaggagt 123000
aaatctcagg ataagtccca aagatagacc aggtaggaaa gggcatttca ggcagaggaa 123060
actttatagg cagatacact gaagtgacgt gaagtagaga atcctaagga aattgcagac 123120
taaatagtag agtgctgatg gagttgtcaa agccatgacc ccggagtgtg gcaaagggca 123180
gctcgtgaaa tgtcttgcac attagcccga agtaaagtgt tttgaagtgc agtccttcga 123240

-continued

```
gtcctgtaat gttagaagaa ataatgctgt cataatccct aaacatatta tgacaagaca 123300
taacacaaat ctatgaagtg ttgtgaaaca ggatggtgca gtctaatgtg aaacaagtgg 123360
tcatttttca ggatgaatct agattccctg ggtgaagga gagtcagagc gtaaatagat 123420
acggaaagtt taatgagctt tgaaaggcaa tctttatcga gtcagaatgt aaaagagtca 123480
caaaatgaat aacacaaatg tattaattta tctaataaat attaactgcc tttaatgtat 123540
ccctgtggga gatgagagtc ttgttcttga gaatttcata acataccaca aacatcaaga 123600
tctttgagtc tgaagaacca aagtaataga attggctgga cgatgttgtg gctacttctg 123660
gccccccagg tgtcttgagt taataatatt gctgatctgg aaatagtagg aaggttaatg 123720
aacaattgca tttcttaatg ttcttgtacg tgtttctttt gtgaactgaa tgttagccta 123780
tttataagac atgccacaaa gtgatctagt aggaactttt taagctcatg ctacaaactt 123840
ggggttgtga aaactaaagc aaataagttg gtatttttag tatgtaatga aaggaggaaa 123900
gttgtggatg agtagaacaa agagataggt ttaacaatca taacacacaa agtcatttgg 123960
tggcctatat ccaaactttc attgattttg ttcatgtttt gtcctagaac cttgagaatc 124020
aggagaatct agtctcttcc ccaacctcag gggtgaagct tgattagtcc aggccagtta 124080
tggtaattcc ataccattgt caagtgactc attctgttat ggacacagga cgacagaatt 124140
ttggcaaata agatatgagg gaaaatcagt tgggtagctt ctgagactgt tttagtcatt 124200
cttatttagg atagaaagat gagaaaatgc ccttttgtgg cttttcagta gtactgcgtg 124260
aggatgtaat atttgaagct gttgcagcca tcttgctatc atgaagggcc agaggatata 124320
gttctacttt ctgatgttgg cagtatggaa gggatggaaa gaacaggagt tatttttttt 124380
ataatggact gaggaattaa ccagctaacc attcttgccc tgccatagct ctaaactctt 124440
acataacata gaaaatgtat ttacaaaatc caatcttgtt ttaattgttt ttcttttcct 124500
tgcagctgaa agcattcttg gggaggaacg catttcttct atcctcttat tttcagtatc 124560
tggaagcctg caaattaaac aaaccacaaa aaaaaaggca gatctatagg aggaagggca 124620
tatatttctt ttcttcttaa aattttattg gagtatgatt gacaaaaaat atgtacatat 124680
ttaatgtaca caactttatg atttcaaaga taagtataca tccatgaagc cagcaccaca 124740
gtctatgcca taaacctatt cattacctac aagagtttac tcctgacttc ttatctatta 124800
ttcttatttc atatgataca aaaaagagaa aataatttaa aaatattgcc acaaagaagc 124860
atcaaaacac aaagatagac aacatgagat ggagagagga acacaataac tgcaaaacat 124920
tcagaaaaac agttaacaaa atggcaatag taagtccttg cctatcaata attactttaa 124980
atgcaagtgg attaaactca ccaataaaaa gacacagagt ggcagaatgt gttaaaaaat 125040
aaaaccagaa tgcaactata tgcagtctcc tttctctttt ctgtatctgc tgcaagtttt 125100
ttctttgtgg ttacaatgag gcttgcataa aactctttat tactgtaaca gtccattttg 125160
actaatgaca acttcaattg catgcaaaaa ctatacttgc actcccctgc cccactttat 125220
taatgtcaga attaacttat ttttgtacta tgtattcatt atccaacttt ctgcagttat 125280
agtttctttc tatgttttgc cttttaagct ctatgctagg gttaagagtg atttacgcac 125340
cctcattact attttacgtt attatgtatt tgtgtatata tttaccttta ccattgagag 125400
ttatgctttc atatattttc atattactgt ttggtgttct ttaatttcaa tttgaagaac 125460
tccttttagc acttcttgca tggcagttct aatggtaata aacttcttag ttttggtttc 125520
tctgggaaag cctttgtatc ttcttcatta ttagaggaaa gattttccag gtatattatt 125580
attggttagc agtttctttc tttcagcact ttgaatatat tatcctattc tctcctagcc 125640
```

-continued

```
tggaaagttt ctgctgaaaa attcattaat agtttcatag ggatccttcc tatgtgatga 125700
gtcacatttt tcttacagct tttaaaattc tctctttgac ttttagcaat ttagtgataa 125760
tgtgtcttag tgtagacctc tagtctttaa gttccacctg ggttttggg ggcttcataa 125820
atctggatgt tcattttcct tttcagattt gggaaatttt cacccattat ttctttaaat 125880
aaggattttg cccctttctc ttttattttt tttcctgagg tacccataag gtaaatattg 125940
atttgcagga tgttgttctg taagtcctgt aggctttctt cactcttttt catttttat 126000
cttttcattc ctctgaagag ataattttaa attacctgta tttgagctaa taaattcatt 126060
tttctgcatg atattctgct gttgaaactc tctatagaaa ttttgaattc agttattttc 126120
tttggtggta gaatttctgt ttggttctct tttatgattt ctatctcttc gaggaacttc 126180
ttgttttgct cctgtatcat tttcctgatt tatttatttg tctatctgtg ttcgcttgta 126240
acttattgag tttaagatga ttattttgaa ttcttatcag gcagttcata gatctccatt 126300
tcttcatggc tggttactgc cattttattt tgttcctttg ttgatgtcat gtttccctga 126360
ttctttgtga attttaggac ttgtatttat gtccatgcat ttgaagacat cattttttcc 126420
agtctttaca gactaatcag tccagtcaga gattctgggt gagctggttg gtccgctggg 126480
ggcaggactg ctgttgatgt ctttgggaag gtagcctgta acctgggttt ctgggagcag 126540
gcctggttct ggtttccact gtggtaggtc tggttttggg gtcatgataa agtctaatat 126600
acacttttct ctccctttct tccacaggtg aactcctgag ccaataagat ctctttgggc 126660
agttcattaa gtgggctagg gaaatactaa tgtggaagtg aaaccatcct ttctactctg 126720
catattgtgc cttttctaat ttatgtgctc tatttatgtg ctgcagtctt tcacctggat 126780
tccagagttc ttatcaagat gttttgtcca tggatgtttg ttaaattaat ttctgtggga 126840
tgacaagggc tggaaccatc tattccacca tattgctggt gtcatttccc catatgttgc 126900
tttatttaca ttaatatttt atatgcttga ggtatcagaa aaagaagtgg aaacccccaaa 126960
aggcagttag accccgaggc atatgtacca ctttaatgaa gggcaataaa ttgcagagaa 127020
gaaatcagca aaaaaaaggg atttgggctc ctaggggcag taaattgtga aaatgtgact 127080
agtattgtag ataaaggctg tttagtatgg tttgtcatac agataagagt tgtttacctc 127140
ttccaggtac aggagaggag aacaccttta aaaatggaga cctatgtcac ttttacaaag 127200
gaaaatttat gctgtgattt taggcagaaa gttgacacca gagaattctt cctgctgctt 127260
ctcaatttcc ttcagctcaa aaatgatcct tatgccaata tggaatattt ttggggtggc 127320
atattctgct cctcttcagc atccttcctg gtatgtgaat tacccaactc ttgtgttctc 127380
agaagttggg cttgagcctt ttgttcaggc ttatgggtac attttgtact ctctaggagc 127440
taaagcagat gggaaggtag tttttagcta agatattttt acaaatcata atttttatgt 127500
ctatagtaaa accaaatttt aagcatcatt acagcaaatc tgaagtggat aaatgaactg 127560
ataaattttt aaaaaaatta agatagtatt aagaaattga catgtagatt ctaaactaag 127620
atttaatagc taacaatgaa gacatcttcc ttatttttat gactgctgag agcaaaaaca 127680
caaagaccta aagcaagtaa ttgaaataaa aaatgatgga ttgggctggc agctattctt 127740
tagatataaa actaaatgca gtctgtctgg aatttaaagg gagtgggtga tccttagccc 127800
ttccttcaga tagacatgca agaaatacaa agtttaaccc ttaataaata aagcctggga 127860
gtaaggaaat tcagaaattt gaatcatatg accaataaaa tgtctctttt tatatcacta 127920
ttgatatcat ttgtgtaagg gtttgaatgg catttaagaa cctcttggtt atatgaaatt 127980
```

-continued gaatttcagt gaaactaggc tgttattttg tgaagtatct gacttagcat tttttaagga 128040
agatatcatt ttaattagtg tatttgaagg tcgagtggat acttttactc tttttaagta 128100
gtggttttct tcacaaactt cggttctgtg tcatatatta ctgatcttta caatgtctct 128160
gagttactgc tgttttccat tcttaaattg ggagaacttt attcctgatt gagaagcaag 128220
aactgaaaat gtcacttttc cctttgaggt gtggaggaaa tcttttggaa atgttcagtc 128280
tctagtttcg taatgtgtaa cttatacttg tatagaacgt taggtcaaaa ttttttttacc 128340 agtggcattt ctcacattca ggtgtaaggg ctcgatgctt gcgtagatac aggaaatcaa 128400
actcacaaaa agtctccact tgttttaggg aattcagtac ccagctgaga gcaattacag 128460
gcaatattaa tatgttggca agaaatgtca gagttcaaat ggccagtctg agtgttcact 128520
ttttccttta tttgctctgt gatcatggct ttagaaggtt ttcttgttaa gaatagttgt 128580
gacctcacct gaattgaaag gtggaagtaa tgtttcttat catgtgtggc atggcctctg 128640
gtcaagtgaa aattattcac tcacttggaa aatgtctttg gtacaggaaa tgatatcctg 128700
aaattcatta agggtttacc attgggttgg attctctata tgaagtgatc acagaacttc 128760
aaacatcatt ctatgaataa cagcttccta gggtgcatgg agaaaaactt catttctca 128820 aatatttatt gggtaccaac acaggagacg ggcctgtact aggttattga tgtctataga 128880
tagttaagga aacttaagaa gtttccttaa ctatctatag tttccttaac tgtacctcaa 128940
ctatatcact tgcagctcat tatgtgtagg tatctctgca tgtatgatct atttccttct 129000
actgctacag actagtagat atcacagttg gcaattctac caaaagaacc tatagtccca 129060
gctactcagg aggctgaggg aggagaatca cttgaacccg ggacacagat gttgcagtga 129120
gccaagatcg cactactgca ctccagcttg gcaacagagc aagattcagt ctcaaaaaag 129180
agagaaaaaa aatgctcctt ttggtttccg atctgtttcc ttagggagaa attgttcccc 129240
tcaagctctc tttctaagag agtggacaga aatgtcttat ctctccagtc ggtaattatg 129300
acttctctgt aagtctacta ctacagacta gtagaaggaa atagatgata catgcagaga 129360
tacctacatg taatgagctg caggtgatat agttgaggta cagttagatg cagataatac 129420
agttgaggta gttatagctg aggtgcaagg gacaaaaatt agacactgtg tgattaaaag 129480
aaaatcatcc atcatctgag caacaactat tcattgaaca cctctaatgt gccaggatca 129540
cgctttgtac aagagttatg atggtgaaca aaatagactt tcagagttta ttcttgaatg 129600
gtaatgtatt aattaaaagg tctcattaat gtttaattac aaactagatt aagtattgtg 129660
gttcaagtgg acagctgggt caggggtgga gtatatctag gatagagaat ttcagttcta 129720
tattttacta attaactggt aaccaggagg tatgttctat acttacattt agctctgtgg 129780
cctgttgtgc ttcaatttcg tcatcttcaa aaccaggaag agctatattc atcttatctc 129840
acaaagctga ttaacataaa tgaaggagcc ttggaaaatg gaaagcatta tacaaatgta 129900
agttgtatag agttccacgg taattgctaa aaatactgag gcaaagataa tcctttgtag 129960
acagaggttt tggttaactt gtgagaatag agttagtaga atgctagaca tagaaaacag 130020
atttcagtga tttcaggaga aaatcagagg gaaggaagaa acatgaggtg ggtccagaag 130080
tggaagtctt caattccttt agaaaaggca catgtagctg gaagcagtgg ctcacgcctg 130140
taatcccagc actttgggag gccgaggcgg gtggatcaca aagtcaagag atcgagatca 130200
tcctggccaa catggtgaaa ccccgtctct actaaaaata caagaattag ccaggcgtag 130260
tggtgggcgc ctgtagtccc agctactcgg gaggctgagg caggagaatc acttgaaccc 130320
aggaggcgga tgttgcagtg agccgagttt gcactactgc actccagcct gtcaacagag 130380

-continued caagactccg tctcaaagaa aaaaaaaaaa aaaacagtcc ccggtgtgaa catggcacgt 130440
gtatacatat gtaacaagcc tgcacattgt gcacatgtac cctaaaactt aaagtataat 130500
aataataaaa taaaaaaaag aaaaagagaa aaaaaaaagc tccttttggg ttccgatctg 130560
tttcctcggg gagaaattat tctcctcaac ctctctttct aagagagtgg acagaaatgt 130620
cttatctctc cagtgggtaa ttataacttc tctgtaagct ataaataggc aaaaaaattc 130680
cctaaggatg tatgcctggg gtgttgtagg ttttagtcat acctgaaagg gttgctcctt 130740
cttccttttt cagagtactc tgtatcgtta tctattcctt tcattttttt tctgaatatt 130800
ttcctaactt attttgtcca catgttctac aggtaaacct taaagattaa attctgttga 130860
ccctgtgctt tcttcagtct aactccttgg cacactgaaa ccacatttga tattgaatgt 130920
tttaacataa tctatttcag gaagtaaaaa aaatcctaga gctctctctt attttccttt 130980
atgttaaata atcaccctct ctgacattgt agctttttaa ggaacacatc atgtagaatt 131040
gataggttct tttggtagaa ttcccaactg tgatatttat ttcatgacta cacatcattc 131100
tcagcaggtc aaaaatcatt gtattatgaa catctaaatt ggttctttaa tatatttttg 131160
ttagcagcag cacatctcct gaaaagcaac actgaagtcg attctgcgga cataaggatg 131220
atttggcatt gacatctgtc agcctgttaa ttactaagga agatttggct gaattaattt 131280
gtttcctggt tagctccttt tctctgctcc attatgccct ttactatgtt gcaaacttga 131340
acaaattaaa gatacattcc aagatatgag aagaattttc atcaaatgta tgaaaatcaa 131400
gtacatgaga aattcagttt ccaaaatata gggcatcatt gtgcagacga acagcttttt 131460
gaacctttct gttgaggaac acttccagtt ctataacatt tcttcagaca tttaatgaca 131520
gtttcctctg tgccaggcac tctctgtaag gtgaaagctc aggctgggaa gaggggtggg 131580
agtagggtga atgggaagcg ggtggggaca aggaaattaa cataagtgga catgcacaac 131640
aaaaaggccc tttcgggcgt taattttgta tcacctgcct gtatttctat tcaaacatga 131700
aaaatttttg aaacaaattt gaagggggag tggtccttca ccaataaggc accaataagg 131760
caggttattt tctcctttgt actggcaacc atcttttctg tagtttatgc tctgctcaca 131820
ccctatgtgc ttgtttccca tctgagataa ccctgcccct tttctgtttt catgaccatt 131880
attcaatgga aaattggaat aaagtaaaac aggacaagcc tgaattactt tgggctcttt 131940
gttatatctc atcatttttt ttggtctctt ttctccacta catttaaaac aaaaaataac 132000
ctttgcctgt gcttttccct cacttctaaa tatgtttttt ttaacctttt ctttcttctc 132060
ttttgtgctt gctttcttag ttaacattac aaattttctg ttttttctaa agctaatttt 132120
aaaaggaggc ctataatatt tgtgtaaagt ttttcattcc tccagtcatc ccatttttcta 132180
tatgacttta atgtgttatc tgccagaaca actagaatag atatctccat tatttctgca 132240
cagatggcag agtgaacaag actttgtcct tagaatttcc atcaacaaaa caaaaccaaa 132300
ccacttacta tatatgtatt gccattcatg tttaagtgct gaaaatggac ttggagactt 132360
atctcagcac tatcacttat gtactctaac tcttctttat ttgagtaggg aatccttctt 132420
gtgacttcct tcagggtgtg gacacattga aagattaatt attcacatat cagctggaaa 132480
aaagtgaggt gacaagtgtt gacatttgcg tttctgaaag aggcacattg ttacatcaaa 132540
aaaaggataa tgccaattag gatttcatat gtgttgtttt attttcacaa ttacaatgtt 132600
agaggaaagc tcaaaagtaa aggcttttgt gaaaatgatc agatgataaa tcttgatacc 132660
tgtgtaagaa gtgaaagcac cagagttttt ttagaagatg aaaaatgaaa aaaaaaaaaa 132720

-continued aaagaaaaag aaacaatttg gcattgttag aaattcttta ttgggagtgg aaaaacatga 132780
aataaaggga aaatagcttt aatcaactcc aaattccttc tttggaagtg ctgtgtgtaa 132840
tctccaataa tggtggtgta catttccccc aactctatta aaaccatcat tatcattgtc 132900
atcttcatca acatggtcat catcattgaa cacacactcc atacaaagta agatgttatg 132960
tgtttgtatt ataagcagag attagacaat aactctaatc acaaggatgc tgtaactagt 133020
agtgtagatg gtagatgtgc acaacaatga agggatgttt gatggtatct aagttgtgta 133080
atcattaggc ttacttgaag agtttcccct aatttttcta tttttctttt tccttttttt 133140
ttttttttc aaacagggtc ttagtctgta cccaagctgg agtgcagtgg cacattcctc 133200
atggctcact ggaggtgcct cagcctcctg ggctcaagca atccccaac ctcagcctcc 133260
ctagtagcta ggactatagg catgccccac accagctcat tatttatttt tttattttt 133320
tgcagaaaca tagtctcact ctttttccca ggctggtctc aaactccagg gctcaagcag 133380
tcctctgtcc tcaacctccc aaagtgctgg gactacaggt atgagccact gtgcctgacc 133440
agaattttc ttgaatgtga tattctcctt cattctatta cacataattt ctctaatctt 133500
cataatttaa ttatcattga atttcagtct atctgattca tgtaaagaca acctgtcatt 133560
ccaaacatga tttgtcctct ttacaaaact aatctgatat gaactgtatt tgattcacta 133620
gagaacagag tatagtgatg cctcaagtta ttgatacctg cattgatcag ggtaactaag 133680
gcttactact ggaacaagca gtgctgtaaa tctcatgggc ttaacatgaa gtctgatatg 133740
gatttgggtg ggggctttac tagggggctt acctctaagc agtgacaaaa ctatgtaggc 133800
tttattcaat tgtgtggctc tgtcatcttt aagtccatca cttcctgcct cagctacaga 133860
agagagaaag aatgaactac caaatgagac tttttaggac tatatcacat gtggcttcaa 133920
cttaagagca acggtagctg ggaaatatca tcttcctgtg tacctcccaa aaaataaaat 133980
gggtttgtga atacatagca ttttctttat tacactatag aatatccaaa tagagatcgg 134040
atattttata gtgtaataaa gaaattggga aattaggagt tagggctgaa tgataaatat 134100
agcctttgaa gacagtgaca atgatataca gttgattagt tggatattgg ataataaaac 134160
ccatcaccta aagaaagagc atagcaaatg attaaaaaca ggatttaaag aatggttttt 134220
acaatgaggg acaatggtag aagcttattg tggtgtggac ttgtaattac ctcttaattt 134280
ccattttttt cttcctttgt aacaaaactc tagtttttg cctaactaaa agactgttgt 134340
gtacccttct ttatagtagg gtataaccac atgactaatg tcacatataa aaatggagaa 134400
cgggtgcaca ttaaagagta ggtaagtggt taatatactt tttctctctc aatcctccca 134460
acctgccctc tttaccttta tctctccaaa ataacatgtt tgttgtttaa tagagatgac 134520
atcgtcctaa tctaaggctt aagattcctg taactcttaa gtcacacttt gccaaatttt 134580
tattcaatca ctgaaggctc acattgcctc tgaaagaaaa aaaaaaagca agtgaaatat 134640
ttctgactgt gagtgttctt atattggcat cttagtgtga acttagggga tatgttagcg 134700
ttgactgttt tctgtatcac ctcaggtgta ttttgtcttt cccctcttga cttcacttac 134760
ccactcactc tgactaatgt cctagcagtg gcaagcatgt agatgtctaa aaatgtagaa 134820
attgtaagaa agaggctgtt tcagggcagc atttggaagt ggctattgtg tagggctaac 134880
catatctctc tcctgccaga ggtcatggcc ttgttgatgg tctctagtca agagcaatcc 134940
cattagtgaa aaaaaaaaaa aaaaagaaaa ccagcactga cagtgactgc ttccaaatat 135000
tctcctgtct gctactatag aatttcctag tgtttcccat cttgtcaatt cctttccctc 135060
accttttta cactgagtga acaactttta tttgaagtgt taggtactaa cccagttctc 135120

-continued tcacccttta ctctgcttcc ttcctttctt aaatgcttcc tgctttgtaa ccctctgcag 135180
ctagtgatac attagtttat gtttgtgttt tctcaagaag tgaaactgtt gtaggttgac 135240
ctattatata gaagtacata ctcctcagta gaaggcaact tatgattgta gaaactgggt 135300
gtttcgtgag aagttgctac ttaactgacc aattaggaaa aggggtacag aaatgattga 135360
gacctccaag gagatacaga ttcatttaag ttgagtgtac tgctgcagac atcattttga 135420
atatctgtat tacgagtaaa tggtggaaat ttgaagacaa gtccatactt tatgaaagta 135480
agagaacaag aaatttgttt ccctaaatct gtgagcatac cctataattc atcagaaaca 135540
gcaaattcac aaacacaaaa ttgacagaaa tatgtaaaac ttttccagca gtttacttct 135600
gaatacatta gaaaatgtga cagaacatag taaatttctt gtcattttac ttcccaaggg 135660
aagtgctagg tttgtaaatc ctagaatatc atcaaattat attttgaaat ttatttcttt 135720
ttgagctaga attttaaaag attacatgtt ttttcacaga atacgttcat ccagttacta 135780
ataatgatgc tgaaggaatg gaaatgtaat ttctagaaat catcactttt caaagtttta 135840
tagtttgtga actggaatac tgaagatgga agtatgattt aatatttggt agaaacagga 135900
gagtttgtta tttgtagctc tgatattaga aattacttga ggtttctgtt accaaacttc 135960
acaaaatata tttcataaaa agcattctta actcaggtta tacatttttt aaaaattatt 136020
ctgaaaggaa ttagatattt aacattgtag ctgacctaaa taaattggag aaaattctta 136080
aacaattatc tttcattttc ccatcaataa atggagcaat aataatacct aattatttat 136140
tgcacaggag tcttgcaata attaattaaa gctttaaagt actttgaaga tgaaaacaat 136200
tttataggcc tcattattaa aggtaatttg ttatggtaac cagtcaaagt cattcatttg 136260
gtcttttaaa cttgttttta aatgctctat tcggatccag gtgttaatta aaaaatttta 136320
aaacaacact taggaaacat atgaaattct gctttctatc ttgatgctta acttgtgaaa 136380
taataggtaa gtttttttc cgaattttgt ttttttcatg tttatacgcc tctctcaaat 136440
cccattgagt gagcgagtat tgctcccagc tcattattac aaaaagaggt ttgccatgtt 136500
aaagccacta agatttttct ttttctgaag ctctttactt aatgcaaaga caaagtgtca 136560
tctatgataa caattctgca tatggaaaac acaaggttat tcatccattt aaacatttat 136620
tgagcaaatg ctatagttta aaaaagataa gccactcggt aaattggaaa atatagtaat 136680
atgtcacttg catgaaattt ttatccaatg aaataatcaa gtaattaaat ttaaggtgaa 136740
agtgattgat gtaatatagg ttaaaagcca gtatggcaaa ggctgaaaca ttacaaagag 136800
aggcatcaaa tgtggttttg ggaagcactc aatttttgtg tagataatat cctagatgta 136860
cctgtatttc ataggaaaga aggcagtagt ggtattctag aacagtggtt ctcaacaagg 136920
gcaatagtcc cctgtccccc attcctggga catttatcaa tttctggaaa tatttttggt 136980
tgtcacaact agggaagtgc tacttgcatc tagtgggaag ctactaaaca tcctacaaaa 137040
cacaggacgg cccaccacaa cagagaatta tccagcccta aatatcaaca aaactgagct 137100
tgaggaagtc tgctcttgtt ggaaaacaca gaactatcaa ggcaccagat ggagaaagta 137160
taagatgtat atcaggaata gcttggcagg agtagacgtt gaaggtaaca ttgaaaatgc 137220
tttaggatag ccttgattat tagattagac tacaaagctg actcattgaa tcactcacgc 137280
actgtgagtc attcaataaa catttatatc tcaggcaata cggacagaga gatagaagat 137340
atagatgctg ctgtaaagtt tacaatttag ttggagacag tcagataaac cacccactgt 137400
gtgaacaaag tgatatctgt caaacaccaa ttctactgtg tctttaaaaa aagttcaatt 137460

-continued aaaaataaat tttggaaaga gtatgcacta catacttctc cacaacttgg gactatatac 137520
aatcttgttt tgtgtatcag tttgccttta tttcagccag catttctttt ggcagtgtac 137580
ttttaattcc cttttatata acaactatta gcaacccatg acgtattgga tagcttccct 137640
tccagactca ctctggaccc ttctctgtgc tattccaggc tcaagatact gatcttcggg 137700
aacttcatgc tgagtgtccc tgtgttcggt tcttgattgt gtttggccca agagggacat 137760
ttataggaga tgagagggtg agaggagaca ggggttgggg catttggtcc ctcaactccc 137820
tcctccaaat agccaggtca ccacagactt gctgcatccc tccactgaag gccacactcc 137880
tttcagatgc cctttcttat agagctaccc tgtctgggtc cttataactg tttcctctcc 137940
ttatcccttc tatctaaagc tggcaatgtt cctcatctgt tgtgagctgt atgctgcttc 138000
actatccctc tttaggaaac tgcctacaca tttgtaaaaa tcctttatta agcactcctc 138060
aaagtgccag tctaggattc tcattgttat atatggggaa catgacttgg gaactgcttg 138120
tatggtagtt gcttttaaaa agagttctgc ataggaagga gtccgaaaag tttaaatttc 138180
atattatgac ttatgcacat ctattgaaga atgtatctgt tagcttattt attcctgcat 138240
gtatgtatgt atctgtatgt atgtatttat ttattttgag atggagtcta gctgtcgccc 138300
aggctggagt gcagtggtgt gatctcagct cagtgcaacc tccacctccc ggcttcaagc 138360
aattctcctg cctcagcctc ccgagtagct gggattatag gaacctgcca ccacacccag 138420
ctaatttgtg tgtggtgtgt gtatttagta gagacagggt ttcgtcatgt tgtccaggct 138480
ggtctcgaac tcctgacttc aagtgatcca cctgcctcgg cctcccaaag tgctgggatt 138540
acaggagtga gccaccatgc tcagcctctt ttatttattt ttaaatgtgg tttagctgtt 138600
ccgcaggacc attctgatgt tctccatata attccatttt tgctatattt ggtttcagtg 138660
aaaatgtaag gttttgaaaa agtgaagtgg ctcaagagtc atgctttatt ctggtagatg 138720
gatttcaaag acgggaagaa ggcatgaggc aaggagacaa acccagatgt acatttaata 138780
atgagtaatt aatactttat tgattatgtt ttcctttatt tttataattct aatgaactga 138840 cgccaatatt tttaaaaagc aagataatga tttgaagaga gttagccatg gcagggaaag 138900
catgaatgga aaagagattg tgctgttata gtgacagtgc ctggaaactc attgaacctg 138960
acagtgtaga aagatgatgt gagataggca gggaaagaca gtagtaaaaa tccaaaattt 139020
aacgtacgga aacaaccatg tctgtggcca ttccactctg aacacgccga tactgtctga 139080
tctcagaggc taagcaccgt ccagcttggt tagtatttgg atgggaagaa acatcttctt 139140
ccccaattcc tttttagtta ccaattatat ctattacttt tatgaatgtt aagagtctac 139200
attgagatta gattagcatg caggggtatg acaatctttt aatggagaag gtaacttctg 139260
gtatctataa actggagaaa aagtgattct tcttacaaga aataaactgc agatgcaggc 139320
actaatagac tgaagcaata actctatttc cctcttttga tctttgaagt atctatatca 139380
aaaaaatctt cttggtggtg gggatatact acatggagat gggccaaaga ctacaaagag 139440
agacttaggt aaaatcttgt ctttgtatga ggattctact tgaattcaat aggcctgtgt 139500
ccctaaagaa aaaaaaatgt atttattgca aaccaattta gcttaagtaa aggtacacat 139560
tttggggttt tattggttgt ggttgttcag ttaaattata cttactgtac tggacaccat 139620
atacgccaat cactgttatc aattctagga atgcacaaat gaataaaata tggtccctgt 139680
cttttctatt ttctgtgaac tttctactta cgtcacaatg gtgcaatggg aaaagaagaa 139740
atggatcatt tattcaaccc ttgataaaag aaagacccct cctagttagc atggtggtag 139800
cagggataat ctgtaaggaa acctaaatcc aatgtgaacc tctgaagaaa gtgaggatgg 139860

-continued ttagagtaat ctagtcttgc ctccacatca ggacatactt gccatgacca gcctgggagt 139920
gtctattttt tttccccatt aaagagggta gcatttcctt ttagttaata ctgagattcc 139980
cccctagaaa ggttctaata attgtagtgt aacaaagtta gtatcaggtt aatatccact 140040
ttaatgggag aatttccaaa actaatatta tcagttttaa tgataccttt ttgatttacg 140100
aaatgtctgt tattcacata gtttttgtta gcagtcaaaa ccaacaaaaa tatttgatga 140160
acccagataa atatttgaga aacttgtatg ctataacact tcattttaaa agatatgtat 140220
tttgtcatct ccaagttttc tttttaaaat tgttattcca acccttcttc ccctcaattt 140280
accagcatca ctaaatgccc accttatttc ccagtagttt atgtgttctc tcatatttta 140340
aaaaggtttc ttgaggtata atttacatat tataaaatta tttatttatt tatttaattc 140400
atttttaaat gtggtttagc tgttccgcag gaccattctg atgttctcta tgtaattcca 140460
tttttgctat atttggtttc agtgaaaatt taaggttttg aaaaagtgaa gtggctcata 140520
aagagtcatg ctttattctg gtagtgtatt caggtgtaca cccattttaa gtgtacagtt 140580
caatgaaatt tagtaaattt ttataattgt gcaaccatca ccacaatcca gttatataac 140640
atttcagtta ccaagaagtt tccctcatgc ccctttgcag ttaattcttg ctcccgctgc 140700
agccctaaca acagccacta atttttctgt ctctataatt ttgccttttc tagaaatttt 140760
gtataaaagg aaccatacaa tatgtagtct tttgtgtcta attatatttg tatgtttttg 140820
aactattaac ttgccacatg tattagtact ttgttccttt tattgatgag tagcattcca 140880
catttggata tattttgttt attcagtcat cagttgatag atgtttggat tatttctagc 140940
atttgcctat tatgaattgt tctgaacaag cgattatgaa taatgatttc tcacacacaa 141000
gtgttatgta aacatatgtt tttatttctc ttgggtagat acctaggact aaaatttctg 141060
ggttatatga taagtatatt cttaactttt aaagaaacta ccaagctacc acttttccaa 141120
tgtgtacgta tcattgtgca ttgccaccag caatgtaaaa tggtttttct acactcttac 141180
caacacttga tattgttagt tgttttgatt ataatcactc tagttggtgt gttgtggtat 141240
catcttgttc aatatccatt ttcccaatgg ttacttatgt tgaacatatt tttatacgct 141300
tttgcatatc tttttcaatg aaatatccac atcttttgct catttttata ttgggttatt 141360
gtcctcttgg attgtaaaag ttcttttttt attccaaata caagcccttt cctagatatg 141420
attggcatat attttttccc agcctgaggc ttgtctttgc tttatcttaa tggtgtcctt 141480
aaaagccatg cttgtgtaaa catatgtatc cacaaacata aacactgtag gagttttatt 141540
ttgttttttt atcttattaa aatggaactg actctatata cttttcagca tcttgatttt 141600
ctcattcaac attacctcat agaaattcac ccattagttt caatttatta tttttaatga 141660
ctgcatacta tttcatggta tgcattcccc cactgatgag cattcaattt gtttctaggt 141720
ttattccaca cccccaacag ccagtaaaac aataaccaca tttgtaccca tttatagatc 141780
cttaagtacg ggtgcttttt atttctgtag tttcaagtcc aggagtaaaa tttttggctc 141840
aaaggcttat atggttttat tttgatttat gttgccagat ggctttctga aacgtatgtg 141900
ataattcact tttctcccaa atgtgtgggc atcctttctc ccatatccac ttaagtcagg 141960
gagctgtcca ttttcaaagg ttgttcagtt aaattgttca gttaaatgtg actgggcatt 142020
tgcattccta tcatgactag caaatttggg cattttcacg tgtttgctag ttgactgaat 142080
ttgctcaatt gttaacttca gtttaaccct ttataaattt ttcctttggg tgttttgtct 142140
ttttttttta gaatataaat atatttggaa ttgtagatat tgggttttgt catttgaatt 142200

-continued gcaaatattt cttccagttg tattgtttga ctattggttt tgcttttgat ctcccttgct 142260
acaagaattt ttaaatttta ttattcctag tcttgaaata tttgtaatat cattactata 142320
tattttctaa ttctttaagg tgggtactag attcctttat ttttgtcttt ctcctttaat 142380
aaaggagtag tgtcctggaa gtgataacat cccagtatca aacacctaga gtccagatct 142440
tggtttctga aggtcattta cttctaaaaa gaaccaagag tgcttggaga aatggctgat 142500
tacaggttgt ggccaagaaa aaacaatcag atctgaatta ttttgtggcg ttagaaacaa 142560
ggaagtactc agagactaat ggagggagtc atgttaaaag gactcagaaa tcacattcaa 142620
ggagccactg ctggtctact ctggaaaaaa tttgaatacc aaaaatagag aataaataac 142680
aatgatggta aaggatcaca aaacatttga ataaacaaaa aaaaatcttg agtcagcaga 142740
gatattccaa aaaaatgaga gactaataaa tgtagggaaa acatgtatat ttaagaatca 142800
ctattgcagc tccagtataa catttgatta ggcaagaaca tggacagagg ctaaaatttt 142860
ggccattaga ttgttgggga acacggtagt ctcacaagga tacaatgttt gataaggttt 142920
ggctgtgtgc ccacccaaat ctcatcttga attgtaattc caaatgttgt gggagggact 142980
ggatgggggt aattgaatca tgggggcggt ttctcctatg ctgttcttgt gatagtgagt 143040
gagttcttat gagatctgat ggttttataa atatcttgca tttctcctgc tatcatttat 143100
tctctctcct gctgccctgt gaagaggtgc cttccaccat gactgtaagt ttcctgaggc 143160
ctctccagcc atgtggaact gtgagtcaat taaacctcta ttattgataa atcatccagt 143220
ctcaggtatt tcatcatagc agcatgagaa cagactaatg cagtaaattg gcaccacaga 143280
gagtgatgtg ctgctataag ggtactcgaa aatgtggaag tggctttgga actgagtagc 143340
aggcagaggt tgaaacagtt gggaggactc agaaaaagaa aggaaaatat gggaaagttt 143400
ggaacttcct ggagacttgg agggctcaga agacaggaat atgtgggaaa atttggaact 143460
tcctagagac ttgttgaatg gctttgacca aaatgctgat agtgatatgg acaatgaaga 143520
ccaggctgaa gtggtctcag atggagatga ggaacttatt gggaattgga gtaaaggtca 143580
ctcttgctat gctttagcaa agagactggc gacattttgc cctagaaatc tgtggaacat 143640
tgaacttgag agatggttta gggtatctga cagaaggaat ttctaagcag caaaccattc 143700
aagaagaagc agagcttaaa tgtttggaaa atttgcagac ttatgatgca atagaaaaga 143760
aaaacccatt ttctgggaat tcaagcctgc tgcagaaatt ttcataaata acaaggagcc 143820
aaatgttaat caccaagaca atgaggaaaa tgtcagagac cttcacagca gcccctcgct 143880
tcacagaccc agaggcctag gagagaaaaa gtgttttgtg ggccaggccc aagcgccccc 143940
cagccctgcc ccccggcagc cttgggacat ggtgcccagt atcccagctg cgtcagctcc 144000
agccttggtt aaaaggagcc aaggtacagc ttgggccatt tcttcagggg tactagcccc 144060
gtgacttggc agcttacatg tggtgttggg cctacgggtg cacagaagtc aagaattgag 144120
gtttaggaac ctccacctag atttcagagg atgtacagaa acccctggat gtgcaggcag 144180
aagtgtgctg cagcggtaga gccctcatgg agaacctctg ttggacaata cgaaagggaa 144240
atgtggggtt ggagcctcca cacagagtcc ccagtggggc actgcctagt ggagctatga 144300
gaattgggac acaattctcc agaccctaga atggtagatc tactggcagc ttgcaccatg 144360
tgcctggaaa agtcacagac actcaatgcc agcctgtgaa agcagccagg agggggcggt 144420
accctgcaaa gccacagggg cagagctgcc taaggctgtg ggaactcatc tcttgcatca 144480
gcgtgacctg gatatgagac atggagtcaa aggaaatcat tttggaactt taaggtttaa 144540
tgactgtcct attggatttg acttgcatgg ggcctctagc tctttggctt tggccaattt 144600

-continued

```
ctcatttgga atggatgtat ttacccaatg gctctacccc attgcatcta ggaagtaact 144660
aactttcttt ttattttgca ggctcatagg tggaagggat ttgccttgtc tcagatgaga 144720
ctttgaactt ggacttttgg gttaatgcta gaatgagtta aaactttggg gaacctttag 144780
gaaggcatgg ttgtgtttta aaacatgagg acatgtgatt tgggaggggc cagaagtgga 144840
atgatatggt ttgggtgtgt cctcacccaa atctaatctt gaattgtaat cccacgtgtc 144900
atgggaggga cccagtggga ggtaattgaa tcatggggt ggtttcctcc atgctgttct 144960
tgtaagagtg agttctcatg agatctaatg gttttatgtg tctggcattt cccttgctgg 145020
cattctctct ctcctgccac cctgtgaaga ggtgccttcc tccatgattg taagtttcct 145080
gaggcctctc cagccataca gaagtacgag tcaattaaac catttttctt tataaattac 145140
gcagtttcag gtatttcttc atagcagtgt gagaacagac taatacagtg ttacttcata 145200
aattgcttac taatcgaaaa ggggaaaatg tattaatacc tttaagatag aaagatctgg 145260
caagtagaca aacttaacgt tgcaagtaat agaacataat attttgtttc tcctctgcta 145320
tgcagtataa agtacctaaa tcattaccaa caaactatgc ttaccaaaaa tgtttattct 145380
aaataaagca tctactgtgg ttctcattta tatagtaagt ataggaatta gagaaacaaa 145440
tgaagtagca ccattatgca tcaatcagac aaatccatga tttgggacat tctctaagtc 145500
aactaatttg gctcttttag aaagtgaaag tcaagagaaa ataaaaatgt aggaggcatg 145560
gcatggtggc tcacacctgt aatcccagca cttagggagg cagaggtggg tggatcactt 145620
aaggccggga gtttcagatc aacctgggca acatagtgag aactcgttct cttaaacaac 145680
aacaacaata aactcttgcc agcagaggtg tgctattaaa aaaaaaaaag taagagaact 145740
atcttgatta aaaatgattt cagagaaata atctttattg caatatgaga atttttcttt 145800
gaatactgaa gttgttttta aagatataaa atttattttg atgaaaattg aggaaacttt 145860
aatatggact gaattagatg acatgaaatt attattaatt tttaacaatt gtgataatgg 145920
tattgtactt atgtagaagc atgcccttat taggatatgt gtgctgaatg taggctttaa 145980
ttgctgcaaa agtcttcctc atgtaaagtc aaaatttttt aggtactaac tattggtctt 146040
cgttccgcca actggagtta aaagcatcag ttgatactgt cacaagaaaa ttatcttctt 146100
tgtattagta aaataattaa aattaaaatg tatatataca aggcagagaa ttacaaaatt 146160
tgggtatcaa tactactata ttaattttat gctactatag tatatgccct tttagatgtt 146220
taatatctgc taacagatat gtttaggtag aaatgatgta tatcaggtat ttctcaccat 146280
ttagatgcca tgaagttgct gtgaattaaa taaacatttg tttggtaaac tgcagtaacc 146340
tattttaaag tgttctttaa aaggtatgta taggccaggc gtgatggctc acacctataa 146400
tcccagcact ttgggaggct gaggtgggca gatgacgagg tcaggagatt gagaccatcc 146460
tggctaacac agtgaaactg cgtctctatt aaaaatacaa aaaattagct gggcgtggtg 146520
gtgggtgcct gtagtcctag ctactcggga ggctgaggca ggagaatggt gtgaacccag 146580
caggcggagc ttgcagtgag ctgagaccgc accactgccc tccagcctgg gcgacagaac 146640
aagactccgt cttaaaaaaa aaaggtatgt atatatacat acatgcacag acacatatat 146700
atttgtgtat cttttttaag attatatcta ttttatatga tgattatata ttatgtgata 146760
tattattata caataatata ttctataaaa ctatttttc ttcaatttat taaaatatta 146820
ttttcatgta atcctggcac tttggcaagc tgaggtggaa ggattgcttc agctcaggag 146880
tttgagacca gcctaggaaa cataaaaccc aactcataaa aattaaaaat atgtatactt 146940
```

-continued

```
ttcggtttta tacttgacag gctttacaag aatttcaagg agatataaaa ataatgcaaa 147000
ttgtctggaa gaactcgcct ctcctctcct tactccaccc tgctattggg aaaaagatta 147060
actgatggtg agtggtgagt ctataatacc atcactccat gttcctggat gttaaaagtc 147120
actcacacat gtgacttctg tctttacaac acatgaagta ggtaaggcca gaattctgct 147180
tccagctaac tgggagaggt agtctgttcc caaagactta aaatatcctc aggtcaggag 147240
tttcaaagtc tacacttaga gggaagaacc aggaagtccg taaagtcata ggtttcaacc 147300
gcatccttca atttagtatt tctaacaaca atgctggtat tttgatatcc atctctttaa 147360
tacctgcttc tatttccaac ttgtttagaa cttgaagagg gagataaggt ttaattttgt 147420
gccttcccca agcccagcat ttagggatgc agagatatta tgtattttaa gcatgtgctg 147480
tagtagccaa tgggaatcca gaatgttgtt gtttatttgc attttaattt actacagaat 147540
tgttgatttt aggccctttg atccaatgct aatttaaatc attttcaata gaacattgtt 147600
tatttccctt catgctttat aactctaaat aataaaaaat accatctttc actttaaagt 147660
ccatattctc caggcattat ttttgagctt cacataggct tagaagaaaa actgatcaac 147720
agtagtgatg tggtggttgt ggaagcagtt gcatagctta gatagctcag gttttaaatc 147780
tcacctttgc cttatgttaa ctgtgtgaac aggttaaaat tactttgatc tctctacacc 147840
tgtttccttg tatgtaaaat gagagtaaca aaagagtagc tgggaagatt agtgagctaa 147900
gacatgcaca gtgattacca tgtctcctgc catatacgcc tcaaaaaattt agctcttatt 147960
atacttgttt ggttcatagt aggtgaagtg tttggtagaa aaattgggaa ttcattcctt 148020
tcttgattag agtgaatgac aatccatttg cagaaagctg cagaaagacc gctccagaaa 148080
tagaatgagg caaccgctct ggagaattga aaactaacgg gagctacgct ccacaaaaga 148140
taaggaaata aaaatgccag gaacaatatt ctgagaagaa gggaaaacaa aagaacagaa 148200
aaattatcag ttatatagcg gggaaaaatc tgaaaggaaa aaatctcaag agaaggggac 148260
taaagaagta taaagctgat tattctatat tgatcgaccc atcaatgtgc taatcaagca 148320
gtaagcagaa ggttgcagga tggaagtatg gattcttcct gaccattcgt tacgcagtag 148380
atgctttctc tacttaatga caacagcaat aggcaactgg aaaatgtcac ttagccagca 148440
tgtccaaatc catcttcctt gactttcctg gtgaaaccac atattttatt ctagatatca 148500
ggttgaccat agaggtaaga catgcagtgc tttggagttt gtattttctt tttttttccc 148560
tttctttttt tattttttat tttttttatt ttttgagact gagtcttgct ctgtcgccca 148620
ggctggagtg cagtggcacg atctcggctc actgcaagct ccgcctgctg ggttcacgcc 148680
attctcctgc ctcagcctcc cgggtagctg ggactacagg cgcccgccac cacgcccggc 148740
taatttttttg tatatttagt agagacgggg tttcaccgtg ttagccagga tggtcttgat 148800
ctcctgacct catgatccgc ccaccttggc ttcccaaagt gctgggatta caggcgtgag 148860
ccaccgcgcc cggcctggag tttgtatttt cttaattctt ttggttggta ctttgcagat 148920
ttggggagca acaattggtg agaaaaacaa tagtattaac atatgtgaaa attcagctgc 148980
taccttttttt atgtaaaaat aattcagctt ttcaattata tgctttcagg tataatctgt 149040
tgtttctata gcatcattag tggcagtatt taaaagtctc taagcctgac agttcacttc 149100
gacagatgca aagaacaata agcactgatt ttcaataagc taataagaag tagtttaaga 149160
aataaattgg cttaatttga gtttacaata atctaaaatt ttgcaaagat ttatttattt 149220
acatatcaca gtgtgctttt gaattagatg tttcttagac taatatgctt attttcagag 149280
gattacaagg atgcagtaga cagcattcca tttgatgtac atagctgcga atacatttaa 149340
```

-continued cattgaaagt ttcaagcact ttcttttaga atttggattt ttcatttcag tctttctagc 149400
aagataactt agagatatgt atgagatata aagtaaatga caaaatagaa tgctatatgg 149460
aggaaaattt gatgaaaata taattgattg agagattttt gttgaacaaa tgaaaccaac 149520
gattttttcc ccatcagaaa ctaattgcat ttctttctta tttccttgga gacacatgtg 149580
gaataaaatg taataaatac tgtacttgtg tgtttactta ccagaatgtt ctcttcagaa 149640
aaagtaatga taccctttca ttgacatcat ccaagtgata atatactttt gtttctgtca 149700
ttggagtaat aataaccttt caaccacatc actgcacagt gcttctttct tttattgtac 149760
ataatgcata aaaataaaga gggtatatta tttcttaagg aaataggttg ttatttaaat 149820
aaattccaag catcagaaaa ctacagttct tgctgatgtg tactaaaatt tctatagata 149880
cttataactt tgtatagaaa tttaatttta atattctttc aattgtcaca tcatacttaa 149940
gtacggatct ccactatttc acatctcaaa aatatgactt aaaaccagtt atagttgttt 150000
ataccccgat gataagggat tagaattttt ttttgccaaa tactccttag gctaagtttc 150060
aaagtctggt ttgtataaaa tattactagc agataaatag tttgttaata aaacatccaa 150120
gcttgtgctg atgggtgaat ttgctataat gtaataaagg ctgacactac tcatagtgag 150180
aatttaacct tttcctcaga ataccttatt catttaaatg aactcacagg tttaatgtaa 150240
aatatttcat atatatttga tacgatcctg tacaaattgt ttcctagcat aataaattga 150300
atacagtgtg aaataaattg tgactttgtt tttttttactt agtatctcaa gtttgaagaa 150360
tataagttct ttatgttttt gcttaagttt gatttacttt atcattaatc ataataatag 150420
gatttgtgct ggatgatgga aatccaaacg gtgttactca gtataataag aaaagtgaac 150480
tacatatgga atgtttaaaa taaagaacta atcttaaacc aatcagattg tttcatgatg 150540
cagacaggaa tctcaggaaa taggcttagt ggaattttct ggcaattaag tataaaattt 150600
tacatgcttt aagtaaatat ttcttaaaca agtgtctatt tctggtctca ttccactctc 150660
caaagagttt catctgagct taataatgtt ggtttgaagg catacttgca aatagagggc 150720
agaaatgtta actctatttc cagatttcta ctattgcaaa cagtctctaa gttaaagcca 150780
aagttgtttt ctattttatt ggagcaaggg aagcctgatt aaagcttttt ttagaataca 150840
tattcactca gcagagcaag aaaacaacct caagactgac atagctgttc taaaagtcat 150900
cttttggttt tattgttgga aagagggatt gctcatcaaa tcactgataa taagaatgct 150960
tagatgacgc tgttatgtag ttgatgttac ttagcatgcc aagtctcttt ctgtacatat 151020
taaaagtgat acgttgttct cagccaagac taataaattt ttttctggta acagctttat 151080
tgagatataa ttcacaaacc atacaattca cccactgaaa ttgtacagtt cgatggtttt 151140
tactatattc acagttaatg caaccatcac tgcaatcaat tttaggacat tttcgtcact 151200
ccaaaaagaa atctcgtatc tattagcaat cgctccttat ttcctcctaa ccacccctca 151260
cccaacctct cagctctagg caaccactaa tttactttct gtctgtatat atttgctatt 151320
gtagacattt aatataattg aaattatata gtatgtggtc tttcgtgact agcttctttc 151380
acttgtcata gtgttttcaa agctcatcca tgttgtagta tatatcagta gtatatcaat 151440
gtgttttatt gacaagtgat attccatcat gtgtatatac cacattttat ttagctcttc 151500
atcagttaaa ggacatttgg gttgtttcca ccctttggct attatgaata atgtcgctat 151560
gaacatttgt gtacacattt ttgagtggac atatgttttc acttctcttt ggtatatgcc 151620
aaggagtgga attgctggat tatatagtaa ctctatgatt accccctctga ggaactgctg 151680

-continued

```
gacagttttg caaagaggtt gtgccatttt tcattcccat aagtgttata tggggattcc 151740
attttctaca tgtcatcacc aacacttgat attatctgtc ttttttttat tatggccata 151800
ctgatggggg tgaagtagta tttcattgtg gttttgcctt acgtttcctt aatgatgttg 151860
acattcatct tttagtgctt tattggctgt tcgaatatct tctaagataa atgtctattc 151920
agatcctttg cctatctaaa aaattgtgtt gtctttttat tgttataata agagatcttt 151980
aaatattctt ttatcaattt tgctttgtgt ggtttactaa ggtaaaaacc ttgggtgtgc 152040
aattaataca ttcaattgtt agcaaaatta ttaaaacaat aacttataat ttttggtcca 152100
cctgaaatag ggaaactaat ttgactcaac ttttctttca attgttgtgg agtctggttg 152160
actgccaaat tttgtaaatt ttaatatttt acccagtaaa aagcttatta aataatagga 152220
tatactgatt agaggttact ttcaagaaat taaatatttt tgtgtcttca gaaagagttc 152280
tccttttgga aagatactat atggataaag aagtaaattt taagtacata ttttttttaaa 152340
gtgcatcagt tattatttaa aggaacattt aaattttagc atttgagcag ctatctttcc 152400
tccttcaaag ttttctcatt atcctttcct tgtacgtatt attatttata ggctgcaaat 152460
gaaacctaaa agaacataaa tggttttcta tttcaacaaa agcaatcacc tccacgtctc 152520
actttcttat ctttaattaa ataagtaaga taaaaagtaa aaatcatggt tgcccctttg 152580
gttttgctgg tctgacccat tatcccagca cattgtggta gagatataat aagcctgctt 152640
tgcctagaag atcacttagg aacaaccaag gcttggggaa gaaatcagtt gccactaaaa 152700
tgtcaaagta tcaagtattt ctgcatgtgt aactagagga aaaggagaga agacagcagt 152760
gcttctgatg aggcccaaga tctctggcat ttgaaagaaa ggtgaaagct gttgatggtc 152820
actttctttg ggtctctttc cttgggtcag gattgtacat gaaagtcgct ttagatacat 152880
tggccagaaa gaatgtgtgt agcctaacac aaacgtgacc tactttttac gaaaggaaga 152940
aattcttggg aggtataact gaaaattatc gtcccaattt acaaactcac tggacagtat 153000
gaatttctct tagggctcct aatctatttc agtcagacag taagtcttcg ccatgaaaac 153060
aaaacgaaat ggactataaa actgaacagg ctgggcttag ttatagatct gattgtttgg 153120
ctatgtgcag ggaaccagca tttaaaaaat aattccagct ttaatctgaa ataaagcaaa 153180
gtctgaatgt atggcatagc ttagtgaaaa aataagctca taaatgtcta taaatgcatt 153240
tataaatata tttaaaaatt tttaaagcag atgcaattct ttgtcacaaa tacggatgtg 153300
attctaaata tcagcaagtt tctgctaaca aaaagatgca aatgaaagtc atgatccaaa 153360
acctgggcat agtaataatt ctggtatctg gtttgagttt tagctccttt cttagctgtc 153420
agcaaaatca tcctctgaac ttctcactct tatgcctgcc cgtctttatt ttaactcata 153480
gacaagcagt tggaattttg ccatttaaca gccaagccct gtggcaggat aataagtaac 153540
agtccactaa catgaatgca gagaaaagca tatgttaggc caggagggat gaaaattgtc 153600
cacatagaag aaaaaataga aaaagcaaga cagaaagaaa aagataaata aaaccttaag 153660
ggcaagaatt ttctgtttac aaatatgctc tcctttagcc tagcttttac aagtgggtga 153720
ctgcattttg cagtcttagt aaatcacgac tgcttaacca tgcatttaaa gctattaaat 153780
taagttacca acagccaatc ccccaaaact tatatgcatg aaaagacata aaaataaaat 153840
aaaacaataa agaaaatttc ttatttaaaa tttaatgttg atatgattaa aaacatatat 153900
caacatctta aaagcaatca gacttcataa tcaaggagta ggcatgttat aataaaaaca 153960
agctctagtt tcatttctgg tgcaggttta atttattatt atttttttaa aagctgaaaa 154020
tggtaggagg tgattcattt gtttggattg aggactacat ctggttcaga gttaatagtc 154080
```

-continued atctaaaagt aaagtatcat ttgagaaggc ttaggggtat gccggaagtt ttaactttta 154140
catcatttgc taatgtgcta gttatctgga agctattaaa ttagaatatc tgattttgct 154200
gagattaaaa agaaatatta gacccatagt taattttttg tgcagaacgc ttccattata 154260
ttctgccaag ttttaaacat ccaatgtaac agcctgtttt tgtttttttt gctttaggaa 154320
atgttcttca atttgccata taggaaatta aaaagtataa catttgaagt aggataatgt 154380
tctgagctta tgttttacaa agctttgaac attaaaactg ttcatggttt aaataatttc 154440
atggttaata tttgtgatgt ataaattcac tggtttcctc tactatggca tgttaaattc 154500
caggtaacct atatctgaag aagaattagt tgtaacaaag attttttttt taatctttct 154560
cgaatgggaa gatccatata gtataggaaa ttgtgagaat actaatgaat tactcagaaa 154620
taaactaaaa ttgtgaaaaa agtaaagaag ttagagatga gagaatgtca tgaccaacga 154680
tggatttaga cttaattgcg tatttggcac attgaagtct aagtccattg ttggtcattt 154740
ataaattttt agactgcagt ttttaatatt tggttttctc ttcattttcc tttcctaaaa 154800
ttatttcctc ttcttccttt tcatctcttc ttttattcct tgtttcccag tgaaattatt 154860
ttctagcaca gcaagacatg gttccactct gaggcgaatt ttaagatgcc gatgttattc 154920
tatttggttt tgcaagctca gggcacacat atacgagtgt gtggagtgtg tgtacgtatc 154980
aaagaagttt ttattctaag aaaattttga atataagttt gaatttatta cttttctctt 155040
ttgcctagta tgttatacaa attctacata gttttagagc caaattacag caatcagttc 155100
acaatccctg tgatcatatt attttcttaa aatttcttgt ttatttgaaa tgactatatt 155160
gacttatttt agctgaaata tagtcacaaa cagatcctct tgtaatgctt ttctcaagat 155220
tccagctgag aaactgcaaa tatgaaaata ccacaactga tttcttcaac tacttattaa 155280
atatcatctt aagttacagt tcaagatcaa cttctttggg acaagcaact atttacttat 155340
gtatgagatt tttaaaaata tcgcttatga ttgttttggt gtatgaagga tcctgtcacc 155400
caggtagtaa gcatagtatc caaccaaagc tcaggaacat gcagtttacc catgtaacaa 155460
acctgcacat gtaccccctg aactccaaag tcgaaaaata aaattaagtc ttccaatagc 155520
ttgttcttta aaaaaaagat tgtttttaaa ttttggaaat aattttctat tgcaacagta 155580
ttaaaagaat gggacttggt ccaagaataa ctcccaaact ggttgtttat ctcataataa 155640
agctgaattg tggaaatcta gaacctaact tcaatacatt gttttccgag aaaaaaaatg 155700
gaacactctt aatttatttc tgatttatca gaattttgct ctccatgtgc aatccaattc 155760
ttacctctgg atgcatgacc tcatagggga aaaaaattgt tcatttctgg ctcgccacaa 155820
tttcatgctc attttaactg agcccttacc agtgcccttc tattttaatt tatctgttgt 155880
tggttctcta acaaaatatc caaaggagta gctgccatga atattttatc tttccaattc 155940
catattccct tccttctcaa cttccatttg tattcctcat caaatgatta ttctccctgt 156000
tgatgtgaaa agatttagga cactttccct cctcctcagc ttgtcaactt gtgatttcct 156060
ttgatttcag agaaagagat gattcttcta taaaaccaac ctatctctct gtccttgacc 156120
cagcttctcc tgtttcataa gagatattac tcttatagat cttcttttct agtctttaca 156180
tacacatttg ttccctcatc cccctctggc tactgtcctc tttcctcttt tcctttagtg 156240
aaaaatgtct tccatgtccc ttgcatctgt atcaccctgg atgtaagttc atttaattgt 156300
tttctctttt tccctttcta cggagattgc cttctcaaaa tcaacttcgt gtcagctcta 156360
gcagtcacat attcactctc agtctggtta attctttagt gcatttcaca acttaaaact 156420

-continued

```
gttttttct tgacttctgg gaaagcacat tatattgccc cataatactc agattcttct 156480
cttactacca cctaaatgct cagtcttttt catatattcc ttttcactcc tctgtgtgtt 156540
atctctacta aatatgaaat ctcagcgatc tcatctaccc cattactgca actctccctt 156600
ctatgtgaaa aagcccaaaa taataatcat ttcccatttt caaagagctt ttccttggat 156660
acttatattt aatctttaat aagaatttat gaggtagata cattcattac acagactacc 156720
aaattcacat tttcagtttc ctactatttg gtcattctcc ataagtcaac tagatattta 156780
ctgcacttag gcattcactg tggtgtagta atgtatcaaa aattaagtct attgtctttt 156840
tatgtcccat ccagtgtccc ttctcaacct tcctgttggt attaaattgg ccaggctact 156900
ggccaagtct gttagttcaa agtcttaaga gtaagcttca tttcaaacag tagaggcttc 156960
caatgggatg aacttggatt attatctgtt ggtgaccctc cccactgtca actcatcctt 157020
tagaagccca ctcaaatgcc agctccttca agagtcatca ccttatcgca atgctcctag 157080
gaacattttc acaactctgt tcctgtggca ctttttgtct ccatcctgat attgctaaat 157140
agtgtggctc tcagacctcg gggtgttggg tcagacaggc tcgtgctcca gtttttgtgc 157200
tgccacttac gaggtggatg acttgttgca agtcaccttt ttaaagcttc gtttttccat 157260
attggtacac agtgttcatg atcataatgc ctagtttgtg ggatgtttaa aaagattaca 157320
tcagataatc atacgcggaa ctggaacata ctaaatgctc aaaaaattgt tagctaactc 157380
actttctata atgtaatatt ctgaacacat gcagaacctg acttttaaga tccagttcct 157440
agttttgtgc ctgaggcttt acaatgctgt gatgctgtga tctggtcatg acttagaata 157500
ctttgattat ctctgctata caatggaatg tattataatt taaataagta tttgtggggc 157560
tggatgctat ggctcatgcc tgtaatccca gcattttggg aggctgaggc ggatggatca 157620
cttgagatca ggaattcgag accagcctgg ccaacatggc gaaaccctgt ctctactaaa 157680
aatacaaaat taagctgggt gttgtggcat gtgcctgtaa tcccagctac tcaggagagt 157740
gaggcaggag aatcacttga acccaggagg cagaggttgc agtgacccaa gatcgcacca 157800
ttgcattcta gcctgggtaa cagaaaggga ctccatctta aaaaaaaaaa aaaaaaaaaa 157860
aaaaaaaaag tatttgtggg atagatggaa aaatttctat aaagatgttc ataaactatt 157920
cttgctaaat tgtaaacaat gattaaaatc aagcatttga acagcagaat ctgattttgt 157980
acatctttgc attttgtata ttacatgagc aaaaccaggg tggattatat ttaaaaattt 158040
tagttatttg ttgattgaat ttactttgat gtcaatcctc catttcttat atatatgcac 158100
tttccaaatc ctattgatca aaaaaatgaa aaatctcatc ttcattaccc tgtaacccaa 158160
agccactcct ctaatcagac cccaactccc tttaagaata accataagtg tctcctactt 158220
ggccctcata cctccagctt ttaactctat taatccattt attacaatga tatacaatag 158280
ataatcttct gtaaacactc atttgaccat gcccttccct tgtttaagaa cttgcaatga 158340
cttgcttttt cctagcacag caaagctaaa tttctccctt gaattttaaa atcctccatc 158400
tgtttctact cttcctatgc aatattattt tccattattc cttaacaagc ttccaccatc 158460
ctactgagac aggtatattt tttgtctcta gtaaactagg ccctgaagat aaaaatttgc 158520
ataaaatatt cagtagcatg ttccttattt tgctctcacc ttctatgctt ttacacatgc 158580
tatttaagtc tcctggaatg ccttctccta aactccatga cccaatacac attttttctc 158640
ccctgtcaac tatttcttca tgaatctccc ccctcttaat gttgttacat agtctctaaa 158700
aataatctaa aatagatgat ttagtcatgt ggaataagat tcagaaggta tcccaggcca 158760
tgtagttaaa gtctcttaac ctcagcaaca cgcctgccag attccctcct tctctgagag 158820
```

-continued atgttctcta tataaacaaa tattatatat attcttccct tatttctctt tcgcccctct 158880
ttttaataca aatgatggag ggagtatcga agctgtccct aaagaggtca caattaagca 158940
gaaacctgaa agaaatgatt gagcatatca ggtaaggatc 158980

<210> SEQ ID NO 33
<211> LENGTH: 405
<212> TYPE: DNA
<213> ORGANISM: Human

<400> SEQUENCE: 33
cttgttgcta ttttagaagg tgtccagtgt gaggtacagc tggtggagtc tgggggaggc 60
ttggtccagc cggggggtc cctgagactc tcctgtgcag cctcgggatt cgtttttaat 120
gtgtattgga tgagttgggt ccgccaggct ccagggaagg ggctggagtg ggtggccaat 180
ataaatcaag atggaagtca gaaatggtat ctggactctg tgaagggccg attcagtatc 240
tccagagaca acgccaagga ctcactttat ctgcaaatac acagcctgag agccgaggac 300
acggctctat attactgtgc gagaggagat tactacgact atagtggtaa ttacattgat 360
gcttttgatg cctggggcca agggacaatg gtcaccgtct cttca 405

<210> SEQ ID NO 34
<211> LENGTH: 1749
<212> TYPE: DNA
<213> ORGANISM: Human

<400> SEQUENCE: 34
gatttgctct gccagcagct gtcggtgccg cgctcgacac cgagtcctag ctaggcgctc 60
acagaatacg cgctccctcc ctccccttc tctgtccccc gcctctcgct caccccggcc 120
cactccagcg gcgactttga gggattccct ctctggcggc ctctgcagca gcacagccgg 180
cctcattcgg ggcactgcga gtatggatct ccaaggaaga ggggtcccca gcatcgacag 240
acttcgagtt ctcctgatgt tgttccatac aatggctcaa atcatggcag aacaagaagt 300
ggaaaatctc tcaggccttt ccactaaccc tgaaaaagat atatttgtgg tgcgggaaaa 360
tgggacgacg tgtctcatgg cagagtttgc agccaaattt attgtacctt atgatgtgtg 420
ggccagcaac tacgtagatc tgatcacaga acaggccgat atcgcattga cccggggagc 480
tgaggtgaag ggccgctgtg gccacagcca gtcggagctg caagtgttct gggtggatcg 540
cgcatatgca ctcaaaatgc tctttgtaaa ggaaagccac aacatgtcca agggacctga 600
ggcgacttgg aggctgagca aagtgcagtt tgtctacgac tcctcggaga aaacccactt 660
caaagacgca gtcagtgctg ggaagcacac agccaactcg caccacctct ctgccttggt 720
cacccccgct gggaagtcct atgagtgtca agctcaacaa accatttcac tggcctctag 780
tgatccgcag aagacggtca ccatgatcct gtctgcggtc cacatccaac cttttgacat 840
tatctcagat tttgtcttca gtgaagagca taaatgccca gtggatgagc gggagcaact 900
ggaagaaacc ttgcccctga ttttggggct catcttgggc ctcgtcatca tggtaacact 960
cgcgatttac cacgtccacc acaaaatgac tgccaaccag gtgcagatcc ctcgggacag 1020
atcccagtat aagcacatgg gctagaggcc gttaggcagg caccccctat tcctgctccc 1080
ccaactggat caggtagaac aacaaaagca cttttccatc ttgtacacga gatacaccaa 1140
catagctaca atcaaacagg cctgggtatc tgaggcttgc ttggcttgtg tccatgctta 1200
aacccacgga agggggagac tctttcggat ttgtagggtg aaatggcaat tattctctcc 1260

-continued

```
atgctgggga ggaggggagg agggtctcag acagctttcg tgctcatggt ggcttggctt   1320

tgactctcca aagagcaata aatgccactt ggagctgtat ctggccccaa agtttaggga   1380

ttgaaaacat gcttctttga ggaggaaacc cctttaggtt cagaagaata tggggtgctt   1440

tgctcccttg gacacagctg gcttatccta tacagttgtc aatgcacaca gaatacaacc   1500

tcatgctccc tgcagcaaga cccctgaaag tgattcatgc ttctggctgg cattctgcat   1560

gtttagtgat tgtcttggga atgtttcact gctacccgca tccagcgact gcagcaccag   1620

aaaacgacta atgtaactat gcagagttgt ttggacttct tcctgtgcca ggtccaagtc   1680

gggggacctg aagaatcaat ctgtgtgagt ctgtttttca aaatgaaata aaacacacta   1740

ttctctggc                                                           1749
```

<210> SEQ ID NO 35
<211> LENGTH: 2320
<212> TYPE: DNA
<213> ORGANISM: Human

<400> SEQUENCE: 35

```
ctcagctgca gttctctgat ggcttgcaca gggtggacca gccccttcc tctatgtgtg      60

tgtctgctgc tgacctgtgg ctttgccgag gcagggaagc tactggtagt gcccatggat    120

gggagccact ggttcaccat gaggtcggtg gtggagaaac tcattctcag gggcatgag    180

gtggttgtag tcatgccaga ggtgagttgg caactgggaa gatcactgaa ttgcacagtg    240

aagacttatt caacttcata taccctggag gatctggacc gggagttcaa ggcttttgcc    300

catgctcaat ggaaagcaca agtacgaagt atatattctc tattaatggg ttcatacaat    360

gacatttttg acttattttt ttcaaattgc aggagtttgt ttaaagacaa aaaattagta    420

gaatacttaa aggagagttc ttttgatgca gtgtttctcg atccttttga taactgtggc    480

ttaattgttg ccaaatattt ctccctcccc tccgtggtct tcgccagggg aatactttgc    540

cactatcttg aagaaggtgc acagtgccct gctcctcttt cctatgtccc cagaattctc    600

ttagggttct cagatgccat gactttcaag gagagagtac ggaaccacat catgcacttg    660

gaggaacatt tattatgcca ccgtttttttc aaaaatgccc tagaaatagc ctctgaaatt    720

ctccaaacac ctgttacgga gtatgatctc tacagccaca catcaatttg gttgttgcga    780

acggactttg ttttggacta tcccaaaccc gtgatgccca acatgatctt cattggtggt    840

atcaactgcc atcagggaaa gccgttgcct atggaatttg aagcctacat taatgcttct    900

ggagaacatg gaattgtggt ttctctttg ggatcaatgg tctcagaaat tccagagaag    960

aaagctatgg caattgctga tgctttgggc aaaatccctc agacagtcct gtggcggtac   1020

actggaaccc gaccatcgaa tcttgcgaac aacacgatac ttgttaagtg gctaccccaa   1080

aacgatctgc ttggtcaccc gatgacccgt gcctttatca cccatgctgg ttcccatggt   1140

gtttatgaaa gcatatgcaa tggcgttccc atggtgatga tgcccttgtt tggtgatcag   1200

atggacaatg caaagcgcat ggagactaag ggagctggag tgaccctgaa tgttctggaa   1260

atgacttctg aagatttaga aaatgctcta aaagcagtca tcaatgacaa aagttacaag   1320

gagaacatca tgcgcctctc cagccttcac aaggaccgcc cggtggagcc gctggacctg   1380

gccgtgttct gggtggagtt tgtgatgagg cacaagggcg cgccacacct gcgccccgca   1440

gcccacgacc tcacctggta ccagtaccat tccttggacg tgattggttt cctcttggcc   1500

gtcgtgctga cagtggcctt catcaccttt aaatgttgtg cttatggcta ccggaaatgc   1560

ttggggaaaa aagggcgagt taagaaagcc cacaaatcca agacccattg agaagtgggt   1620
```

-continued

```
gggaaataag gtaaaatttt gaaccattcc ctagtcattt ccaaacttga aaacagaatc   1680
agtgttaaat tcattttatt cttattaagg aaatactttg cataaattaa tcagccccag   1740
agtgctttaa aaaattctct taaataaaaa taatagactc gctagtcagt aaagatattt   1800
gaatatgtat cgtgccccct ccggtgtctt tgatcaggat gacatgtgcc atttttcaga   1860
ggacgtgcag acaggctggc attctagatt acttttctta ctctgaaaca tggcctgttt   1920
gggagtgcgg gattcaaagg tggtcccacc gctgccccta ctgcaaatgg cagttttaat   1980
cttatctttt ggcttctgca gatggttgca attgatcctt aaccaataat ggtcagtcct   2040
catctctgtc ctgcttcata ggtgccacct tgtgtgttta aagaagggaa gctttgtacc   2100
tttagagtgt aggtgaaatg aatgaatggc ttggagtgca ctgagaacag catatgattt   2160
cttgctttgg ggaaaaagaa tgatgctatg aaattggtgg gtggtgtatt tgagaagata   2220
atcattgctt atgtcaaatg gagctgaatt tgataaaaac ccaaaataca gctatgaagt   2280
gctgggcaag tttacttttt ttctgatgtt tcctacaact                         2320
```

```
<210> SEQ ID NO 36
<211> LENGTH: 2722
<212> TYPE: DNA
<213> ORGANISM: Human

<400> SEQUENCE: 36

catagagcca gcgggcgcgg gcgggacggg cgccccgcgg ccggacccag ccagggcacc     60
acgctgcccg gccctgcgcc gccaggcact tctttccggg gctcctaggg acgccagaag    120
gaagtcaacc tctgctgctt ctccttggcc tgcgttggac cttccttttt ttgttgtttt    180
tttttgtttt tccccttttct tcctttttgaa ttaactggct tcttggctgg atgttttcaa    240
cttctttcct ggctgcgaac ttttccccaa ttgttttcct tttacaacag ggggagaaag    300
tgctctgtgg tccgaggcga gccgtgaagt tgcgtgtgcg tggcagtgtg cgtggcagga    360
tgtgcgtgcg tgtgtaaccc gagccgcccg atctgtttcg atctgcgccg cggagccctc    420
cctcaaggcc cgctccacct gctgcggtta cgcggcgctc gtgggtgttc gtgcctcgga    480
gcagctaacc ggcgggtgct gggcgacggt ggaggagtat cgtctcgctg ctgcccgagt    540
cagggctgag tcacccagct gatgtagaca gtggctgcct tccgaagagt gcgtgtttgc    600
atgtgtgtga ctctgcggct gctcaactcc caacaaacca gaggaccagc cacaaactta    660
accaacatcc ccaaacccga gttcacagat gtgggagagc tgtagaaccc tgagtgtcat    720
cgactgggcc ttcttatgat tgttgtttta agattagctg aagatctctg aaacgctgaa    780
ttttctgcac tgagcgtttt gacagaattc attgagagaa cagagaacat gacaagtact    840
tctagctcag cactgctcca actactgaag ctgattttca aggctactta aaaaaatctg    900
cagcgtacat taatggattt ctgttgtgtt taaattctcc acagattgta ttgtaaatat    960
tttatgaagt agagcatatg tatatattta tatatacgtg cacatacatt agtagcacta   1020
cctttggaag tctcagctct tgcttttcgg gactgaagcc agttttgcat gataaaagtg   1080
gccttgttac gggagataat tgtgttctgt tgggacttta gacaaaactc acctgcaaaa   1140
aactgacagg cattaactac tggaacttcc aaataatgtg tttgctgatc gttttactct   1200
tcgcataaat attttaggaa gtgtatgaga attttgcctt caggaacttt tctaacagcc   1260
aaagacagaa cttaacctct gcaagcaaga ttcgtggaag atagtctcca ctttttaatg   1320
cactaagcaa tcggttgcta ggagcccatc ctgggtcaga ggccgatccg cagaaccaga   1380
```

-continued

```
acgttttccc ctcctggact gttagtaact tagtctccct cctcccctaa ccaccccgc   1440

ccccccccac cccccgcagt aataaaggcc cctgaacgtg tatgttggtc tcccgggagc   1500

tgcttgctga agatccgcgc ccctgtcgcc gtctggtagg agctgtttgc agggtcctaa   1560

ctcaatcggc ttgttgtgat gcgtatcccc gtagatgcca gcacgagccg ccgcttcacg   1620

ccgccttcca ccgcgctgag cccaggcaag atgagcgagg cgttgccgct gggcgccccg   1680

gacgccggcg ctgccctggc cggcaagctg aggagcggcg accgcagcat ggtggaggtg   1740

ctggccgacc acccgggcga gctggtgcgc accgacagcc ccaacttcct ctgctccgtg   1800

ctgcctacgc actggcgctg caacaagacc ctgcccatcg ctttcaaggt ggtggcccta   1860

ggggatgttc cagatggcac tctggtcact gtgatggctg gcaatgatga aaactactcg   1920

gctgagctga gaaatgctac cgcagccatg aagaaccagg ttgcaagatt taatgacctc   1980

aggtttgtcg gtcgaagtgg aagagggaaa agcttcactc tgaccatcac tgtcttcaca   2040

aacccaccgc aagtcgccac ctaccacaga gccatcaaaa tcacagtgga tgggccccga   2100

gaacctcgaa gacatcggca gaaactagat gatcagacca agcccgggag cttgtccttt   2160

tccgagcggc tcagtgaact ggagcagctg cggcgcacag ccatgagggt cagcccacac   2220

cacccagccc ccacgcccaa ccctcgtgcc tccctgaacc actccactgc ctttaaccct   2280

cagcctcaga gtcagatgca ggaggaagac acagcaccct ggagatgtta aggcagaagt   2340

cagttcttct gtccatccct ctccccagcc aggatagagc tatcttttcc atctcatcct   2400

cagaagagac tcagaagaaa gatgacagcc ctcagaatgc acgttatgag gaaggcagaa   2460

tgtgggtctg taattcctcc gtgtcccttc tccccctctg caaaccgtcg taacaataat   2520

agttcctaac acatgggaca attgtgagga ttaaatgagt tagcctgcag aaatcacttg   2580

atgcacagca catgggaagc attgtgtgta tttattaatc cttcacaaag tctttgagat   2640

atatttttat caaatattta gcatggatcc cggtacactt tcaatactta ataaatggtc   2700

aatgttattc tttttcacta tt                                            2722
```

<210> SEQ ID NO 37
<211> LENGTH: 631
<212> TYPE: DNA
<213> ORGANISM: Human
<220> FEATURE:
<221> NAME/KEY: misc_feature
<222> LOCATION: (524)..(524)
<223> OTHER INFORMATION: any kind of base
<220> FEATURE:
<221> NAME/KEY: misc_feature
<222> LOCATION: (592)..(592)
<223> OTHER INFORMATION: any kind of base
<220> FEATURE:
<221> NAME/KEY: misc_feature
<222> LOCATION: (547)..(547)
<223> OTHER INFORMATION: any kind of base
<220> FEATURE:
<221> NAME/KEY: misc_feature
<222> LOCATION: (600)..(600)
<223> OTHER INFORMATION: any kind of base
<220> FEATURE:
<221> NAME/KEY: misc_feature
<222> LOCATION: (519)..(519)
<223> OTHER INFORMATION: any kind of base

<400> SEQUENCE: 37

```
ttattctcta ccttgttcca catctggcat tttttgtgca tcttccaact taagtacaca     60

gcagcaagtg ctctacatct ttgggtagct acacagaacc ccactgtggc tcactgtgga    120

cacaccattg aaaaccttgt atgtaggtca cttagtacaa ggaggaacac aactgttgaa    180
```

-continued gaagtaccta aaaattgaat tacttgaaca aagtgtggga catttgctgt tttgatggat 240
tttaccacac tgtcttccca tttatgctta ccagcaatac ataggaacac ttgggtccct 300
gcagtcaggg tgtggaaatg gcagatgagt tcagccctaa ggtgcatttt tcttactagg 360
aggagatgga gtgtatttta tgggatataa gcattagcta catttcctgt cctgttcaca 420
tcctttgccc atgtgtctat gaggttattg atctttctta ctgatttatt ggtagctctt 480
acttaagagg taattagcct tttgcctgtg gagagtttnt tgtnttgcca tttgtccttt 540
tttaatnttt tttggttatt ggcccatttg tcttttggac tctgatgtgg tnttgctgan 600
ttcctttgat gtattctagt tatctgactt t 631

<210> SEQ ID NO 38
<211> LENGTH: 1761
<212> TYPE: DNA
<213> ORGANISM: Human

<400> SEQUENCE: 38
gtttagagta ctaggttatt tatgttttac aaagtttgaa tcttctataa actaagaaag 60
gggatgatcc ttagatttgc attaaaatat agaagtcttt taaagtaaat gtgaaccttg 120
tctaagtact gtaatccaca caacacatta taagaagcaa accagcatct taaggaatta 180
taaaattacc ctatttaaaa gccatgctat tgttctgcta ttaccagatt tattgtgcca 240
cacaaaagga tcatgtgtgt cagcaggggc cgtttggaac aaacctagtc attaatgagt 300
aagatactcc tgttagttca gggaccaagt tttatgaccc agaggcttaa tgatgtttgg 360
atatatttca aatcggcgtg cttacctcac tgatttaaat tattttctaa atagtggcca 420
ttgtagacct gactcaggct gaagctaaat agagaacaat ttagaaagtt aactaacaat 480
acagtgcatt ctacccgtag gcccaccatg cccttctgcc cctggctgat ttgatcctgt 540
gtctgatccc attgcaccct gactgggcag tccctacaga accagtgtta atttgaaggg 600
cctccactca ggctccaaat gtggcagcca aagagaacaa tccagggaac ctacatttat 660
ttttaaggac aaatatttcc tcctcagtgg tcctaatgtt cagggcttta gagggaaccc 720
aggtggtctc ttcaccctgt gtcctagaat gggagagtaa gtagacagtg gtgataaccc 780
cacactgctt ataagtgcat ctttatagta tttggggctt tcctacccct ttagccttct 840
gtacctagta ccatattcca gttttaaaga actggcagaa tgtgatggat aacagaggaa 900
gagctcaatt tatgtttatt ggaagaacat tttacttaaa tgatttgagg ggtgggaggg 960
agtgaactac tgagtttgcc agagtgaaaa tccatctgaa aaactcagct acctttagtt 1020
tttagtcctc atttttggtc ttgtctctgc ggactgtgaa gaatcacaat gctctatatg 1080
ccctggactg tgtggcaaat gcaggttgca gcgtgtgtgt tacatgagga tcttccacaa 1140
tttcagaatg cacgccagag ctgaaggggg aaacttggta acttgcccat tattctctgc 1200
ttttagccag agttaaacag actgatgggt ctggtagcca acaacttggc aacttccact 1260
ccttctcacc tcgtgagatt aagggctgtg aaaagaaatc tagtctaact ccaacagaaa 1320
tctgtctctg ttaagtgttt taccttctgt aagtagagat ggtagagcca agatttttct 1380
tttggtaatt tccctgtcta taaagtgaga ccaaagggat atctgttccc tgttaccttt 1440
ttggagaatt cataacattt gaagatcaaa aaattgaatg ataaatatga atggcttttc 1500
aattctgtgg actttgtacc atttggcttc accttgtact gcaagatgaa tttgtaaaca 1560
aaacaaaatt ggactgtctg gaaagctaaa gttctgaaat atggaatgta ctgcctctaa 1620

-continued

```
tttttctttg tcttcctctc actggcattt ttttctctcc caggtttctt aagaataatg   1680

ttttttaaag gaggcttttt gcccatcaag aataaaaaga aataaaacca aagggttacc   1740

ggaaaaaaaa aaaaaaaaaa a                                             1761
```

<210> SEQ ID NO 39
<211> LENGTH: 2414
<212> TYPE: DNA
<213> ORGANISM: Human

<400> SEQUENCE: 39

```
ggggtgaggg cagcagctcg ccacagctgc cagccatctg tccattcacc catctgtcca     60

tctggcagcc cgctgttcag acctgtctgt ctgtccgccc atctctgtaa gcccatctct    120

gtcccattgt ctatctgacc atctttctct tactgtcctc tttgtctagc tatctggcct    180

atctgtcgat ccatcttcgt gtctgtcttc agccccccacc tgtttttgtc catctgtcca    240

attacctgtg actctgtgca tcttcttgtc cattcatctg cccacccatc cgtccctccg    300

tctgcccacc agccgcccct ctcctcctgg gctgcagagc catggcccgg ggctacgggg    360

ccacggtcag cctagtcctg ctgggtctgg ggctggcgct ggctgtcatt gtgctggctg    420

tggtcctctc tcgacaccag gccccatgtg gcccccaggc ctttgcccac gctgctgttg    480

ccgccgactc caaggtctgc tcggatattg gacgagccat cctccagcag cagggctcac    540

ccgtggatgc caccatcgcg gctctggtct gcaccagcgt cgtcaaccct cagagcatgg    600

gcctgggcgg aggggtcatc ttcaccatct acaatgtgac aacagggaag gtggaggtca    660

tcaatgcccg ggagacggtg ccggccagcc acgccccgag cctgctggac cagtgtgcac    720

aggctctgcc actgggcaca ggggcccagt ggatcggggt gcccggggag ctccgtggct    780

atgccgaggc ccaccgccgc catggccgcc tgccctgggc gcagctgttc cagcccacca    840

tcgcgctgct ccgagggggg catgtggtgg cccctgtcct cagccgtttc ctgcacaaca    900

gcatcctgcg gccttccttg caggcgtcaa ccctgcgcca gctcttcttc aacgggacag    960

aacccctgag gcctcaggac ccactcccat ggcctgcact ggccaccacc ctggagaccg   1020

tggccacaga gggcgtggag gtcttctaca cggggaggct gggccagatg ctggtggagg   1080

acattgccaa ggaagggagc cagctgacgc tgcaggacct ggccaagttc cagcccgagg   1140

tggtggatgc cctggaggtg cccctggggg actataccct gtactcacca ccgccgcctg   1200

cagggggtgc cattctcagc tttatcctca acgtgctaag agggttcaac ttctcaacag   1260

agtctatggc caggcctgaa gggagggtga acgtgtacca ccaccttgta gagacgctca   1320

agtttgccag gggcagaggg tggaggctgg gggaccctcg aagccacccg aagctccaga   1380

atgcctcccg ggacctgctg ggggagaccc tggcccagct catccgccaa cagatcgatg   1440

gccgggggga ccaccagctc agccactaca gcttggccga ggcctggggc cacgggacag   1500

gcacgtccca tgtgtctgtg ctgggggagg atggcagcgc cgtggctgcc accagcacca   1560

tcaacacacc ctttggagcg atggtgtatt caccacggac aggcatcatc ctcaacaacg   1620

agctcctgga cttatgcgag cgatgcccct ggggttccgg caccaccccc tcacctgtga   1680

gtggagacag ggtgggtgga gctcccggaa ggtgctggcc cccagttcca ggcgagcgtt   1740

ccccatcctc catggtgccc tccatcttga tcaacaaagc ccaggggtcg aagctagtga   1800

ttggcggggc tggcggggag ctcatcatct ctgctgtggc ccaggccatc atgagcaagc   1860

tgtggcttgg ctttgacctg agagcggcca ttgcagcccc catcctgcat gtcaacagca   1920

agggctgtgt ggagtacgag cccaacttca gccaggaggt gcagagggga ctccaagacc   1980
```

-continued

```
gtggccagaa ccagacccag aggcccttct tcctgaacgt ggtccaggct gtgtcccagg   2040
aggggcctg tgtgtacgcc gtctcggacc tgaggaagag tggggaggcc gcaggctact   2100
aagacactgc tctgcccaga gctgaagtct ggccccacca tgagtcctgt gtccaggccg   2160
gacatggctg gggaccaac tactctggca ggatctggac ccctggcagg ggagtccagc   2220
tgagagtgga agaggtggcg gggaccagct gggcagatga gaggctgagc ctcatcccta   2280
accccctttc ccagagcccc tggtggtcct gaaccggccc ctctatccct ccgcaggcct   2340
cttacctggg gccactctcc caccctctcg atctgtatat cctccagtcc aagattaaag   2400
aagaggcgga ctgt                                                     2414
```

<210> SEQ ID NO 40
<211> LENGTH: 2146
<212> TYPE: DNA
<213> ORGANISM: Human

<400> SEQUENCE: 40

```
cggggacggt gcgccagtgc cccctccgcg agccccaacc agtagacggt tccctgtctc     60
ccgcgcccca atttcgattt tcaaacgcaa ctcctacagg attctgagac cccgtcccat    120
ctcccatatc ccatttccag ctgcaaatta ctgcagaatc tgaacccagg aaagaaaccc    180
atttgccgac cccctcttcc ctctccagac aggtggagag cgggtgaggg tctcgctcgg    240
ctttccccct gcacctttcc caccctcccg cccgtccctg gggtcctcc gtcaccgcgg    300
ccatggccca gaagccgaag gtggaccccc acgtcgggcg gctgggatac ctgcaggcgc    360
tggtcacgga attccaggag acccaaagcc aagacgccaa ggagcaagtc ctcgccaacc    420
tcgccaactt cgcttatgac cccagcaact acgagtatct gcggcagctg caggtcctgg    480
atttatttct cgattcgctg tcggaggaga atgagaccct ggtggagttt gctattggag    540
gcctgtgcaa cctgtgccca gacagggcca acaaggagca catcctgcac gcaggaggtg    600
tcccactcat catcaactgc ctatccagcc ccaatgagga gacggtgctg tctgccatca    660
ccacgctcat gcacctgagc ccgccgggcc gcagctttct cccagagctg accgccacgc    720
ccgtggtgca gtgcatgctt cgcttctccc tctcggccag cgccaggctc cggaacctgg    780
cacagatctt cctggaggac ttctgctccc cccgccaggt ggccgaggcc cgcagccggc    840
aggcgcactc tgccctgggt atcccactgc cgaggagcgt ggccccacgg cagcgctgat    900
ccatggagac tgcgagaccg tggcacccct actgctgggg accacagtcc tgatgtggac    960
gcagggaacg gggagcacat actgccccat tggtgccttt tcagccatct gaaaggcggg   1020
ttctttcagc aggacaggca tttacactga tgaaacgcca ctgggagtga ggaagccaga   1080
ctccagagac acggagaaga tcaaactgga gctgcgttca taggctggca ctctcaatcc   1140
tacatcaggt gccaccacca ccagactcag gccctggtgt aagaagcggc caagtgcctg   1200
gacccagagg ctttgcagga cagtgttctc aggagctggg cctgaggctt aggagagctg   1260
ccttcgctgc aggaaatcag ggattatccc ttaacagaag tgtctggagt agttttcagg   1320
tataggaatg agatgcctcg tggtgaaagg atctcaccct gggaagatgt ggtgcccccct   1380
ccagggctct ggaggatgga tgcctccccc aggggctctc caagctgggc atttgggcct   1440
ggtggatgcc aacctggata acctgtggcc cagcattgac tgtccaccca gccttgctgt   1500
taggcaccat gactccaaga tgaagatgtg gtccctgccc ttgagtgaca gcccagggac   1560
ttaatgtggc catcgggcat caagcacaag gccatgcagg tgatgatacg tcggaataga   1620
```

-continued

```
ggcaccagcc ctggtaactg catcttctcc ccttgccacc ccatggcccc ggctgaaagc   1680

ttcggccctc ctctgctgtc actcaatgat ggggagccct accccagaag tgtatcccac   1740

gagggcatca gggacgcagt gagtgttgct caagggagtc aggaagagac ggcaacgtaa   1800

aggatgtggc tccatgtcca tggtgccccc tggtcaacat aaggagcgtg ggatccgatg   1860

gaaaggtgga gctcagggaa aatgggggtc cttgcctctc gtgtaccccc tcaaggctga   1920

ccccttagat ggcccaggaa tggcaggtgc tacaaaaatg gtacccacgt gggcatggaa   1980

atggggcaga ttaggggacc actggactca gaggggaggg aagggctcat cagcacccgc   2040

tcagggagcc tgtcccttta tgttcccaaa taaagggtcc tagaagacta gaaagccaag   2100

gtcttttatt aaaggtcccg actggtaaaa aaaaaaaaaa aaaaaa                  2146
```

<210> SEQ ID NO 41
<211> LENGTH: 8789
<212> TYPE: DNA
<213> ORGANISM: Human

<400> SEQUENCE: 41

```
atgtctgaca aaatgtcgag tttcctacat attggagaca tttgttctct gtacgcggag     60

ggatcgacaa atggatttat tagcaccttg ggcctggttg atgatcgttg tgttgtacag    120

ccagaaaccg gggaccttaa caatccacct aagaaattca gagactgcct ctttaagcta    180

tgtcccatga accgctactc tgcccaaaag cagttctgga aagccgctaa gcctggggcc    240

aacagcacca cagacgcagt gctactcaac aaactgcacc acgctgcaga cttggaaaag    300

aagcagaatg agacagaaaa caggaaattg ctggggaccg taatccagta tggcaatgtg    360

atccagctcc tgcatttgaa aagtaataaa tacctaacag tgaataagag gcttcctgct    420

ctgttggaga agaatgccat gagagtcaca ttggacgagg ctggaaatga agggtcctgg    480

ttttatattc agccattcta caagctgcga tccattggag acagcgtggt cataggtgac    540

aaggtggttc tgaaccccgt caatgctggt cagcccctac atgctagcag ccatcaactg    600

gtagataacc caggctgcaa tgaggtcaat tccgtcaact gcaatacaag ctggaaaata    660

gtccttttca tgaaatggag tgataacaaa gacgacatat taaagggggg tgacgtggtg    720

aggctgtttc atgctgagca ggagaagttt ctcacctgtg acgaacacag gaagaagcag    780

cacgtcttcc tgagaaccac gggccggcag tcggccacat ctgccaccag ttcaaaagcc    840

ctgtgggagg tggaggtggt ccagcatgac ccatgtcggg gcggagcagg gtattggaac    900

agccttttcc gtttcaagca tctggccacg gggcattact tggcagcaga ggtggaccct    960

gatcaggacg cctctcgaag taggttgcgg aatgcccaag aaaagatggt atactccctg   1020

gtctctgtgc ctgaaggcaa tgacatctcc tccattttcg agctagatcc caccactctg   1080

cgtggaggtg acagccttgt cccaaggaac tcttatgttc ggctcagaca cctatgtact   1140

aatacctggg ttcacagcac aaatattcct attgacaagg aagaagaaaa gcccgtgatg   1200

ctgaaaattg gcacctctcc tgtgaaggag gataaggaag catttgccat agttccggtt   1260

tctcctgctg aagttcggga cctggacttc gccaatgatg ccagcaaggt gctgggctcc   1320

attgctggga agctagagaa gggcaccatc acccagaatg aaaggaggtc tgtaaccaag   1380

ctgctagaag atttggttta cttcgtcact ggtggaacta attctggtca agatgttctc   1440

gaagttgtct tctccaagcc caacagagaa cggcagaaac tgatgagaga acagaatatt   1500

ctcaagcaga tcttcaagtt gttacaagcc ccattcacag actgcggtga tggcccaatg   1560

cttcggctgg aagagctcgg ggaccagcgg cacgctcctt tcagacacat ctgccggctc   1620
```

-continued

```
tgctacaggg tgctgagaca ctcgcagcaa gactacagga agaaccagga gtatatagcc   1680
aagcagtttg gcttcatgca gaagcagatt ggctatgatg tgttggctga agacactatc   1740
actgccctgc tccacaataa tcggaaactc ctggaaaaac acattaccgc ggcagagatt   1800
gacacatttg tcagcctggt gcgaaagaac agggagccca gattcttaga ttacctctcc   1860
gacctctgtg tctccatgaa caaatcaatt ccagtgaccc aggaactgat atgtaaagct   1920
gtgctgaacc ccaccaacgc tgacatcctg attgagacca aattggttct ttctcgtttt   1980
gaatttgaag gtgtctcttc cactggagag aatgctctgg aggcaggaga agacgaggaa   2040
gaggtgtggc tgttttggag ggacagcaac aaagagattc gcagcaagag tgtgagggaa   2100
ttggctcagg atgctaaaga agggcagaag gaggaccgag acgttctcag ctactacaga   2160
tatcagctga acctctttgc gaggatgtgt ctggaccgcc aatacctggc catcaacgaa   2220
atctcaggcc agctggatgt cgatctcatt ctccgctgca tgtctgacga gaacctgccc   2280
tatgacctca gggcgtcctt ctgccgcctc atgcttcaca tgcatgtgga ccgagatccc   2340
caggaacaag tcaccccgt gaaatatgcc cgcctctggt cggagattcc ctcggagatc   2400
gccattgacg actatgatag tagtggagct tccaaagatg aaattaagga gagatttgct   2460
cagaccatgg agtttgtgga ggagtattta agagatgtgg tttgtcagag gttccctttc   2520
tctgataaag agaagaataa gcttacgttt gaggttgtaa atttagctag gaatctcata   2580
tactttggtt tctacaactt ctctgacctt ctacgattaa ctaagatcct tctggccata   2640
ttggactgtg tacatgtgac aacaatcttc cccattagca agatggcgaa aggagaagag   2700
aataaaggta acaatgatgt ggagaagctg aagagcagta acgtgatgag atctattcat   2760
ggcgtgggag agctgatgac ccaggtggtg ctccggggag gaggcttttt gcccatgact   2820
cccatggctg ctgcccctga aggcaatgtg aagcaggcag agcctgagaa ggaggacatc   2880
atggtcatgg acaccaagct gaagatcatt gagatactcc agtttatttt gaatgtgagg   2940
ttggattata ggatctcctg cctcctgtgt atatttaagc gagagtttga tgaaagcaat   3000
tcccagactt cagaaacatc ctccggaaac agcagccaag aagggccaag taatgtacca   3060
ggtgctcttg actttgaaca cattgaagaa caagcagaag gcatctttgg aggaagtgag   3120
gagaacaccc cactggactt ggatgaccac ggcggcagaa cctttctccg tgtcctgctc   3180
cacttgacga tgcatgacta cccacccctg gtgtcagggg ccctgcagct cctcttccgg   3240
cacttcagcc agaggcagga ggtgctccag gccttcaaac aggttcaact gctggttacc   3300
agccaagatg tggacaacta caaacagatc aaacaagact tggatcaact gaggtccatc   3360
gtggaaaagt cagagctttg ggtgtacaaa gggcagggcc ccgatgagac tatggatggt   3420
gcatctggag aaaatgaaca taagaaaacg gaggagggaa ataacaagcc acaaaagcat   3480
gaaagcacca gcagctacaa ctacagagtg gtcaaagaga ttttgattcg gcttagcaaa   3540
ctctgtgttc aagagagtgc ctcagtgaga aagagcagga agcagcaaca gcgtctgctc   3600
cggaacatgg gcgcgcacgc cgtggtgctg gagctgctgc agattcccta tgagaaggcc   3660
gaagatacca agatgcaaga gataatgagg ttggctcatg aatttttgca gaatttctgc   3720
gcaggcaacc agcagaatca agctttgcta cataaacaca taaacctgtt tctcaaccca   3780
gggatcctgg aggcagtaac catgcagcac atcttcatga acaatttcca gctttgcagt   3840
gagatcaacg agagagttgt tcagcacttc gttcactgca tagagactca cggtcggaat   3900
gtccagtata taaagttctt acagacaatt gtcaaggcag aagggaaatt tattaaaaaa   3960
```

-continued

```
tgccaagaca tggttatggc cgagctggtc aattcgggag aggatgtcct cgtgttctac   4020
aacgacagag cctctttcca gactctgatc cagatgatgc ggtcagaacg ggatcggatg   4080
gatgagaaca gccctctcat gtaccacatc cacttggtcg agctcctggc tgtgtgcacg   4140
gagggtaaga atgtctacac agagatcaag tgcaactccc tgctcccgct ggatgacatc   4200
gttcgcgtgg tgacccacga ggactgcatc cctgaggtta aaattgcata cattaacttc   4260
ctgaatcact gctatgtgga tacagaggtg gaaatgaagg agatttatac cagcaatcac   4320
atgtggaaat tgtttgagaa tttccttgta gacatctgca gggcctgtaa caacactagt   4380
gacaggaaac atgcagactc gattttggag aagtatgtca ccgaaatcgt catgagtatt   4440
gttactactt tcttcagctc tcccttctca gaccagagta cgactttgca gactcgccag   4500
cctgtctttg tgcaactgct gcaaggcgtg ttcagggttt accactgcaa ctggttaatg   4560
ccaagccaaa aagcctccgt ggagagctgt attcgggtgc tgtctgatgt agccaagagc   4620
cgggccattg ccattcccgt ggacctggac agccaagtca acaacctctt tctcaagtcc   4680
cacagcattg tgcagaaaac agccatgaac tggcggctct cagcccgcaa tgccgcacgc   4740
agggactctg ttctggcagc ttccagagac taccggaata tcattgagag attgcaggac   4800
atcgtctccg cgctggagga ccgtctcagg cccctggtgc aggcagagtt atctgtgctc   4860
gtggatgttc tccacagacc cgagctgctt ttcccagaga acacagacgc cagaaggaaa   4920
tgtgaaagtg gcggtttcat ttgcaagtta ataaagcata caaaacagct gctagaagaa   4980
aatgaagaga agctctgcat taaggtccta cagaccctga gggaaatgat gaccaaagat   5040
agaggctatg gagaaaagct aatttccatt gatgaattgg ataatgctga gcttcctcca   5100
gctccggatt ctgagaacgc cactgaggag cttgaaccaa gtccacccct gcggcagctg   5160
gaagaccata aaaggggtga ggcgctcagg caagttctgg tcaaccgtta ctatggaaac   5220
gtcagacctt cgggacgaag agagagcctt accagctttg gcaatggccc actgtcagca   5280
ggaggacccg gcaagcccgg gggaggaggg ggaggttccg gatccagctc tatgagcagg   5340
ggtgagatga gtctggccga ggttcagtgt caccttgaca aggaggggc ttccaatcta    5400
gttatcgacc tcatcatgaa cgcatccagt gaccgagtgt tccatgaaag cattctcctg   5460
gccattgccc ttctggaagg aggcaacacc accatccagc actccttttt ctgtcgcttg   5520
acagaagata agaagtcaga gaaattcttt aaggtgtttt atgaccggat gaaggtggcc   5580
cagcaagaaa tcaaagcaac agtgacagtg aacaccagtg acttgggaaa taaaaagaaa   5640
gacgatgagg tagacaggga tgccccatca cggaaaaaag ctaaagagcc cacaacacag   5700
ataacagaag aggtccggga tcagctcctg gaggcctccg ctgccaccag gaaagccttc   5760
accactttca ggagggaggc tgatcccgac gaccactacc agcctggaga gggcacccag   5820
gccactgccg acaaggccaa ggacgacctg gagatgagcg cggtcatcac catcatgcag   5880
cccatcctcc gcttccttca gctcctgtgt gaaaaccaca accgagacct gcagaacttc   5940
ctccgttgcc aaaataacaa gaccaactac aatttggtat gtgagaccct gcagtttctg   6000
gactgtattt gtggaagcac aactggaggc cttggtcttc tgggcttgta tataaatgaa   6060
aagaacgtag cgcttatcaa ccaaaccctg gaaagtctga ccgaatactg tcaaggacct   6120
tgccatgaga accagaactg catagccacc catgaatcca atggcattga catcatcaca   6180
gccctgatcc tcaatgatat caatcctttg ggaaagaaga ggatggacct tgtgttagaa   6240
ctgaagaaca atgcctcgaa gttgctcctg gccatcatgg aaagcaggca cgacagtgaa   6300
aacgcagaga ggatacttta taacatgagg cccaaggaac tggtggaagt gatcaagaaa   6360
```

-continued

```
gcctacatgc aaggtgaagt ggaatttgag gatggagaaa acggtgagga tggggcggcg   6420
tcccccagga acgtggggca caacatctac atattagccc atcagttggc tcggcataac   6480
aaagaacttc agagcatgct gaaacctggt ggccaagtgg acggagatga agccctggag   6540
ttttatgcca agcacacggc gcagatagag attgtcagat tagaccgaac aatggaacag   6600
atagtctttc ccgtgcccag catatgtgaa ttcctaacca aggagtcaaa actacgaatt   6660
tactatacta cggagagaga cgaacaaggc agcaaaatca atgatttctt tctgcggtct   6720
gaagacctct tcaatgaaat gaattggcag aagaaactga gagcccagcc cgtgttgtac   6780
tggtgtgccc gcaacatgtc tttctggagc agcatttcgt ttaacctggc cgtcctgatg   6840
aacctgctgg tggcgttttt ctacccgttt aagggagtcc gaggaggaac cctggagccc   6900
cactggtcgg gactcctgtg gacagccatg ctcatctctc tggccatcgt cattgccctc   6960
cccaagcccc atggcatccg ggccttaatt gcctccacaa ttctacgatt gatattttca   7020
gtcgggttac aacccacgtt gtttcttctg ggcgctttca atgtatgcaa taaaatcatc   7080
tttctaatga gctttgtggg caactgtggg acattcacaa gaggctaccg agccatggtt   7140
ctggatgttg agttcctcta tcacttgttg tatctggtga tctgtgccat ggggctcttt   7200
gtccatgaat tcttctacag tctgctgctt tttgatttag tgtacagaga agagactttg   7260
cttaatgtca ttaaaagtgt cactcgcaat ggacggccca tcatcctgac agcagttctg   7320
gctctgatcc tcgtttacct gttctcaata gtgggctatc ttttcttcaa ggatgacttt   7380
atcttggaag tagataggct gcccaatgaa acagctgttc cagaaaccgg cgagagtttg   7440
gcaagcgagt tcctgttctc cgatgtgtgt agggtggaga gtggggagaa ctgctcctct   7500
cctgcaccca gagaagagct ggtccctgca gaagagacgg aacaggataa agagcacaca   7560
tgtgagacgc tgctgatgtg cattgtcact gtgctgagtc acgggctgcg gagcgggggt   7620
ggagtaggag atgtactcag gaagccgtcc aaagaggaac ccctgtttgc tgctagagtt   7680
atttatgacc tcttgttctt cttcatggtc atcatcattg ttcttaacct gatttttggg   7740
gttatcattg acacttttgc tgacctgagg agtgagaagc agaagaagga agagatcttg   7800
aagaccacgt gctttatctg tggcttggaa agagacaagt ttgacaacaa gactgtcacc   7860
tttgaagagc acatcaagga agaacacaac atgtggcact atctgtgctt catcgtcctg   7920
gtgaaagtaa aggactccac cgaatatact gggcctgaga gttacgtggc agaaatgatc   7980
aaggaaagaa accttgactg gttccccagg atgagagcca tgtcattggt cagcagtgat   8040
tctgaaggag aacagaatga gctgagaaac ctgcaggaga agctggagtc caccatgaaa   8100
cttgtcacga acctttctgg ccagctgtcg gaattaaagg atcagatgac agaacaaagg   8160
aagcagaaac aaagaattgg tcttctagga catcctcctc acatgaatgt caacccacaa   8220
caaccagcat aagcaaatga aagaaaggaa ttgtatttac cttttataat tattattagt   8280
gtgggaatgg ctaatgagtt ctgattcacc cacgaaggtt acatttatgc tgaatacatt   8340
tgtaaatact cagttttata ctgtatgtat atgattgcta ctctaaaggt ttggatatat   8400
gtattgtaat tagaattgtt ggcatgatga catttcattt gtgccaaaaa tattaaaaat   8460
gcctttttttg gaaggactaa cagaaagcac ctgatttgca cttgaaccag attatagatt   8520
taaaagtata tgacatgtat tttgtattta aaactagaat agccagtatt tatgtttttt   8580
ataaaactgt gcaatacgaa ttatgcaatc acaatacatt tgtagctccc gagtgtccta   8640
aagggagtgc acttctttga agctggtgtg ttaatactat gtaataaatg gttaactttc   8700
```

-continued

```
aaatgatgct gctgccaaaa ttatattaat agagagtttc aggcccctgg gaattcctgc   8760

agcccggggg atccccgggt accgagctc                                     8789
```

<210> SEQ ID NO 42
<211> LENGTH: 4394
<212> TYPE: DNA
<213> ORGANISM: Human

<400> SEQUENCE: 42

```
aaactcccag ggcccgccca ggacccccaa gccgccgcgg acgcagccca ggatggcggc     60

ccaggtgact ctggaggacg cgctgtccaa cgtggacctc ctggaggagc tgcccctgcc    120

cgaccagcag ccctgcatcg agcccccgcc atcctcgctg ctctaccagc caaatttcaa    180

cactaacttt gaagacagaa atgcatttgt tactggcatc gcaagataca ttgaacaagc    240

caccgtccac tctagcatga acgagatgct ggaggagggc caagaatatg ctgtcatgct    300

gtacacctgg aggagctgct cccgggccat cccacaggtg aaatgtaacg agcagcctaa    360

cagagtggaa atctacgaga aaaccgtgga ggttctggag cctgaggtca caaaactgat    420

gaatttcatg tacttccaga gaaatgccat tgagcgtttc tgcggggaag tgaggcgcct    480

gtgccatgcc gagaggagga aggacttcgt gtcagaagcc tacctgatca cactgggcaa    540

attcatcaac atgttcgctg tgctggacga gctgaagaac atgaagtgca gtgtgaagaa    600

cgaccactca gcgtacaaga gggccgctca gtttttacgt aaaatggcag atccacagtc    660

catccaggaa tcgcagaatc tgtccatgtt cctggccaat cataacaaga tcacacagtc    720

tctgcagcag cagctcgaag tgatttctgg ctacgaagag ctcctggcag atattgtgaa    780

tctgtgtgtg gattactacg agaacaggat gtatttgacg cccagtgaga aacacatgct    840

tctcaaagtc atgggatttg gtctgtacct gatggatggg agtgtcagta acatctataa    900

gttggatgcc aagaaaagaa taaacttatc caaaatcgac aagtacttca agcaactcca    960

ggtggttcca ctatttgggg acatgcaaat agaactggca agatatatca agaccagcgc   1020

ccactacgag gaaaataaat ctcgatggac gtgcacatcc tccggcagca gccctcagta   1080

caacatctgc gagcagatga tccagatccg cgaggaccac atgcgcttca tttcggagct   1140

ggcgcgctac agcaacagcg aggtggtcac gggctcgggc cgccaggagg cccagaagac   1200

ggacgcggag taccgcaagc tcttcgacct ggcgctgcag ggcctgcagc tgttgtcgca   1260

gtggagcgcg cacgtgatgg aagtgtattc ctggaagctt gtgcacccca ccgacaagta   1320

ctccaacaag gactgccccg acagcgctga agagtacgag cgtgccacgc gctacaacta   1380

caccagcgag gagaagtttg ccctagtgga ggtgatcgcc atgatcaaag gcctgcaggt   1440

gctgatgggc aggatggaga gcgtgttcaa ccacgccatc cggcacaccg tctatgccgc   1500

actgcaggac ttctcccagg tgacccttag ggagccgctg cggcaggcca tcaagaagaa   1560

gaagaacgtc atccagagtg tcctgcaggc catcaggaag accgtgtgtg actgggagac   1620

ggggcatgag cccttcaatg acccagcctt gcggggcgag aaggacccca agagcggctt   1680

cgacataaaa gtaccacgcc gcgccgtggg accctccagc actcagcttt acatggtgag   1740

aaccatgcta gagtccctca ttgcagacaa aagtggttcc aagaaaacct tgagaagtag   1800

ccttgagggg cccaccatat tggacataga aaaatttcat cgagagtcat tcttctacac   1860

tcacttgata aatttcagtg aaacgctgca gcagtgctgt gacctttcgc agctgtggtt   1920

ccgagagttc ttcctggagc tgaccatggg caggaggatc cagttcccca ttgagatgtc   1980

gatgccctgg atcctgacgg accacatcct ggagaccaag gaggcatcga tgatggagta   2040
```

-continued

```
cgtgctctac tccctggacc tgtacaatga cagcgcccac tacgcgctca ccaggttcaa   2100
caagcagttc ctgtacgacg aaattgaggc cgaggtgaat ctatgttttg accaatttgt   2160
ttacaagcta gcagaccaga tatttgccta ttataaggtt atggcaggaa gtttgcttct   2220
tgataaacgg ttacgatcag aatgcaagaa tcagggagcc acgatccacc tcccgccgtc   2280
taaccgctac gagacgctgc tgaagcagag gcatgtgcag ctcctcggca gatcaataga   2340
cctcaatcgt ctgatcaccc agcgcgtctc agcagccatg tataagtccc tagaactggc   2400
gattggacga tttgaaagtg aagatttgac ctccatagtt gagctggatg gcctgttgga   2460
aatcaaccgc atgacccaca agctgctgag ccggtacctg acgctggacg gcttcgacgc   2520
catgttccgg gaggccaacc acaacgtgtc agcgccctac gggaggatca ccctgcacgt   2580
cttctgggag ctcaactatg acttcctgcc caactactgc tacaacggct ctaccaaccg   2640
gtttgttcgg acagtgttac cattttctca ggaatttcaa agagataagc agcctaatgc   2700
acagcctcag tatctgcatg gatccaaggc tttgaacttg gcctactcca gcatttacgg   2760
cagctaccgg aacttcgtgg gacctccaca ctttcaagtc atctgccggc ttctcggcta   2820
ccagggtatc gccgtggtca tggaggagct gctgaaggtc gtcaagagcc tgctgcaagg   2880
cacaatcctg cagtacgtga agacgctgat ggaggtgatg cccaagatct gccgcctgcc   2940
ccggcacgag tacggctctc ctggtatcct ggagttcttc caccaccagc tgaaggacat   3000
cgtggagtac gcagagctga agacggtgtg cttccagaac ctgcgggagg tggggaacgc   3060
catcctcttc tgcctgctca tcgagcagag cctgtcttta gaagaagtgt gtgacctgct   3120
gcacgcggct cctttccaga acatcttgcc gcgagtccat gtgaaagagg gggagagact   3180
tgatgccaaa atgaaaagac tagaatcaaa gtacgccccg ctgcatcttg tcccactgat   3240
tgaaagactg gggacccctc agcaaattgc catcgcaaga gagggggacc tgctgacaaa   3300
ggagcgcctc tgctgcggcc tgtccatgtt tgaggtcatc ctgacacgga tccggagctt   3360
tctggatgac cccatctggc gcgggcctct gcccagcaat ggggtcatgc atgtggacga   3420
gtgtgtggag tttcacagac tgtggagtgc catgcagttt gtctactgca ttcccgtggg   3480
gacacacgag ttcacagtcg agcagtgctt tggtgatggg ctacactggg ctggctgtat   3540
gatcatcgta cttcttgggc agcagcggcg ttttgctgtg ctggatttct gctaccatct   3600
acttaaagtc cagaaacatg atggcaaaga tgagattatt aaaaatgtgc ctttgaagaa   3660
gatggtggag agaattcgca agttccagat tctcaatgat gagatcatca ccatcctgga   3720
taagtacctg aagtcaggcg acggggaggg cacgccagtg gagcatgtgc gctgcttcca   3780
gccgcccatc caccagtccc tcgccagcag ctgagggcac gcgctgcact ccgtaactca   3840
acatggcatg cctttctctc cgtaaactat ttagtgagat ttttagggac tatttttcag   3900
tatctctgta cctgttaaag gggtgcttt tcgatctaaa aacttaattt tataaaattg   3960
acttattttt ctagactaaa attgtatatg cttttggtaa ttaggaactc ttgagaatat   4020
tggctgctga ttgttgccat cacgttccta caaaattgtt tttctatggg atgttctggc   4080
agctgtgtca taaaatgctg ctgggttcat tcattcattc cataagaaac ttaataccag   4140
caaatgcatt aaatcccttg ccagttacca ttaactataa ctatttagct tttgtttagg   4200
gatctttctg atggtctttt atgagcaatc ttagttctaa gtcattgttc ccatcccttt   4260
tttgtgtgtt tcagaaaata gtgaacttga ttcccctgct tccactaaat ccagttgtga   4320
caaaatctaa cgtgacatca gatcgaaagg ttatagaaat aaaactaatg agatctaaaa   4380
```

-continued

```
aaaaaaaaaa aaaa                                                       4394

<210> SEQ ID NO 43
<211> LENGTH: 1166
<212> TYPE: DNA
<213> ORGANISM: Human

<400> SEQUENCE: 43

gcaagaatgg tgcctgtcct gctgtctctg ctgctgcttc tgggtcctgc tgtcccccag      60

gagaaccaag atggtcgtta ctctctgacc tatatctaca ctgggctgtc caagcatgtt     120

gaagacgtcc ccgcgtttca ggcccttggc tcactcaatg acctccagtt ctttagatac     180

aacagtaaag acaggaagtc tcagcccatg ggactctgga gacaggtgga aggaatggag     240

gattggaagc aggacagcca acttcagaag gccagggagg acatctttat ggagaccctg     300

aaagacattg tggagtatta caacgacagt aacgggtctc acgtattgca gggaaggttt     360

ggttgtgaga tcgagaataa cagaagcagc ggagcattct ggaaatatta ctatgatgga     420

aaggactaca ttgaattcaa caaagaaatc ccagcctggg tccccttcga cccagcagcc     480

cagataacca agcagaagtg ggaggcagaa ccagtctacg tgcagcgggc caaggcttac     540

ctggaggagg agtgccctgc gactctgcgg aaatacctga aatacagcaa aaatatcctg     600

gaccggcaag atcctccctc tgtggtggtc accagccacc aggccccagg agaaaagaag     660

aaactgaagt gcctggccta cgacttctac ccagggaaaa ttgatgtgca ctggactcgg     720

gccggcgagg tgcaggagcc tgagttacgg ggagatgttc ttcacaatgg aaatggcact     780

taccagtcct gggtggtggt ggcagtgccc ccgcaggaca cagcccccta ctcctgccac     840

gtgcagcaca gcagcctggc ccagcccctc gtggtgccct gggaggccag ctaggaagca     900

agggttggag gcaatgtggg atctcagacc cagtagctgc ccttcctgcc tgatgtggga     960

gctgaaccac agaaatcaca gtcaatggat ccacaaggcc tgaggagcag tgtgggggga    1020

cagacaggag gtggatttgg agaccgaaga ctgggatgcc tgtcttgagt agacttggac    1080

ccaaaaaatc atctcacctt gagcccaccc ccaccccatt gtctaatctg tagaagctaa    1140

taaataatca tccctccttg cctagc                                         1166

<210> SEQ ID NO 44
<211> LENGTH: 5221
<212> TYPE: DNA
<213> ORGANISM: Human

<400> SEQUENCE: 44

cggccgcccg ggcaggtttt gtagactttc atagccaaag aaaccggctt cggcttcttt      60

aaaatccccg acgactcacc tgattaacct gctgcagttc tgaccctgcc aagagctgac     120

aatttactgg ttcatcaatg aaacaatatt aaattatgaa gatgtaagga aaaaatccta     180

cgctaacact gtcgcagttt gaaaggcttc tctgcagaat gtcaaacaaa gatcgacaca     240

ttgattccag ctgttcgtcc ttcatcaaga cggaaccttc cagcccagcc tccctgacgg     300

acagcgtcaa ccaccacagc cctggtggct cttcagacgc cagtgggagc tacagttcaa     360

ccatgaatgg ccatcagaac ggacttgact cgccacctct ctacccttct gctcctatcc     420

tgggaggtag tgggcctgtc aggaaactgt atgatgactg ctccagcacc attgttgaag     480

atccccagac caagtgtgaa tacatgctca actcgatgcc caagagactg tgtttagtgt     540

gtggtgacat cgcttctggg taccactatg ggtagcatc atgtgaagcc tgcaaggcat      600

ctttcaagag gaaaatacaa gccaatatag aatacagctg ccctgccacg aatgaatgtg     660
```

-continued

```
aaatcacaaa gcgcagacgt aaatcctgcc aggcttgccg cttcatgaag tgtttaaaag    720
tgggcatgct gaaagaaggg gtgcgtcttg acagagtacg tggaggtcgg cagaagtaca    780
agcgcaggat agatgcggag aacagcccat acctgaaccc tcagctggtt cagccagcca    840
aaaagccata taacaagatt gtctcacatt tgttggtggc tgaaccggag aagatctatg    900
ccatgcctga ccctactgtc cccgacagtg acatcaaagc cctcactaca ctgtgtgact    960
gtgccgaccg agagttggtg gttatcattg gatgggcgaa gcatatccca ggcttctcca   1020
cgctgtccct ggcggaccag atgagccttc tgcagagtgc ttggatggaa attttgatcc   1080
ttggtttcgt ataccggtct ctttcgtttg aggatgaact tgtctatgca gacgattata   1140
taatggacga agaccagtcc aaattagcag gccttcttga tctaaataat gctatcctgc   1200
agctggtaaa gaaatacaag agcatgaagc tggaaaaaga agaatttgtc accctcaaag   1260
ctatagctct tgctaattca gactccatgc acatagaaga tgttgaagcc gttcagaagc   1320
ttcaggatgt cttacatgaa gcgctgcagg attatgaagc tggccagcac atggaagacc   1380
ctcgtcgagc tggcaagatg ctgatgacac tgccactcct gaggcagacc tctaccaagg   1440
ccgtgcagca tttctacaac atcaaactag aaggcaaagt cccaatgcac aaactttttt   1500
tggaaatgtt ggaggccaag gtctgctaaa agctccctgg gccttccatc cttcattgtt   1560
gaaaagggga aataaaccca agagtgatgt cgaagaaact tagagtttag ttaacaacat   1620
caaaaatcaa cagactgcac tgataattta gcagcaagac tatgaagcag ctttcagatt   1680
cctccatagg ttcctgatga gtttctttct actttctcca tcatcttctt tcctctttct   1740
tcccacattt ctctttctct ttattttta tcctttctt ctttcacctc ccttatttct   1800
ttgcttcttt cattcctagt tcccattctc ctttatttc ttcccgtctg cctgccttct   1860
ttcttttctt tacctactct cattcctctc ttttctcatc cttcccttt tttctaaatt   1920
tgaaatagct ttagtttaaa aaaaaatcct cccttccccc tttcctttcc ctttctttcc   1980
tttttccctg tccttttccc tttcctttcc tttcctcttg accttctttc catctttctt   2040
tttcttcctt ctgctgctga acttttaaaa gaggtctcta actgaagaga gatggaagcc   2100
agccctgcca aaggatggag atccataata tggatgccag tgaacttatt gtgaaccata   2160
ccgtccccaa tgactaagga atcaaagaga gagaaccaac gttcctaaaa gtacagtgca   2220
catatacaaa ttgactgagt gcagtattag atttcatggg agcagcctct aattagacaa   2280
cttaagcaac gttgcatcgg ctgcttctta tcattgcttt tccatctaga gcagttacag   2340
ccatttgatc ccttaattgt tttttcaagt ctcccaggta tttgttagtt tagctactat   2400
gtaacttttt cagggaatag tttaagcttt attcagtcat gcaatactaa agagaaataa   2460
gaatactgca attttgtgct ggctttgaac aattacgaac aataatgaag gacaaatgaa   2520
tcctgaagga agatttttaa aaatgttttg tttcttctta caaatggaga ttttttgta   2580
ccagctttac cacttttcag ccatttatta atatgggaat ttaacttact caagcaatag   2640
ttgaagggaa ggtgcatatt atcacggttg caatttatgg ttgtgtgccc agtctggtcc   2700
ccaaacatca atttcttaac atgagctcca gtttacctaa atgttcactg acacaaagga   2760
tgagattaca cctacagtga ctctgagtag tcacatatat aagcactgca catgagatat   2820
agatccgtag aattgtcagg agtgcacctc tctacttggg aggtacaatt gccatatgat   2880
ttctagctgc catggtggtt aggaatgtga tacatgcctg tttgcaaagt cacagaccat   2940
tgcctcagaa ggagctgtga gccagtattc atttaagagg caataaggca aatgccagaa   3000
```

-continued

```
ttaaaaaaaa aaaatcatca aagacagaaa atgcctgacc aaattctaaa acctaatcca   3060
tataagttta ttcatttagg aatgttcgtt taaattaatc tgcagttttt accaagagct   3120
aagccaatat atgtgctttt caaccagtat tgtcacagca tgaaagtcac agtcaggttc   3180
cagactgtta agaggtgtaa tctaatgaag aaatcaatta gatgccccga aatctacagt   3240
cgctgaataa ccaataaaca gtaacctcca tcaaatgcta taccaatgga ccagtgttag   3300
tagctgctcc ctgtattatg tgaacagtct tattctatgt acacagatgt aattaaaatt   3360
gtaatcctaa caaacaaaag aaatgtagtt cagcttttca atgtttcatg tttgctgtgc   3420
ttttctgaat tttatgttgc attcaaagac tgttgtcttg ttcttgtggt gtttggattc   3480
ttgtggtgtg tgcttttaga cacagggtag aattagagac aatattggat gtacaattcc   3540
tcaggagact acagtagtat attctattcc ttaccagtaa taaggttctt cctaataata   3600
attaagagat tgagactcca aacaagtatt cattatgaac agatacacat caaaatcata   3660
ataatatttt cagaacaagg aataatttct ctaatggttt attatagaat accaatgtat   3720
agcttagaaa taaaactttg aatatttcaa gaatatagat aagtctaatt tttaaatgct   3780
gtatatatgg ctttcactca atcatctctc agatgttgtt attaactcgc tctgtgttgt   3840
tgcaaaactt tttggtgcag attcgtttcc aaaactattg ctactttgtg tgctttaaac   3900
aaaataccttt gggttgatga aacatcaacc cagtgctagg aatactgtgt atctatcatt   3960
agctatatgg gactatattg tagattgtgg tttctcagta gagaagtgac tgtagtgtga   4020
ttcttgataa atcatcatta gcaattcatt cagatggtca ataacttgaa atttatagct   4080
gtgataggag ttcagaaatt ggcacatccc tttaaaaata acaacagaaa atacaactcc   4140
tgggaaaaaa aggtgctgat tctataagat tatttatata tgtgagtgtt taaaaagatt   4200
attttccaga aagtttgtgc agggtttaag ttgctactat tcaactacac tatatataaa   4260
taagatatat acaatatata cattgttttc actgtatcac attaaagtac ttgggcttca   4320
gaagtaagaa gccaaccaac tgaaaacctg agatggagat atgttcaaag aatgagatac   4380
aattttttag ttttcagttt aagtaactct cagcattaca aaagagtaag tatctcacaa   4440
ataggaaata aaactaaaac gtagatttaa aaaagaactg cacgggcttt agggtaaatg   4500
ctcatcttaa acctcactag agggaagtct tctcaagttt caagcaagac catttactta   4560
atgtgaagtt ttggaaagtt ataaaggtgt atgttttagc catatgatcc taaatttaat   4620
tttgctcttt taggttcgtt cttatttaaa gcaatatgat tgtgtgactc cttgtagtta   4680
cacttgtgtt tcaatcagat cagattgttg tatttattcc actattttgc atttaaatga   4740
taacataaca gatataaaaa atttaaaact gctatttttc ttatagaaga gaaaatgggt   4800
gttggtgatt gtattttaat tatttaagcg tctctgttta cctgcctagg aaaacatttt   4860
atggcagtct tatgtgcaaa gatcgtaaaa ggacaaaaaa tttaaactgc ttataataat   4920
ccaggagttg cattatagcc agtagtaaaa aaaataataa taataataat aaaaccatgt   4980
ctatagctgt agatgggctt cacatctgta aagcaatcaa ttgtatattt ttgtgatgtg   5040
taccatactg tgtgctccag caaatgtcca tttgtgtaaa tgtatttatt ttatattgta   5100
tatattgtta aatgcaaaaa ggagatatga ttctgtaact ccaatcagtt cagatgtgta   5160
acccaaatat tatgcctttc aggatgatgg tagagcaata ttaaacaagc ttccactttt   5220
g                                                                   5221
```

<210> SEQ ID NO 45
<211> LENGTH: 1174

-continued

<212> TYPE: DNA
<213> ORGANISM: Human

<400> SEQUENCE: 45
ggcacgaggg ggccggagga gggacgcgcc ggagcgggac cgacgggacc gagcgagcga 60
ccgacgcgcc acccgccgac gcctcagccg cttggggccc gcacggaccc tctacttcag 120
tgtagaatga gccaaggaga ctcaaaccca gcagctattc cgcatgcagc agaagatatt 180
caaggagatg accgatggat gtctcagcac aacagatttg ttttggactg taaagacaaa 240
gagcctgatg tactgttcgt gggagactcc atggtgcagt taatgcagca atatgagata 300
tggcgagagc ttttttcccc acttcatgca ctgaattttg gaattggggg agatacaaca 360
agacatgttt tgtggagact aaagaatgga gaactggaga atattaagcc taaggtcatt 420
gttgtctggg taggaacaaa taaccacgaa aatacagcag aagaagtagc aggtgggatc 480
gaggccattg tacaacttat caacacaagg cagccacagg ccaaaatcat tgtattgggt 540
ttgttacctc gaggtgagaa acccaatcct ttgaggcaaa agaacgccaa ggtgaaccaa 600
ctcctcaagg tttcgctgcc gaagcttgcc aacgtgcagc tcctggatac cgacgggggt 660
tttgtgcact cggacggtgc catctcctgc cacgacatgt ttgattttct gcatctgaca 720 ggaggggggct atgcaaagat ctgcaaaccc ctgcatgaac tgatcatgca gttgttggag 780
gaaacacctg aggagaaaca aaccaccatt gcctgactgg ctcttatcag tgttaatagc 840
atctcagctt cctcagatca gttctatcac tggcactaca gaatccttct ctttcttaag 900
gcactttgca ttgtagaatg ttcctggatg ttcatatcta gtgtttgaag ggaggaggg 960 atttaaactg gtcctgtaca tagaaggttt gtttgacaga ggagaaaaat tagccaagga 1020
agattgttgt ttaaattcat ttgaaaccag aaggggactt tttagttgta tgtgtaacac 1080
attcattgaa ttattatcac tgttttcttg ggacaacatc aagcctaaat actgaacaat 1140
atgaagatta aaaaaaaaaa aaaaaaaaaa aaaa 1174

<210> SEQ ID NO 46
<211> LENGTH: 1619
<212> TYPE: DNA
<213> ORGANISM: Human

<400> SEQUENCE: 46
ggggatatgg cggggccttt gtctctcgct gtcgccggag tcccaggtct gtcttcactg 60
ctctgtgtcc tctgctccta gaggcccagc ctctgtggcg ctgttaccag cagtattgga 120
gatccacagc taagatgcca ggacccccta gaagcctaga aatgggactg ttgacattta 180
gggatgtggc catagaattc tctctggagg agtggcaaca cctggacatt gcacagcaga 240
atttatatag aaatgtgatg ttagagaact acagaaacct ggccttcctg ggtattgctg 300
tctctaagcc agacctgatc acctgtctgg aacaagggaa agagccctgg aatatgaagc 360
gacatgagat ggtggatgaa cccccaggta tgtgtcctca ttttgctcaa gacctttggc 420
cagagcaggg catggaagat tcttttcaaa aagcaatact gagaagatat ggaaaatatg 480
gacatgagaa tttacagtta agaaaaggct gtaaaagtgt ggatgagtat aaggtgaaca 540
aagaaggtta taatggactt aaccagtgtt tcacaactgc ccagagcaaa gtatttcaat 600
gtgataaata tttgaaagtc ttctataaat ttttaaattc aaacagacct aagataagac 660
atactgaaaa gaaatctttc aaatgtaaaa aacgtgtcaa attattttgc atgctttcac 720
ataaaaccca acacaaaagc atttatcata gagagaagtc ctacaaatgt aaagaatgtg 780

-continued

```
gaaaaacctt taattggtcc tcaaccctta ctaatcatag gaaaatttat actgaagaga    840

aaccttacaa atgtgaagaa tataacaaat ctcctaagca actctcaacc cttactacac    900

atgaaataat tcatgctgga gagaaactct acaaatgtga agaatgtggc aaagctttta    960

atcggtcctc aacttttact aaacataagg taattcatac tggagtaaaa ccctacaaat   1020

gtgaagaatg tggcaaagca tttttctggt cctcaaccct aactaaacat aagagaattc   1080

atactggaga gcaaccctac aaatgggaaa aatttggcaa agcctttaat cggtcctcgc   1140

acctcaccac agataagata actcatactg gagagaaatc ttacaagtat gaataatgtg   1200

ccaaagccta agaaaaccct caattcttaa tagatataag attattccta ctggagagaa   1260

actacaaacc tgagagaggc gctaatgctt ttgacagtac ctaaaacttt aaagaaaatc   1320

attctgctga aaaatcctag aaatgtgaag aatgtgaaaa agcctttaaa tgattgtcac   1380

acttgattgt aggtaagata attcatactg gagaaaacta ccagtgtgaa caacgtggcc   1440

aagcttcgac aatgctcaca ccctattgca caggaaagca tttatacttg agaagaaatg   1500

tacaaatatt ggcaaagtaa aaaatccatt aacacctgct cacatcttac tcaaaattgt   1560

agagttcata gtaaataaaa gcattaaaat tcaaaaaaaa aaaaaaaaaa aaaaaaaaa    1619
```

<210> SEQ ID NO 47
<211> LENGTH: 534
<212> TYPE: DNA
<213> ORGANISM: Human

<400> SEQUENCE: 47

```
tttttacaac atatatcttt aattaaattt atattggtgg gtttaaaaaa cattaagtca     60

ggagatgata gctagggaaa taaggtatcc tgtgagtatt tataacaaaa tatttaaaat    120

ttaaaaagaa taagaaacat caattggctt tttgtaactt aaaagagact aaccaagtgt    180

tgtttcccag ttctgtacaa gcagaggcca caggaggatt cttacataag aagcacaggg    240

aaaagaattg ttaattctgc gtgtgtgttt ttgtttctca gaattgtttg gaagaacttt    300

gtccagtcag aaatgagtaa aaacaagatg taagaaacat taaaacaggg ggcatatggt    360

cttaagagat aatcttggag aatatagcaa aagacaaatt gctccattag atattataat    420

ttggtatgta acatgaacat ttaaaattct gattaaagtg actaaaaggg tttgtttttt    480

aaaaaaaatc aaaacagaac ttacgggata aaactcagaa taaatttact ctca          534
```

<210> SEQ ID NO 48
<211> LENGTH: 4763
<212> TYPE: DNA
<213> ORGANISM: Human
<220> FEATURE:
<221> NAME/KEY: misc_feature
<222> LOCATION: (3847)..(3847)
<223> OTHER INFORMATION: any kind of base

<400> SEQUENCE: 48

```
cccctcaccc cactcaactg ccccgggccc ccgcgcgcgc ggccgcccct ccactcaccc     60

tgtgtcggcc ccgctcccct ctccccccacc aggcgagcag gcgagcgggc agagcccgcg    120

gcggaggtcg gcgcggctcc ggggttcatg gtgacgaggc ggcggccgct cgagcccagc    180

ggcggcgggc ggcgggagct ggggcgcggg cccgggccgc ctctcccaga gcgcggggcc    240

gggcggcggg cgcgcccagg cagcggctgc gagcgccccc ccgcgccgcg cccccgcgcc    300

ccccgcgccg cgccccccgcg cgcttggctt gcggggggcc gggcctgcgg gcggccgccg    360

cgccgcgcac ccatggacgg cccggccatc atcacccagg tgaccaaccc caaggaggac    420
```

-continued

```
gagggccggt tgccgggcgc gggcgagaaa gcctcccagt gcaacgtcag cttaaagaag    480
cagaggagcc gcagcatcct tagctccttc ttctgctgct tccgtgatta caatgtggag    540
gcccctccac ccagcagccc cagtgtgctt ccgccactgg tggaggagaa tggtgggctt    600
cagaagccac cagctaagta ccttcttcca gaggtgacgg tgcttgacta tggaaagaaa    660
tgtgtggtca ttgatttaga tgaaacattg gtgcacagtt cgtttaagcc tattagtaat    720
gctgatttta ttgttccggt tgaaatcgat ggaactatac atcaggtgta tgtgctgaag    780
cggccacatg tggacgagtt cctccagagg atggggcagc tttttgaatg tgtgctcttt    840
actgccagct tggccaagta tgcagaccct gtggctgacc tcctagaccg ctggggtgtg    900
ttccgggccc ggctcttcag agaatcatgt gtttttcatc gtgggaacta cgtgaaggac    960
ctgagtcgcc ttgggcggga gctgagcaaa gtgatcattg ttgacaattc ccctgcctca   1020
tacatcttcc atcctgagaa tgcagtgcct gtgcagtcct ggttcgatga catgacggac   1080
acggagctgc tggacctcat cccccttcttt gagggcctga gccgggagga cgacgtgtac   1140
agcatgctgc acagactctg caataggtag ccctggcctc tgcctgcctc ccgcctgtgc   1200
actctggaac ctctggcctc aggggacctg cctgtcctca gctccctggg agctgaaagt   1260
gaggatactc cgtgctccag gccacagggt gaatgtggcc atgcctacct gttttgtttt   1320
tttaagaaca gaaacaacta ttttaaaaga actcttttaa gaaatttcat aaagggacat   1380
gcattttact gggtttgctt ttcttaaaac ataccaaaaa agaaaaaaat agaaaaaaaa   1440
aaaaaaaaag ctgatctcta tcagactctt caactgtcct ccctccaagc agaccacctg   1500
tccccttcta tcccagctca gagcagctga cccaactcag aatctctttc ctacaggatg   1560
aaagtgcctt ttgaatgtta tttttaagcc gagagttaat tttctacac aacatatttc   1620
cagacatctt ttagtctttt attgtcttag atactataag aagatgaaca tgacaatttt   1680
ctagaacctg gtagcgtgtg tgtgtggttg gcggggggtg ctgagggagg ggagtgagtc   1740
acaggagcct gtcccccaac aggtgtgact gctctgacaa cctgtggcat gctgcagggt   1800
caggctcctg ataggaggat ttcatgacta tgtcattgtc tccactcatt tttgacccag   1860
tttggaatgt atctgcaatt gtgtggctca acactttagg aaacatagat tattttatat   1920
tattatttct gatggtgaca agtttgtctt gaggtcacat tttctccttg aaaagtgaca   1980
tcctgtcact tctgctctca cactactgcc atacatttgt gttttttttgt tgttattgtt   2040
tgggtagagc agttacaaga aaccctaaaa cccttggata taaaagaaat ctgtttattg   2100
atttttaaat ctttcctttc caaaagctgg atacacatgg agctgtttgg gaattttcct   2160
tgctgctacc gcgctgccac caaatggaat tgaccagcgg ctgttacact gttctttgcc   2220
actgtgccta tgctcagaat atgctcactg ctaagctaca aactcggaca gggtcagaaa   2280
cagaggtgtc ccatcccatt gcagcctcca ccacctgtaa ccccttcctg gcattggcca   2340
ctgaagggta caaaggcaaa aggaccacag caccacttag gtgtagcatg gattttaaac   2400
tgcagtcagt atcagatcct gtttgataaa taagctgact gttctctctt gagaacctgt   2460
ggcctcaacc agccaccaag ctgatgtggc ccaagctcca tctcttggtc ttctcctttg   2520
aagcacagcc tatttctgag ccaagggttg gggaagcctg tctagatgtg ggactcattg   2580
ccccaaacca gggagaggaa gagctcccac agggagagcc caggctctct ttgcagcctt   2640
tcccagtttg gtgtttaaag cagtgccatg ttccttgttt gacaacaaga cagtctgtaa   2700
agtattgctc ttaaaaacaa ttaaaaagaa ccctttcata ttggcaccat tgccttagtc   2760
```

-continued

```
ctctgtgggt tggtcttcag ccagcattct ggtgggagtg actggcatta acaagactgg   2820

aaatcggggg tcaaagtaaa atatctttgt tttgctttca ttcacaaagt aatgaagcca   2880

gctgccaatt acatcctccc aacagcactt tggtctgtga ctgctgtgtg atattcagaa   2940

gggaagtagt attcaggggg taaacaggtc tcccagcatt ctgagtgttc caaaccagta   3000

atccacatgc caattcaaat agaacagccc cttgctagat attaccacag ataatgacag   3060

tacatggtag aactgcccat gccacaaata tttatttgga aaagtagtca ttaaatgaac   3120

ccactgcctt aaatgtcttg aatgttgcag tcaagtgtct gtcatgtgtt gatatccaca   3180

cagaattagg ccctaatgag agccttagac cctcaaccat gccccctcg ttggcatcac   3240

agggccttat ttggaagagc ggggcaaaga ggatggaaat cataaaatat ttcatgggaa   3300

tcgaacctag ggatagtgct ccacttctga cgatggagtg aagacacttg gcagacttga   3360

gccagacact tcacctagta gttcctgaaa ctgtgagcac cactgcacta agccagtgcg   3420

gagctgttag ggacgggccc agctcctgca cacggacaca gaatgtctgg agagggcagc   3480

aggcctctga gggttctgga atctgtgcca ccttatttga ccacactcca aaattctgtt   3540

tttattttaa cccttgaatc tgctttatgt acataatcaa aatatctata tctatatcta   3600

tatctatatc tatatatttt taatcatcta catgtaaatg aagcaataga attctaacat   3660

aaggccaaga aatgagacga atgtttgggg tttatgtttt ttaaggtaaa tacgggtatt   3720

gtttttaatt attaccatgt attaaattgt gggctttgaa acctaatgaa acctgttagc   3780

cacttctctg tgccatatac ttcccatgtt accaaaatac gcccaactct ttagccaaaa   3840

gagaacnctg acctcctgag tttccatgct cctttctgtc aggtttaaat gtagtcttct   3900

ggagaagtat ttttgacatt gagctctggg acaggacacc ttgggtttgt ggactgcagc   3960

ccactatgat gttattactt ctctggccag gcctccagtg gaagtgcaca ggcactccca   4020

atgttgttaa tgctctgtct tccatttgtt ctggaatcct acgtgttggt ctgtggttcc   4080

atgcattagc tgtttgtaaa taatgcattt gcatactgaa aaaggaatgc cacctgccac   4140

agttgatggt gagaagctcc tttgacgtgg tgcaattttg atgagatgtc tctggggaca   4200

cgaggatgcc ctaatgatgc tgacttgtca tggttgcagc atttgaactt ttggtgttaa   4260

aaaaaaaaac ctgtaagtct gtaacctggc aacattttac aaccctgtat ttttaaagat   4320

ggctttctaa taaaaaatcc agaaccacac agccctatgg tcaaacaatc ctacgtttgt   4380

gcctctgctt ttaaaggtgc tgtgctggac agttggcatg ccagggttcg agaagagtga   4440

atggcttgac gtccttgcag ttaactgtgc aaaattggct ggctgcctct gttcctactg   4500

tactgtaact ttgatcatgt ctgttcctat tccattctcc caggagcttc tctgcagact   4560

gacacaccct cccccacccc gggtagtgga gatgctggtg tctgggtagt catggatttc   4620

tgctgacatt tgaatgtgat aaacaatcca gcattactta ggaaatgcta catgcggaat   4680

gtgcacgttt ccaggggcga gtattgtcaa tcaaaaggtt tgcaatgatt tccttcctgc   4740

caaaaataaa catgtgaaac tgc                                           4763
```

<210> SEQ ID NO 49
<211> LENGTH: 10300
<212> TYPE: DNA
<213> ORGANISM: Human

<400> SEQUENCE: 49

```
aactgctagt ggctgagtcc ctggcggggc gcggcggtgg aaggtgtcgc gtacgggctt     60

cccgagctga cgtggcttga attgggaggg gggcagctgg agcctcaggc ggcagcgctt    120
```

-continued

```
ctagaaatgc tgagccgatt atcaggatta gcaaatgttg ttttgcatga attatcagga   180
gatgatgaca ctgatcagaa tatgagggct cccctagacc ctgaattaca ccaagaatct   240
gacatggaat ttaataatac tacacaagaa gatgttcagg agcgcctggc ttatgcagag   300
caattggtgg tggagctaaa agatattatt agacagaagg atgttcaact gcagcagaaa   360
gatgaagctc tacaggaaga gagaaaagct gctgataaca aaattaaaaa actaaaactt   420
catgcgaagg ccaaattaac ttctttgaat aaatacatag aagaaatgaa agcacaagga   480
gggactgttc tgcctacaga acctcagtca gaggagcaac tttccaagca tgacaagagt   540
tctacagagg aagagatgga aatagaaaag ataaaacata agctccagga gaaggaggaa   600
ctaatcagca ctttgcaagc ccagcttact caggcacagg cagaacaacc tgcacagagt   660
tctacagaga tggaagaatt tgtaatgatg aagcaacagc tccaggagaa ggaagaattc   720
attagcactt tacaagccca gctcagccag acacaggcag agcaagctgc acagcaggtg   780
gtccgagaga aagatgcccg ctttgaaaca caagttcgtc ttcatgaaga tgagcttctt   840
cagttagtaa cccaggcaga tgtggaaaca gagatgcaac agaaattgag ggtgctgcaa   900
aggaagcttg aggaacacga agaatccttg gtgggccgtg ctcaggtcgt tgacttgctg   960
caacaggagc tgactgctgc tgagcagaga aaccagattc tctctcagca gttacagcag  1020
atggaagctg agcataatac tttgaggaac actgtggaaa cagaaagaga ggagtccaag  1080
attctactgg aaaagatgga acttgaagtg gcagagagaa aattatcctt ccataatctg  1140
caggaagaaa tgcatcatct tttagaacag tttgagcaag caggccaagc ccaggctgaa  1200
ctagagtctc ggtatagtgc tttggagcag aagcacaaag cagaaatgga agagaagacc  1260
tctcatattt tgagtcttca aaagactgga caagagctgc agtctgcctg tgatgctcta  1320
aaggatcaaa attcaaagct tctccaagat aagaatgaac aggcagttca gtcagcccag  1380
accattcagc aactggaaga tcagctccag caaaaaatcca aagaaattag ccaatttcta  1440
aatagactgc ccttgcaaca acatgaaaca gcatctcaga cttctttccc agatgtttat  1500
aatgagggca cacaggcagt cactgaggag aatattgctt ctttgcagaa gagagtggta  1560
gaactagaga atgaaaaggg agccttgctc cttagttcta tagagctgga ggagctgaaa  1620
gctgagaatg aaaaactgtc ttctcagatt actctcctag aggctcagaa tagaactggg  1680
gaggcagaca gagaagtcag tgagatcagc attgttgata ttgccaacaa gaggagctct  1740
tctgctgagg aaagtggaca agatgttcta gaaaacacat tttctcagaa acataaagaa  1800
ttatcagttt tattgttgga aatgaaagaa gctcaagagg aaattgcatt tcttaaatta  1860
cagctccagg gaaaaagggc tgaggaagca gatcatgagg tccttgacca gaaagaaatg  1920
aaacagatgg agggtgaggg aatagctcca attaaaatga aagtatttct tgaagataca  1980
gggcaagatt ttcccttaat gccaaatgaa gagagcagtc ttccagcagt tgaaaaagaa  2040
caggcgagca ctgaacatca aagtagaaca tctgaggaaa tatctttaaa tgatgctgga  2100
gtagaattga aatcaacaaa gcaggatggt gataaatccc tttctgctgt accagatatt  2160
ggtcagtgtc atcaggatga gttggaaagg ttaaaaagtc aaattttgga gctcgagcta  2220
aactttcata aagcacaaga aatctatgag aaaaatttag atgagaaagc taaggaaatt  2280
agcaacctaa accagttgat tgaggagttt aagaaaaatg ctgacaacaa cagcagtgca  2340
ttcactgctt tgtctgaaga aagagaccag cttctctctc aggtgaagga acttagcatg  2400
gtaacagaat tgagggctca ggtaaagcaa ctggaaatga accttgcaga agcagaaagg  2460
```

-continued

```
caaagaagac ttgattatga aagccaaact gcccatgaca acctgctcac tgaacagatc   2520
catagtctca gcatagaagc caaatctaaa gatgtgaaaa ttgaagtttt acagaatgaa   2580
ctggatgatg tgcagcttca gttttctgag cagagtaccc tgataagaag cctgcaaagc   2640
cagctgcaaa ataaggaaag tgaagtgctt gagggggcag aacgtgtaag gcatatctca   2700
agtaaagtgg aagaactgtc ccaggctctt tcacagaagg aacttgaaat aacaaaaatg   2760
gatcagctct tactagagaa aaagagagat gtggaaaccc tccaacaaac catcgaggag   2820
aaggatcaac aagtgacaga aatcagcttt agtatgactg agaaaatggt tcagcttaat   2880
gaagagaagt tttctcttgg ggttgaaatt aagactctta aagaacagct aaatttatta   2940
tccagagctg aggaagcaaa aaaagagcag gtggaagaag ataatgaagt ttcttctggc   3000
cttaaacaaa attatgatga gatgagccca gcaggacaaa taagtaagga agaacttcag   3060
catgaatttg accttctgaa gaaagaaaat gagcagagaa agagaaagct ccaggcagct   3120
cttattaaca gaaaggagct tctgcaaaga gtcagtagat tggaagaaga attagccaac   3180
ttgaaagatg aatctaagaa agaaatccca ctcagtgaga ctgagagggg agaagtggaa   3240
gaagataaag aaaacaaaga atactcagaa aaatgtgtga cttctaagtg ccaagaaata   3300
gaaatttatt taaaacagac aatatctgag aaagaagtgg aactacagca tataaggaag   3360
gatttggaag aaaagctggc agctgaagag caattccagg ctctggtcaa acagatgaat   3420
cagaccttgc aagataaaac aaaccaaata gatttgctcc aagcagaaat cagtgaaaac   3480
caagcaatta tccagaagtt aatcacaagt aacacggatg caagtgatgg ggactccgta   3540
gcacttgtaa aggaaacagt ggtgataagt ccaccttgta caggtagtag tgaacactgg   3600
aaaccagaac tagaagaaaa gatactggcc cttgaaaaag aaaaggagca acttcaaaag   3660
aagctacagg aagccttaac ctcccgcaag gcaattctta aaaaggcaca ggagaaagaa   3720
agacatctca gggaggagct aaagcaacag aaagatgact ataatcgctt gcaagaacag   3780
tttgatgagc aaagcaagga aaatgagaat attggagacc agctaaggca actccagatt   3840
caagtaaggg aatccataga cggaaaactc ccaagcacag accagcagga atcgtgttct   3900
tccactccag gtttagaaga acctttattc aaagccacag aacagcatca cactcaacct   3960
gttttagagt ccaacttgtg cccagactgg ccttctcatt ctgaagatgc gagtgctctg   4020
cagggcggaa cttctgttgc ccagattaag gcccagctga aggaaataga ggctgagaaa   4080
gtagagttag aattgaaagt tagttctaca acaagtgagc ttactaaaaa atcagaagag   4140
gtatttcagt tacaagagca gataaataaa cagggtttag aaatcgagag tctaaagaca   4200
gtatcccatg aagctgaagt ccatgccgaa agcctgcagc agaaattgga aagcagccaa   4260
ctacaaattg ctggcctaga acatctaaga gaattgcaac ctaaactgga tgaactgcaa   4320
aaactcataa gcaaaaagga agaagacgtt agctaccttt ctggacaact tagtgagaaa   4380
gaagcagctc tcactaaaat acagacagag ataatagaac aagaagattt aattaaggct   4440
ctgcatacac agctagaaat gcaagccaaa gagcatgatg agaggataaa gcagctacag   4500
gtggaacttt gtgaaatgaa gcaaaaacca gaagagattg gagaagaaag tagagcaaag   4560
caacaaatac aaaggaaact gcaagctgcc cttatttccc gaaaagaagc actaaaagaa   4620
aacaaaagtc tccaagagga attgtctttg gccagaggta ccattgaacg tctcaccaag   4680
tctctggcag atgtggaaag ccaagtttct gctcaaaata aagaaaaaga tacggtctta   4740
ggaaggttag ctcttcttca agaagaaaga gacaaactca ttacagaaat ggacaggtct   4800
ttattggaaa atcagagtct cagcagctcc tgtgaaagtc taaaactagc tctagagggt   4860
```

-continued

```
cttactgaag acaaggaaaa gttagtgaag gaaattgaat ctttgaaatc ttctaagatt   4920
gcagaaagta ctgagtggca agagaaacac aaggagctac aaaaagagta tgaaattctt   4980
ctgcagtcct atgagaatgt tagtaatgaa gcagaaagga ttcagcatgt ggtggaagct   5040
gtgaggcaag agaaacaaga actgtatggc aagttaagaa gcacagaggc aaacaagaag   5100
gagacagaaa agcagttgca ggaagctgag caagaaatgg aggaaatgaa agaaaagatg   5160
agaaagtttg ctaaatctaa acagcagaaa atcctagagc tggaagaaga gaatgaccgg   5220
cttagggcag aggtgcaccc tgcaggagat acagctaaag agtgtatgga aacacttctt   5280
tcttccaatg ccagcatgaa ggaagaactt gaaagggtca aaatggagta tgaaaccctt   5340
tctaagaagt ttcagtcttt aatgtctgag aaagactctc taagtgaaga ggttcaagat   5400
ttaaagcatc agatagaaga taatgtatct aaacaagcta acctagaggc caccgagaaa   5460
catgataacc aaacgaatgt cactgaagag ggaacacagt ctataccagg tgagactgaa   5520
gagcaagact ctctgagtat gagcacaaga cctacatgtt cagaatcggt tccatcagcg   5580
aagagtgcca accctgctgt aagtaaggat ttcagctcac atgatgaaat taataactac   5640
ctacagcaga ttgatcagct caaagaaaga attgctggat tagaggagga gaagcagaaa   5700
aacaaggaat ttagccagac tttagaaaat gagaaaaata ccttactgag tcagatatca   5760
acaaaggatg gtgaactaaa aatgcttcag gaggaagtaa ccaaaatgaa cctgttaaat   5820
cagcaaatcc aagaagaact ctccagagtt accaaactaa aggagacagc agaagaagag   5880
aaagatgatt tggaagagag gcttatgaat caattagcag aacttaatgg aagcattggg   5940
aattactgtc aggatgttac agatgcccaa ataaaaaatg agctattgga atctgaaatg   6000
aagaacctta aaaagtgtgt gagtgaattg gaagaagaaa agcagcagtt agtcaaggaa   6060
aaaactaagg tggaatcaga aatacgaaag gaatatttgg agaaaataca aggtgctcag   6120
aaagaacccg gaaataaaag ccatgcaaag gaacttcagg aactgttaaa agaaaaacaa   6180
caagaagtaa agcagctaca gaaggactgc atcaggtatc aagagaaaat tagtgctctg   6240
gagagaactg ttaaagctct agaatttgtt caaactgaat ctcaaaaaga tttggaaata   6300
accaaagaaa atctggctca agcagttgaa caccgcaaaa aggcacaagc agaattagct   6360
agcttcaaag tcctgctaga tgacactcaa agtgaagcag caagggtcct agcagacaat   6420
ctcaagttga aaaaggaact tcagtcaaat aaagaatcag ttaaaagcca gatgaaacaa   6480
aaggatgaag atcttgagcg aagactggaa caggcagaag agaagcacct gaaagagaag   6540
aagaatatgc aagagaaact ggatgctttg cgcagagaaa aagtccactt ggaagagaca   6600
attggagaga ttcaggttac tttgaacaag aaagacaagg aagttcagca acttcaggaa   6660
aacttggaca gtactgtgac ccagcttgca gcctttacta agagcatgtc ttccctccag   6720
gatgatcgtg acagggtgat agatgaagct aagaaatggg agaggaagtt tagtgatgcg   6780
attcaaagca aagaagaaga aattagactc aaagaagata attgcagtgt tctaaaggat   6840
caacttagac agatgtccat ccatatggaa gaattaaaga ttaacatttc caggcttgaa   6900
catgacaagc agatttggga gtccaaggcc cagacagagg tccagcttca gcagaaggtc   6960
tgtgatactc tacaggggga aaacaaagaa cttttgtccc agctagaaga gacacgccac   7020
ctataccaca gttctcagaa tgaattagct aagttggaat cagaacttaa gagtctcaaa   7080
gaccagttga ctgatttaag taactcttta gaaaaatgta aggaacaaaa aggaaacttg   7140
gaagggatca taaggcagca agaggctgat attcaaaatt ctaagttcag ttatgaacaa   7200
```

-continued

```
ctggagactg atcttcaggc ctccagagaa ctgaccagta ggctgcatga agaaataaat   7260
atgaaagagc aaaagattat aagcctgctt tctggcaagg aagaggcaat ccaagtagct   7320
attgctgaac tgcgtcagca acatgataaa gaaattaaag agctggaaaa cctgctgtcc   7380
caggaggaag aggagaatat tgttttagaa gaggagaaca aaaaggctgt tgataaaacc   7440
aatcagctta tggaaacact gaaaaccatc aaaaaggaaa acattcagca aaaggcacag   7500
ttggattcct ttgttaaatc catgtcttct ctccaaaatg atcgagaccg catagtgggt   7560
gactatcaac agctggaaga gcgacatctc tctataatct tggaaaaaga ccaactcatc   7620
caagaggctg ctgcagagaa taataagctt aaagaagaaa tacgaggctt gagaagtcat   7680
atggatgatc tcaattctga gaatgccaag ctagatgcag aactgatcca atatagagaa   7740
gacctgaacc aagtgataac aataaaggac agccaacaaa agcagcttct tgaagttcaa   7800
cttcagcaaa ataaggagct ggaaaataaa tatgctaaat tagaagaaaa gctgaaggaa   7860
tctgaggaag caaatgagga tctgcggagg tcctttaatg ccctacaaga agagaaacaa   7920
gatttatcta aagagattga gagtttgaaa gtatctatat cccagctaac aagacaagta   7980
acagccttgc aagaagaagg tactttagga ctctatcatg cccagttaaa agtaaaagaa   8040
gaagaggtac acaggttaag tgctttgttt tcctcctctc aaaagagaat tgcagaactg   8100
gaagaagaat tggtttgtgt tcaaaaggaa gctgccaaga aggtaggtga aattgaagat   8160
aaactgaaga aagaattaaa gcatcttcat catgatgcag ggataatgag aaatgaaact   8220
gaaacagcag aagagagagt ggcagagcta gcaagagatt tggtggagat ggaacagaaa   8280
ttactcatgg tcaccaaaga aaataaaggt ctcacagcac aaattcagtc ttttggaagg   8340
tctatgagtt ccttgcaaaa tagtagagat catgccaatg aggaacttga tgaactgaaa   8400
aggaaatatg atgccagtct gaaggaattg gcacagttga aagaacaggg actcttaaac   8460
agagagagag atgctcttct ttctgaaacc gccttttcaa tgaactccac tgaggagaat   8520
agcttgtctc accttgagaa acttaaccaa cagctcctat ccaaagatga gcaattgctt   8580
cacttgtcct cacaactaga agattcttat aaccaagtgc agtccttttc caaggctatg   8640
gccagtctgc agaatgagag agatcacctg tggaatgagc tggagaaatt tcgaaagtca   8700
gaggaaggga agcagaggtc tgcagctcag ccttccacca gcccagctga agtacagagt   8760
ttaaaaaaag ctatgtcttc actccaaaat gacagagaca gactactgaa ggaattgaag   8820
aatctgcagc agcaatactt acagattaat caagagatca ctgagttaca tccactgaag   8880
gctcaacttc aggagtatca agataagaca aaagcatttc agattatgca agaagagctc   8940
aggcaggaaa acctctcctg gcagcatgag ctgcatcagc tcaggatgga gaagagttcc   9000
tgggaaatac atgagaggag aatgaaggaa cagtacctta tggctatctc agataaagat   9060
cagcagctca gtcatctgca gaatcttata agggaattga ggtcttcttc ctcccagact   9120
cagcctctca aagtgcaata ccaaagacag gcatccccag agacatcagc ttccccagat   9180
gggtcacaaa atctggttta tgagacagaa cttctcagga cccagctcaa tgacagctta   9240
aaggaaattc accaaaagga gttaagaatt cagcaactga acagcaactt ctctcagcta   9300
ctggaagaga aaaacaccct ttccattcag ctctgcgata ccagtcagag tcttcgtgag   9360
aaccagcagc actatggtga ccttttaaat cactgtgcag tcttggagaa gcaggttcaa   9420
gagctgcagg cggggccact aaatatagat gttgctccag gagctcccca ggaaaagaat   9480
ggagttcaca gaaagagtga ccctgaggaa ctaagggaac cgcagcaaag cttttctgaa   9540
gctcagcagc agctatgcaa caccagacag gaagtgaatg aattaaggaa gctgctggaa   9600
```

-continued gaagaacgag accaaagagt ggctgctgag aatgctctct ctgtggccga ggagcagatc 9660
agacggttag agcacagtga atgggactct tcccggactc ctatcattgg ctcctgtggc 9720
actcaggagc aggcactgtt aatagatctt acaagcaaca gttgtcgaag gacccggagt 9780
ggcgttggat ggaagcgagt cctgcgttca ctctgtcatt cacggacccg agtgccactt 9840
ctagcagcca tctactttct aatgattcat gtcctgctca ttctgtgttt tacgggccat 9900
ctatagactt agttgttact ctttggacca ctcccttcaa aacttggaat tctctcacct 9960
ctaacatcag aacatcaatt ccagtggaac agtcttccca tttacaggtc ttctctccaa 10020
ctcttcacgg aaagtgcctg caaaaacaga ggtggatacg aggacaggtt ggagctgcag 10080
ggactggcga gtctgctttc ttctactgcc ctgagcctga acgcttctgc ttaatctgag 10140
aatcacattt ggtttgttga gcctaatatt tgttgagatt ttgcaggacc ctgatctttt 10200
gtggtcctgt aaaagatact gaggaatgtc tttcagccaa gccaagagga tggtttcaat 10260
aaacctaata atctgaagtt cagctttttt ttttttttt 10300

<210> SEQ ID NO 50
<211> LENGTH: 2357
<212> TYPE: DNA
<213> ORGANISM: Human

<400> SEQUENCE: 50
gaggagacgc gctttgtgct gggcgccggc cgcgccagcc acggcctgcg gcgcccgcgg 60
caccatgatc tccaccaagg agaagaacaa gatcccgaag gacagcatga cgcttctgcc 120
ctgcttctac ttcgtggagc tgcccatagt ggcttcttcc atcgtatcct tgtacttcct 180
ggagctgacc gacctcttca agccggccaa ggtgggcttc cagtgctatg accgcactct 240
ctccatgccc tacgtggaga ccaacgagga gctcatcccg ctgctgatgc tgctcagctt 300
ggccttcgcg gcccctgccg cctcgatcat ggtggccgag ggcatgttgt actgtctgca 360
gtcccggctg tggggccgtg ccgggggggcc cgccggggcg gagggcagca tcaacgccgg 420
cggctgcaac ttcaactcct tcctgcggcg tacggtgcgg tttgtgggtg tccacgtgtt 480
cggcctgtgt gccacagccc tggtgacgga cgtgatccag ctggccacgg gttaccacac 540
tcccttcttc ctcaccgtct gcaagcccaa ctacactctc ctgggcacgt cctgcgaggt 600
caacccctac atcacgcagg acatctgctc cggccacgac atccacgcca tcctgtctgc 660
acggaagacc ttcccgtccc agcacgccac gctgtcagcc ttcgccgcgg tctatgtgtc 720
ggtgagtccg gcacctcact gcccttccca ggccctcttg ctgacccgtg gggagccctc 780
cctgacccca acccccatgc cccagatgta cttcaactcg gtcatctcgg acaccaccaa 840
gctgctgaag cccatcctgg tcttcgcctt tgccatcgcc gcgggcgtat gcgggctcac 900
gcagatcacg cagtaccgca gccaccctgt ggacgtgtat gccggcttcc tcatcggggc 960
gggcatcgct gcctacctgg cctgccacgc ggtgggcaac ttccaggccc cacctgcaga 1020
gaagcccgcg gccccggccc ccgccaagga cgcgctgcgg gccctgacgc agcggggcca 1080
cgactcggtt tatcagcaga ataagtcggt gagcaccgac gagctggggc ccccagggcg 1140
gctggagggc gcgccccggc ccgtggcccg cgagaagacc tcgctgggca gcctgaagcg 1200
cgccagcgtg gacgtggacc tgctggcccc gcgcagcccc atggccaagg agaacatggt 1260
gaccttcagc cacacgctgc ccagggccag cgcgccctcg ctggacgacc ccgcgcgccg 1320
ccacatgacc atccacgtgc cgctggacgc ctcgcgctcc aagcagctca tcagcgagtg 1380

-continued

```
gaagcagaag agcctggagg gccgcggcct ggggctgccc gacgacgcca gccccgggca   1440

cctgcgcgcg cccgccgaac ccatggcgga ggaggaggaa gaggaggagg acgaagagga   1500

agaggaggag gaggaagagg aggaggacga gggcccggcc ccgccctcgc tctaccccac   1560

cgtgcaggcg cggccggggc tggggcctcg ggtcatcctc ccaccgcgcg cggggccgcc   1620

gccgctggtg cacatcccgg aggagggcgc gcagacgggg gccggcctgt cccccaaaag   1680

cggcgccggg gtgcgcgcca agtggctcat gatggccgag aagagcgggg cggcagtggc   1740

caaccctccg cggctgctgc aggtcatcgc catgtccaag gctccgggcg cgccgggccc   1800

caaggcggcc gagacggcgt cgtcgtccag cgccagctcc gactcctcgc agtaccggtc   1860

gccgtcggac cgcgactccg ccagcatcgt gaccatcgac gcgcacgcgc cgcaccaccc   1920

cgtggtgcac ctgtcggccg gcggcgcgcc ctgggagtgg aaggcggcgg gcggcggggc   1980

caaggcggag gccgacggcg gctacgagct gggggacctg gcgcgcggct tccgcggcgg   2040

ggccaagccc ccgggcgtgt cccccggctc gtcggtcagc gacgtggacc aggaggagcc   2100

gcggttcggg gccgtggcca ccgtcaacct ggccacgggc gaggggctgc cccgctggg   2160

cgcggccgat ggggcgctgg gcccgggcag ccgggagtcc acgctgcggc gccacgcggg   2220

cggcctgggg ctggcggagc gcgaggcgga ggcggaggcc gagggctact tccgcaagat   2280

gcaggcgcgc cgcttccccg actagcgcgg cggggccggg ggcgggcggg gggcgggccg   2340

agggcgcggg cggccgc                                                  2357
```

<210> SEQ ID NO 51
<211> LENGTH: 3496
<212> TYPE: DNA
<213> ORGANISM: Human

<400> SEQUENCE: 51

```
aagattttac tgacaatttg gagctagatg aagaaggagc aggcgggttc acggctaaag     60

caatcgttca gagagacaga gtggatgaag aggccttgaa tttcccctac gaggatgact    120

ttgacaacga tgtggatgct ctgctggaag aaggcctttg tgcccccaaa aagaggcgaa    180

cagaggaaaa atatggcgga gacagcgacc atctgtccga tggagagaca agtgtgcagc    240

cgatgatgac caagattaaa acagtgctca aaagtcgtgg ccgcccacct acagagccgc    300

tgcccgacgg gtggatcatg acattccata actctggagt cccggtgtac ctacacagag    360

agtctcgggt ggtcacctgg tccaggccat acttcttggg aacgggaagc atacggaaat    420

acgaccctcc tctgagtagc atcccttgtc tgcattataa gaaaatgaag gacaacgagg    480

aacgggagca aagcagtgac ctcaccccta gtggggatgt gtcccccgtc aagcccctga    540

gccgatctgc agagctggag tttcccctgg atgagcctga ctctatgggt gctgacccgg    600

ggcccccgga cgagaaagac ccactagggg ctgaggcagc ccctggggcc ctggggcagg    660

tgaaggccaa agtcgaggtg tgcaaagatg aatccgttga tctcgaggaa tttcgaagct    720

acctggagaa gcgttttgac tttgagcaag ttactgtgaa aaaattcagg acttgggctg    780

agcggcggca attcaatcgg gaaatgaagc ggaagcaggc ggagtccgag aggcccatct    840

tgccagccaa tcagaagctc attactttat cagtgcaaga tgcacccaca aagaaagagt    900

ttgttattaa ccccaacggg aaatccgagg tctgcatcct gcacgagtac atgcagcgtg    960

tcctcaaggt ccgccctgtc tataatttct ttgaatgtga gaacccaagt gagccttttg   1020

gtgcctcggt gaccattgat ggtgtgactt acggatctgg aactgcaagc agcaaaaaac   1080

ttgcgaagaa taaagctgcc cgagctacac tggaaatcct catccctgac tttgttaaac   1140
```

-continued

```
agacctctga agagaagccc aaagacagtg aagaactcga gtattttaac cacatcagca   1200
tcgaggactc gcgggtctac gagctgacca gcaaggctgg gctgttgtct ccatatcaga   1260
tcctccacga gtgccttaaa agaaaccatg ggatgggtga cacgtctatc aagtttgaag   1320
tggttcctgg gaaaaaccag aagagtgaat acgtcatggc gtgtggcaag cacacagtgc   1380
gcgggtggtg taagaacaag agagttggaa agcagttagc ctcacagaag atccttcagc   1440
tgctgcaccc acatgtcaag aactgggggt ctttactgcg catgtatggc cgtgagagca   1500
gcaagatggc caagcaggag acatcggaca agagtgtgat tgagctgcag cagtatgcca   1560
agaagaacaa gcccaacctg cacatcctca gcaagctcca agaggagatg aagaggctag   1620
ctgaggaaag ggaggagact cgaaagaagc ccaagatgtc cattgtggcg tccgcccagc   1680
ctggcggtga gcccctgtgc accgtggacg tgtgagggag gtggcacggg ccagggcgcg   1740
ggggccgcca gccgcacttc tgaggagacc agcagtcatg catcgtgcac cacagtgtca   1800
ggcctccaac ccacgctcct tccctgtggc caacctgtgg gcccggcctt agggtggaga   1860
ctttagtgta cagggacagc catggccaca cagcacacat gtggagcagc ggctctccct   1920
ggaaagctcc aggcctgaat ggatggactc agcgactgca ccagtggcag ctggtgactg   1980
tggacagtgg tggaccctgc ttctgtgcac ctgctgcagg ctctttttat gaaggctttc   2040
atgaatttta gtatgtaata cgcactgacg acacatgatg cttggatgac agatgagagg   2100
ggatggctga gtcctgtggc tggcccgtga tgccaggtgg cccatgtgcc cagggcgcct   2160
gcagggctgc tacagggacc tggtcaggag gtgcacatgg tgccctgccc tcacccaccc   2220
tctgtgtttc cccttctttg aaaaggtaga agagaaagga atattttaaa ccttttggc    2280
ttaaacagaa ttttagcatc agaactagct ttctgggatt ggaggcaaac catcaaggtg   2340
gtccctctcc agtctggaca cgatgccagc aaggatgacg tcctgccacc tcctggagtt   2400
accctggcct cctagggtcc ctttttctga tgaagtctta attccctaaa agcgcctctt   2460
tggacactga ggccctctct gcctttcctg gcctccggca acagtttttt tacaaagatt   2520
ttttgcagtc gagtccatat gtccacccat tgatttttaa agcttttgtg atattttagc   2580
attttgaaag actttcacag tgagagtaga aggtagattt ggaatcatgc attttagcaa   2640
gtggacttgt tgaaacagga agcaagggcc ttcagtgtag cccattcttg atccagagct   2700
gttgcctgtg acagcggttt ctctggatgt caaaggcagc tgcctggtgc ccagcttgct   2760
tctcgactgg tggcccctat gggtgggtgt gcgatggaaa tgtgttcctg ccggagtctg   2820
aggcaccagg gtgtgctcaa aggctggccc tggtggtgga ctggcacctg tgcagagtgc   2880
cgtgtgcttg tggtgcgcca tctgaagcaa gagtccagcg ttctgccgtg tctgtccccc   2940
accatgcccc ctacaggcgg tactgatggc gctttttttt tttttttct gtcaggaaaa    3000
caatgttggc ctgtgggccg cccacaacat atccttccct cactacctgt gtgaccaagg   3060
ttggcttctg ttgacctttt aaaaaagaaa ccctcaactc aaattgctat aattagacac   3120
ttgcttctgt cttgcctcct gtctgcagct gtgaatagtc atttgactgt gactgttgcc   3180
cttagccagc cagatgcgcc tgtgaaccaa agcttcgtgc acatgtgttc ccctaaaggt   3240
tggggagcct cgctgtgtct tgctgttccc aggcaccacc acagcaggtg ctgccatact   3300
cttgtggtct ctgtgcgccc cccccccccc cacccgtctg ccaagcatgg gtatgaatcg   3360
tgcacacagc catgcttcaa ggccggggca ggggagcctg tgctgatgcc atccagggca   3420
ctgggctgtg cctggaaggc gagccttgat tgtctgaaca cataaagcaa actgtccaga   3480
```

-continued

```
aaaaaaaaaa aaaaaa                                                   3496

<210> SEQ ID NO 52
<211> LENGTH: 3508
<212> TYPE: DNA
<213> ORGANISM: Human

<400> SEQUENCE: 52

gcaacagccc agccctagct tgggagcgga cccacacgaa ctgctcaaag gcttggagcg     60

ggtctagtaa ggcgaacgga ctgcttccgg ccagaggtcc cgggcggagg aggaagctgt    120

ggctgccggc ggtgggacgc cccggccgct cagccccccgg gcactgctgt ggggcgttca    180

gctttccaca cttggggcaa agcaagccgc gaggaggaac cagacagtcc tgttagttgt    240

ggccagccct cattccctgg aaatggcaaa caaggggaac aagaagcgtc ggcagttctc    300

tctggaggag aaaatgaaag ttgtgggagc tgtagactca ggcaagagga aaggtgatgt    360

ggcaaaagaa tttggtatca ctccctctac tttatctaca ttcttaaagg atcgcaccaa    420

atttgaagaa aaggtgcggg aggcatccgt gggaccccag cggaaaagga tgaggagcgc    480

tctttatgat gacattgata aggctgtttt tgcttggttt caagaaatcc atgccaaaaa    540

cattcttgtg actggttctg tcattcggaa aaaagcacta aacttggcca acatgcttgg    600

ctatgacaat tttcaagcaa gtgtgggctg gctgaacaga tttagagatc gccacggaat    660

tgctttgaaa gcagtctgta gagaagatag tgacaggtta atgaatggtc taggaataga    720

taagattaat gagtggcatg caggggaaat tataaaactg attgctgact acagcccaga    780

tgatatcttt aatgctgatg agacaggagt gtttttccag ttgcttcccc agcacacact    840

tgctgctaaa ggagaccact gtagaggggg caagaaagca aagcagcggt tgacagcact    900

cttttgttgc aatgcctcgg ggactgaaaa aatgagacca ttgattgttg gtaggtcagc    960

cagcccacac tgcctcaaga acattcattc cctcccttgt gattaccgag ccaaccagtg   1020

ggcttggatg acaagggatc tgtttaatga gtggctgatg caagtggatg ccaggatgaa   1080

gagggcggaa cgccggatcc tcttgctcat agacaactgc tctgctcata acatgcttcc   1140

acacttggaa aggattcagg ttgggtatct gccctccaac tgtactgctg tcctgcagcc   1200

actgaatctt ggcataattc acaccatgaa agtactgtac cagagccacc ttctaaaaca   1260

gatcctcctc aagctcaaca gcagtgagga tcaagaagag gtggacatca agcaggccat   1320

cgacatgatt gctgcagcgt ggtggtcagt caagccatcc acagtggtga aatgttggca   1380

gaaggcaggc atcgtcccta tggaatttgc agaatgtgac acagaatcag cagccagtga   1440

accagacatt gccattgaaa agttgtggca cacagtggct attgccacct gtgtcccaaa   1500

tgaagtaaat ttccaggact ttgttactgc agatgatgat ctcattatct ctcaggacac   1560

agacatcatc caggacatgg tggctggcga aaataccagt gaagcaggaa gtgaagatga   1620

aggggaggta tctttaccag agcaaccaaa agtcaccatc acagaagcca tatcaagtgt   1680

acagaaactt agacagttcc tttccacttg tgtagacatt cctgatgcca tttttggaca   1740

attaaatggc atagatgaat atttaatgaa aagagtgaca caaaccctta ttgattccaa   1800

aattacagat ttcctccaaa caaaataatg caggaattta tttcagaaaa tgtagtttac   1860

aagaataaag atttctttag ataggttgtt gagccaattt aagtaaagca atgttattgt   1920

gacaacattc cagtactctg aaatagccag gaaacttctt tgaatggaat ttgactaata   1980

tgtgtgtttt cttttctttt gtttttggct gtctctggtc cttgattcaa gatgtatttt   2040

gattcatcca agggtttcca aacttgtctg caaattagga tcacttgaga atcctttaaa   2100
```

-continued

```
aattccaaag ctcaggccat atcccaggcc tattaaatca caatctttgg tgacgggtca   2160
caggcattgg tagttttgaa gctctccagg tgattccaat gtgcagacaa atttgaaaac   2220
tgaaccaacc acaggaacat caagtacact gtgggcctgg gtccagcttc tttccagtaa   2280
gtgtatctca ggggcttcca aatttagctt acatcagaat cacttggaag gcttgttaaa   2340
acccaaggct gctaggccca cccccagagt ttgatacagt agacctcagg tgggacccaa   2400
aaatttgcat ttctaacaca ttctcagctg atgcagtcca ggctccatgc tttgaaaacc   2460
actggtctag ctttagatag gatattgagc caatttaaat aaagcaatat actggtctag   2520
ctgagttcta gaacttctct ctttagctgg ccatctgaat actcccccat cactaattgt   2580
taaaaaaaga atcaactgtt cttactctag agctcttttt tcctttctgc tgatttgctg   2640
gaagcactac aagacttctg tttgttcgtt cgtttgtttg tttgtttgtt tttaaagatg   2700
gggtcttgtt atattgccta ggctggaatg cagtggttat tcacaggcat gattataaca   2760
cactactctc tctaactcct ggcctcaagc catcctccca aatagatggg actactgatg   2820
cacactgcca tgctggcctt acgaaatgtt ttaataggca tttcactaat agggatctgg   2880
agtacaagga aatacagtgc atttaagaca taggctgggc atggtggctc atgcctgtaa   2940
tcccagcaca ttgggaagat cacttgaggc aaggagtttg agaccagact ggccaacaca   3000
gcgagacccc catctctaaa aaaaaaaaaa ttaataagac atggatacaa ccagggaggg   3060
aggttataat aatagagcat cctgttaatc agaatcatgg gggagaacat acagcccagc   3120
gtgcctctca ctttccagaa agggtgagag gatcattaga gagttcatta gagagtattt   3180
attcctaata agtcagataa atgtcagttt catttttaga agtttcacac aatacctgct   3240
aatggtgtga tgtcattttt ccccctgctt caggttaatt ttttggatat ttcagaaacc   3300
catagcaatt cagtgatttt tctttttgta gtagctcagt caaaacaggt aacagcagat   3360
taatcataga aaatgttgct tccacattaa caaaacaatc actgaaaaac agcagatgtt   3420
taaatagatt attttatagc ttattttgga tattttttct tttaataaac taatatgatc   3480
atttgaatta aaaaaaaaaa aaaaaaaa                                      3508
```

<210> SEQ ID NO 53
<211> LENGTH: 1391
<212> TYPE: DNA
<213> ORGANISM: Human

<400> SEQUENCE: 53

```
tgcactcacc tcctagagac caggctgcca tcatgctctg gaagcttgtg gagaatgtca     60
agtacgaaga tatctatgag gaccggcacg atggtgtccc gagccacagc tcgcggctct    120
cccagctggg ctcggtgtcc caaggaccct actcgagcgc cccgccgctg tcccacaccc    180
cgtcgtcgga cttccagccg ccctacttcc cacccccccta ccagccgctc ccctaccacc    240
agagccagga cccctactcc cacgtcaacg accccctactc cctgaaccca ctgcaccagc    300
cccagcaaca tccctggggg caacggcagc ggcaagaagt gggttcggaa gccggctctc    360
tcctgcccca gcctcgggcc gccttgcccc agctctcggg ccttgacccc cggagggact    420
accactcggt ccgccggccg gacgtgctgc tgcattcggc gcaccacggc ctggacgcgg    480
gcatgggtga cagcctctcg ctgcacggcc tcggccatcc cggaatggaa gacgtccagt    540
cagttgaaga tgccaataac agcggcatga atctattgga ccagtctgtc attaaaaaag    600
ttccagttcc tcccaaatcg gtgacttctc taatgatgaa taaagacggc ttcctgggag    660
```

-continued

```
gcatgtctgt caacaccggc gaggtgtttt gctccgtccc aggccgtttg tctctgctca    720

gttcaacttc gaagtacaaa gtaactgtgg gagaagttca gagacggctg tcgccccctg    780

aatgcctcaa tgcatctctc ctcggcggag tcctcagaag agccaaatcg aaaaatgggg    840

ggagatcttt gcgagaaagg ctagaaaaaa tcggtttgaa tttacccgcg ggcaggcgca    900

aagcagcaaa tgtcacgtta ctcacctccc tggtggaagg agaagctgtt cacttagcta    960

gggattttgg gtacatttgc gaaacggagt ttcccgccaa agccgtctct gagtatttga   1020

accggcagca cacagacccg agtgacctgc actcccgaaa gaatatgctg ttggccacca   1080

agcaactttg taaagaattt acggatctac tggcgcagga ccggacaccg atagggaaca   1140

gccgacccag ccccatcctg gagccgggga tccagagctg cctcacgcac ttcagcctca   1200

tcacgcacgg cttcggcgcc ccggccattt gcgccgcgct cacggccctg cagaactatc   1260

tcaccgaggc gctcaaaggc atggacaaga tgttcttgaa caacaccacc actaacaggc   1320

acacgtctgg ggaaggccca ggtagtaaaa ctggcgacaa ggaggagaaa cacaggaaat   1380

gaaaaatttt t                                                        1391
```

<210> SEQ ID NO 54
<211> LENGTH: 4862
<212> TYPE: DNA
<213> ORGANISM: Human

<400> SEQUENCE: 54

```
acgcagctcc gccccgcgtc cgacccgcgg atcccgcggc gtccggcccg ggtggtctgg     60

atcgcggagg gaatgccccg gagggcggag aactgggacg aggccgaggt aggcgcggag    120

gaggcaggcg tcgaagagta cggccctgaa gaagacggcg gggaggagtc gggcgccgag    180

gagtccggcc cggaagagtc cggcccggag gaactgggcg ccgaggagga gatggaggcc    240

gggcggccgc ggcccgtgct gcgctcggtg aactcgcgcg agccctccca ggtcatcttc    300

tgcaatcgca gtccgcgcgt cgtgctgccc gtatggctca acttcgacgg cgagccgcag    360

ccctacccaa cgctgccgcc tggcacgggc cgccgcatcc acagctaccg aggtcacctt    420

tggctcttca gagatgcagg gacacacgat gggcttctgg ttaaccaaac tgaattattt    480

gtgccatctc tcaatgttga cggacagcct atttttgcca atatcacact gccagtgtat    540

actctgaaag agcgatgcct ccaggttgtc cggagcctag tcaagcctga gaattacagg    600

agactggaca tcgtcaggtc gctctacgaa gatctggaag accacccaaa tgtgcagaaa    660

gacctggagc ggctgacaca ggagcgcatt gcacatcaac ggatgggaga ttgaagattt    720

ctgttgaaac ttacactgtt tcatctcagc ttttgatggt actgatgagt cttgatctag    780

atacaggact ggttccttcc ttagtttcaa agtgtctcat tctcagagta aaataggcac    840

cattgcttaa aagaaagtta actgacttca ctaggcattg tgatgtttag gggcaaacat    900

cacaaaatgt aatttaatgc ctgcccatta gagaagtatt tatcaggaga aggtggtggc    960

atttttgctt cctagtaagt caggacagct tgtatgtaag gaggtttata taagtaattc   1020

agtgggaatt gcagcatatc gtttaatttt aagaaggcat tggcatctgc ttttaatgga   1080

tgtataatac atccattcta catccgtagc ggttggtgac ttgtctgcct cctgctttgg   1140

gaagactgag gcatccgtga ggcagggaca agtctttctc ctctttgaga ccccagtgcc   1200

tgcacatcat gagccttcag tcagggtttg tcagaggaac aaaccagggg acactttgtt   1260

agaaagtgct tagaggttct gcctctattt ttgttggggg gtgggagagg ggaccttaaa   1320

atgtgtacag tgaacaaatg tcttaaaggg aatcattttt gtaggaagca tttttttataa   1380
```

-continued

```
ttttctaagt cgtgcacttt ctcggtccac tcttgttgaa gtgctgtttt attactgttt   1440
ctaaactagg attgacattc tacagttgtg ataatagcat ttttgtaact tgccatccgc   1500
acagaaaata cgagaaaatc tgcatgtttg attatagtat taatggacaa ataagttttt   1560
gctaaatgtg agtatttctg ttcctttttg taaatatgtg acattcctga ttgatttggg   1620
tttttttgtt gttgttgttt tgttttgttt tgtttttttg ggatggagkc tcactcttgt   1680
cacccaggct ggagtgcagt ggcgccatct cggctcactg caacctctgc ctcctgagtt   1740
cacgtaatcc tcctgagtag ctgggattac aggtgcctgc caccacgctg gccaattttt   1800
gtacttttag tagagacagt gtttcgccat gttggccagg ctggtttcaa actcctgacc   1860
tcaggtgatc cgcccacctc agcctcccaa aatggtggga ttacaggtgt gtgggccacc   1920
gtgcctggct gattcagcat tttttatcag gcaggaccag gtggacttcc acctccagcc   1980
tctggtccta ccaatggatt catggagtag cctggactgt ttcatagttt tctaaatgta   2040
caaattctta taggctagac ttagattcat taactcaaat tcaatgcttc tatcagactc   2100
agtttttttgt aactaataga tttttttttc cacttttgtt ctactccttc cctaatagct   2160
ttttaaaaaa atctccccag tagagaaaca tttggaaaag acagaaaact aaaaaggaag   2220
aaaaaagatc cctattagat acacttctta aatacaatca cattaacatt ttgagctatt   2280
tccttccagc ctttttaggg cagattttgg ttggttttta catagttgag attgtactgt   2340
tcatacagtt ttataccctt tttcatttaa ctttataact taaatattgc tctatgttag   2400
tataagcttt tcacaaacat tagtatagtc tccctttttat aattaatgtt tgtgggtatt   2460
tcttggcatg catctttaat tccttatcct agcctttggg cacaattcct gtgctcaaaa   2520
atgagagtga cggctggcat ggtggctccc gcctgtaatc ccagtacttt gggaagccaa   2580
ggtaagagga ttgcttgagc ccagaacttc aagatgagcc tgggctcata gtgagaaccc   2640
gtctatacaa aaaattttta aaaattagca tggcggcaca catctgtaat cctagctact   2700
tggcaggctg aggtgagaag atcattggag tttaggaatt ggaggcggca gtgagtcatg   2760
agtatgccgc tgcactccag cctgggggac agagcaagac cctgcctcaa aaaaaaaaaa   2820
aaaaaaaatt caggccggga atggtggttc acgcctgtaa tcccagcact ttgggggggtc   2880
gaggtgggca gatcacctga ggtcaggagt tcgagaccag cctggccaac atggtaaaac   2940
cccatttcta ctaaaaaata caagaattag ctgggtgtgg tggcgcatgc ctgtaatcct   3000
agctactcag gaggctgagg caggagaatc acttgacccc aggaggcgaa gattgcagtg   3060
agctgatatc gcaccattgt actccagcct gtgtgacaga gcaatactct tgtcccaaaa   3120
aaaaaaaaaa ttcaaatcag agtgaagtga atgagacact ccagttttcc ttctactccg   3180
aattttagct cctcctttca acattcaaca aatagtcttt tttttttttt ttttttttg   3240
gggatggagt ctccctctgt tgcccaggct ggagtgcaga ggtgcgatct ctgctcacta   3300
caagctctgc ctcccgagtt caagtgattc tcctggctca ccctcctgag ctgggattac   3360
aggcgcctgc caccatgcct ggctaatttt gtgtttttag tggagacggg gtttcaccat   3420
gttgtccagg atggtcttga tctcctgacc ttgtgatcca cccacctcag cctcccaaag   3480
tggtgggatt acaggtgtga gccaccgcgt ccagccagct ttattatttt ttttaagctg   3540
tctttgtgtc aaaatgatag ttcatgctcc tcttgttaaa acctgcaggc cgagcacagt   3600
ggctcatgcc tgtaatccca gcattttggg agaccaaggc ggatggatca cctgaggtca   3660
ggagctcaag accagcctgg ctaacatggt gaaacctcat ctccacttaa aatacaaaaa   3720
```

-continued

```
ttgccggccg cggcggctca tgcctgtaat cccagcactt tgggaggcct aggcgggtgg   3780

atcacgacgt caggaaatcg agaccatcct ggctaacacg ggtgaaaccc cgtctctatt   3840

aaaaaataga aaaaattagg cgggcgtggt ggtgagcgcc tgtagtccca gctactcgag   3900

agcctgaggc aggagaatgg catgaacctg gaaggtggag cttgcagtga gctgagatgg   3960

tgccactgca ctctaacctg ggcgacagag tgagactccg tctcaaaaaa aaaaacaaaa   4020

accaaaactt atccaggtgt ggcggtgggc gcctgtgagg caggcgaatc tcttgaaccc   4080

gggaggcgga ggttgcagtg agccaagatc acaccattgc actccagcct gggaaacaag   4140

agtgaaattc catctcaaaa ccaaattttc aaaaaaaaaa catgccgctt gagtactgtg   4200

tttttggtgt tgtccaagga aaattaaaac ctgtagcatg aataatgttt gttttcattt   4260

cgaatcttgt gaatgtatta aatatatcgc tcttaagaga cggtgaagtt cctatttcaa   4320

gtttttttg ttttgttttg tttttaagct gtttttaat acattaaatg gtgctgagta   4380

aaggaaatag gcagggtgtg ttgtgtggtg ttttaactag gcgcttctct ctcagagagt   4440

tttgaaacct gtttacataa aggcccaaga tgggaaggag atccaaacat aagccaccag   4500

cctcattcca agtctcttct ctttccaacc ctggattttt ttttttatt taacattgtt   4560

tcttttagct ttattttct tataaaagaa atgtatcact ataaaaaatt acacactaca   4620

gaaaaatatt aagaagaaaa acattcacat cggaaacaaa gtttttccc atgaaaacag   4680

aacccaaaag ggtaagtggt tagtatttca ccagcaatta tgttgagaat aaggccaggc   4740

gaggtggctc acgcctgtaa tctcagcact ttgggaggcc agggcaggca gatcatctga   4800

ggtcaggagt ttgagaccag cctggccaac atggtgaaac cctatctcta ctaaaaatta   4860

aa                                                                  4862
```

<210> SEQ ID NO 55
<211> LENGTH: 3568
<212> TYPE: DNA
<213> ORGANISM: Human

<400> SEQUENCE: 55

```
atagttttca ggttaagaaa gccagaatct ttgttcagcc acactgactg aacagacttt     60

tagtggggtt acctggctaa cagcagcagc ggcaacggca gcagcagcag cagcagcagc    120

agcagcagca gcagggctcc tgggataact caggcatagt tcaacactat gggtcctcct    180

ctgaagctct tcaaaaacca gaaataccag gaactgaagc aggaatgcat caaagacagc    240

agacttttct gtgatccaac atttctgcct gagaatgatt ctcttttcta caaccgactg    300

cttcctggaa aggtggtgtg gaaacgtccc caggacatct gtgatgaccc ccatctgatt    360

gtgggcaaca ttagcaacca ccagctgacc caagggagac tggggcacaa gccaatggtt    420

tctgcatttt cctgtttggc tgttcaggag tctcattgga caaagacaat tcccaaccat    480

aaggaacagg aatgggaccc tcaaaaaaca gaaaaatacg ctgggatatt tcactttcgt    540

ttctggcatt ttggagaatg gactgaagtg gtgattgatg acttgttgcc caccattaac    600

ggagatctgg tcttctcttt ctccacttcc atgaatgagt tttggaatgc tctgctggaa    660

aaagcttatg caaagctgct aggctgttat gaggccctgg atggtttgac catcactgat    720

attattgtgg acttcacggg cacattggct gaaactgttg acatgcagaa aggaagatac    780

actgagcttg ttgaggagaa gtacaagcta ttcggagaac tgtacaaaac atttaccaaa    840

ggtggtctga tctgctgttc cattgagtct cccaatcagg aggagcaaga agttgaaact    900

gattggggtc tgctgaaggg ccatacctat accatgactg atattcgcaa aattcgtctt    960
```

-continued

```
ggagagagac ttgtggaagt cttcagtgct gagaaggtgt atatggttcg cctgagaaac   1020
cccttgggaa gacaggaatg gagtggcccc tggagtgaaa tttctgaaga gtggcagcaa   1080
ctgactgcat cagatcgcaa gaacctgggg cttgttatgt ctgatgatgg agagttttgg   1140
atgagcttgg aggacttttg ccgcaacttt cacaaactga atgtctgccg caatgtgaac   1200
aaccctattt ttggccgaaa ggagctggaa tcggtgttgg gatgctggac tgtggatgat   1260
gatcccctga tgaaccgctc aggaggctgc tataacaacc gtgatacctt cctgcagaat   1320
ccccagtaca tcttcactgt gcctgaggat gggcacaagg tcattatgtc actgcagcag   1380
aaggacctgc gcacttaccg ccgaatggga agacctgaca attacatcat tggctttgag   1440
ctcttcaagg tggagatgaa ccgcaaattc cgcctccacc acctctacat ccaggagcgt   1500
gctgggactt ccacctatat tgacacccgc acagtgtttc tgagcaagta cctgaagaag   1560
ggcaactatg tgcttgtccc aaccatgttc cagcatggtc gcaccagcga gtttctcctg   1620
agaatcttct ctgaagtgcc tgtccagctc agggaactga ctctggacat gcccaaaatg   1680
tcctgctgga acctggctcg tggctacccg aaagtagtta ctcagatcac tgttcacagt   1740
gctgaggacc tggagaagaa gtatgccaat gaaactgtaa acccatattt ggtcatcaaa   1800
tgtggaaagg aggaagtccg ttctcctgtc cagaagaata cagttcatgc catttttgac   1860
acccaggcca ttttctacag aaggaccact gacattccta ttatagtaca ggtctggaac   1920
agccgaaaat tctgtgatca gttcttgggg caggttactc tggatgctga ccccagcgac   1980
tgccgtgatc tgaagtctct gtacctgcgt aagaagggtg gtccaactgc caaagtcaag   2040
caaggccaca tcagcttcaa ggttatttcc agcgatgatc tcactgagct ctaaatctgc   2100
aatcccagag aatcctgaca aagcgtgcca cccttttatt ttccgtcagg tgccaggtct   2160
tagttaagat tcacaatctt tagaaagaat gagattcaca ataattaact cttcctctct   2220
tctgataaat tccccatacc tcccaatcca agtagcatct gtagctacat aacctatata   2280
cctccagcag ctggacatgg ggaggcgaca gtcctatcta gacatcatac acatttgcca   2340
agaaaggatc tctggggctt ccgggggtga gattcaagca ggacaataac aagaggctgg   2400
acaccctaca gatgtctttg atgttttcag ttgtttgata tatctcccct gtagggcatg   2460
ttgaggaagg aggagggctg atcaaggcca agctggtcta gcctgacatc ctagctcctg   2520
actgaacact atagacttcc cagcagcatt tcacccagca gccagagccg gctttaagtc   2580
cccaaccctt acagacacca ctgccaccac caccaaccac gaccaccacc accaccacca   2640
ctcaccacca tcatcacctc cggaaagtgt agtcctgccc taacccaagt cacccccgac   2700
agtaaatttt accttcatgt tgagaaagct tcctggtgct taatcaagag ctggagttca   2760
atgagtccta gacagtgaga ggggcctgag cttcagctca atggaagcct gctgtgtgcc   2820
acaagacgga aaagtggaag aagctgcagt gggagacaaa gcctcggtcc cccacccatc   2880
cacacacacc tacactcaca cacgcgcaca tgggcgcgca cgaactacca ttcaggcagt   2940
cagtgggcaa gaggaaagat aagtaagtac catacacacc taaaagatga gagaattcat   3000
ccagacatat tacagccagt ttggggcccc tgactgcaat gtgaaacctc tcgctgctgc   3060
taggtttaca aacaagccca ttgtcctgtg cctcctaata tcatttgtac tgaagacccc   3120
atctggggac ttgagacttt ggtcccagcc cagactcctc agacttttct ctcagttggg   3180
atgcttcact cgctgggggt gtttgtttgc cctctcattt ttcagtactt ctacagaatt   3240
ttctctagag tcagtcatta tgaaatgtac ttccctccat cttaacctat caactttctg   3300
```

-continued

```
cccctccttc aaggcccagt ataaatgcca cctcctccat gaagccttcc ctaattccac   3360

cccaaacccc caccttcaac aatatttcaa cgcttctgca atgatgaaaa agaaacatag   3420

ttgtagtact tagcctacct agaccagcaa gcattcattt ttagctcgct catttttttac   3480

catgttttcc agtctgttta acttctgcag tgccttcact acactgcctt acataaacca   3540

aatcacaata aagttcatat tcagtaca                                      3568
```

<210> SEQ ID NO 56
<211> LENGTH: 1955
<212> TYPE: DNA
<213> ORGANISM: Human

<400> SEQUENCE: 56

```
gaattcacca agcgttggat tgttcaccca ctaataggga acgtgagctg ggtttagacc     60

gtcgtgagac aggttagttt taccctactg atgatgtgtt gttgccatgg taatcctgct    120

cagtacgaga ggaaccgcag gttcagacat ttggtgtatg tgcttggctg aggagccaat    180

ggggcgaacg taccatctgt gggattatga ctgaacgcct ctaagtcaga atcccgccca    240

ggcgaacgat acggcagcgc cgcggagcct cggttggcct cggatagccg gtcccccgcc    300

tgtccccgcc ggcgggccgc ccccccctcc agcgccccgc gcgcgcggga gggcgcgtgc    360

cccgccgcgc gccgggaccg gggtccggtg cggagtgccc ttcgtcctgg gaaacggggc    420

gcggccggaa aggcggccgc cccctcgccc gtcacgcacc gcacgttcgt ggggaacctg    480

gcgctaaacc attcgtagac gacctgcttc tgggtcgggg tttcgtacgt agcagagcag    540

ctccctcgct gcgatctatt gaaagtcagc cctcgacaca agggtttgtc cgcgcgcgcg    600

gcggcgtgcg tgcgggggc ccggcggggc gtgcgcgtcc ggcgccgtcc gtccttccgt    660

tcgtcttcct ccctcccggc ctctccgccg accgcgggcg tggtgggggg gtgggggggg    720

gacgcgcgac cccggtcggc gcgccccgct tcttcggttc ccgcctcctc cccgttcacc    780

gcggggcggc tcgtccgctc cgggccggga cggggtccgg ggagcgtggt ttgggagccg    840

cggaggcggc cgcgccgagc cgggcccgtg cgcggtcccc gtcccggggg ttggccgcgc    900

gggccccggt ggggccaccc ggggtcccgg ccctcgcgcg tccttcctct cgctcctccg    960

cacgggtcga ccagcagacc gcgggtggtg ggcggcgggc ggcgaggccg cacgggcgtc   1020

cccgcacccg gccgacctcc gctcgtgacc tctcctcggt cgggctccgg ggtcgaccgc   1080

ctgccccgcg ggcgtgagac tcagccgctg tctcgccgtg tcccgggtcg accggcgggc   1140

ttctccaccg agcggcgtgt aggagtgccc gtcgggacga accgcaaccg gagcgtcccc   1200

gtctcggtcg gcacctccgg ggtcgaccag ctgccgcccg cgagctccgg acttagccgg   1260

cgcctgcacg tgtcccgggt cgaccagcag gcggccgcga cgtgcggcgc accgacgaga   1320

gggcgtgcat tcccgttcgc gcgcccggac cctccaccgg cctgggcccg acggtggagc   1380

tgggaccacg cggaactccc tctcctacat ttttttcagc cccaccgcga gtttgcgtcc   1440

gcgggatttt aagagggagt cactgctgcc gtcagccagt aatgcttcct ccttttttgc   1500

ttttaggttt tgctcttgcc tttttttttt tttttttctt tctttctttc tttctttctt   1560

tctttctttc tttctttctt tctttctcgc tctcgcctct cgctctctcc ctcgctcgtt   1620

ttctttctct ttctctttct ctctctctct ctctctctct ctctctgtct ctcgctctcg   1680

ccctctctct ctctctcttc tctctgtctc tctctgtctc tctctctctc tctctctctc   1740

tctctctctc tctctctctc tctctctccc tccccctccc tccctctctc cccttccttg   1800

gtgccttctc ggctcttgac acttagccgc tgtctcgccg tgtcccgggt cgaccggcgg   1860
```

-continued

```
gccttctcca ccgagcggcg tgtaagagtg cccgtcggga cgagccggac ccgccgcgtc   1920

cccgtctcgg tcggcactcc ggggtcgacc agctg                              1955
```